US006809209B2

(12) United States Patent
Rodriguez

(10) Patent No.: US 6,809,209 B2
(45) Date of Patent: Oct. 26, 2004

(54) NITROGEN-CONTAINING GROUP-13 ANIONIC COMPOUNDS FOR OLEFIN POLYMERIZATION

(75) Inventor: George Rodriguez, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 60 days.

(21) Appl. No.: 10/239,030

(22) PCT Filed: Apr. 3, 2001

(86) PCT No.: PCT/US01/10697

§ 371 (c)(1),
(2), (4) Date: Sep. 17, 2002

(87) PCT Pub. No.: WO01/81435

PCT Pub. Date: Nov. 1, 2001

(65) Prior Publication Data

US 2003/0083515 A1 May 1, 2003

Related U.S. Application Data

(60) Provisional application No. 60/196,013, filed on Apr. 7, 2000.

(51) Int. Cl.[7] .............................. C07F 5/06; C07F 5/00; B01J 31/00; C08F 4/64
(52) U.S. Cl. ........................... 556/1; 502/103; 502/117; 526/160; 526/943; 556/12; 556/173; 556/174; 556/187; 556/189; 568/2; 568/6
(58) Field of Search ............................ 568/2, 6; 556/1, 556/12, 173, 174, 187, 189; 502/103, 117; 526/160, 943

(56) References Cited

U.S. PATENT DOCUMENTS

| | | | |
|---|---|---|---|
| 4,543,399 A | 9/1985 | Jenkins, III et al. | 526/70 |
| 4,588,790 A | 5/1986 | Jenkins, III et al. | 526/70 |
| 4,871,705 A | 10/1989 | Hoel | 502/117 |
| 4,892,851 A | 1/1990 | Ewen et al. | 502/104 |
| 4,937,299 A | 6/1990 | Ewen et al. | 526/119 |
| 5,001,205 A | 3/1991 | Hoel | 526/128 |
| 5,017,714 A | 5/1991 | Welborn, Jr. | 556/12 |
| 5,028,670 A | 7/1991 | Chinh et al. | 526/73 |
| 5,153,157 A | 10/1992 | Hlatky et al. | 502/117 |
| 5,198,401 A | 3/1993 | Turner et al. | 502/155 |
| 5,241,025 A | 8/1993 | Hlatky et al. | 526/129 |
| 5,278,119 A | 1/1994 | Turner et al. | 502/155 |
| 5,278,264 A | 1/1994 | Spaleck et al. | 526/127 |
| 5,296,433 A | 3/1994 | Siedle et al. | 502/117 |
| 5,296,434 A | 3/1994 | Karl et al. | 502/117 |
| 5,304,614 A | 4/1994 | Winter et al. | 526/127 |
| 5,308,816 A | 5/1994 | Tsutsui et al. | 502/108 |
| 5,318,935 A | 6/1994 | Canich et al. | 502/117 |
| 5,324,800 A | 6/1994 | Welborn et al. | 526/160 |
| 5,352,749 A | 10/1994 | DeChellis et al. | 526/68 |
| 5,382,638 A | 1/1995 | Bontemps et al. | 526/67 |

(List continued on next page.)

FOREIGN PATENT DOCUMENTS

| | | |
|---|---|---|
| DE | 196 32 557 A1 | 2/1998 |
| EP | 0 129 368 A | 12/1984 |
| EP | 0 277 003 | 8/1988 |
| EP | 0 277 004 | 8/1988 |
| EP | 0 418 044 A | 3/1991 |
| EP | 0 577 581 A2 | 1/1994 |
| EP | 0 578 838 A1 | 1/1994 |
| EP | 0 591 756 A | 4/1994 |
| EP | 0 570 982 | 1/1997 |
| EP | 0 500 944 | 10/1998 |
| WO | WO 91/09882 | 7/1991 |
| WO | WO 92/00333 | 1/1992 |
| WO | WO 92/10066 | 6/1992 |
| WO | WO 93/02099 | 2/1993 |
| WO | WO 93/14132 | 7/1993 |
| WO | WO 93/19103 | 9/1993 |
| WO | WO 94/01471 | 1/1994 |
| WO | WO 94/03506 | 2/1994 |
| WO | WO 95/07941 | 3/1995 |
| WO | WO 95/07942 | 3/1995 |
| WO | WO 96/08519 | 3/1996 |
| WO | WO 96/23010 | 8/1996 |
| WO | WO 96/33227 | 10/1996 |
| WO | WO 96/40805 | 12/1996 |
| WO | WO 97/19959 | 6/1997 |
| WO | WO 97/22635 | 6/1997 |
| WO | WO 97/22639 | 6/1997 |
| WO | WO 97/29845 | 8/1997 |
| WO | WO 97/35893 | 10/1997 |
| WO | WO 97/48735 | 12/1997 |
| WO | WO 98/55518 | 12/1998 |
| WO | WO 99/06412 | 2/1999 |
| WO | WO 99/06413 | 2/1999 |
| WO | WO 99/06449 | 2/1999 |
| WO | WO 99/30822 | 6/1999 |
| WO | WO 99/42467 | 8/1999 |
| WO | WO 99/43717 | 9/1999 |
| WO | WO 99/45042 | 9/1999 |

*Primary Examiner*—Porfirio Nazario-Gonzalez
(74) *Attorney, Agent, or Firm*—Charles E. Runyan

(57) ABSTRACT

The invention addresses an composition of matter comprising a cation [Ct]⁺ and an anion [A]⁻, the anion comprises a core Group-13 element bound to partially or completely fluorinated fluoroaryl ligands, at least one of the fluoroaryl ligands is substituted with a Group-15 element that has been rendered essentially inert for subsequent chemical reaction through its unbonded electron pair by substituting an electron-withdrawing group on it. [Ct]⁺ may be selected from anilinium and ammonium cations, trityl carbenium cations, Group-11 metal cations, silylium cations, the cations of the hydrated salts of Group-1 or -2 metals, and derivatives of the foregoing anilinium, ammonium, trityl carbenium, and silylium cations containing $C_1-C_{20}$ hydrocarbyl, hydrocarbylsilyl, or hydrocarbylamine substituents for one or more hydrogen atoms of said cations. The compositions can be used to activate olefin polymerization catalysts, and can be prepared to dissolve in aliphatic solvents. Syntheses and polymerization are illustrated.

38 Claims, No Drawings

U.S. PATENT DOCUMENTS

| | | | |
|---|---|---|---|
| 5,387,568 A | 2/1995 | Ewen et al. | 502/104 |
| 5,405,922 A | 4/1995 | DeChellis et al. | 526/68 |
| 5,408,017 A | 4/1995 | Turner et al. | 526/134 |
| 5,436,304 A | 7/1995 | Griffin et al. | 526/68 |
| 5,447,895 A | 9/1995 | Marks et al. | 502/117 |
| 5,453,471 A | 9/1995 | Bernier et al. | 526/68 |
| 5,462,999 A | 10/1995 | Griffin et al. | 526/68 |
| 5,463,999 A | 11/1995 | Taruya et al. | 123/647 |
| 5,470,993 A | 11/1995 | Devore et al. | 556/11 |
| 5,491,246 A | 2/1996 | Rosen et al. | 556/7 |
| 5,502,017 A | 3/1996 | Marks et al. | 502/103 |
| 5,502,124 A | 3/1996 | Crowther et al. | 526/127 |
| 5,504,049 A | 4/1996 | Crowther et al. | 502/117 |
| 5,512,693 A | 4/1996 | Rosen et al. | 556/7 |
| 5,635,573 A | 6/1997 | Harrington et al. | 526/170 |
| 5,688,634 A | 11/1997 | Mixon et al. | 430/296 |
| 5,763,556 A | 6/1998 | Shaffer et al. | 526/384.4 |
| 5,767,208 A | 6/1998 | Turner et al. | 526/160 |
| 5,834,393 A | 11/1998 | Jacobsen et al. | 502/152 |
| 5,851,945 A | 12/1998 | Turner et al. | 502/103 |
| 5,869,723 A | 2/1999 | Hinokuma et al. | 556/402 |
| 5,895,771 A | 4/1999 | Epstein et al. | 502/103 |

NITROGEN-CONTAINING GROUP-13 ANIONIC COMPOUNDS FOR OLEFIN POLYMERIZATION

This application claims the benefit of Provisional Application No. 60/196,013, filed Apr. 7, 2000.

TECHNICAL FIELD

This invention relates to polymerization cocatalyst compounds containing weakly coordinating Group-13 element anions and to the preparation of olefin polymers using catalyst systems based on organometallic transition-metal cationic compounds stabilized by these anions.

BACKGROUND

The term "noncoordinating anion" (NCA) is now accepted terminology in the field of olefin and vinyl monomer, coordination, insertion, and carbocationic polymerization. See, for example, EP 0 277 003, EP 0 277 004, U.S. Pat. No. 5,198,401, U.S. Pat. No. 5,278,119, and Baird, Michael C., et al, *J. Am. Chem. Soc.* 1994, 116, 6435–6436. The noncoordinating anions are described to function as electronic stabilizing cocatalysts, or counterions, for essentially active, cationic metallocene polymerization catalysts. The term noncoordinating anion applies both to truly noncoordinating anions and to coordinating anions that are labile enough to undergo replacement by olefinically or acetylenically unsaturated monomers at the insertion site. These noncoordinating anions can be effectively introduced into a polymerization medium as Bronsted acid salts containing charge-balancing countercations, as ionic cocatalyst compounds, or mixed with an organometallic catalyst before adding it to the polymerization medium. See also, the review articles by S. H. Strauss, "The Search for Larger and More Weakly Coordinating Anions", *Chem. Rev.*, 93, 927–942 (1993).

U.S. Pat. No. 5,502,017, to Marks et al., addresses ionic metallocene polymerization catalysts for olefin polymerization containing a weakly coordinating anion comprising boron substituted with halogenated aryl substituents preferably containing silylalkyl substitution, such as tert-butyldimethyl-silyl. Marks et al. disclose the weakly coordinating anion as the cocatalyst. The silylalkyl substitution is said to increase the solubility and thermal stability of the resulting metallocene salts. Examples 3–5 describe synthesis of and polymerization with the cocatalyst compound triphenylcarbenium tetrakis (4-dimethyl-t-butylsilyl-2,3,5,6-tetrafluorophenyl)borate.

In view of the above, there is a continuing need for olefin polymerization activators both to improve the industrial economics of solution polymerization and to provide alternative activating compounds for ionic, olefin polymerization catalyst systems.

BRIEF SUMMARY

The invention provides anion-containing cocatalyst precursor compounds which can be combined with organometallic catalyst precursor compounds to form active olefin polymerization catalysts for insertion, coordination, or carbocationic polymerization. Olefin polymerization can proceed by catalyst formation followed by or in situ catalyst formation essentially concurrent with, contacting the catalyst with appropriate monomers: those having accessible olefinic or acetylenic unsaturation or having olefinic unsaturation capable of cationic polymerization. The invention catalysts are suitable for preparing polymers and copolymers from olefinically and acetylenically unsaturated monomers. The anions $[A]^-$ of the cocatalyst precursors are those containing a Group-13 element core to which fluoroaryl ligands are connected, at least one of these fluoroaryl ligands is substituted with a Group-15 element containing a lone-pair electron functionality.

Additionally, the Group-15 element is attached to an electron withdrawing ligand that causes the lone-pair to become essentially inert, i.e., it will not strongly coordinate to the activated catalyst.

Preferred invention cocatalyst precursor compounds can be represented by the following formula:

$[Ct]^+[M(ArF)_n\{(ArF)E(ArF)(R)\}_{4-n}]^-$, where $[Ct]^+$ is a cation capable of abstracting an alkyl group, or breaking a carbon-metal connection, M is a Group-13 element, ArF is a fluorinated aryl group, E is a Group-15 element, n equals 0 to 3, and R is a $C_1$–$C_{20}$ hydrocarbyl or hydrocarbylsilyl substituent.

DETAILED DESCRIPTION

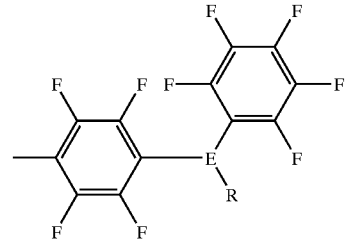

Exemplary ArF ligands and substituents of the above invention specifically include fluorinated aryl(fluoroaryl) groups, preferably perfluorinated aryl groups, and include substituted ArF groups having substituents in addition to fluorine, such as fluorinated hydrocarbyl groups. Preferred fluorinated aryl groups include phenyl, biphenyl, napthyl and their derivatives. The disclosures of U.S. Pat. Nos. 5,198,401, 5,296,433, 5,278,119, 5,447,895, 5,688,634, 5,895,771, WO 93/02099, WO 97/29845, WO 99/43717, WO 99/42467 and WO 99/45042 teach suitable ArF groups. It is preferred that at least one third of the hydrogen atoms connected to aromatic ligands be fluorine substituted, and more preferred that the aryl ligands be perfluorinated. Perfluorinated means that each aryl hydrogen atom, is substituted with fluorine or fluorcarbyl substituents, e.g., trifluoromethyl. The goal of the fluorination is to remove abstractable hydrogen from the NCA. The above chemical drawing illustrates a representative ligand structure on boron. E is preferably nitrogen and R is selected as desired for the polymerization sought. Additional ligands using nitrogen as E are illustrated below.

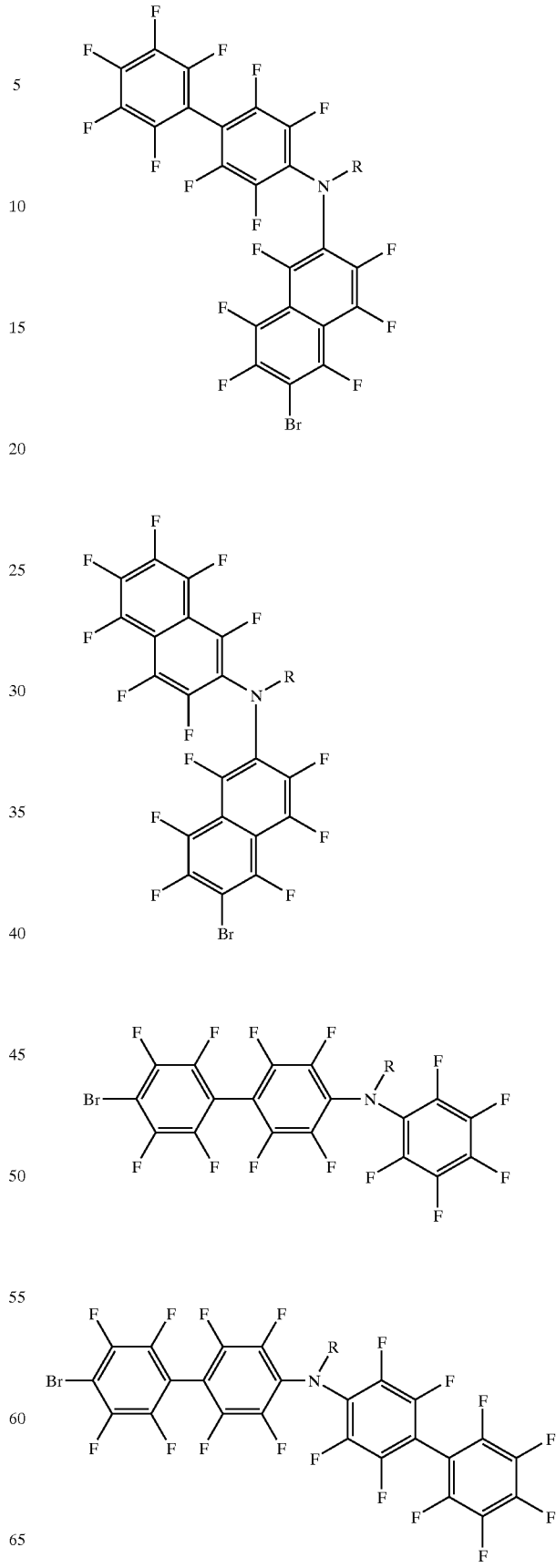

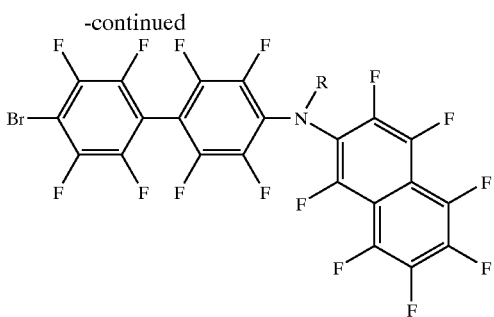

Essentially any of the defined R groups will be effective for olefin polymerization such as by solution, bulk, slurry and gas phase polymerization processes. Exemplary R groups include methyl, ethyl, n-propyl, iso-propyl, n-butyl, cyclohexyl, benzyl, trimethylsilyl, triethylsilyl, tri-n-propylsilyl, tri-isopropylsilyl, etc. Particular advantage in solution polymerization can be realized by selecting R such that solubility in aliphatic solvents is effectively achieved. The term "effective solubility", and equivalent phraseology, is used here to mean having sufficient solubility so that enough cocatalyst precursor can be dissolved in an aliphatic solvent (such as hexane) to activate industrially useful quantities of catalyst precursor, while bypassing slurry techniques and aromatic solvents. For example the selection of triethylsilyl, or higher carbon-number alkyl groups on silicon, provides effective solubility where trimethylsilyl is much less effective in doing so.

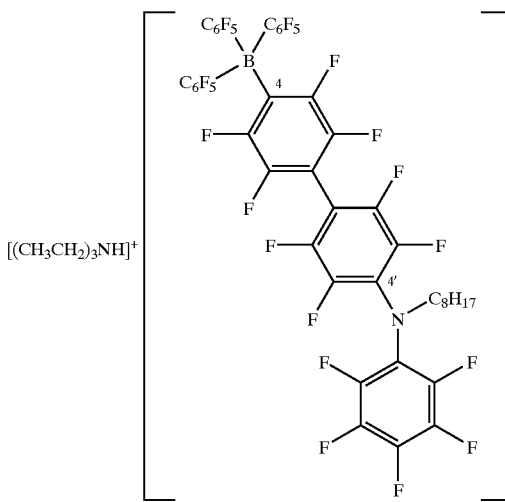

The ionic cocatalyst depicted above is referred to as [N,N,N-triethyl ammonium]+(4'-((perfluorophen-1-yl)(octyl)amino)perfluorbiphen-4-yl)tris(perfluorophen-1-yl)borate. The anion is named as a borate, in this case, trisperfluorophenylborate. (Note that the designation "-1-yl" is normally omitted from phenyl when it is named. The designation "-1-yl" is used to denote that a radical moiety is connecting to a central atom at the radical's one position. When phenyl is the radical, it, by convention, always has the connection point labeled 1, therefore no connection point need be labeled.) The borate has a fourth ligand: a perfluorinated biphenyl ligand that is itself substituted with a substituted amino group. This biphenyl radical connects to the boron atom at the radical's "4" position. This gives rise to "perfluorobiphen-4-yl". The biphenyl ligand is substituted at its "4'" position by an amino group. Specifically, the amino group is (octyl)-(perfluorophen-1-yl)amino. Hence, the portion of the name shown as "(4'-(perfluorophen-1-yl)(octyl)amino)".

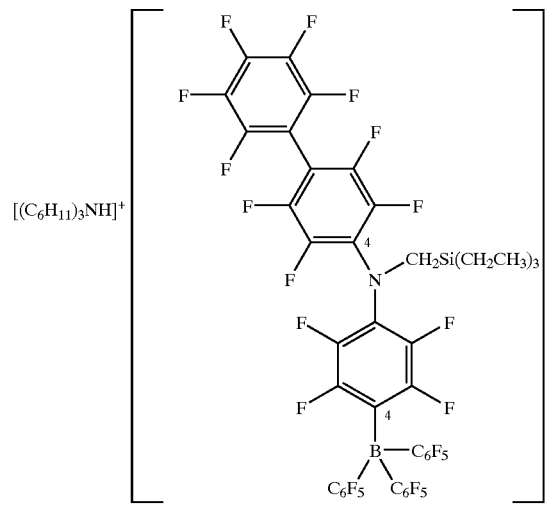

The ionic cocatalyst depicted above is referred to as [N,N,N-tricyclohexyl ammonium]+[(4-((perfluorobiphen-4-yl)(triethylsilylmethyl)amino)perfluorphen-1-yl) tris (perfluorophenyl)borate]. In this case, the anion is again named as a borate: tris(perfluorophenyl)borate. The borate has a fourth ligand: a perfluorinated phenyl ligand that is itself substituted with a substituted amino group. This phenyl radical connects to the boron atom at the radical's "1" position. This gives rise to "perfluorophen-1-yl". The phenyl ligand is substituted at its "4" position by an amino group. Specifically, the amino group is (triethyl(silyl)methyl)(perfluorobiphen-4-yl)amino. Hence, the portion of the name shown as "(4-(triethyl(silyl)methyl)(perfluorobiphen-4-yl)amino)".

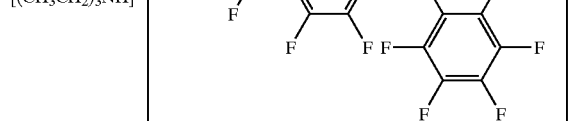

The ionic cocatalyst depicted above is referred to as [N,N,N-triethyl ammonium]+[(7-((perfluorophenyl)(octyl)phosphino)perfluornaphth-2-yl bis(perfluorophenyl)(perfluoronaphthyl)aluminate]. In this case, the anion is named as an aluminate: bisperfluorophenyl (perfluoronaphthyl)aluminate. The aluminate has a fourth ligand: a perfluorinated naphthyl ligand that is itself substituted with a substituted phosphino group. This napthyl radical connects to the aluminum atom at the radical's "2"

position. This gives rise to "perfluoronaphth2-yl". The naphthyl ligand is substituted at its "7" position by a phosphino group. Specifically, the phosphino group is (octyl)(perfluorophen-1-yl)phosphino. Hence, the portion of the name shown as "(7-(perfluorophen-1-yl)-(octyl) phosphino)".

Effective cationic groups (Ct+)(also referred to as activating cations) are those known to abstract a ligand (Q) such as monoanionic hydride, alkyl, or other hydrocarbyl or hydrocarbylsilyl ligands from organometallic catalyst precursors leaving active catalyst. An activating cation is suitable for abstracting an alkyl group or breaking a carbon-metal connection in an olefin polymerization catalyst precursor. Preferably, Ct+ doesn't interfere with polymerization. Useful cationic groups for this invention include, but are not limited to, nitrogen-containing groups such as ammonium salts of U.S. Pat. No. 5,198,401, and WO 97/35893, the trityl carbenium groups of U.S. Pat. No. 5,387,568, the silylium cationic groups of WO 96/08519. Additionally, suitable cations include nitrogen- and carbon-based cations described in WO 97/35893, and in copending U.S. applications Ser. Nos. 09/694,595 (22 Oct. 1999 priority), 60/160,942 (22 Oct. 1999 priority), 09/734,296 (9 Dec. 1999 priority), and 60/169,768 (9 Dec. 1999 priority). Thus, hydrocarbyl, hydrocarbyl-amine, hydrocarbyl-silyl, preferably $C_1-C_{20}$, and Group-1-,-2-,-11- and -12-based cationic groups suit this invention. An example of a hydrocarbyl-amine is [N-pentafluorophenyl pyrrolidine]. When based on Group-15 elements, the cationic moiety should be a tertiary amine or phosphine, though specialized secondary amines or phosphines are conceivable.

The invention cocatalyst compositions may be prepared by synthetic methods well within the skills of organic and organometallic chemists. In a typical procedure, pentafluoroaniline in an aprotic polar solvent is combined with pentafluorobromobenzene in the presence of a base. Other possible amines may be used. For example, 4-amino-nonafluorobiphenyl or 2-amino-heptafluoronaphthyl are useful alternatives. After work-up, the fluoroamine halobenzene combination affords N-(4-bromotetrafluorophenyl)-penta-fluoroaniline. Metalation of this secondary amine with a metal hydride provides the corresponding secondary metal amide, which is then treated with a chloroalkyl, bromoalkyl, or chlorotrialkylsilane. The resulting product is the corresponding tertiaryamine. In a one-pot procedure, this tertiary amine is first reacted with an alkyl lithium (e.g., n-butyl lithium), and then with one quarter of an equivalent of boron trichloride. This sequence of reactions provides $Li(Et_2O)_{2.5}$ $[4-(C_6F_5N\{SiR_3\})—C_6F_4]_4B$. Reacting this lithium salt with a dialkylanilinium chloride affords the corresponding dialkylanilinium borate. A specific example of this reaction sequence is shown in Scheme 1.

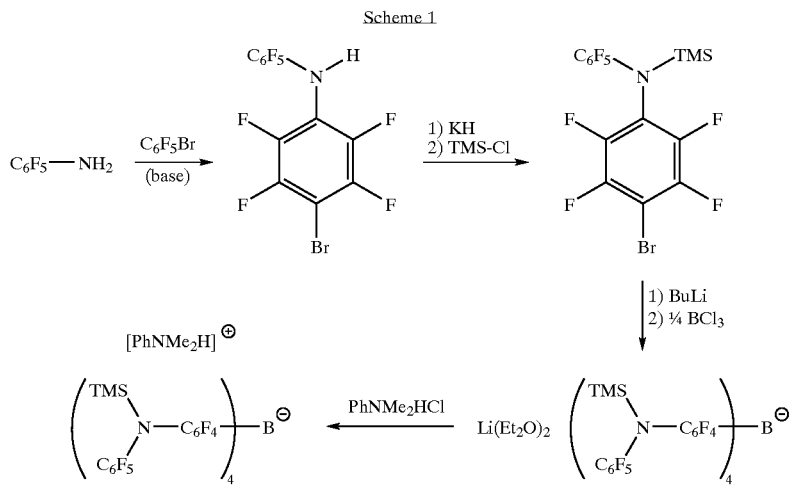

Scheme 1

Catalyst precursor compounds suitable for olefin polymerization catalysis by coordination or insertion polymerization will include the known organo-metallic, transition metal compounds useful in traditional Ziegler-Natta polymerization, particularly the metallocenes known to be useful in polymerization. A requirement for the catalyst precursor is that is must be susceptible to activation by invention cocatalysts. Catalyst precursor typically useful with invention cocatalyst precursors include Group-3⁻10 transition metal compounds in which at to least one metal ligand can be abstracted by the cocatalyst precursors, particularly those ligands include hydride, hydrocarbyl and hydrocarbylsilyl, and lower-alkyl-substituted $(C_1-C_{10})$ derivatives of those. Examples include hydride, methyl, benzyl, dimethyl-butadiene, etc. Abstractible ligands and transition metal compounds comprising them include those metallocenes described in, for example, U.S. Pat. No. 5,198,401 and WO 92/00333. Syntheses of these compounds are well known from the published literature. Additionally, where the metal ligands include labile halogen, amido or alkoxy ligands (for example, biscyclopentadienyl zirconium dichloride), which may not allow for ready abstraction with this invention's cocatalyst precursors, the ligands can be converted into abstractable ones through known routes such as alkylation with lithium or aluminum hydrides, alkyls, alkylalumoxanes, Grignard reagents, etc. See also EP 0 500 944 and EP 0 570 982 for the reaction of organoaluminum compounds with dihalo-substituted metallocenes prior to catalyst activation.

Additional description of metallocene compounds with, or that can be alkylated to contain, at least one abstractable ligand to form a catalytically active transition-metal cation appear in the patent literature, e.g., EP-A-0 129 368, U.S. Pat. Nos. 4,871,705, 4,937,299, 5,324,800, 5,470,993, 5,491,246, 5,512,693, EP-A-0 418 044, EP-A-0 591 756, WO-A-92/00333, WO-A-94/01471 and WO 97/22635.

Such metallocenes can be described for this invention as mono- or biscyclopentadienyl-substituted Group-3, -4, -5, or -6 transition metals in which the ligands may themselves be substituted with one or more groups, and may bridge to each other or through a heteroatom to the transition metal. The size and constituency of the ligands and bridging elements are not critical to the preparation of this invention's catalyst systems, but should be chosen in the literature-described manner to enhance activity and to select the desired polymer characteristics. Preferably, the cyclopentadienyl rings (including substituted, cyclopentadienyl-based, fused-ring systems, such as indenyl, fluorenyl, azulenyl, or their substituted analogs), when bridged to each other, will be lower-alkyl substituted ($C_1$–$C_6$) in the 2 position (without or without a similar 4-position substituent in the fused ring). The cyclopentadienyl rings may additionally comprise alkyl, cycloalkyl, aryl, alkylaryl, and arylalkyl substituents, the latter as linear, branched, or cyclic structures including multi-ring structures, for example, those of U.S. Pat. Nos. 5,278,264 and 5,304,614. Such substituents should each have essentially hydrocarbyl characteristics and will typically contain up to 30 carbon atoms, but may contain heteroatoms, such as 1–5 non-hydrogen or non-carbon atoms, e.g., N, S, O, P, Ge, B and Si.

Essentially any known metallocene catalyst is suitable for preparing linear polyethylene or ethylene-containing copolymers (where copolymer means a polymer prepared using at least two different monomers), see again WO-A-92/00333 and U.S. Pat. Nos. 5,001,205, 5,198,401, 5,324,800, 5,304,614 and 5,308,816, for specific listings. Criteria for selecting metallocene catalysts suitable for making isotactic or syndiotactic polypropylene are well known in the art, both patent and academic literature, see for example *Journal of Organometallic Chemistry* 369, 359–370 (1989). Likewise, synthetic methods for these metallocenes are also known. Typically, the catalysts are stereorigid, asymmetric, chiral, or bridged chiral metallocenes. See, for example, U.S. Pat. No. 4,892,851, U.S. Pat. No. 5,017,714, U.S. Pat. No. 5,296,434, U.S. Pat. No. 5,278,264, WO-A-(PCT/US92/10066) WO-A-93/19103, EP-A2-0 577 581, EP-A1-0 578 838, and academic literature "The Influence of Aromatic Substituents on the Polymerization Behavior of Bridged Zirconocene Catalysts", Spaleck, W., et al, *Organometallics* 1994, 13, 954–963, and "ansa-Zirconocene Polymerization Catalysts with Annelated Ring Ligands-Effects on Catalytic Activity and Polymer Chain Lengths", Brinzinger, H., et al, *Organometallics* 1994, 13, 964–970, and documents referred to therein. Though many of these references deal with alumoxane-activated catalyst systems, analogous metallocenes can be activated with the cocatalysts of this invention. In catalyst systems lacking abstractable ligands, at least one non-abstractable ligand must first be replaced with an abstractable one. Replacement by alkylation, as described above, serves as one example. Additionally, the metallocenes should contain a group into which the ethylene group, —C=C—, may insert, for example, hydride, alkyl, alkenyl, or silyl. See additional description; G. G. Hlatky, "Metallocene catalysts for olefin polymerization Annual review of 1996", *Coordination Chemistry Reviews*, 181, 243–296 (Elsevier Science, 1999).

Representative metallocene compounds can have the formula:

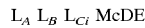

where, Mc is a Group-3–10 metal, preferably Group-3–6 metal; $L_A$ is a substituted or unsubstituted cyclopentadienyl ligand, connected to Mc; and $L_B$ is a ligand as defined for $L_A$, or is J, a heteroatom ligand connected to Mc. The $L_A$ and $L_B$ ligands may bridge to each other through a Group-13–16-element-containing bridge. $L_{Ci}$ is an optional, neutral, non-oxidizing ligand connected to Mc (i equals 0 to 3); and D and E are the same or different labile ligands, optionally bridged to each other, $L_A$, or $L_B$. Each of D and E are connected to Mc.

D and E's identity is functionally constrained. The first constraint is that upon activation, either the D—Mc or the E—Mc connection must break—D or E should be chosen to facilitate this. Another constraint is that a polymerizable molecule must be able to insert between Mc and whichever of D or E remains.

Cyclopentadienyl encompasses substituted and unsubstituted, 5-carbon aromatic ring ligands and heteroatom analogs thereof. Cyclopentadienyl also encompasses fused-ring systems including but not limited to indenyl and fluorenyl. Also, the use of heteroatom-containing rings or fused rings, where a non-carbon, Group-13,-14,-15 or -16 atom replaces a ring carbon is considered for this specification to be within the terms "cyclopentadienyl." See, for example, the background and teachings of WO 98/37106, having priority with U.S. Ser. No. 08/999,214, filed Dec. 29, 1997, and WO 98/41530, having priority with U.S. Ser. No. 09/042,378, filed Mar. 13, 1998. Substituted cyclopentadienyl structures means that one or more hydrogen atoms is replaced by a hydrocarbyl, hydrocarbylsilyl, or heteroatom-containing similar structure. The hydrocarbyl structures specifically include $C_1$–$C_{30}$ linear, branched, cyclic alkyl, and cycloaromatic fused and pendant rings. These rings may also be substituted with similar structures.

Non-limiting representative metallocene compounds include mono-cyclopentadienyl compounds such as pentamethylcyclopentadienyltitanium iso-propoxide, pentamethylcyclopentadienyltribenzyl titanium, dimethylsilyltetramethyl-cyclopentadienyl-tert-butylamido titanium dichloride, pentamethyl-cyclopentadienyl titanium trimethyl, dimethylsilyltetramethylcyclopentadienyl-t-butylamido zirconium dimethyl, dimethylsilyltetramethylcyclopentadienyl-dodecylamido hafnium dihydride, dimethylsilyltetramethylcyclopentadienyl-dodecylamido hafnium dimethyl, unbridged biscyclopentadienyl compounds such as bis(1,3-butyl, methylcyclopentadienyl) zirconium dimethyl, pentamethylcyclo-pentadienyl-cyclopentadienyl zirconium dimethyl, (tetramethylcyclopentadienyl)-(n-propylcyclopentadienyl) zirconium dimethyl; bridged bis-cyclopentadienyl compounds such as dimethylsilylbis(tetrahydroindenyl) zirconium dichloride and silacyclobutyl (tetramethylcyclopentadienyl)(n-propyl-cyclopentadienyl) zirconium dimethyl; bridged bis-indenyl compounds such as dimethylsily-bisindenyl zirconium dichloride, dimethylsily-bisindenyl hafnium dimethyl, dimethylsilyl-bis(2-methylbenzindenyl)zirconium dichloride, dimethylsilylbis (2-methylbenzindenyl)zirconium dimethyl; and fluorenyl ligand-containing compounds, e.g., diphenylmethyl (fluorenyl)(cyclopentadienyl)zirconium dimethyl; and the additional mono- and biscyclopentadienyl compounds such as those listed and described in U.S. Pat. Nos. 5,017,714, 5,324,800, WO 92/00333 and EP-A-0 591 756.

Particular advantage in solution polymerization can be achieved by using aliphatic-solvent-soluble precursor compounds, e.g., bis(para-triethylsilyl-phenyl) methylene (2,7-(di-tert-butyl)fluorenyl)(cyclopentadienyl)hafnium dimethyl is particularly notable in solution polymerization. But the solubilizing effect of the aliphatic-solvent-soluble anion compounds of the invention will tend to offset low solubility of typical organometallic cations useful in olefin polymerization. See, applications U.S. Ser. Nos. 09/426,099 (priority Oct. 22, 1999), 09/694,595 (priority Oct. 22, 1999), and 60/160,942 (priority Oct. 22, 1999) for background as to soluble catalysts and specific metallocene and precursor cocatalyst cations useful with the current invention.

Representative traditional Ziegler-Natta transition-metal compounds include tetrabenzyl zirconium, tetra bis (trimethylsilylmethyl)zirconium, oxo-tris (trimethylsilylmethyl)vanadium, tetrabenzyl hafnium, tetrabenzyl titanium, bis(hexamethyl disilazido)dimethyl titanium, tris(trimethylsilylmethyl) niobium dichloride, tris (trimethylsilylmethyl) tantalum dichloride. Again, important features of such compositions for coordination polymerization are having ligands capable of abstraction and having ligands into which the ethylene (olefinic) group can insert. These features enable ligand abstraction from the catalyst precursor to form the invention catalysts.

Additional organometallic transition-metal compounds suitable as olefin polymerization catalysts in accordance with the invention will be any of those Group 3–10 that can be converted by ligand abstraction or σ-bond scission into a catalytically active cation and stabilized in that charged state by a noncoordinating or weakly coordinating anion sufficiently labile to be displaced by an olefinically unsaturated monomer such as ethylene.

Exemplary compounds include those described in the patent literature. International patent publications WO 96/23010, WO 97/48735 and Gibson, et al., *Chem. Comm.*, pp. 849–850 (1998), which disclose diimine-based ligands for Group-8–10 compounds that undergo ionic activation and polymerize olefins. Transition-metal polymerization catalyst systems from Group-5–10 metals, in which the active transition-metal center is highly oxidized and stabilized by low-coordination-number, polyanionic, -ligand systems, are described in U.S. Pat. No. 5,502,124 and its divisional U.S. Pat. No. 5,504,049. See also the Group-5 organo-metallic catalyst compounds of U.S. Pat. No. 5,851, 945 and the tridentate-ligand-containing, Group-5–10, organometallic catalysts of copending U.S. application Ser. No. 09/302,243, filed Apr. 29, 1999, and its equivalent PCT/US99/09306. Group-11 catalyst precursor compounds, activatable with ionizing cocatalysts, useful for olefins and vinyl-group-containing polar monomers are described and exemplified in WO 99/30822 and its priority documents, including U.S. patent application Ser. No. 08/991,160, filed Dec. 16, 1997.

U.S. Pat. No. 5,318,935 describes bridged and unbridged, bisamido transition-metal catalyst compounds of Group-4 metals insertable polymerization of α-olefins. Bridged bis (arylamido) Group-4 compounds for olefin polymerization are described by D. H. McConville., et al., in *Organometallics* 1995, 14, 5478–5480. Synthetic methods and compound characterization are presented. Further work appearing in D. H. McConville, et al, *Macromolecules* 1996, 29, 5241–5243, describes bridged bis(arylamido) Group-4 compounds that are polymerization catalysts for 1-hexene. Additional invention-suitable transition metal compounds include those described in WO 96/40805. Cationic Group-3- or Lanthanide-metal complexes for olefin coordination polymerization of olefins are disclosed in co-pending U.S. application Ser. No. 09/408,050, filed Sep. 29, 1999, and its equivalent PCT/US99/22690. The catalyst precursors are stabilized by a mono-anionic bidentate ligand and two monoanionic ligands and can be activated with this invention's ionic cocatalysts.

The literature contains many additional descriptions of suitable organo-metallic and organometalloid, catalyst-precursor compounds. Compounds that contain abstractable ligands or that can be alkylated to contain abstractable ligands are suitable for the practice of this invention. See, for instance, V. C. Gibson, et al; "The Search for New-Generation Olefin Polymerization Catalysts: Life Beyond Metallocenes", *Angew. Chem. Int. Ed.*, 38, 428–447 (1999).

When using the above catalysts of the invention, the catalyst system will generally employ one or more scavenging agents that remove polar impurities from the reaction environment and increase catalyst activity. Any polymerization reaction components, particularly solvents, monomers, and catalyst feeds, can inadvertently introduce impurities and adversely affect catalyst activity and stability. Impurities decrease or eliminate catalytic activity, particularly with ionizing-anion-activated catalyst systems. The polar impurities, or catalyst poisons, include water, oxygen, metal impurities, etc. Preferably, these impurities are removed from or reduced in the reaction components before their addition to the reaction vessel. Impurities can be removed by chemically treating the components or by impurity-separation steps. Such treatment or separation can occur during or after synthesis of the components. In any case, the polymerization process will normally employ minor amounts of scavenging agent. Typically, these scavengers will be organometallic such as the Group-13 compounds of U.S. Pat. Nos. 5,153,157, 5,241,025 and WO-A-91/09882, WO-A-94/03506, WO-A-93/14132, and that of WO 95/07941. Exemplary compounds include triethyl aluminum, triethyl borane, triisobutyl aluminum, methylalumoxane, and isobutyl aluminumoxane. Those compounds having bulky or $C_6$–$C_{20}$ linear hydrocarbyl substituents bound to the metal or metalloid center are preferred because they coordinate to the active catalyst less. Examples include triethylaluminum, but more preferably, bulky compounds such as triisobutylaluminum, triisoprenylaluminum, and long-chain, linear-alkyl-substituted aluminum compounds, such as tri-n-hexylaluminum, tri-n-octylaluminum, or tri-n-dodecylaluminum. When alumoxane is used as activator, any excess over the amount needed to activate the catalysts can act as a poison scavenger and additional organometallic compounds may not be necessary. Alumoxanes also may be used in scavenging amounts with other activation means, e.g., methylalumoxane and triisobutyl-aluminoxane with boron-based activators. The amount of such compounds to be used is minimized during polymerization to that amount effective to enhance activity (and with that amount necessary for activation of the catalyst compounds if used in a dual role) since excess amounts may poison catalysts.

This invention's catalyst system can polymerize those unsaturated monomers conventionally recognized as coordination polymerizable using metal-locenes. Typical conditions include solution, slurry, gas-phase, and high-pressure polymerization. The catalysts may be supported on inorganic oxide or polymeric supports and as such will be particularly useful in those operating modes employing fixed-bed, moving-bed, fluid-bed, slurry, or solution processes conducted in single, series, or parallel reactors. Invention catalyst pre-polymerization may also be used for further polymer-particle morphological control in art-recognized slurry- or gas-phase-reaction processes. WO 98/55518, describes a preferred invention support method for gas-phase or slurry polymerization.

Alternative embodiments of this invention's olefin polymerization methods employ the catalyst system in liquid phase (solution, slurry, suspension, bulk phase, or combinations thereof), in high-pressure liquid or supercritical fluid phase, or in gas phase. These processes may also be employed in singular, parallel, or series reactors. The liquid processes comprise contacting olefin monomers with the catalyst system described above in a suitable diluent or solvent and allowing those monomers to react long enough to produce the invention copolymers. Both aliphatic and aromatic hydrocarbyl solvents are suitable; hexane is preferred. Bulk and slurry processes are typically done by contacting the supported catalysts with a liquid monomer slurry. Gas-phase processes typically use a supported catalyst and are conducted in any manner suitable for ethylene homo-polymers or copolymers prepared by coordination polymerization. Illustrative examples may be found in U.S. Pat. Nos. 4,543,399, 4,588,790, 5,028,670, 5,382,638, 5352, 749, 5,408,017, 5,436,304, 5,453,471, and 5,463,999, 5,767, 208 and WO 95/07942.

The polymerization reaction temperature can go as low as about 40° C. Preferably, the minimum reaction temperature is about 60° C. The temperature can go as high as about 250° C., but preferably does not exceed 220° C. The minimum reaction pressure is about 1 mm Hg, preferably about 0.1 bar, and most preferably 1.0 bar. The maximum pressure is less than or equal to about 2500 bar, preferably 1600 bar or lower, but most preferably 500 bar or less.

For homogenous solution polymerization best results may be obtained when the quantity and type of solvent used to introduce the catalyst is controlled as well as the manner of introduction. Generally it is believed preferable to achieve full solution and avoid slurried systems, and hence fairly high concentrations of the catalyst, at low temperatures and use low solvent amounts. The difficulty of meeting these objectives varies with the solubility of the non-coordinating anion and transition metal components.

The invention is especially suitable for use with solution polymerization using bridged fluorenyl metallocene hafnium compounds at polymerization temperatures in excess of 110° C., for elastomeric olefin copolymers, and more preferably more than 160° C. and up to 250° C. for plastomeric ethylene copolymers.

Invention catalyst systems can produce several types of linear polyethylene including high- and ultra-high-molecular-weight polyethylenes, including both homo- and copolymers with other alpha-olefin monomers or alpha-olefinic or non-conjugated diolefins, e.g. $C_3$–$C_{20}$ olefins, diolefins, or cyclic olefins. The polyethylenes are produced by adding ethylene, and optionally one or more other monomers, with the invention catalyst that has been slurried with a solvent, such as hexane or toluene, to a reaction vessel under low pressure (typically<50 bar), at a typical temperature of 40–250° C. Cooling typically removes polymerization heat. Gas-phase polymerization can be conducted, for example, in a continuous fluid-bed, gas-phase reactor operated at a minimum of 2000 kPa and up to 3000 kPa. The minimum temperature is 60° C.; the maximum temperature is 160° C. The gas-phase reaction uses hydrogen as a reaction modifier at a concentration of no less than 100 PPM. The hydrogen gas concentration should not exceed 200 PPM. The reaction employs a $C_4$–$C_8$ comonomer feedstream and a $C_2$ feed-stream. The $C_4$–$C_8$ feedstream goes down to 0.5 mol %. It also may go up to 1.2 mol %. Finally, the $C_2$ feedstream has a minimum concentration of 25 mol %. Its maximum concentration is 35 mol %. See, U.S. Pat. Nos. 4,543,399, 4,588,790, 5,028,670 and 5,405, 922 and 5,462,999.

High-molecular-weight, low-crystallinity, ethylene-α-olefin elastomers (including ethylene-cyclic-olefin and ethylene-α-olefin-diolefin elastomers) can be prepared using this invention's catalysts under traditional solution polymerization processes or by introducing ethylene gas into invention catalyst slurries with α-olefin, cyclic olefin, or either or both mixed with other polymerizable and non-polymerizable compounds functioning as polymerization diluents. Typical ethylene pressures will be between 10 and 1000 psig (69–6895 kPa) and the polymerization diluent temperature will typically be between 40 and 160° C. The process can be carried out in one or more stirred tank reactors, operated individually, in series or parallel. See the general disclosure of U.S. Pat. No. 5,001,205 for general process conditions. See also, international application WO 96/33227 and WO 97/22639.

Other olefinically unsaturated monomers besides those specifically described above may be polymerized using the invention catalysts, for example, styrene, alkyl-substituted styrenes, isobutylene and other geminally disubstituted olefins, ethylidene norbornene, norbornadiene, dicyclopentadiene, and other olefinically-unsaturated monomers, including other cyclic olefins, such as cyclopentene, norbornene, alkyl-substituted norbornenes, and vinyl group-containing polar monomers capable of coordinating polymerization. See, for example, U.S. Pat. Nos. 5,635,573, 5,763,556, and WO 99/30822. Additionally, alpha-olefinic macromers of up to 1000 mer units or more may be incorporated by copolymerization yielding branch-containing olefin polymers. Additionally, oligomerization, dimerization, hydrogenation, olefin/carbon monoxide copolymerization, hydro-formulation, hydrosilation, hydroamination, and related catalytic reactions employing organometallic cationic complexes can be accomplished using the invention cocatalyst complexes with selected organometallic compounds suitably selected as known in the art.

The invention catalyst compositions can be used as described above individually for coordination polymerization or can be mixed with other known olefin-polymerization catalyst compounds to prepare polymer blends. By selection of monomers and coordination catalyst compounds, polymer blends can be prepared under polymerization conditions analogous to those using individual catalyst compositions. Polymers having increased MWD for improved processing and other traditional benefits available from polymers made with mixed catalyst systems can thus be achieved.

Blended polymer formation can be achieved ex situ through mechanical blending or in situ through using mixed catalyst systems. It is generally believed that in situ blending provides a more homogeneous product and allows the blend to be produced in one step. In situ blending with mixed catalyst systems involves combining more than one catalyst in the same reactor to simultaneously produce multiple, distinct polymer products. This method requires additional catalyst synthesis, and the various catalyst components must be matched for their activities, the polymer products they generate at specific conditions, and their response to changes in polymerization conditions.

Non-exhaustive List of Invention Non-coordinating Anions

2'-((propyl)(4,5,6tri-fluoro-naphthyl)phos-phino)per-fluoro-biphen-4-yl)(pentalfluoro-pyrenyl)(tetrafluoro-fluorenyl)(pentafluoro-anthracenyl)-borate; 2'-((tri-iso-propyl-silyloctyl)-(per-fluoro-biphenyl)amino)per-fluoro-biphen-4-yl)(per-fluoro-naphthyl)-(pentalfluoro-pyrenyl)-(2,3,5-tri-fluoro-phenyl)borate; 2'-((tri-n-propyl-silyl) (pentalfluoro-pyrenyl)arsino)per-fluoro-biphen-4-yl)(per-fluoro-phenyl)-(2',3',5'-tri-fluoro-biphenyl)-(per-fluoro-naphthyl)-borate; 3-((3-ethyl-nonyl)(per-fluoroanthracenyl)amino)per-fluoro-phenyl)(per-fluoro-pyrenyl)-(per-fluoro-biphenyl)-(per-fluoro-naphthyl)-borate; 3-((3-ethyl-nonyl)(per-fluoro-fluorenyl)amino)per-fluoro-phenyl)(per-fluoro-phenyl)-(4,5,6-tri-fluoro-naphthyl)-(per-fluoro-naphthyl)-borate; 3-((triethyl-silyl-propyl)(2,3,4-tri-fluoro-phenyl)amino)per-fluoro-phenyl)(per-fluoro-biphenyl)-(per-fluoro-phenyl)-(pentalfluoro-pyrenyl)-aluminate; 3'-((benzyl)(pentafluoro-pyrenyl)amino)per-fluoro-biphen-4-yl)(5,6,7,8-tetrafluoro-naphthyl)-(per-fluoro-phenyl)-(pentafluoro-anthracenyl)-aluminate; 3-((butyl)(per-fluoro-phenyl)amino)per-fluoro-phenyl)(2',3',4'-tri-fluoro-biphenyl)-(per-fluoro-biphenyl)-(pentafluoro-anthracenyl)-borate; 3'-((diethyl-nonly-silyl)(per-fluoro-phenyl)amino)per-fluoro-biphen 4-yl)(per-fluoro-anthracenyl)-(2',3',4'-tri-fluoro-biphenyl)-(2,3,5-tri-fluoro-phenyl)-borate; 3-((hexyl)(per-fluoro-biphenyl)amino)per-fluoro-phenyl)(per-fluoro-fluorenyl)-(per-fluoro-anthracenyl)-(4,5,6-tri-fluoro-naphthyl)-borate; 3-((iso-propyl)(2',3',4'-tri-fluoro-biphenyl)amino)per-fluoro-phenyl)(2,3,4-tri-fluoro-phenyl)-(2',3',4'-tri-fluoro-biphenyl)-(2',3',5'-tri-fluoro-biphenyl)-borate; 3'-((iso-propyl)(per-fluoro-biphenyl)phos-phino)per-fluoro-biphen-4-yl)(pentalfluoro-pyrenyl)-(5,6,7,8-tetrafluoro-naphthyl)-(per-fluoro-biphenyl)-borate; 3'-((methyl)(per-fluoro-biphenyl)amino)per-fluoro-biphen-4-yl)(2,3,6-tri-fluoro-phenyl)-(2',3',4'-tri-fluoro-biphenyl)-(per-fluoro-phenyl)-aluminate; 3'-((methyl-diethyl-silyl-octyl)(per-fluoro-fluorenyl)amino)per-fluoro-biphen-4-yl)(per-fluoro-pyrenyl)-(pentalfluoro-pyrenyl)-(per-fluoro-phenyl)-aluminate; 3-((methyl-ethyl-hexyl-silyl)(2',3',4'-tri-fluoro-biphenyl)amino)per-fluoro-phenyl)(per-fluoro-pyrenyl)-(per-fluoro-biphenyl)-(pentafluoro-anthracenyl)-borate; 3-((n-butyl)-(2',3',5'-tri-fluoro-biphenyl)amino)per-fluoro-phenyl)(2,3,5-tri-fluoro-phenyl)-(per-fluoro-naphthyl)-(per-fluoro-fluorenyl)-aluminate; 3-((n-butyl)(per-fluoro-naphthyl)amino)per-fluoro-phenyl)(5,6,7,8-tetrafluoro-naphthyl)-(per-fluoro-phenyl)-(per-fluoro-fluorenyl)-borate; 3-((octyl)(per-fluoro-phenyl)amino)per-fluoro-phenyl)(2,3,6-tri-fluoro-phenyl)-(2',3',5'-tri-fluoro-biphenyl)-(per-fluoro-biphenyl)-borate; 3-((octyl)(per-fluoro-phenyl)phos-phino)per-fluoro-phenyl)(pentafluoro-pyrenyl)-(2,3,4-tri-fluoro-phenyl)-(per-fluoro-phenyl)-aluminate; 3-((propyl)(per-fluoro-biphenyl)phos-phino)per-fluoro-phenyl)bis(2,3,6-tri-fluoro-phenyl)-(per-fluoro-phenyl)-borate; 3'-((propyl)(per-fluoro-pyrenyl)amino)per-fluoro-biphen-4-yl)(2,3,6-tri-fluoro-phenyl)-(4,5,6,7-tetrafluoro-naphthyl)-(per-fluoro-phenyl)-borate; 3-((triethyl-silyl-ethyl)-(4,5,6-tri-fluoro-naphthyl)phos-phino)per-fluoro-phenyl)bis(per-fluoro-biphenyl)-(4,5,6-tri-fluoro-naphthyl)-borate; 3'-((triethyl-silyl-ethyl)(pentalfluoro-pyrenyl)amino)per-fluoro-biphen-4-yl)-(2,3,5-tri-fluoro-phenyl)-(t4,5,6-tri-fluoro-naphthyl)-aluminate; 3'-((triethyl-silyl-ethyl)(per-fluoro-biphenyl)amino)per-fluoro-biphen-4-yl)(2',3',4'-tri-fluoro-biphenyl)-(pentalfluoro-pyrenyl)-(per-fluoro-pyrenyl)-borate; 3-((tri-iso-propyl-silyl-octyl)(per-fluoro-anthracenyl)phos-phino)per-fluoro-phenyl)(2',3',5'-tri-fluoro-biphenyl)(4,5,7-tri-fluoro-naphthyl)-(2,3,4-tri-fluoro-phenyl)-borate: 3'-((trimethyl-silyl)(per-fluoro-biphenyl)amino)per-fluoro-biphen-4-yl)(pentalfluoropyrenyl)-(4,5,6,7-tetrafluoro-naphthyl)-(per-fluoro-biphenyl)-borate; 3'-(tripropyl-silyl)(4,5,6,7-tetrafluoro-naphthyl)amino)per-fluoro-biphen-4-yl)-(pentafluoro-anthracenyl)3per-fluoro-biphenyl)-(2,3,4-tri-fluoro-phenyl)-aluminate; 3-((tri-n-propyl-silyl)(pentafluoro-anthracenyl)amino)fluoro-phen-1-yl)(2,3,4-tri-fluoro-phenyl)-(per-fluoro-naphthyl)-(2',3',4'-tri-fluoro-biphenyl)-borate; 3-((tri-n-propyl-silyl)(per-fluoro-biphenyl)-arsino)per-fluoro-phenyl)(4,5,6,7-tetrafluoro-naphthyl)-(per-fluoro-anthracenyl)-(5,6,7,8-tetrafluoro-naphthyl)-borate; 3-((tri-n-propyl-silyl-hexyl)(per-fluoro-phenyl)phos-phino)per-fluoro-phenyl)(2,3,6-tri-fluoro-phenyl)-(pentafluoro-anthracenyl)-(4,5,7-tri-fluoro-naphthyl)-borate; 3-((tri-n-propyl-silyl-hexyl)(per-fluoro-pyrenyl)phos-phino)per-fluoro-phenyl)(per-fluoro-phenyl)-(2',3',5'-tri-fluoro-biphenyl)-(per-fluoro-anthracenyl)-borate; 4'-((3-ethyl-nonyl)-(pentalfluoro-pyrenyl)amino)per-fluoro-biphen-4-yl)(5,6,7,8-tetrafluoro-naphthyl)-(per-fluoro-naphthyl)-(pentalfluoro-pyrenyl)-borate; 4-((3-ethyl-nonyl)(per-fluoro-phenyl)phos-phino)per-fluoro-phenyl)(2,3,4-tri-fluoro-phenyl)-(5,6,7,8-tetrafluoro-naphthyl)-(4,5,7-tri-fluoro-naphthyl)-aluminate; 4'-((triethyl-silyl-propyl)(per-fluoro-phenyl)amino)fluoro-biphen-4-yl)(per-fluoro-anthracenyl)-(2',3',5'-tri-fluoro-biphenyl)-(per-fluoro-phenyl)-borate; 4-((triethyl-silyl-propyl)-(per-fluoro-phenyl)amino)per-fluoro-phenyl)(per-fluoro-naphthyl)-(per-fluoro-biphenyl)-(per-fluoro-fluorenyl)-aluminate; 4-((2,2-dimethyl-octyl)(2',3',5'-tri-fluoro-biphenyl)phos-phino)per-fluoro-phenyl)(per-fluoro-pyrenyl)-(per-fluoro-biphenyl)-(per-fluoro-phenyl)-borate; 4'-((2,2-dimethyl-octyl)(per-fluoro-phenyl)amino)per-fluoro-biphen-4-yl)(per-fluoro-anthracenyl)-(2',3',4'-tri-fluoro-biphenyl)-(2,3,5-tri-fluoro-phenyl)-borate; 4'-((2,2-dimethyl-octyl)(per-fluoro-phenyl)arsino)per-fluoro-biphen-4-yl)(2,3,6-tri-fluoro-phenyl)-(2',3',5'-tri-fluoro-biphenyl)-(2,3,4-tri-fluoro-phenyl)-borate; 4'-((benzyl)(4,5,6-tri-fluoro-naphthyl)amino)per-fluoro-biphen-3-yl)-(4,5,7-tri-fluoro-naphthyl)-(per-fluoro-fluorenyl)-(4,5,6-tri-fluoro-naphthyl)-aluminate; 4'-((benzyl)(5,6,7,8-tetrafluoro-naphthyl)amino)per-fluoro-biphen-4-yl)(per-fluoro-biphenyl)-(per-fluoro-anthracenyl)-(4,5,7-tri-fluoro-naphthyl)-borate; 4'-((benzyl)(per-fluoro-pyrenyl)amino)per-fluoro-biphen-3-yl)(2',3',5'-tri-fluoro-biphenyl)-(pentalfluoro-pyrenyl)-(per-fluoro-fluorenyl)-aluminate; 4'-((butyl)(per-fluoro-anthracenyl)amino)per-fluoro-biphen-4-yl)bis(4,5,6-tri-fluoro-naphthyl)-(per-fluoro-phenyl)-borate; 4'-((diethyl-nonly-silyl)(2,3,6-tri-fluoro-phenyl)amino)per-fluoro-biphen-4-yl)(4,5,6,7-tetrafluoro-naphthyl)(tetrafluoro-fluorenyl)-(per-fluoro-biphenyl)-borate; 4-((diethyl-nonly-silyl)(4,5,7-tri-fluoro-naphthyl)phos-phino)per-fluoro-phenyl)(2',3',5'-tri-fluoro-biphenyl)-(per-fluoro-anthracenyl)-(per-fluoro-fluorenyl)-borate; 4'-((hexyl)(2',3',4'-tri-fluoro-biphenyl)amino)fluoro-biphen-4-yl)(4,5,6,7-tetrafluoro-naphthyl)-(per-fluoro-anthracenyl)-(per-fluoro-fluorenyl)-borate; 4'-((hexyl)(per-fluoro-anthracenyl)amino)per-fluoro-biphen-4-yl)(2,3,6-tri-fluoro-phenyl)-(per-fluoro-phenyl)-(4,5,6,7-tetrafluoro-naphthyl)-borate; 4'-((iso-propyl)(per-fluoro-anthracenyl)phos-phino)per-fluoro-biphen-3-yl)-(per-fluoro-biphenyl)-(per-fluoro-anthracenyl)-(tetrafluoro-fluorenyl)-aluminate; 4-((methyl-diethyl-silyl-octyl)(2',3',5'-tri-fluoro-biphenyl)amino)per-fluoro-phenyl)(per-fluoro-phenyl)-(per-fluoro-pyrenyl)-(per-fluoro-fluorenyl)-borate; 4'-((methyl-diethyl-silyl)-(pentalfluoro-pyrenyl)amino)per-fluoro-biphen-3-yl)(per-fluoro-phenyl)-(per-fluoro-pyrenyl)-(4,5,6,7-tetrafluoro-naphthyl)-borate; 4'-((methyl-diethyl-silyl-octyl)(per-fluoro-anthracenyl)phos-phino)per-fluoro-biphen-4-yl)(per-fluoro-fluorenyl)-(per-fluoro-phenyl)-(pentafluoro-anthracenyl)-aluminate; 4'-((methyl-diethyl-silyl-octyl)(per-fluoro-biphenyl)amino)per-fluoro-biphen-4-yl)(2,3,4-tri-fluoro-phenyl)-(tetrafluoro-fluorenyl)(5,6,7,8-tetrafluoro-naphthyl)-borate; 4-((methyl-ethyl-hexyl-silyl)(pentalfluoro-pyrenyl)amino)per-fluorophenyl)(pentalfluoroanthracenyl)(2,3,6-tri-fluoro-phenyl)-(per-fluoro-naphthyl)-borate; 4'-((methyl-ethyl-hexyl-silyl)(per-fluoro-phenyl)amino)per-fluoro-biphen-4-yl)-(tetrafluorofluorenyl)-(2,3,4-tri-fluoro-phenyl)-(per-fluoro-anthracenyl)-borate; 4'-((methyl-ethyl-hexyl-silyl)(per-fluoro-phenyl)arsino)per-fluoro-biphen-3-yl)(5,6,7,8-tetrafluoro-naphthyl)-(per-fluoro-biphenyl)-(2,3,5-tri-fluoro-phenyl)-aluminate; 4'-((methyl-ethyl-hexyl-silyl)(per-fluoro-pyrenyl)amino)per-fluoro-biphen-3-yl)(per-fluoro-anthracenyl)-(2,3,6-tri-fluoro-phenyl)-(2,3,4-tri-fluoro-phenyl)-borate; 4'-((nonyl)(4,5,7-tri-fluoro-naphthyl)amino)per-fluoro-biphen-3-yl)(per-fluoro-biphenyl)-(4,5,7-tri-fluoro-naphthyl)-(2,3,5-tri-fluoro-phenyl)-borate; 4'-((octyl)(5,6,7,8-tetrafluoro-naphthyl)amino)per-fluoro-biphen-3-yl)(per-fluoro-biphenyl)-(5,6,7,8-tetrafluoro-naphthyl)-(per-fluoro-fluorenyl)-aluminate; 4-((octyl)(pentafluoro-anthracenyl)amino)per-fluoro-phenyl)(per-fluoro-anthracenyl)-(per-fluoro-pyrenyl)-(2,3,5-tri-fluoro-phenyl)-borate; 4'-((propyl)(2',3',5'-tri-fluoro-biphenyl)amino)per-fluoro-biphen-4-yl)(2',3',4'-tri-fluoro-biphenyl)-(per-fluoro-naphthyl)-(per-fluoro-phenyl)-aluminate; 4-((propyl)(per-fluoro-anthracenyl)amino)-per-fluoro-phenyl)(4,5,6-tri-fluoro-naphthyl)-(per-fluoro-pyrenyl)-(4,5,6,7-tetrafluoro-naphthyl)-borate; 4'-((triethylsilyl)(2',3',5'-tri-fluoro-biphenyl)amino)per-fluoro-biphen-3-yl)(2,3,5-tri-fluoro-phenyl)-(pentalfluoro-pyrenyl)-(per-fluoro-phenyl)-aluminate; 4'-((triethylsilyl)(pentalfluoro-pyrenyl)amino)per-fluoro-biphen-3-yl)(per-fluoro-phenyl)-(4,5,7-tri-fluoro-naphthyl)-(tetrafluoro-fluorenyl)-borate; 4'-((triethylsilyl)(per-fluoro-biphenyl)amino)per-fluoro-biphen-3-yl)bis(per-fluoro-anthracenyl)-(per-fluoro-pyrenyl)-borate; 4'-((triethyl-silyl-ethyl)(2,3,5-tri-fluoro-phenyl)-amino)per-fluoro-biphen-4-yl)(per-fluoro-naphthyl)-(per-fluoro-biphenyl)-(per-fluoro-phenyl)-borate; 4-((triethyl-silyl-ethyl)(4,5,7-tri-fluoro-naphthyl)amino)per-fluoro-phenyl)(pentalfluoro-pyrenyl)-(per-fluoro-biphenyl)-(pentafluoro-anthracenyl)-borate; 4'-((triethyl-silyl-ethyl)(per-fluoro-anthracenyl)phos-phino)fluoro-biphen-3-yl)(tetrafluoro-fluorenyl)-(per-fluoro-biphenyl)-(2,3,6-tri-fluoro-phenyl)-borate; 4-((triethyl-silyl-ethyl)(per-fluoro-biphenyl)amino)per-fluoro-phenyl)(2',3',5'-tri-fluoro-biphenyl)-(4,5,6,7-tetrafluoro-naphthyl)-(per-fluoro-pyrenyl)-borate; 4'-((tri-iso-propyl-silyl)(2',3',4'-tri-fluoro-biphenyl)phos-phino)per-fluoro-biphen-3-yl)(5,6,7,8-tetrafluoro-naphthyl)-(per-fluoro-pyrenyl)-(pentalfluoro-pyrenyl)-aluminate; 4-((tri-iso-propyl-silyl)(per-fluoro-biphenyl)amino)per-fluoro-phenyl)(4,5,7-tri-fluoro-naphthyl)-(per-fluoro-naphthyl)-(2',3',5'-tri-fluoro-biphenyl)-borate; 4-((tri-iso-propyl-silyl)(per-fluoro-biphenyl)amino)-per-fluoro-phenyl)bis(pentalfluoro-pyrenyl)-(per-fluoro-pyrenyl)-borate; 4'-((tri-iso-propyl-silyl-octyl)(2,3,4-tri-fluoro-phenyl)phos-phino)per-fluoro-biphen-3-yl)(2,3,5-tri-fluoro-phenyl)-(4,5,6,7-tetrafluoro-naphthyl)-(tetrafluoro-fluorenyl)-borate; 4'-((tri-iso-propyl-silyl-octyl)(per-fluoro-phenyl)amino)fluoro-biphen-4-yl)(per-fluoro-biphenyl)-(2,3,4-tri-fluoro-phenyl)-(tetrafluoro-fluorenyl)-borate; 4-((tri-iso-propyl-silyl-octyl)(per-fluoro-phenyl)amino)per-fluoro-phenyl)(2,3,4-tri-fluoro-phenyl)-(4,5,6-tri-fluoro-naphthyl)-(per-fluoro-phenyl)-borate; 4'-((trimethyl-silyl)(2,3,4-tri-fluoro-phenyl)arsino)fluoro-biphen-4-yl)(4,5,6,7-tetrafluoro-naphthyl)-(per-fluoro-biphenyl)-(4,5,7-tri-fluoro-naphthyl)-aluminate; 4'-((trimethyl-silyl)(4,5,6-tri-fluoro-naphthyl)amino)per-fluoro-biphen-4-yl)(per-fluoro-anthracenyl)-(per-fluoro-naphthyl)-(2',3',4'-tri-fluoro-biphenylaluminate; 4-((trimethyl-silyl)(per-fluoro-phenyl)amino)per-fluoro-phenyl)-(per-fluoro-pyrenyl)(5.6,7,8-tetrafluoro-naphthyl)-(2',3',4'-tri-fluoro-biphenyl)-barate; 4'-((tri-n-propyl-silyl)(per-fluoro-phenyl)amino)per-fluoro-biphen-4-yl)(per-fluoro-phenyl)-(per-fluoro-biphenyl)-(4,5,6-tri-fluoro-naphthyl)-borate; 4'-((tri-n-propyl-silyl-hexyl)(per-fluoro-anthracenyl)-amino)per-fluoro-biphen-4-yl)bis(2,3,5-t-fluoro-phenyl)-(per-fluoro-fluorenyl)-borate; 4'-((tri-n-propyl-silyl-hexyl)(per-fluoro-phenyl)arsino)per-fluoro-biphen-3-yl)(5,6,7,8-tetrafluoro-naphthyl)-(per-fluoro-phenyl)-(4,5,6-tri-fluoro-naphthyl)-borate; 5-((3-ethyl-nonyl)(per-fluoro-fluorenyl)amino)per-fluoro-inden-2-yl)(per-fluoro-fluorenyl)-(per-fluoro-biphenyl)-(4,5,6-tri-fluoro-naphthyl)-aluminate; 5-((3-ethyl-nonyl)(per-fluoro-phenyl)phos-phino)fluoro-inden-1-yl)-(2,3,6-tri-fluoro-phenyl)-(4,5,7-tri-fluoro-naphthyl)-(per-fluoro-phenyl)-aluminate; 5-((triethyl-silyl-propyl)(4,5,6,7-tetrafluoro-naphthyl)phos-phino)per-fluoro-napth-1-yl)(4,5,6-tri-fluoro-naphthyl)-(5,6,7,8-tetrafluoro-naphthyl)-(per-fluoro-phenyl)-borate; 5-((triethyl-silyl-propyl)-(pentafluoro-anthracenyl)amino)per-fluoro-napth-3-yl)(per-fluoro-biphenyl)-(2,3,5-tri-fluoro-phenyl)-(2',3',4'-tri-fluoro-biphenyl)-borate; 5-((triethyl-silyl-propyl)(per-fluoro-biphenyl)amino)-per-fluoro-inden-2-yl)(4,5,6,7-tetrafluoro-naphthyl)-(per-fluoro-pyrenyl)-(pentafluoro-pyrenyl)-borate; 5-((triethyl-silyl-propyl)(per-fluoro-fluorenyl)amino)per-fluoro-napth-1-yl)(pentafluoro-pyrenyl)-(tetrafluoro-fluorenyl)-(2',3',5'-tri-fluoro-biphenyl)-borate; 5-((2,2-dimethyl-octyl)(per-fluoro-naphthyl)amino)per-fluoro-inden-1-yl)(per-fluoro-biphenyl)-(tetrafluoro-fluorenyl)-(per-fluoro-phenyl)-aluminate; 5-((2,2-dimethyl-octyl)(per-fluoro-phenyl)amino)fluoro-inden-2-yl)-(per-fluoro-fluorenyl)-(per-fluoro-biphenyl)-(4,5,6-tri-fluoro-naphthyl)-aluminate; 5-((2,2-dimethyl-octyl)(per-fluoro-phenyl)amino)per-fluoro-napth-2-yl)(4,5,7-tri-fluoro-naphthyl)-(per-fluoro-fluorenyl)-(per-fluoro-biphenyl)-borate; 5-((benzyl)(2,3,6-tri-fluoro-phenyl)phos-phino)-per-fluoro-inden-2-yl)(per-fluoro-biphenyl)-(per-fluoro-fluorenyl)-(pentalfluoro-pyrenyl)-borate; 5-((benzyl)(per-fluoro-anthracenyl)amino)per-fluoro-napth-2-yl)(per-fluoro-fluorenyl)-(2,3,5-tri-fluoro-phenyl)-(2',3',4'-tri-fluoro-biphenyl)-borate; 5-((cyclo-hexyl)(2',3',4'-tri-fluoro-biphenyl)-amino)per-fluoro-napth-2-yl)(per-fluoro-naphthyl)-(per-fluoro-biphenyl)(pentalfluoro-pyrenyl)-borate; 5-((cyclo-hexyl)(2,3,4-tri-fluoro-phenyl)amino)per-fluoro-naphth-3-yl)(per-fluoro-phenyl)-(2,3,5-tri-fluoro-phenyl)-(2',3',5'-tri-fluoro-biphenyl)-borate; 5-((cyclo-hexyl)(per-fluoro-biphenyl)amino)per-fluoro-napth-3-yl)(per-fluoro-phenyl)-(per-fluoro-fluorenyl)aluminate; 5-((diethyl-nonly-silyl)(per-fluoro-fluorenyl)phos-phino)per-fluoro-napth-3-yl)(5,6,7,8-tetrafluoro-naphthyl)-(4,5,6,7-tetrafluoro-naphthyl)-(tetrafluoro-fluorenyl)-borate; 5-((diethyl-nonly-silyl)(per-fluoro-phenyl)amino)per-fluoro-napth-3-yl)(per-fluoro-phenyl)-(per-fluoro-fluorenyl)-(4,5,6-tri-fluoro-naphthyl)-borate; 5-((ethyl)(per-fluoro-biphenyl)amino)per-fluoro-naphth-1-yl)(4,5,6-tri-fluoro-naphthyl)-(per-fluoro-naphthyl)-(2',3',5'-tri-fluoro-biphenyl)-borate; 5-((ethyl)(per-fluoro-biphenyl)arsino)per-fluoro-inden-2-yl)(2',3',4'-tri-fluoro-biphenyl)-(per-fluoro-biphenyl)-(per-fluoro-pyrenyl)-borate; 5-((ethyl)(per-fluoro-fluorenyl)amino)per-fluoro-napth-2-yl)(2,3,4-tri-fluoro-phenyl)-(per-fluoro-fluorenyl)-(per-fluoro-naphthyl)-borate; 5-((ethyl)(per-fluoro-phenyl)arsino)per-fluoro-napth-3-yl)(2,3,5-tri-fluoro-phenyl)-(per-fluoro-biphenyl)-(per-fluoro-phenyl)-aluminate; 5-((hexyl)(per-fluoro-biphenyl)phos-phino)per-fluoro-inden-2-yl)(5,6,7,8-tetrafluoro-naphthyl)-(2',3',5'-tri-fluoro-biphenyl)pentalfluoro-pyrenyl)-borate; 5-((hexyl)(per-fluoro-biphenyl)phos-phino)per-fluoro-napth-1-yl)(4,5,7-tri-fluoro-naphthyl)-(per-fluoro-phenyl)per-fluoro-fluorenyl)borate; 5-((hexyl)(per-fluoro-phenyl)amino)-per-fluoro-napth-2-yl)(per-fluoro-phenyl)(2',3',5-tri-fluorobiphenyl)-(per-fluoro-fluorenyl)-borate; 5-((iso-propyl)(2', 3',4'-tri-fluoro-biphenyl)amino)per-fluoro-inden-1-yl)(2,3, 4-tri-fluoro-phenyl)-(per-fluoro-phenyl)-(pentalfluoro-pyrenyl)-aluminate; 5-(((iso-propyl)(per-fluoro-phenyl)amino)per-fluoro-inden-1-yl)(2,3,6-tri-fluoro-phenyl)-(per-fluoro-phenyl)-(tetrafluoro-fluorenyl)-aluminate; 5-((methyl)(4,5,6,7-tetrafluoro-naphthyl)amino)per-fluoro-napth-1-yl)(per-fluoro-biphenyl)-(2',3',5'-tri-fluoro-biphenyl)-(pentalfluoro-pyrenyl)-borate; 5-((methyl)(4,5,6,7-tetrafluoro-naphthyl)amino)per-fluoro-napth-2-yl)(pentalfluoro-pyrenyl)-(per-fluoro-naphthyl)-(per-fluoro-anthracenyl)-borate; 5-((methyl)(4,5,6-tri-fluoro-naphthyl)phos-phino)per-fluoro-napth-1-yl)(4,5,6,7-tetrafluoro-naphthyl)-(2,3,6-tri-fluoro-phenyl)-(2,3,5-tri-fluoro-phenyl)-borate; 5-((methyl)(4,5,7-tri-fluoro-naphthyl)arsino)per-fluoro-napth-2-yl)(per-fluoro-anthracenyl)-(per-fluoro-biphenyl)-(2,3,5-tri-fluoro-phenyl)-borate; 5-((methyl)(per-fluoro-fluorenyl)amino)per-fluoro-napth-3-yl)(2,3,4-tri-fluoro-phenyl)-(2,3,6-tri-fluoro-phenyl)-(per-fluoro-phenyl)-aluminate; 5-((methyl)(per-fluoro-fluorenyl)phos-phino)per-fluoro-inden-2-yl)-(2',3',4'-tri-fluoro-biphenyl)-(4,5,7-tri-fluoro-naphthyl)-(per-fluoro-phenyl)-aluminate; 5-((methyl)-(per-fluoro-phenyl)amino)per-fluoro-napth-2-yl)bis(per-fluoro-biphenyl)-(2,3,4-tri-fluoro-phenyl)-borate; 5-((methyl-diethyl-silyl)(2',3',5'-tri-fluoro-biphenyl)phos-phino)per-fluoro-napth-1-yl)(4,5,6-tri-fluoro-naphthyl)-(per-fluoro-fluorenyl)-(per-fluoro-phenyl)-borate; 5-((methyl-diethyl-silyl-octyl)(per-fluoro-biphenyl)amino)per-fluoro-napth-2-yl)(2,3,5-tri-fluoro-phenyl)-(tetrafluoro-fluorenyl)-(per-fluoro-biphenyl)-borate; 5-((methyl-ethyl-hexyl-silyl)(pentafluoro-anthracenyl)-amino)per-fluoro-inden-1-yl)(pentalfluoro-pyrenyl)-(per-fluoro-biphenyl)-(2,3,5-tri-fluoro-phenyl)-borate; 5-((n-butyl)(4,5,7-tri-fluoro-naphthyl)phos-phino)per-fluoro-napth-2-yl)bis(2,3,6-tri-fluoro-phenyl)-(per-fluoro-anthracenyl)-borate; 5-((octyl)(per-fluoro-anthracenyl)amino)per-fluoro-inden-1-yl)(per-fluoro-biphenyl)-(2',3',5'-tri-fluoro-biphenyl)-(pentafluoro-anthracenyl)-borate; 5-((triethylsilyl)(pentalfluoro-pyrenyl)amino)per-fluoro-napth-2-yl)(pentalfluoro-pyrenyl)-(tetrafluoro-fluorenyl)-(pentafluoro-anthracenyl)-borate; 5-((triethylsilyl)(per-fluoro-anthracenyl)-amino)per-fluoro-napth-2-yl)(per-fluoro-anthracenyl)-(4,5,6-tri-fluoro-naphthyl)-(per-fluoro-pyrenyl)-barate; 5-((triethylsilyl)(per-fluoro-naphthyl)amino)per-fluoro-napth-3-yl)(4,5,7-tri-fluoro-naphthyl)-(tetrafluoro-fluorenyl)-(2',3',4'-tri-fluoro-biphenyl)aluminate; 5-((triethylsilyl)-(per-fluoro-pyrenyl)amino)per-fluoro-inden-2-yl)bis(per-fluoro-biphenyl)-(5,6,7,8-tetrafluoro-naphthyl)-borate; 5-((triethyl-silyl-ethyl)(pentalfluoro-pyrenyl)phos-phino)per-fluoro-napth-2-yl)-(per-fluoro-biphenyl)-(4,5,6-tri-fluoro-naphthyl)-(2,3,4-tri-fluoro-phenyl)-aluminate; 5-((triethyl-silyl-ethyl)(per-fluoro-biphenyl)amino)per-fluoro-inden-2-yl)(5,6,7,8-tetrafluoro-naphthyl)-(2,3,5-tri-fluoro-phenyl)-(tetrafluoro-fluorenyl)-aluminate; 5-((tri-iso-propyl-silyl)(2',3',4'-tri-fluoro-biphenyl)arsino)fluoro-napth-2-yl)(2',3',5'-tri-fluoro-biphenyl)-(4,5,6,7-tetrafluoro-naphthyl)-(2,3,5-tri-fluoro-phenyl)-borate; 5-((tri-iso-propyl-silyl)(4,5,6-tri-fluoro-naphthyl)arsino)per-fluoro-napth-1-yl)(4,5,6-tri-fluoro-naphthyl)-(per-fluoro-anthracenyl)-(per-fluoro-fluorenyl)-aluminate; 5-((tri-iso-propyl-silyl)(per-fluoro-phenyl)amino)fluoro-napth-2-yl)(pentalfluoro-pyrenyl)-(2,3,5-tri-fluoro-phenyl)-(4,5,6-tri-fluoronaphthyl)-borate; 5(tri-iso-propyl-silyl)(per-fluoro-pyrenyl)amino)per-fluoro-napth-3-yl)bis(per-fluoro-biphenyl)-(2,3,5-tri-fluoro-phenyl)-aluminate; 5-((tri-iso-propyl-silyl)(2',3',5'-tri-fluoro-biphenyl)phos-phino)fluoro-napth-1-yl)-(5,6,7,8-tetrafluoro-naphthyl)per-fluoro-phenyl)(4,5,7-tri-fluoro-naphthylaluminate; 5(tri-iso-propyl-silyl-octyl)(5,6,7,8-tetrafluoro-naphthyl)amino)per-fluoro-inden-1-yl)(per-fluoro-anthracenyl)-(per-fluoro-pyrenyl)-(2,3,5-tri-fluoro-phenyl)-aluminate; 5-((tri-iso-propyl-silyl-octyl)(per-fluoro-fluorenyl)amino)per-fluoro-napth-3-yl)(per-fluoro-phenyl)-(4,5,6-tri-fluoro-naphthyl)-(per-fluoro-anthracenyl)-aluminate; 5-((tri-iso-propyl-silyl-octyl)(per-fluoro-naphthyl)phos-phino)per-fluoro-napth-3-yl)(4,5,7-tri-fluoro-naphthyl)-(2',3',4'-tri-fluoro-biphenyl)-(per-fluoro-biphenyl)-borate; 5-((trimethyl-silyl)(per-fluoro-fluorenyl)amino)per-fluoro-inden-2-yl)(per-fluoro-phenyl)-(per-fluoro-anthracenyl)-(per-fluoro-biphenyl)-aluminate; 5-((tri-n-propyl-silyl)(2',3',4'-tri-fluoro-biphenyl)amino)fluoro-inden-1-yl)(per-fluoro-anthracenyl)-(per-fluoro-fluorenyl)-(2',3',5'-tri-fluoro-biphenyl)-borate; 5-((tri-n-propyl-silyl)(per-fluoro-phenyl)-amino)per-fluoro-napth-3-yl)(5,6,7,8-tetrafluoro-naphthyl)-(2,3,4-tri-fluoro-phenyl)-(per-fluoro-fluorenyl)-aluminate; 5-((tri-n-propyl-silyl)(per-fluoro-pyrenyl)amino)per-fluoro-napth-1-yl)-(2',3',5'-tri-fluoro-biphenyl)-(pentalfluoro-pyrenyl)-(per-fluoro-phenyl)-borate; 5-((tri-n-propyl-silyl-hexyl)(2',3',4'-tri-fluoro-biphenyl)amino)per-fluoro-inden-2-yl)(per-fluoro-phenyl)-(pentafluoro-anthracenyl)-(tetrafluoro-fluorenyl)-borate; 5-((tri-n-propyl-silyl-hexyl)(pentalfluoro-pyrenyl)phos-phino)per-fluoro-inden-1-yl)(per-fluoro-naphthyl)-(tetrafluoro-fluorenyl)-(per-fluoro-anthracenyl)-aluminate; 5-((tri-n-propyl-silyl-hexyl)(per-fluoro-anthracenyl)amino)per-fluoro-inden-1-yl)(2',3',4'-tri-fluoro-biphenyl)-(2,3,4-tri-fluoro-phenyl)-(per-fluoro-biphenyl)-borate; 5-((tri-n-propyl-silyl-hexyl)(per-fluoro-biphenyl)amino)per-fluoro-napth-2-yl)(per-fluoro-biphenyl)-(per-fluoro-naphthyl)-(2,3,5-tri-fluoro-phenyl)-aluminate; 5-((tri-n-propyl-silyl-hexyl)-(per-fluoro-pyrenyl)amino)per-fluoro-inden-2-yl)(per-fluoro-phenyl)-(per-fluoro-anthracenyl)-(4,5,6,7-tetrafluoro-naphthyl)-borate; 6-((3-ethyl-nonyl)(pentalfluoro-pyrenyl)amino)per-fluoro-naphth-2-yl)(per-fluoro-phenyl)-(2',3',4'-tri-fluoro-biphenyl)-(tetrafluoro-fluorenyl)-borate; 6-((3-ethyl-nonyl)(per-fluoro-phenyl)phos-phino)per-fluoro-napth-2-yl)(5,6,7,8-tetrafluoro-naphthyl)-(pentafluoro-anthracenyl)-(4,5,7-tri-fluoro-naphthyl)-aluminate; 6-((triethyl-silyl-propyl)(2',3',5'-tri-fluoro-biphenyl)amino)per-fluoro-fluoren-1-yl)(per-fluoro-phenyl)-(4,5,6,7-tetrafluoro-naphthyl)-(2,3,5-tri-fluoro-phenyl)-borate; 6-((triethyl-silyl-propyl)(pentalfluoro-pyrenyl)phos-phino)per-fluoro-napth-3-yl)(2',3',5'-tri-fluoro-biphenyl)-(per-fluoro-fluorenyl)-(per-fluoro-pyrenyl)-aluminate; 6-((triethyl-silyl-propyl)(per-fluoro-biphenyl)phos-phino)per-fluoro-napth-3-yl)(per-fluoro-anthracenyl)-(4,5,7-tri-fluoro-naphthyl)-(2,3,4-tri-fluoro-phenyl)-borate; 6-((triethyl-silyl-propyl)(per-fluoro-naphthyl)amino)fluoro-napth-3-yl)bis(per-fluoro-anthracenyl)-(2',3',5'-tri-fluoro-biphenyl-aluminate; 6-((triethyl-silyl-propyl)(per-fluoro-phenyl)amino)per-fluoro-fluoren-1-yl)(per-fluoro-anthracenyl)-(2',3',5'-tri-fluoro-biphenyl)-(per-fluoro-naphthyl)-borate; 6-((triethyl-silyl-propyl)(per-fluoro-pyrenyl)phos-phino)per-fluoro-anth-racen-2-yl)-(2',3',5'-tri-fluoro-biphenyl)-(5,6,7,8-tetrafluoro-naphthyl)-(per-fluoro-phenyl)-borate; 6-((2,2-dimethyl-octyl)(per-fluoro-fluorenyl)phos-phino)per-fluoro-napth-2-yl)(per-fluoro-phenyl)-(4,5,6,7-tetrafluoro-naphthyl)-(per-fluoro-anthracenyl)-borate; 6-((benzyl)(5,6,7,8-tetrafluoro-naphthyl)amino)per-fluoro-anth-racen-2-yl)(per-fluoro-phenyl)-(per-fluoro-naphthyl)(2',3',4'-tri-fluoro-biphenyl)-aluminate; 6-((benzyl)(per-fluoro-biphenyl)amino)per-fluoro-napth-2-yl)(per-fluoro-fluorenyl)-(per-fluoro-anthracenyl)-(tetrafluoro-fluorenyl)-aluminate;

6-((benzyl)(per-fluoro-phenyl)amino)per-fluoro-napth-3-yl)(per-fluoro-anthracenyl)(per-fluoro-biphenyl)(4,5,6-tri-fluoro-naphthyl)-borate; 6-((butyl)(2,3,6-tri-fluoro-phenyl)amino)fluoro-fluoren-2-yl)(per-fluoro-biphenyl)-(per-fluoro-anthracenyl)-(pentafluoro-anthracenyl)-borate; 6-((butyl)-(pentafluoro-anthracenyl)amino)fluoro-napth-3-yl)(2',3',5'-tri-fluoro-biphenyl)-(per-fluoro-biphenyl)-(per-fluoro-phenyl)-aluminate; 6-((butyl)(per-fluoro-phenyl)amino)per-fluoro-fluoren-2-yl)(per-fluoro-pyrenyl)-(pentafluoro-anthracenyl)-(per-fluoro-fluorenyl)-borate; 6-((butyl)(per-fluoro-phenyl)amino)per-fluoro-napth-2-yl)(4,5,7-tri-fluoro-naphthyl)-(per-fluoro-phenyl)-(per-fluoro-fluorenyl)-borate; 6-((butyl)(per-fluoro-phenyl)phos-phino)per-fluoro-anth-racen-2-yl)-(2,3,4-tri-fluoro-phenyl)-(per-fluoro-biphenyl)-(2,3,6-tri-fluoro-phenyl)-aluminate; 6-((cyclo-hexyl)(2,3,6-tri-fluoro-phenyl)phos-phino)per-fluoro-anth-racen-2-yl)(2,3,4-tri-fluoro-phenyl)-(pentafluoro-anthracenyl)-(per-fluoro-biphenyl)-borate; 6-((cyclo-hexyl)(4,5,6,7-tetrafluoro-naphthyl)amino)per-fluoro-inden-2-yl)bis(per-fluoro-anthracenyl)-(per-fluoro-pyrenyl)-aluminate; 6-((cyclo-hexyl)(per-fluoro-fluorenyl)amino)per-fluoro-anth-racen-2-yl)bis(5,6,7,8-tetrafluoro-naphthyl)-(per-fluoro-fluorenyl)-aluminate; 6-((cyclo-hexyl)(per-fluoro-naphthyl)-arsino)per-fluoro-inden-2-yl)(4,5,6,7-tetrafluoro-naphthyl)-(2',3',5'-tri-fluoro-biphenyl)-(per-fluoro-phenyl)-borate; 6-((cyclo-hexyl)(per-fluoro-phenyl)amino)per-fluoro-anth-racen-1-yl)(per-fluoro-biphenyl)-(2',3',4'-tri-fluoro-biphenyl)-(4,5,6-tri-fluoro-naphthyl)-borate; 6-((cyclo-hexyl)-(per-fluoro-phenyl)amino)per-fluoro-anth-racen-2-yl)(per-fluoro-naphthyl)-(pentalfluoro-pyrenyl)-(2,3,5-tri-fluoro-phenyl)-borate; 6-((cyclo-hexyl)(per-fluoro-phenyl)amino)per-fluoro-napth-2-yl)(4,5,6,7-tetrafluoro-naphthyl)-(per-fluoro-biphenyl)-(per-fluoro-phenyl)-borate; 6-((cyclo-hexyl)(per-fluoro-phenyl)arsino)fluoro-fluoren-1-yl)(per-fluoro-anthracenyl)-(per-fluoro-phenyl)-(per-fluoro-naphthyl)-borate; 6-((diethyl-nonly-silyl)(2,3,4-tri-fluoro-phenyl)amino)per-fluoro-fluoren-2-yl)(per-fluoro-naphthyl)-(pentafluoro-anthracenyl)-(per-fluoro-biphenyl)-aluminate; 6-((diethyl-nonly-silyl)(per-fluoro-phenyl)amino)per-fluoro-inden-2-yl)(per-fluoro-phenyl)-(2,3,4-tri-fluoro-phenyl)-(4,5,6-tri-fluoro-naphthyl)-borate; 6-((diethyl-nonly-silyl)(per-fluoro-phenyl)arsino)per-fluoro-napth-3-yl)(per-fluoro-anthracenyl)-(4,5,6,7-tetrafluoro-naphthyl)-(2',3',4'-tri-fluoro-biphenyl)-borate; 6-((diethyl-nonly-silyl)(per-fluoro-phenyl)phos-phino)per-fluoro-anth-racen-1-yl)(2,3,5-tri-fluoro-phenyl)-(4,5,6-tri-fluoro-naphthyl)-(per-fluoro-naphthyl)-borate; 6-((diethyl-nonly-silyl)(per-fluoro-phenyl)phos-phino)per-fluoro-anth-racen-1-yl)(2,3,6-tri-fluoro-phenyl)-(per-fluoro-pyrenyl)-(per-fluoro-fluorenyl)-borate; 6-((diethyl-nonly-silyl)(per-fluoro-pyrenyl)phos-phino)per-fluoro-naphth-2-yl)(2,3,4-tri-fluoro-phenyl)-(4,5,7-tri-fluoro-naphthyl)-(per-fluoro-anthracenyl)-borate; 6-((diethyl-nonly-silyl)(tetrafluoro-fluorenyl)-amino)per-fluoro-fluoren-1-yl)(per-fluoro-biphenyl)-(5,6,7,8-tetrafluoro-naphthyl)-(per-fluoro-phenyl)-borate; 6-((ethyl)(2',3',4'-tri-fluoro-biphenyl)phos-phino)per-fluoro-anth-racen-1-yl)-(4,5,6,7-tetrafluoro-naphthyl)-(2',3',4'-tri-fluoro-biphenyl)-(per-fluoro-phenyl)-borate; 6-((ethyl)-(per-fluoro-biphenyl)amino)per-fluoro-fluoren-1-yl)(per-fluoro-pyrenyl)-(per-fluoro-fluorenyl)-(tetrafluoro-fluorenyl)-borate; 6-((hexyl)(2',3',4'-tri-fluoro-biphenyl)amino)per-fluoro-napth-1-yl)-(per-fluoro-naphthyl)-(per-fluoro-biphenyl)-(pentalfluoro-pyrenyl)-borate; 6-((hexyl)(2,3,4-tri-fluoro-phenyl)amino)fluoro-napth-3-yl)(per-fluoro-pyrenyl)(pentafluoro-pyrenyl)-(per-fluoro-anthracenyl)-borate; 6-((hexyl)(per-fluoro-anthracenyl)amino)per-fluoro-anth-racen-1-yl)(per-fluoronaphthyl)-(per-fluoro-biphenyl)-(4,5,6,7-tetrafluoro-naphthyl)-aluminate; 6-(hexyl)(per-fluoro-anthracenyl)amino)per-fluoro-napth-1-yl)(pentalfluoro-pyrenyl)-(4,5,7-tri-fluoro-naphthyl)-(per-fluoro-phenyl)-borate; 6-((hexyl)(per-fluoro-biphenyl)amino)per-fluoro-anth-racen-1-yl)(per-fluoro-biphenyl)-(4,5,6,7-tetrafluoro-naphthyl)-(tetrafluoro-fluorenyl)-aluminate; 6-((hexyl)(per-fluoro-biphenyl)phos-phino)per-fluoro-fluoren-2-yl)(4,5,6-tri-fluoro-naphthyl)-(2,3,4-tri-fluoro-phenyl)-(per-fluoro-biphenyl)-borate; 6-((hexyl)(per-fluoro-phenyl)amino)per-fluoro-anth-racen-2-yl)(per-fluoro-phenyl)-(pentalfluoro-pyrenyl)-(2',3',4'-tri-fluoro-biphenyl)-borate; 6-((hexyl)(per-fluoro-phenyl)phos-phino)per-fluoro-napth-1-yl)bis(4,5,7-tri-fluoro-naphthyl)-(per-fluoro-biphenyl-aluminate; 6-((hexyl)(per-fluoro-pyrenyl)amino)per-fluoro-fluoren-2-yl)(2,3,5-tri-fluoro-phenyl)-(per-fluoro-biphenyl)-(per-fluoro-phenyl)-borate; 6-((hexyl)-(per-fluoro-pyrenyl)amino)per-fluoro-fluoren-2-yl)(per-fluoro-phenyl)-(per-fluoro-fluorenyl)-(4,5,7-tri-fluoro-naphthyl)-borate; 6-((hexyl)(tetrafluoro-fluorenyl)amino)fluoro-fluoren-2-yl)(per-fluoro-phenyl)-(per-fluoro-anthracenyl)-(per-fluoro-pyrenyl)aluminate; 6-((iso-propyl)(per-fluoro-anthracenyl)amino)per-fluoro-inden-2-yl)(2',3',5'-tri-fluoro-biphenyl)-(per-fluoro-pyrenyl)-(pentafluoro-anthracenyl)-borate; 6-((iso-propyl)(per-fluoro-biphenyl)amino)per-fluoro-fluoren-2-yl)bis(per-fluoro-anthracenyl)-(per-fluoro-pyrenyl)-borate; 6-((iso-propyl)(per-fluoro-naphthyl)phos-phino)fluoro-inden-2-yl)(4,5,6-tri-fluoro-naphthyl)-(tetrafluoro-fluorenyl)-(per-fluoro-biphenyl)-borate; 6-((iso-propyl)(per-fluoro-phenyl)amino)per-fluoro-fluoren-1-yl)(per-fluoro-phenyl)-(per-fluoro-anthracenyl)-(per-fluoro-pyrenyl)-aluminate; 6-((iso-propyl)(per-fluoro-phenyl)amino)per-fluoro-napth-3-yl)(per-fluoro-phenyl)-(per-fluoro-pyrenyl)-(pentalfluoro-pyrenyl)-borate; 6-((iso-propyl)(per-fluoro-phenyl)arsino)per-fluoro-fluoren-2-yl)-(4,5,7-tri-fluoro-naphthyl)-(4,5,6,7-tetrafluoro-naphthyl)-(2',3',4'-tri-fluoro-biphenyl)-borate; 6-((methyl)(2,3,4-tri-fluoro-phenyl)amino)fluoro-fluoren-2-yl)(2,3,6-tri-fluoro-phenyl)-(per-fluoro-naphthyl)-(4,5,6-tri-fluoro-naphthyl)-borate; 6-((methyl)(per-fluoro-biphenyl)phos-phino)per-fluoro-fluoren-1-yl)(per-fluoro-fluorenyl)-(4,5,6-tri-fluoro-naphthyl)-(5,6,7,8-tetrafluoro-naphthyl)-borate; 6-((methyl)(per-fluoro-biphenyl)phos-phino)per-fluoro-napth-1-yl)(per-fluoro-biphenyl)-(per-fluoro-phenyl)(per-fluoro-fluorenyl)-aluminate; 6-((methyl)(per-fluoro-fluorenyl)arsino)per-fluoro-inden-2-yl)(per-fluoro-phenyl)-(pentafluoro-anthracenyl)-(per-fluoro-naphthyl)-borate; 6-((methyl)(per-fluoro-phenyl)amino)per-fluoro-anth-racen-2-yl)(5,6,7,8-tetrafluoro-naphthyl)-(per-fluoro-naphthyl)-(pentalfluoro-pyrenyl)-borate; 6-((methyl)(per-fluoro-phenyl)amino)per-fluoro-napth-2-yl)(5,6,7,8-tetrafluoro-naphthyl)-(2,3,4-tri-fluoro-phenyl)-(4,5,7-tri-fluoro-naphthyl)-borate; 6-((methyl)(per-fluoro-phenyl)phos-phino)fluoro-napth-3-yl)-(per-fluoro-fluorenyl)-(pentalfluoro-pyrenyl)-(2,3,4-tri-fluoro-phenyl)-borate; 6-((methyl)(per-fluoro-pyrenyl)amino)per-fluoro-fluoren-2-yl)(pentalfluoro-pyrenyl)-(2',3',4'-tri-fluoro-biphenyl)-(2,3,4-tri-fluoro-phenyl)-borate; 6-((methyl-diethyl-silyl-octyl)(2',3',5'-tri-fluoro-biphenyl)amino)-fluoro-fluoren-2-yl)(2,3,6-tri-fluoro-phenyl)(2',3',5'-tri-fluoro-biphenyl)-(per-fluoro-fluorenyl)-borate; 6-((methyl-diethyl-silyl-octyl)(per-fluoro-biphenyl)amino)fluoro-anth-racen-2-yl)(per-fluoro-phenyl)(4,5,7-tri-fluoro-naphthyl)-(pentafluoro-anthracenyl)-aluminate; 6-((methyl-diethyl-silyl-octyl)(per-fuoro-phenyl)amino)per-fluoro-naphth-3-yl)(5,6,7,8-tetrafluoro-naphthyl)-(2,3,5-tri-fluoro-phenyl)(tetrafluoro-fluorenyl)-aluminate; 6-((methyl-diethyl-silyl-octyl)(perfluorophenyl)amino)per-fluoro-napth-3-yl)(2,3,6-tri-fluoro-phenyl)-(tetrafluoro-fluorenyl)-(per-fluoro-anthracenyl)-borate; 6-((methyl-diethyl-silyl-octyl)(per-fluoro-pyrenyl)amino)per-fluoro-napth-2-yl)(4,5,6,7-tetrafluoro-naphthyl)-(per-fluoro-pyrenyl)-(4,5,6-tri-fluoro-naphthyl)-borate; 6-((methyl-ethyl-hexyl-silyl)(2,3,4-tri-fluoro-phenyl)phosphino)per-fluoro-napth-3-yl)bis(pentalfluoro-pyrenyl)-(2,3,5-tri-fluoro-phenyl-aluminate; 6-((methyl-ethyl-hexyl-silyl)(4,5,6,7-tetrafluoro-naphthyl)arsino)per-fluoro-napth-1-yl)(4,5,6-tri-fluoro-naphthyl)-(5,6,7,8-tetrafluoro-naphthyl)-(per-fluoro-fluorenyl)-borate; 6-((methyl-ethyl-hexyl-silyl)(4,5,7-tri-fluoro-naphthyl)amino)fluoro-anth-racen-2-yl)(per-fluoro-biphenyl)-(per-fluoro-fluorenyl)-(per-fluoro-pyrenyl)-borate; 6-((methyl-ethyl-hexyl-silyl)(per-fluoro-biphenyl)amino)per-fluoro-napth-3-yl)(per-fluoro-phenyl)-(per-fluoro-anthracenyl)-(2',3',5'-tri-fluoro-biphenyl)-borate; 6-((n-butyl)-(2',3',4'-tri-fluoro-biphenyl)amino)per-fluoro-napth-1-yl)(pentafluoro-anthracenyl)-(2,3,4-tri-fluoro-phenyl)-(per-fluoro-biphenyl)-borate; 6-((n-butyl)(2,3,4-tri-fluoro-phenyl)arsino)per-fluoro-fluoren-1-yl)(tetrafluoro-fluorenyl)-(per-fluoro-biphenyl)-(per-fluoro-pyrenyl)-borate; 6-((n-butyl)(5,6,7,8-tetrafluoro-naphthyl)arsino)per-fluoro-napth-1-yl)(per-fluoro-phenyl)-(4,5,6,7-tetrafluoro-naphthyl)-(per-fluoro-naphthyl)-aluminate; 6-((n-butyl)(per-fluoro-biphenyl)amino)per-fluoro-anth-racen-1-yl)(2',3',4'-tri-fluoro-biphenyl)-(4,5,6-tri-fluoro-naphthyl)-(per-fluoro-phenyl)-borate; 6-((n-butyl)(per-fluoro-biphenyl)amino)per-fluoro-napth-2-yl)(per-fluoro-fluorenyl)-(per-fluoro-anthracenyl)-(tetrafluoro-fluorenyl)-aluminate; 6-((n-butyl)(per-fluoro-fluorenyl)amino)per-fluoro-anth-racen-1-yl)(per-fluoro-pyrenyl)-(per-fluoro-biphenyl)-(2,3,4-tri-fluoro-phenyl)-borate; 6-((n-butyl)(per-fluoro-phenyl)phos-phino)per-fluoro-fluoren-2-yl)bis(per-fluoro-biphenyl)-(pentafluoro-anthracenyl)-borate; 6-((nonyl)(per-fluoro-anthracenyl)amino)per-fluoro-naphth-3-yl)(4,5,6-tri-fluoro-naphthyl)-(per-fluoro-pyrenyl)-(2,3,6-tri-fluoro-phenyl)-borate; 6-((nonyl)(per-fluoro-biphenyl)amino)per-fluoro-anth-racen-1-yl)(per-fluoro-anthracenyl)-(2',3',4'-tri-fluoro-biphenyl)-(per-fluoro-fluorenyl)borate; 6-((nonyl)(per-fluoro-biphenyl)amino)per-fluoro-anth-racen-2-yl)(5,6,7,8-tetrafluoro-naphthyl)-(2,3,6-tri-fluoro-phenyl)-(per-fluoro-pyrenyl)-borate; 6-((nonyl)(per-fluoro-biphenyl)arsino)per-fluoro-napth-3-yl)(4,5,6-tri-fluoro-naphthyl)-(5,6,7,8-tetrafluoro-naphthyl)-(per-fluoro-phenyl)-borate; 6-((nonyl)(per-fluoro-biphenyl)phos-phino)per-fluoro-anth-racen-2-yl)(per-fluoro-phenyl)(4,5,6,7-tetrafluoro-naphthyl)-(per-fluoro-naphthyl)-aluminate; 6-((nonyl)(per-fluoro-fluorenyl)amino)per-fluoro-anth-racen-1-yl)(2',3',5'-tri-fluoro-biphenyl)-(per-fluoro-pyrenyl)-(4,5,6-tri-fluoro-naphthyl)-borate; 6-((nonyl)(per-fluoro-naphthyl)amino)per-fluoro-fluoren-2-yl)(2,3,5-tri-fluoro-phenyl)-(5,6,7,8-tetrafluoro-naphthyl)-(4,5,6-tri-fluoro-naphthyl)-borate; 6-((nonyl)(per-fluoro-pyrenyl)amino)per-fluoro-inden-2-yl)(per-fluoro-biphenyl)-(2',3',4'-tri-fluoro-biphenyl)-(per-fluoro-fluorenyl)-borate; 6-((nonyl)(tetrafluoro-fluorenyl)amino)per-fluoro-napth-1-yl)(per-fluoro-pyrenyl)-(pentalfluoro-pyrenyl)-(per-fluoro-anthracenyl)-aluminate; 6-((octyl)(4,5,6,7-tetrafluoro-naphthyl)phos-phino)per-fluoro-fluoren-2-yl)(2,3,6-tri-fluoro-phenyl)-(per-fluoro-phenyl)-(4,5,6,7-tetrafluoro-naphthyl)-borate; 6-((octyl)(4,5,7-tri-fluoro-naphthyl)arsino)per-fluoro-naphth-3-yl)(per-fluoro-fluorenyl)-(4,5,6-tri-fluoro-naphthyl)-(pentalfluoro-pyrenyl)borate; 6-((octyl)(per-fluoro-biphenyl)arsino)per-fluoro-napth-2-yl)(per-fluoro-naphthyl)(per-fluoro-biphenyl)pentafluoro-anthracenyl)-aluminate; 6-((octyl)(tetrafluoro-fluorenyl)amino)per-fluoro-napth-2-yl)(2',3',4'-tri-fluorobiphenyl)(4,5,6,7-tetrafluoro-naphthyl)(4,5,7-tri-fluoronaphthyl)-aluminate; 6-((octyl)(tetrafluoro-fluorenyl)phos-phino)per-fluoro-inden-2-yl)bis(per-fluoro-anthracenyl)-(5,6,7,8-tetrafluoro-naphthyl)-borate; 6-((propyl)(2',3',4'-tri-fluoro-biphenyl)amino)per-fluoro-napth-1-yl)(2',3',4'-tri-fluoro-biphenyl)-(2,3,5-tri-fluoro-phenyl)-(per-fluoro-phenyl)-aluminate; 6-((propyl)(2,3,4-tri-fluoro-phenyl)amino)per-fluoro-anth-racen-2-yl)(2',3',4'-tri-fluoro-biphenyl)-(per-fluoro-fluorenyl)-(per-fluoro-phenyl)-borate; 6-((propyl)(per-fluoro-fluorenyl)amino)per-fluoro-fluoren-2-yl)(tetrafluoro-fluorenyl)-(per-fluoro-phenyl)-(4,5,6-tri-fluoro-naphthyl)-borate; 6-((propyl)(per-fluoro-fluorenyl)phos-phino)per-fluoro-fluoren-2-yl)-(4,5,6,7-tetrafluoro-naphthyl)-(4,5,6-tri-fluoro-naphthyl)-(per-fluoro-fluorenyl)-aluminate; 6-((propyl)(per-fluoro-phenyl)phos-phino)per-fluoro-napth-3-yl)(4,5,6-tri-fluoro-naphthyl)-(per-fluoro-phenyl)-(per-fluoro-biphenyl)-aluminate; 6-((propyl)(per-fluoro-pyrenyl)amino)per-fluoro-anth-racen-2-yl)(4,5,7-tri-fluoro-naphthyl)-(pentafluoro-anthracenyl)-(per-fluoro-phenyl)-borate; 6-((propyl)(per-fluoro-pyrenyl)arsino)fluoro-napth-1-yl)(per-fluoro-pyrenyl)-(per-fluoro-phenyl)-(4,5,6-tri-fluoro-naphthyl)-borate; 6-((propyl)(tetrafluoro-fluorenyl)amino)per-fluoro-fluoren-2-yl)(per-fluoro-anthracenyl)-(4,5,6-tri-fluoro-naphthyl)-(per-fluoro-pyrenyl)-borate; 6-((triethylsilyl)(pentalfluoro-pyrenyl)arsino)per-fluoro-inden-2-yl)(per-fluoro-biphenyl)-(2,3,4-tri-fluoro-phenyl)-(per-fluoro-phenyl)-aluminate; 6-((triethylsilyl)(per-fluoro-biphenyl)amino)per-fluoro-anth-racen-2-yl)(2,3,4-tri-fluoro-phenyl)-(2,3,5-tri-fluoro-phenyl)-(4,5,6-tri-fluoro-naphthyl)-borate; 6-((triethylsilyl)(per-fluoro-fluorenyl)phos-phino)fluoro-anth-racen-2-yl)(per-fluoro-biphenyl)-(per-fluoro-phenyl)-(4,5,6,7-tetrafluoro-naphthyl)-borate; 6-((triethyl-silyl-ethyl)-(4,5,6,7-tetrafluoro-naphthyl)amino)per-fluoro-fluoren-2-yl)(per-fluoro-anthracenyl)-(per-fluoro-naphthyl)-(4,5,6-tri-fluoro-naphthyl)-borate; 6-((triethyl-silyl-ethyl)(4,5,6,7-tetrafluoro-naphthyl)phosphino)per-fluoro-inden-2-yl)(per-fluoro-naphthyl)-(per-fluoro-fluorenyl)-(per-fluoro-phenyl)-borate; 6-((triethyl-silyl-ethyl)(per-fluoro-biphenyl)amino)per-fluoro-fluoren-2-yl)-(per-fluoro-biphenyl)-(pentafluoro-anthracenyl)-(per-fluoro-phenyl)-borate; 6-((triethyl-silyl-ethyl)(per-fluoro-phenyl)phos-phino)per-fluoro-anth-racen-1-yl)bis(per-fluoro-biphenyl)-(4,5,6-tri-fluoro-naphthyl)-borate; 6-((tri-iso-propyl-silyl)(2',3',5'-tri-fluoro-biphenyl)amino)per-fluoro-anth-racen-1-yl)(2',3',4'-tri-fluoro-biphenyl)-(per-fluoro-anthracenyl)-(2,3,4-tri-fluoro-phenyl)-borate; 6-((tri-iso-propyl-silyl)(per-fluoro-phenyl)amino)per-fluoro-napth-2-yl)(per-fuoro-pyrenyl)-(pentafluoro-anthracenyl)-(per-fluoro-phenyl)-borate; 6-((tri-iso-propyl-silyl)-(tetrafluoro-fluorenyl)phos-phino)per-fluoro-anth-racen-1-yl)(per-fluoro-fluorenyl)-(4,5,7-tri-fluoro-naphthyl)-(per-fluoro-pyrenyl)-borate; 6-((tri-iso-propyl-silyl-octyl)(per-fluoro-anthracenyl)arsino)per-fluoro-fluoren-1-yl)(2',3',4'-tri-fluoro-biphenyl)-(per-fluoro-fluorenyl)-(4,5,6,7-tetrafluoro-naphthyl)-aluminate; 6-((tri-isopropyl-silyl-octyl)(per-fluoro-phenyl)amino)-per-fluoro-anth-racen-1-yl)(per-fluoro-fluorenyl)-(4,5,6,7-tetrafluoro-naphthyl)-(per-fluoro-naphthyl)-borate; 6-((tri-isopropyl-silyl-octyl)(per-fluoro-phenyl)phos-phino)per-fluoro-napth-2-yl)(per-fluoro-phenyl)-(2',3',4'-tri-fluoro-biphenyl)-(2,3,6-tri-fluoro-phenyl)-borate; 6-((trimethyl-silyl)(2,3,6-tri-fluoro-phenyl)amino)per-fluoro-anthracen-2-yl)(per-fluoro-biphenyl)-(2,3,4-tri-fluoro-phenyl)-(tetrafluoro-fluorenyl)-borate; 6-(trimethyl-silyl)(4,5,7-tri-fluoro-naphthyl)amino)per-fluoro-anth-racen-1-yl)(2,3,6-tri-fluoro-phenyl)(2,3,4-tri-fluoro-phenyl)-(per-fluoro-biphenyl)-aluminate;

6-((trimethyl-silyl)(per-fluoro-anthracenyl)amino)per-fluoro-anth-racen-2-yl)(4,5,6,7-tetrafluoro-naphthyl)-(per-fluoro-fluorenyl)-(2',3',4'-tri-fluoro-biphenyl)-borate; 6-((trimethyl-silyl)(per-fluoro-biphenyl)amino)fluoro-napth-3-yl)(per-fluoro-biphenyl)-(4,5,7-tri-fluoro-naphthyl)-(2',3',5'-tri-fluoro-biphenyl)-aluminate; 6-((trimethyl-silyl)(per-fluoro-pyrenyl)phos-phino)per-fuoro-napth-3-yl)(2,3,6-tri-fluoro-phenyl)-(4,5,6,7-tetrafluoro-naphthyl)-(4,5,6-tri-fluoro-naphthyl)-borate; 6-((tri-n-propyl-silyl)(2,3,5-tri-fluoro-phenyl)amino)per-fluoro-napth-3-yl)(per-fluoro-pyrenyl)-(4,5,7-tri-fluoro-naphthyl)-(per-fluoro-fluorenyl)-aluminate; 6-((tri-n-propyl-silyl)(pentafluoro-anthracenyl)amino)per-fluoro-napth-2-yl)(per-fluoro-phenyl)-(per-fluoro-biphenyl)-(2,3,5-tri-fluoro-phenyl)-borate; 6-((tri-n-propyl-silyl)(per-fluoro-anthracenyl)amino)per-fluoro-anth-racen-2-yl)(2',3',5'-tri-fluoro-biphenyl)-(2,3,6-tri-fluoro-phenyl)-(per-fluoro-biphenyl)-borate; 6-((tri-n-propyl-silyl)(per-fluoro-fluorenyl)amino)per-fluoro-fluoren-1-yl)(2,3,4-tri-fluoro-phenyl)-(2,3,6-tri-fluoro-phenyl)-(per-fluoro-phenyl)-borate; 6-((tri-n-propyl-silyl)(per-fluoro-phenyl)phos-phino)per-fluoro-naphth-3-yl)(per-fluoro-phenyl)-(pentalfluoro-pyrenyl)-(2,3,4-tri-fluoro-phenyl)-aluminate; 6-((tri-n-propyl-silyl-hexyl)(2,3,4-tri-fluoro-phenyl)amino)per-fluoro-napth-1-yl)(per-fluoro-naphthyl)-(5,6,7,8-tetrafluoro-naphthyl)-(per-fluoro-pyrenyl)-aluminate; 6-((tri-n-propyl-silyl-hexyl)(4,5,6,7-tetrafluoro-naphthyl)amino)-per-fluoro-anth-racen-1-yl)bis(per-fluoro-biphenyl)-(4,5,6,7-tetrafluoro-naphthyl)-aluminate; 6-((tri-n-propyl-silyl-hexyl)(4,5,6,7-tetrafluoro-naphthyl)phos-phino)fluoro-anth-racen-1-yl)(per-fluoro-phenyl)-(tetrafluoro-fluorenyl)-(per-fluoro-anthracenyl)-borate; 6-((tri-n-propyl-silyl-hexyl)(per-fluoro-biphenyl)phos-phino)per-fluoro-anth-racen-1-yl)(per-fluoro-pyrenyl)-(2',3',4'-tri-fluoro-biphenyl)-(per-fluoro-naphthyl)-borate; 6-((tri-n-propyl-silyl-hexyl)(per-fluoro-phenyl)-amino)per-fluoro-napth-3-yl)bis(per-fluoro-anthracenyl)-(per-fluoro-pyrenyl)-borate; 6-((tri-n-propyl-silyl-hexyl)(per-fluoro-pyrenyl)amino)per-fluoro-napth-3-yl)bis(2',3',4'-tri-fluoro-biphenyl)-(per-fluoro-pyrenyl)-borate; 7-((3-ethyl-nonyl)(5,6,7,8-tetrafluoro-naphthyl)arsino)per-fluoro-napth-2-yl)(4,5,6-tri-fluoro-naphthyl)-(5,6,7,8-tetrafluoro-naphthyl)-(2',3',5'-tri-fluoro-biphenyl)-borate; 7-((3-ethyl-nonyl)(pentalfluoro-pyrenyl)amino)per-fluoro-fluoren-1-yl)(per-fluoro-fluorenyl)-(per-fluoro-phenyl)-(per-fluoro-biphenyl)borate; 7-((3-ethyl-nonyl)(pentalfluoro-pyrenyl)arsino)per-fluoro-inden-2-yl)(2,3,6-tri-fluoro-phenyl)-(tetrafluoro-fluorenyl)-(per-fluoro-anthracenyl)-borate; 7-((3-ethyl-nonyl)(per-fluoro-biphenyl)phos-phino)per-fluoro-fluoren-1-yl)-(per-fluoro-anthracenyl)-(per-fluoro-fluorenyl)-(4,5,6-tri-fluoro-naphthyl)-borate; 7-((3-ethyl-nonyl)(per-fluoro-phenyl)arsino)per-fluoro-napth-3-yl)(2,3,6-tri-fluoro-phenyl)-(per-fluoro-biphenyl)-(2,3,4-tri-fluoro-phenyl)-borate; 7-((triethyl-silyl-propyl)(2,3,4-tri-fluoro-phenyl)-amino)per-fluoro-pyren-2-yl)(per-fluoro-phenyl)-(per-fluoro-biphenyl)-(per-fluoro-anthracenyl)-borate; 7-((triethyl-silyl-propyl)(2,3,6-tri-fluoro-phenyl)amino)per-fluoro-anth-racen-1-yl)-(2',3',5'-tri-fluoro-biphenyl)-(per-fluoro-phenyl)-(2',3',4'-tri-fluoro-biphenyl)-aluminate; 7-((triethyl-silyl-propyl)(4,5,6-tri-fluoro-naphthyl)amino)per-fluoro-pyren-2-yl)(per-fluoro-biphenyl)-(per-fluoro-naphthyl)-(per-fluoro-phenyl)-borate; 7-((triethyl-silyl-propyl)(per-fluoro-fluorenyl)-amino)per-fluoro-napth-3-yl)(per-fluoro-phenyl)-(4,5,7-tri-fluoro-naphthyl)-(pentafluoro-anthracenyl)aluminate; 7-((triethyl-silyl-propyl)(per-fluoro-fluorenyl)phos-phino)per-fluoro-napth-1-yl)(pentalfluoro-pyrenyl)-(per-fluoro-anthracenyl)-(2,3,6-tri-fluoro-phenyl)-aluminate; 7-((triethyl-silyl-propyl)(per-fluorophenyl)amino)per-fluoro-napth-1-yl)(2,3,4-tri-fluoro-phenyl)-(4,5,6-tri-fluoro-naphthyl)-(4,5,6,7-tetrafluoro-naphthyl)-aluminate; 7-((triethyl-silyl-propyl)(per-fluoro-phenyl)amino)per-fluoro-napth-3-yl)(2,3,5-tri-fluoro-phenyl)-(per-fluoro-phenyl)-(per-fluoro-biphenyl)-borate; 7-((2,2-dimethyl-octyl)(2,3,5-tri-fluoro-phenyl)amino)per-fluoro-fluoren-2-yl)(pentafluoro-anthracenyl)-(per-fluoro-phenyl)-(per-fluoro-biphenyl)-borate; 7-((2,2-dimethyl-octyl)(4,5,6,7-tetrafluoro-naphthyl)amino)per-fluoro-anth-racen-1-yl)(per-fluoro-anthracenyl)-(2',3',4'-tri-fluoro-biphenyl)-(per-fluoro-phenyl)-aluminate; 7-((2,2-dimethyl-octyl)-(4,5,6-tri-fluoro-naphthyl)phos-phino)per-fluoro-anth-racen-1-yl)(2,3,4-tri-fluoro-phenyl)-(per-fluoro-biphenyl)-(pentafluoro-anthracenyl)-borate; 7-((2,2-dimethyl-octyl)(pentafluoro-anthracenyl)phos-phino)per-fluoro-napth-1-yl)(per-fluoro-fluorenyl)-(5,6,7,8-tetrafluoro-naphthyl)-(per-fluoro-anthracenyl)-aluminate; 7-((2,2-dimethyl-octyl)(pentalfluoro-pyrenyl)-amino)per-fluoro-napth-1-yl)(per-fluoro-naphthyl)-(tetrafluoro-fluorenyl)-(pentalfluoro-pyrenyl)-borate; 7-((2,2-dimethyl-octyl)(per-fluoro-fluorenyl)arsino)fluoro-napth-1-yl)(per-fluoro-phenyl)-(per-fluoro-naphthyl)-(pentalfluoro-pyrenyl)-borate; 7-((2,2-dimethyl-octyl)(per-fluoro-naphthyl)-amino)per-fluoro-anth-racen-1-yl)bis(per-fluoro-anthracenyl)-(pentalfluoro-pyrenyl-aluminate; 7-((2,2-dimethyl-octyl)(per-fluoro-pyrenyl)phos-phino)per-fluoro-fluoren-1-yl)bis(5,6,7,8-tetrafluoro-naphthyl)-(per-fluoro-phenyl)-borate; 7-((benzyl)(per-fluoro-anthracenyl)amino)per-fluoro-anth-racen-1-yl)(per-fluoro-pyrenyl)-(per-fluoro-anthracenyl)-(2,3,5-tri-fluoro-phenyl)-borate; 7-((benzyl)(per-fluoro-biphenyl)amino)per-fluoro-napth-1-yl)(tetrafluoro-fluorenyl)-(pentalfluoro-pyrenyl)-(2,3,5-tri-fluoro-phenyl)-borate; 7-((benzyl)(per-fluoro-biphenyl)amino)-per-fluoro-pyren-1-yl)(2',3',4'-tri-fluoro-biphenyl)-(tetrafluoro-fluorenyl)-(4,5,6,7-tetrafluoro-naphthyl)-borate; 7-((butyl)(pentalfluoro-pyrenyl)amino)per-fluoro-fluoren-2-yl)(pentafluoro-anthracenyl)-(per-fluoro-biphenyl)-(2,3,4-tri-fluoro-phenyl)-aluminate; 7-((butyl)(per-fluoro-phenyl)amino)per-fluoro-anth-racen-1-yl)(per-fluoro-pyrenyl)-(2',3',4'-tri-fluoro-biphenyl)-(per-fluoro-biphenyl)-aluminate; 7-((cyclo-hexyl)(2',3',4'-tri-fluoro-biphenyl)amino)per-fluoro-pyren-1-yl)(4,5,6,7-tetrafluoro-naphthyl)-(tetrafluoro-fluorenyl)-(pentafluoro-anthracenyl)-borate; 7-((cyclo-hexyl)(2',3',4'-tri-fluoro-biphenyl)phos-phino)per-fluoro-pyren-2-yl)(per-fluoro-fluorenyl)-(tetrafluoro-fluorenyl)-(per-fluoro-phenyl)-aluminate; 7-((cyclo-hexyl)(2,3,4-tri-fluoro-phenyl)-amino)per-fluoro-inden-2-yl)(per-fluoro-fluorenyl)-(2,3,6-tri-fluoro-phenyl)(per-fluoro-biphenyl)-aluminate; 7-((cyclo-hexyl)(2,3,4-tri-fluoro-phenyl)amino)per-fluoro-pyren-2-yl)(2,3,4-tri-fluoro-phenyl)-(per-fluoro-fluorenyl)-(per-fluoro-naphthyl)-borate; 7-((cyclo-hexyl)(4,5,6-tri-fluoro-naphthyl)amino)per-fluoro-fluoren-2-yl)(per-fluoro-biphenyl)-(tetrafluoro-fluorenyl)-(per-fluoro-phenyl)-aluminate; 7-((cyclo-hexyl)(5,6,7,8-tetrafluoro-naphthyl)arsino)per-fluoro-fluoren-2-yl)-(per-fluoro-biphenyl)-(pentalfluoro-pyrenyl)-(per-fluoro-phenyl)-aluminate; 7-((cyclo-hexyl)-(5,6,7,8-tetrafluoro-naphthyl)arsino)per-fluoro-napth-3-yl)(per-fluoro-anthracenyl)-(4,5,6,7-tetrafluoro-naphthyl)-(per-fluoro-biphenyl)-borate; 7-((cyclo-hexyl)(5,6,7,8-tetrafluoro-naphthyl)phos-phino)fluoro-inden-2-yl)bis(pentafluoro-anthracenyl)-(4,5,6,7-tetrafluoro-naphthyl)-borate; 7-(cyclo-hexyl)(pentalfluoro-pyrenyl)amino)per-fluoro-pyren-2-yl)bis(per-fluoro-biphenyl)-(2,3,4-tri-fluoro-phenyl)-borate; 7-((cyclo-hexyl)(per-fluoro-biphenyl)amino)per-fluoro-fluoren-1-yl)(per-fluoronaphthyl)-(2',3',4'-tri-fluoro-biphenyl)-(per-fluoro-fluorenyl)-borate; 7-((cyclo-hexyl)(per-fluoro-biphenyl)amino)per-fluoro-fluoren-1-yl)bis(per-fluoro-anthracenyl)-(per-fluoro-fluorenyl-aluminate; 7-((cyclo-hexyl)(per-fluoro-biphenyl)arsino)per-fluoro-napth-1-yl)bis(4,5,6,7-tetrafluoro-naphthyl)-(4,5,6-tri-fluoro-naphthyl)borate; 7-((cyclo-hexyl)(per-fluoro-fluorenyl)amino)fluoro-pyren-1-yl)(2,3,4-tri-fluoro-phenyl)-(per-fluoro-naphthyl)-(per-fluoro-phenyl)-aluminate; 7-((cyclo-hexyl)(per-fluoro-phenyl)amino)per-fluoro-anth-racen-1-yl)(per-fluoro-fluorenyl)-(5,6,7,8-tetrafluoro-naphthyl)-(per-fluoro-anthracenyl)-borate; 7-((cyclo-hexyl)(per-fluoro-phenyl)amino)per-fluoro-fluoren-1-yl)bis(2,3,4-tri-fluoro-phenyl)-(4,5,7-tri-fluoro-naphthyl-aluminate; 7-((cyclo-hexyl)(tetrafluoro-fluorenyl)amino)per-fluoro-pyren-1-yl)(2,3,6-tri-fluoro-phenyl)-(2,3,4-tri-fluoro-phenyl)-(per-fluoro-phenyl)-borate; 7-((diethyl-nonly-silyl)(5,6,7,8-tetrafluoro-naphthyl)amino)per-fluoro-napth-2-yl)(tetrafluoro-fluorenyl)-(per-fluoro-naphthyl)-(per-fluoro-biphenyl)-borate; 7-((diethyl-nonly-silyl)-(pentalfluoro-pyrenyl)amino)per-fluoro-naphth-1-yl)(per-fluoro-naphthyl)-(per-fluoro-phenyl)-(per-fluoro-biphenyl)-borate; 7-((diethyl-nonly-silyl)(per-fluoro-fluorenyl)amino)per-fluoro-inden-2-yl)(per-fluoro-phenyl)-(per-fluoro-naphthyl)-(2',3',5'-fluoro-biphenyl)-borate; 7-((diethyl-nonly-silyl)(per-fluoro-phenyl)phos-phino)per-fluoro-pyren-2-yl)(tetrafluoro-fluorenyl)-(per-fluoro-naphthyl)-(per-fluoro-biphenyl)-borate; 7-((diethyl-nonly-silyl)(per-fluoro-pyrenyl)amino)-per-fluoro-inden-2-yl)(4,5,6-tri-fluoro-naphthyl)-(per-fluoro-anthracenyl)-(per-fluoro-phenyl)-borate; 7-((ethyl)(2,3,6-tri-fluoro-phenyl)amino)per-fluoro-napth-1-yl)(2,3,4-tri-fluoro-phenyl)-(tetrafluoro-fluorenyl)-(5,6,7,8-tetrafluoro-naphthyl)-borate; 7-((ethyl)(4,5,7-tri-fluoro-naphthyl)-amino)per-fluoro-napth-2-yl)(pentafluoro-anthracenyl)-(2',3',5'-tri-fluoro-biphenyl)-(per-fluoro-biphenyl)-borate; 7-((ethyl)(per-fluoro-anthracenyl)amino)per-fluoro-inden-2-yl)(2,3,6-tri-fluoro-phenyl)-(4,5,6-tri-fluoro-naphthyl)-(per-fluoro-fluorenyl)-aluminate; 7-((ethyl)(per-fluoro-naphthyl)amino)per-fluoro-napth-1-yl)(per-fluoro-fluorenyl)-(2,3,4-tri-fuoro-phenyl)-(2',3',5'-tri-fluoro-biphenyl)-aluminate; 7-((ethyl)(per-fluoro-pyrenyl)amino)per-fluoro-anth-racen-1-yl)(per-fluoro-phenyl)-(per-fluoro-anthracenyl)-(2',3',5'-tri-fluoro-biphenyl)-borate; 7-((ethyl)(per-fluoro-pyrenyl)amino)per-fluoro-fluoren-1-yl)(2,3,4-tri-fluoro-phenyl)-(2,3,6-tri-fluoro-phenyl)-(per-fluoro-phenyl)borate; 7-((hexyl)(per-fluoro-biphenyl)phos-phino)per-fluoro-napth-2-yl)-(pentafluoro-anthracenyl)-(per-fluoro-biphenyl)-(2,3,4-tri-fluoro-phenyl)-borate; 7-((hexyl)(per-fluoro-phenyl)amino)fluoro-napth-3-yl)(2,3,5-tri-fluoro-phenyl)-(per-fluoro-phenyl)-(4,5,7-tri-fluoro-naphthyl)-aluminate; 7-((hexyl)(per-fluoro-phenyl)amino)per-fluoro-fluoren-1-yl)(per-fluoro-pyrenyl)-(4,5,6,7-tetrafluoro-naphthyl)-(per-fluoro-phenyl)-borate; 7-((hexyl)(per-fluoro-phenyl)amino)per-fluoro-napth-1-yl)bis(per-fluoro-biphenyl)-(4,5,6-tri-fluoro-naphthyl-aluminate; 7-((hexyl)(per-fluoro-phenyl)amino)per-fluoro-napth-2-yl)(pentalfluoro-pyrenyl)-(4,5,7-tri-fluoro-naphthyl)-(per-fluoro-phenyl)-borate; 7-((hexyl)(per-fluoro-phenyl)amino)per-fluoro-napth-3-yl)(tetrafluoro-fluorenyl)-(pentafluoro-anthracenyl)-(per-fluoro-naphthyl)-borate; 7-((hexyl)(tetrafluoro-fluorenyl)amino)per-fluoro-napth-1-yl)(2,3,4-tri-fluoro-phenyl)-(5,6,7,8-tetrafluoro-naphthyl)-(per-fluoro-pyrenyl)-borate; 7-((iso-propyl)(pentalfluoro-pyrenyl)arsino)-per-fluoro-napth-1-yl)bis(per-fluoro-anthracenyl)(per-fluoro-biphenyl)-borate; 7-((iso-propyl)-(per-fluoro-biphenyl)amino)per-fluoro-inden-2-yl)(per-fluoro-phenyl)per-fluoro-fluorenyl)-(2',3',5'-tri-fluoro-biphenyl)-aluminate; 7-(iso-propyl)(per-fluoro-biphenyl)amino)per-fluoro-napth-3-yl)(per-fluoro-phenyl)-(4,5,6,7-tetrafluoro-naphthyl)-(per-fluoro-naphthyl)aluminate; 7-((methyl)(2,3,5-tri-fluoro-phenyl)amino)per-fluoro-anth-racen-1-yl)(per-fluoro-fluorenyl)-(per-fluoro-anthracenyl)-(tetrafluoro-fluorenyl)-aluminate; 7-((methyl)(2,3,5-tri-fluoro-phenyl)amino)-per-fluoro-napth-1-yl)bis(2,3,6-tri-fluoro-phenyl)-(per-fluoro-pyrenyl)-borate; 7-((methyl)-(4,5,6,7-tetrafluoro-naphthyl)amino)per-fluoro-pyren-2-yl)(2,3,5-tri-fluoro-phenyl)-(per-fluoro-fluorenyl)-(5,6,7,8-tetrafluoro-naphthyl)-borate; 7-((methyl)(per-fluoro-phenyl)amino)per-fluoro-pyren-2-yl)(per-fluoro-naphthyl)-(per-fluoro-fluorenyl)-(per-fluoro-phenyl)-aluminate; 7-((methyl)(per-fluoro-pyrenyl)amino)per-fluoro-pyren-2-yl)(per-fluoro-biphenyl)-(per-fluoro-naphthyl)-(tetrafluoro-fluorenyl)-borate; 7-((methyl-diethyl-silyl-octyl)(5,6,7,8-tetrafluoro-naphthyl)amino)per-fluoro-inden-2-yl)(2',3',4'-tri-fluoro-biphenyl)-(per-fluoro-phenyl)-(2,3,4-tri-fluoro-phenyl)-aluminate; 7-((methyl-diethyl-silyl-octyl)(per-fluoro-anthracenyl)amino)per-fluoro-napth-2-yl)(2,3,5-tri-fluoro-phenyl)-(per-fluoro-fluorenyl)-(per-fluoro-biphenyl)-borate; 7-((methyl-diethyl-silyl-octyl)(per-fluoro-biphenyl)amino)per-fluoro-napth-1-yl)(per-fluoro-anthracenyl)-(pentafluoro-anthracenyl)-(per-fluoro-phenyl)-aluminate; 7-((methyl-diethyl-silyl-octyl)(per-fluoro-fluorenyl)amino)per-fluoro-pyren-1-yl)(per-fluoro-anthracenyl)-(2',3',5'-tri-fluoro-biphenyl)-(per-fluoro-biphenyl)-aluminate; 7-((methyl-diethyl-silyl-octyl)(per-fluoro-phenyl)amino)per-fluoro-napth-3-yl)(per-fluoro-pyrenyl)-(2,3,4-tri-fluoro-phenyl)-(per-fluoro-anthracenyl)-borate; 7-((methyl-diethyl-silyl-octyl)(per-fluoro-phenyl)arsino)fluoro-napth-2-yl)-(per-fluoro-pyrenyl)-(per-fluoro-phenyl)-(2,3,4-tri-fluoro-phenyl)-borate; 7-((methyl-diethyl-silyl-octyl)(per-fluoro-phenyl)arsino)per-fluoro-napth-3-yl)(2',3',5'-tri-fluoro-biphenyl)-(per-fluoro-pyrenyl)-(per-fluoro-biphenyl)-aluminate; 7-((methyl-ethyl-hexyl-silyl)(4,5,6,7-tetrafluoro-naphthyl)arsino)per-fluoro-napth-2-yl)(per-fluoro-phenyl)-(2,3,4-tri-fluoro-phenyl)-(per-fluoro-biphenyl)-borate; 7-((methyl-ethyl-hexyl-silyl)(per-fluoro-phenyl)amino)per-fluoro-inden-2-yl)-(2,3,5-tri-fluoro-phenyl)-(per-fluoro-pyrenyl)-(2',3',4'-tri-fluoro-biphenyl)-borate; 7-((methyl-ethyl-hexyl-silyl)(per-fluoro-phenyl)amino)per-fluoro-pyren-2-yl)(per-fluoro-fluorenyl)-(per-fluoro-pyrenyl)(2,3,4-tri-fluoro-phenyl)-borate; 7-((n-butyl)(2,3,5-tri-fluoro-phenyl)amino)per-fluoro-pyren-1-yl)(per-fluoro-anthracenyl)-(2,3,4-tri-fluoro-phenyl)-(per-fluoro-biphenyl)-borate; 7-((n-butyl)(5,6,7,8-tetrafluoro-naphthyl)amino)per-fluoro-fluoren-2-yl)(per-fluoro-anthracenyl)-(4,5,6,7-tetrafluoro-naphthyl)-(per-fluoro-biphenyl)-aluminate; 7-((n-butyl)(per-fluoro-biphenyl)amino)per-fluoro-inden-2-yl)(2',3',5'-tri-fluoro-biphenyl)-(4,5,6-tri-fluoro-naphthyl)-(2,3,6-tri-fluoro-phenyl)-borate; 7-((n-butyl)(per-fluoro-pyrenyl)amino)per-fluoro-pyren-1-yl)(per-fluoro-phenyl)-(tetrafluoro-fluorenyl)-(4,5,7-tri-fluoro-naphthyl)-aluminate; 7-((nonyl)(4,5,6,7-tetrafluoro-naphthyl)amino)per-fluoro-napth-3-yl)(2,3,5-tri-fluoro-phenyl)-(4,5,6,7-tetrafluoro-naphthyl)-(2,3,6-tri-fluoro-phenyl)-aluminate; 7-((nonyl)(4,5,6-tri-fluoro-naphthyl)arsino)per-fluoro-fluoren-2-yl)(per-fluoro-naphthyl)-(per-fluoro-fluorenyl)-(per-fluoro-pyrenyl)-borate; 7-((nonyl)(per-fluoro-phenyl)phos-phino)per-fluoro-fluoren-2-yl)(per-fluoro-naphthyl)-(per-fluoro-phenyl)-(4,5,6,7-tetrafluoro-naphthyl)-aluminate; 7-((nonyl)(per-fluoro-pyrenyl)amino)per-fluoro-napth-1-yl)(2',3',5'-tri-fluoro-biphenyl)-(per-fluoro-anthracenyl)-(per-fluoro-fluorenyl)borate; 7-((octyl)(2,3,4-tri-fluoro-phenyl)amino)per-fluoro-pyren-2-yl)(per-fluoro-phenyl)(2',3',4'-tri-fluoro-biphenyl)-

(per-fluoro-naphthyl)-borate; 7-((octyl)(4,5,6,7-tetrafluoro-naphthyl)amino)per-fluoro-naphth-1-yl)(2',3',5'-tri-fluorobiphenyl)-(4,5,6-tri-fluoro-naphthyl)-(per-fluoro-anthracenyl)-borate; 7-((octyl)(4,5,7-tri-fluoro-naphthyl)amino)per-fluoro-pyren-2-yl)(per-fluoro-phenyl)-(4,5,7-tri-fluoro-naphthyl)-(per-fluoro-naphthyl)-aluminate; 7-((octyl)(per-fluoro-anthracenyl)amino)per-fluoro-anth-racen-1-yl)(per-fluoro-phenyl)-(per-fluoro-fluorenyl)-(4,5,7-tri-fluoro-naphthyl)-borate; 7-((octyl)(per-fluoro-biphenyl)amino)per-fluoro-naphth-2-yl)bis(4,5,7-tri-fluoro-naphthyl)-(per-fluoro-biphenyl)-borate; 7-((octyl)(per-fluoro-biphenyl)arsino)per-fluoro-inden-2-yl)(per-fluoro-fluorenyl)-(tetrafluoro-fluorenyl)-(per-fluoro-phenyl)-borate; 7-((octyl)(per-fluoro-biphenyl)phos-phino)per-fluoro-napth-3-yl)bis(pentafluoro-anthracenyl)-(per-fluoro-phenyl)-borate; 7-((octyl)(per-fluoro-naphthyl)arsino)per-fluoro-anth-racen-1-yl)(4,5,7-tri-fluoro-naphthyl)-(per-fluoro-biphenyl)-(per-fluoro-phenyl)-borate; 7-((octyl)-(per-fluoro-phenyl)amino)per-fluoro-napth-2-yl)(per-fluoro-biphenyl)-(4,5,6,7-tetrafluoro-naphthyl)-(per-fluoro-phenyl)-aluminate; 7-((octyl)(per-fluoro-phenyl)amino)per-fluoro-napth-3-yl)(5,6,7,8-tetrafluoro-naphthyl)-(4,5,6,7-tetrafluoro-naphthyl)-(per-fluoro-phenyl)-aluminate; 7-((propyl)(2,3,4-tri-fluoro-biphenyl)phos-phino)per-fluoro-fluoren-2-yl)(per-fluoro-pyrenyl)-(per-fluoro-naphthyl)-(per-fluoro-anthracenyl)-borate; 7-((propyl)(pentafluoro-anthracenyl)phos-phino)per-fluoro-fluoren-2-yl)(per-fluoro-phenyl)-(per-fluoro-biphenyl)-(4,5,6-tri-fluoro-naphthyl)-borate; 7-((propyl)(pentafluoro-anthracenyl)phos-phino)per-fluoro-inden-2-yl)(2,3,5-tri-fluoro-phenyl)-(4,5,6-tri-fluoro-naphthyl)-(per-fluoro-naphthyl)-borate; 7-((propyl)(per-fluoro-biphenyl)arsino)per-fluoro-inden-2-yl)(per-fluoro-phenyl)-(2,3,6-tri-fluoro-phenyl)-(pentafluoro-pyrenyl)-borate; 7-((propyl)(per-fluoro-fluorenyl)amino)per-fluoro-napth-2-yl)(2,3,5-tri-fluoro-phenyl)-(4,5,6,7-tetrafluoro-naphthyl)-(tetrafluoro-fluorenyl)-borate; 7-((triethylsilyl)(2',3',4'-tri-fluoro-biphenyl)arsino)per-fluoro-napth-3-yl)(4,5,6,7-tetrafluoro-naphthyl)-(2,3,4-tri-fluoro-phenyl)-(per-fluoro-fluorenyl)-borate; 7-((triethylsilyl)(4,5,7-tri-fluoro-naphthyl)phos-phino)per-fluoro-pyren-2-yl)(per-fluoro-phenyl)-(per-fluoro-anthracenyl)-(per-fluoro-naphthyl)-aluminate; 7-((triethylsilyl)(per-fluoro-biphenyl)phos-phino)per-fluoro-pyren-1-yl)(per-fluoro-anthracenyl)-(2,3,4-tri-fluoro-phenyl)-(per-fluoro-biphenyl)borate; 7-((triethylsilyl)(per-fluoro-phenyl)amino)-per-fluoro-pyren-2-yl)(per-fluoro-anthracenyl)-(per-fluoro-biphenyl)-(per-fluoro-phenyl)-borate; 7-((triethyl-silyl-ethyl)(2',3',4'-tri-fluoro-biphenyl)amino)per-fluoro-napth-3-yl)(per-fluoro-phenyl)-(per-fluoro-pyrenyl)-(per-fluoro-fluorenyl)-borate; 7-((triethyl-silyl-ethyl)(per-fluoro-biphenyl)amino)per-fluoro-napth-1-yl)bis(per-fluoro-biphenyl)-(2,3,4-tri-fluoro-phenyl)-borate; 7-((triethyl-silyl-ethyl)(per-fluoro-biphenyl)phos-phino)per-fluoro-pyren-1-yl)(per-fluoro-fluorenyl)-(per-fluoro-anthracenyl)-(5,6,7,8-tetrafluoro-naphthyl)-aluminate; 7-((triethyl-silyl-ethyl)(per-fluoro-fluorenyl)amino)per-fluoro-napth-1-yl)(per-fluoro-pyrenyl)-(4,5,6,7-tetrafluoro-naphthyl)-(4,5,7-tri-fluoro-naphthyl)-borate; 7-((triethyl-silyl-ethyl)(per-fluoro-phenyl)amino)per-fluoro-napth-1-yl)(per-fluoro-anthracenyl)-(2',3',4'-tri-fluoro-biphenyl)-(per-fluoro-phenyl)-aluminate; 7-((tri-iso-propyl-silyl)(2',3',4'-tri-fluoro-biphenyl)amino)fluoro-inden-2-yl)(2,3,4-tri-fluoro-phenyl)-(4,5,6-tri-fluoro-naphthyl)-(per-fluoro-biphenyl)-aluminate; 7-((tri-iso-propyl-silyl)(pentalfluoro-pyrenyl)phos-phino)per-fluoro-pyren-1-yl)(per-fluoro-fluorenyl)-(pentalfluoro-pyrenyl)-(pentafluoro-anthracenyl)borate; 7-(tri-iso-propyl-silyl)(per-fluoro-pyrenyl)arsino)per-fluoro-napth-1-yl)(tetrafluoro-fluorenyl)(per-fluoro-naphthyl)pentafluoro-anthracenyl)-borate; 7-((tri-iso-propyl-silyl)(2',3',5'-tri-fluoro-biphenyl)amino)per-fluoro-pyren-2-yl)(per-fluoro-pyrenyl)-(pentalfluoro-pyrenyl)-(per-fluoro-phenyl)-aluminate; 7-((tri-iso-propyl-silyl-octyl)-(pentalfluoro-pyrenyl)amino)per-fluoro-anth-racen-1-yl)bis(4,5,7-tri-fluoro-naphthyl)-(per-fluoro-phenyl)-aluminate; 7-((tri-iso-propyl-silyl-octyl)(per-fluoro-anthracenyl)amino)per-fluoro-napth-3-yl)(2',3',5'-tri-fluoro-biphenyl)-(per-fluoro-pyrenyl)-(2,3,4-tri-fluoro-phenyl)-aluminate; 7-((tri-iso-propyl-silyl-octyl)(per-fluoro-biphenyl)phos-phino)per-fluoro-pyren-2-yl)(per-fluoro-phenyl)-(4,5,6-tri-fluoro-naphthyl)-(per-fluoro-anthracenyl)-borate; 7-((tri-iso-propyl-silyl-octyl)(per-fluoro-phenyl)amino)per-fluoro-fluoren-1-yl)(2,3,5-tri-fluoro-phenyl)-(4,5,6,7-tetrafluoro-naphthyl)-(tetrafluoro-fluorenyl)-borate; 7-((tri-iso-propyl-silyl-octyl)(per-fluoro-phenyl)arsino)-per-fluoro-fluoren-1-yl)(4,5,7-tri-fluoro-naphthyl)-(per-fluoro-fluorenyl)-(pentafluoro-anthracenyl)-borate; 7-((tri-iso-propyl-silyl-octyl)(per-fluoro-pyrenyl)amino)per-fluoro-naphth-1-yl)(per-fluoro-fluorenyl)-(5,6,7,8-tetrafluoro-naphthyl)-(per-fluoro-anthracenyl)-aluminate; 7-((trimethyl-silyl)(2',3',4'-tri-fluoro-biphenyl)phos-phino)per-fluoro-fluoren-1-yl)(per-fluoro-pyrenyl)-(2',3',5'-tri-fluoro-biphenyl)-(per-fluoro-biphenyl)-borate; 7-((trimethyl-silyl)(4,5,6,7-tetrafluoro-naphthyl)phos-phino)per-fluoro-napth-2-yl)(per-fluoro-biphenyl)-(pentafluoro-anthracenyl)-(per-fluoro-phenyl)-aluminate; 7-((trimethyl-silyl)(per-fluoro-biphenyl)phos-phino)-per-fluoro-pyren-2-yl)(pentafluoro-anthracenyl)-(per-fluoro-anthracenyl)-(per-fluoro-phenyl)-borate; 7-((trimethyl-silyl)(per-fluoro-fluorenyl)amino)per-fluoro-pyren-2-yl)(5,6,7,8-tetrafluoro-naphthyl)-(2,3,4-tri-fluoro-phenyl)-(per-fluoro-anthracenyl)-borate; 7-((trimethyl-silyl)(per-fluoro-phenyl)phos-phino)per-fluoro-napth-2-yl)(per-fluoro-fluorenyl)-(per-fluoro-phenyl)-(4,5,7-tri-fluoro-naphthyl)-borate; 7-((trimethyl-silyl)(per-fluoro-pyrenyl)amino)per-fluoro-napth-3-yl)(per-fluoro-biphenyl)-(2,3,6-tri-fluoro-phenyl)-(per-fluoro-pyrenyl)-borate; 7-((tri-n-propyl-silyl)(2,3,5-tri-fluoro-phenyl)amino)per-fluoro-pyren-1-yl)(per-fluoro-naphthyl)-(2,3,5-tri-fluoro-phenyl)-(per-fluoro-anthracenyl)-aluminate; 7-((tri-n-propyl-silyl)(2,3,6-tri-fluoro-phenyl)amino)per-fluoro-inden-2-yl)(2',3',5'-tri-fluoro-biphenyl)-(per-fluoro-anthracenyl)-(per-fluoro-pyrenyl)-borate; 7-((tri-n-propyl-silyl)(per-fluoro-fluorenyl)amino)per-fluoro-napth-2-yl)(per-fluoro-fluorenyl)-(per-fluoro pyrenyl)(2,3,5-tri-fluoro-phenyl)-borate; 7-((tri-n-propyl-silyl)(per-fluoro-fluorenyl)amino)-per-fluoro-pyren-2-yl)(per-fluoro-fluorenyl)-(pentafluoro-anthracenyl)(per-fluoro-pyrenyl)-borate; 7-(tri-n-propyl-silyl)(per-fluoro-phenyl)amino)fluoro-napth-3-yl)(2,3,4-tri-fluoro-phenyl)-(per-fluoro-biphenyl)-(pentafluoro-anthracenyl)-borate; 7-((tri-n-propyl-silyl)(per-fluoro-phenyl)-amino)per-fluoro-pyren-1-yl)(2',3',5'-tri-fluoro-biphenyl)-(tetrafluoro-fluorenyl)-(per-fluoro-pyrenyl)-aluminate; 7-((tri-n-propyl-silyl)(per-fluoro-phenyl)phos-phino)fluoro-napth-2-yl)-(2',3',5'-tri-fluoro-biphenyl)-(per-fluoro-biphenyl)-(per-fluoro-anthracenyl)-borate; 7-((tri-n-propyl-silyl-hexyl)(per-fluoro-biphenyl)amino)fluoro-pyren-2-yl)(4,5,7-tri-fluoro-naphthyl)-(2',3',4'-tri-fluoro-biphenyl)-(per-fluoro-biphenyl)-borate; 7-((tri-n-propyl-silyl-hexyl)(per-fluoro-biphenyl)phos-phino)fluoro-napth-2-yl)(per-fluoro-phenyl)-(pentafluoro-anthracenyl)(5,6,7,8-tetrafluoro-naphthyl)-aluminate; 7-((tri-n-propyl-silyl-hexyl)(per-fluoro-fluorenyl)amino)fluoro-pyren-2-yl)(tetrafluoro-fluorenyl)-(per-fluoro-biphenyl)-(per-fluoro-pyrenyl)-borate; 7-((tri-n-propyl-silyl-hexyl)(per-fluoro-fluorenyl)

amino)per-fluoro-anth-mcen-1-yl)bis(per-fluoro-biphenyl)-(per-fluoro-phenyl)-borate; 7-((tri-n-propyl-silyl-hexyl)(per-fluoro-fluorenyl)phos-phino)per-fluorouoren-2-yl)(per-fluoro-phenyl)-(tetrafluoro-fluorenyl)(4,5,7-tri-fluoro-naphthyl)-aluminate; 7-((tri-n-propyl-silyl-hexyl)(per-fluoro-phenyl)amino)per-fluoro-napth-1-yl)(4,5,7-tri-fluoro-naphthyl)-(per-fluoro-fluorenyl)-(tetrafluoro-fluorenyl)-borate; 7-((tri-n-propyl-silyl-hexyl)(per-fluoro-phenyl)amino)per-fluoro-napth-2-yl)(per-fluoro-biphenyl)-(per-fluoro-anthracenyl)-(pentalfluoro-pyrenyl)-aluminate; 7-((tri-n-propyl-silyl-hexyl)(per-fluoro-phenyl)-arsino)fluoro-fluoren-1-yl)(5,6,7,8-tetrafluoro-naphthyl)-(4,5,6,7-tetrafluoro-naphthyl)-(per-fluoro-phenyl)-aluminate; 7-((tri-n-propyl-silyl-hexyl)(per-fluoro-phenyl)arsino)per-fluoro-napth-2-yl)(tetrafluoro-fluorenyl)-(2,3,6-tri-fluoro-phenyl)-(2',3',5'-tri-fluoro-biphenyl)-borate; 7-((tri-n-propyl-silyl-hexyl)(per-fluoro-pyrenyl)phos-phino)per-fluoro-inden-2-yl)(tetrafluoro-fluorenyl)-(per-fluoro-anthracenyl)-(per-fluoro-fluorenyl)-aluminate; 8-((2,2-dimethyl-octyl)(pentalfluoro-pyrenyl)arsino)per-fluoro-napth-3-yl)(per-fluoro-pyrenyl)-(2',3',4'-tri-fluoro-biphenyl)-(per-fluoro-biphenyl)-aluminate; 8-((2,2-dimethyl-octyl)(per-fluoro-pyrenyl)amino)per-fluoro-napth-3-yl)-(2',3',4'-tri-fluoro-biphenyl)-(per-fluoro-anthracenyl)-(per-fluoro-pyrenyl)-aluminate; 8-((2,2-dimethyl-octyl)(tetrafluoro-fluorenyl)phos-phino)per-fluoro-napth-3-yl)(per-fluoro-phenyl)-(per-fluoro-biphenyl)-(pentafluoro-anthracenyl)-aluminate; 8-((benzyl)(per-fluoro-anthracenyl)-amino)per-fluoro-napth-3-yl)(5,6,7,8-tetrafluoro-naphthyl)-(2',3',4'-tri-fluoro-biphenyl)-(per-fluoro-phenyl)-aluminate; 8-((butyl)(2',3',5'-tri-fluoro-biphenyl)amino)per-fluoro-napth-3-yl)-(2,3,5-tri-fluoro-phenyl)-(per-fluoro-biphenyl)-aluminate; 8-((cyclohexyl)(per-fluoro-anthracenyl)phos-phino)per-fluoro-pyren-2-yl)bis(4,5,7-tri-fluoro-naphthyl)-(per-fluoro-biphenyl)-borate; 8-((hexyl)(per-fluoro-fluorenyl)amino)per-fluoro-pyren-2-yl)bis(per-fluoro-anthracenyl)-(2,3,4-tri-fluoro-phenyl)-borate; 8-((hexyl)(per-fluoro-phenyl)phos-phino)per-fluoro-pyren-2-yl)(4,5,6-tri-fluoro-naphthyl)-(2,3,6-tri-fluoro-phenyl)-(per-fluoro-pyrenyl)-aluminate; 8-((iso-propyl)(2',3',5'-tri-fluoro-biphenyl)amino)per-fluoro-napth-3-yl)(per-fluoro-phenyl)-(2,3,4-tri-fluoro-phenyl)-(per-fluoro-biphenyl)borate; 8-((iso-propyl)(4,5,6-tri-fluoro-naphthyl)arsino)per-fluoro-pyren-2-yl)(pentafluoro-anthracenyl)-(per-fluoro-biphenyl)(4,5,6,7-tetrafluoro-naphthyl)-borate; 8-((methyl)(4,5,6-tri-fluoro-naphthyl)-arsino)per-fluoro-pyren-2-yl)bis(per-fluoro-biphenyl)-(per-fluoro-fluorenyl)-borate; 8-((methyl)-(5,6,7,8-tetrafluoro-naphthyl)arsino)per-fluoro-napth-3-yl)(pentalfluoro-pyrenyl)-(5,6,7,8-tetrafluoro-naphthyl)-(per-fluoro-phenyl)-borate; 8-((methyl-ethyl-hexyl-silyl)(2,3,4-tri-fluoro-phenyl)amino)per-fluoro-naphth-3-yl)bis(pentafluoro-anthracenyl)-(2,3,5-tri-fluoro-phenyl)-borate; 5-((methyl-ethyl-hexyl-silyl)(4,5,6-tri-fluoro-naphthyl)amino)per-fluoro-napth-3-yl)(per-fluoro-pyrenyl)-(tetrafluoro-fluorenyl)-(4,5,6,7-tetrafluoro-naphthyl)-borate; 8-((methyl-ethyl-hexyl-silyl)(5,6,7,8-tetrafluoro-naphthyl)amino)per-fluoro-napth-3-yl)(2',3',5'-tri-fluoro-biphenyl)-(per-fluoro-biphenyl)-(5,6,7,8-tetrafluoro-naphthyl)-borate; 8-((methyl-ethyl-hexyl-silyl)(per-fluoro-naphthyl)phos-phino)per-fluoro-pyren-2-yl)(pentalfluoro-pyrenyl)-(pentafluoro-anthracenyl)-(4,5,6,7-tetrafluoro-naphthyl)-borate; 8-((n-butyl)(per-fluoro-phenyl)arsino)per-fluoro-napth-3-yl)(per-fluoro-anthracenyl)-(per-fluoro-phenyl)-(per-fluoro-naphthyl)-borate; 8-((nonyl)(per-fluoro-anthracenyl)phos-phino)per-fluoro-pyren-2-yl)(per-fluoro-biphenyl)-(per-fluorofluorenyl)(per-fluoro-anthracenyl)borate; 8-((nonyl)(per-fluoro-phenyl)amino)per-fluoro-napth-3-yl)(per-fluoro-biphenyl)-(2,3,5-tri-fluoro-phenyl)-(4,5,7-tri-fluoro-naphthyl)-borate; 8-((octyl)(2,3,6-tri-fluoro-phenyl)phos-phino)per-fluoro-napth-3-yl)(tetrafluoro-fluorenyl)(2,3,4-tri-fluoro-phenyl)-(pentalfluoro-pyrenyl)-aluminate; 8-((propyl)(pentafluoro-anthracenyl)amino)per-fluoro-pyren-2-yl)(per-fluoro-anthracenyl)-(2,3,6-tri-fluoro-phenyl)-(2',3',4'-tri-fuoro-biphenyl)-borate; 8-((propyl)(per-fluoro-phenylphosphino)per-fluoro-napth-3-yl)(per-fluoro-pyrenyl)-(per-fluoro-fluorenyl)-(pentafluoro-anthracenyl)-borate; 8-((triethylsilyl)(per-fluoro-anthracenyl)-amino)perfuoro-pyren-2-yl)(per-fluoro-pyrenyl)-(5,6,7,8-tetrafluoro-naphthyl)-(per-fluoro-anthracenyl)-borate; 8-((triethylsilyl)(per-fluoro-phenyl)amino)per-fluoro-pyren-2-yl)(2',3',5'-tri-fluoro-biphenyl)-(per-fluoro-phenyl)-(pentalfluoro-pyrenyl)-aluminate; 8-((triethyl-silyl-ethyl)-(pentafluoro-anthracenyl)amino)per-fluoro-pyren-2-yl)(per-fluoro-biphenyl)-(pentalfluoro-pyrenyl)-(per-fluoro-fluorenyl)-aluminate; 8-((tri-iso-propyl-silyl-octyl)(4,5,6,7-tetrafluoro-naphthyl)arsino)per-fluoro-pyren-2-yl)(2,3,4-tri-fluoro-phenyl)-(2,3,5-tri-fluoro-phenyl)-(per-fluoro-naphthyl)-borate; 8-((trimethyl-silyl)(per-fluoro-fluorenyl)amino)per-fluoro-napth-3-yl)-(4,5,7-tri-fluoro-naphthyl)-(pentalfluoro-pyrenyl)-(per-fluoro-biphenyl)-aluminate; 8-((trimethylsilyl)(per-fluoro-phenyl)amino)per-fluoro-pyren-2-yl)bis(2,3,4-tri-fluoro-phenyl)-(4,5,7-tri-fluoro-naphthyl-aluminate; 8-((tri-n-propyl-silyl)(4,5,6,7-tetrafluoro-naphthyl)amino)per-fluoro-pyren-2-yl)(per-fluoro-fluorenyl)-(per-fluoro-biphenyl)-(per-fluoro-anthracenyl)-aluminate; 8-((tri-n-propyl-silyl-hexyl)(2',3',4'-tri-fluoro-biphenyl)phos-phino)per-fluoro-napth-3-yl)(per-fluoro-phenyl)-(4,5,6-tri-fluoro-naphthyl)-(per-fluoro-anthracenyl)-borate Non-exhaustive List of Invention Cocatalyst Precursors

[N,N,N-(ethyl)(methyl)(octyl)ammonium]+[5-((benzyl)(perfluorophenyl)phosphino)per-fluoronapth-1-yl)(tetrafluorofluorenyl)(2',3',4'-trifluorobiphenyl)(perfluorobiphenyl)aluminate]⁻; [tri-N-(n-butyl)ammonium]+[7-((triethylsilylethyl)(perfluoropyrenyl)phosphino)perfluoropyren-2-yl)(perfluorophenyl)(perfluorobiphenyl)(perfluorofluorenyl)aluminate]⁻; [N,N,N-(ethyl)(methyl)-(isopropyl)ammonium]+[6-((hexyl)(perfluorobiphenyl)arsino)fluorofluoren-1-yl)(perfluoropyrenyl)(perfluoroanthracenyl)(perfluorobiphenyl)aluminate]⁻; [tri-N-octylammonium]+[6-((triethylsilyl)(perfluoroanthracenyl)amino)perfluoroinden-2-yl)(perfluorobiphenyl)(2,3,6-tri-fluorophenyl)(pentafluoroanthracenyl)aluminate]⁻; [N,N,N-(dimethyl)(t-butyl)ammonium]+[7-((tri-isopropylsilyloctyl)(tetrafluorofluorenyl)phosphino)perfluoronapth-3-yl)(perfluoro-anthracenyl)(perfluorobiphenyl)(perfluoronaphthyl)aluminate]⁻; [tri-N-(n-butyl)ammonium]+[7-((ethyl)(2',3',4'-trifluorobiphenyl)amino)perfluoroanthracen-1-yl)(perfluorobiphenyl)(perfluoroanthracenyl)(4,5,6,7-tetrafluoronaphthyl)aluminate]⁻; [tri-N-(dimethylphenylammonium]+[7-((cyclohexyl)(perfluoroanthracenyl)phosphino)perfluoronapth-2-yl)(perfluoroanthracenyl)(per-fluorofluorenyl)(2,3,4-trifluorophenyl)aluminate]⁻; [N,N,N-(ethyl)(methyl)(t-butyl)-ammonium]+[8-((trimethylsilyl)(perfluorophenyl)arsino)perfluoropyren-2-yl)(perfluorofluorenyl)-(2',3',4'-trifluorobiphenyl)(5,6,7,8-tetrafluoronaphthyl)aluminate]⁻; [tri-N-octylammonium]+[6-((n-butyl)(perfluorobiphenyl)phosphino)perfluoroanthracen-1-yl)bis(5,6,7,8-tetrafluoronaphthyl)(perfluorofluorenyl)aluminate]⁻; [tri-N-(t-butyl)ammonium]+[3-((nonyl)(perfluoro-pyrenyl)phosphino)perfluorophenyl)bis(perfluorobiphenyl)(2,3,5-trifluorophenylaluminate]⁻; [N,N,N-(ethyl)(methyl)

(isopropyl)ammonium]+[5-((ethyl)(4,5,7-trifluoronaphthyl)amino)per-fluoronaphth-2-yl)(pentafluoropyrenyl)(perfluorophenyl)(perfluoroanthracenyl)aluminate]⁻; [N,N,N-(ethyl)(methyl)(octyl)ammonium]+[4'-((benzyl)(perfluorophenyl)amino)perfluorobiphen-4-yl)(4,5,7-trifluoronaphthyl)(perfluorophenyl)(tetrafluorofluorenyl)aluminate]⁻; [tri-N-methyl-ammonium]+[6-((nonyl)(2,3,5-trifluorophenyl)phosphino)perfluoroanthracen-2-yl)bis(perfluoro-anthracenyl)(perfluoropyrenyl)aluminate]⁻; [tri-N-propylammonium]+[8-((3-ethylnonyl)(per-fluorophenyl)amino)perfluoronaphth-3-yl)(2,3,4-trifluorophenyl)(2,3,6-trifluorophenyl)(perfluoro-phenyl)aluminate]⁻; [tri-N-ethylammonium]+[7-((trimethylsilyl)(perfluorobiphenyl)amino)per-fluoroanthracen-1-yl)(perfluoropyrenyl)(perfluorofluorenyl)(perfluorophenyl)aluminate]⁻; [tri-N-ethylammonium]+[7-((ethyl)(perfluorofluorenyl)amino)perfluoropyren-2-yl)(perfluoropyrenyl)-(perfluorofluorenyl)(4,5,6-trifluoronaphthyl)aluminate]⁻; [N,N,N-(dimethyl)(t-butyl)-ammonium]+[5-((tri-isopropylsilyl)(perfluorobiphenyl)amino)perfluoronapth-1-yl)(perfluoro-anthracenyl)(perfluorobiphenyl)(2,3,5-trifluorophenyl)aluminate]⁻; [tri-N-(dimethylphenyl-ammonium]+[6-((tri-n-propylsilylhexyl)(perfluorophenyl)phosphino)perfluorofluoren-2-yl)(per-fluorophenyl)(perfluorobiphenyl)(4,5,6-trifluoronaphthyl)aluminate]⁻; [tri-N-methyl-ammonium]+[6-((ethyl)(4,5,6,7-tetrafluoronaphthyl)amino)perfluoronapth-1-yl)bis(perfluoro-anthracenyl)(2,3,6-trifluorophenyl)aluminate]⁻; [tri-N-(t-butyl)ammonium]+[5-((tri-isopropylsilyl-octyl)(2,3,5-trifluorophenyl)amino)perfluoroinden-1-yl)(perfluoropyrenyl)(perfluorophenyl)-(2',3',4'-trifluorobiphenyl)aluminate]⁻; [N,N,N-(ethyl)(methyl)(isopropyl)ammonium]+[6-((diethylnonlysilyl)(4,5,6,7-tetrafluoronaphthyl)amino)fluoronapth-3-yl)(2,3,4-trifluorophenyl)-(perfluorophenyl)(perfluoroanthracenyl)aluminate]⁻; [tri-N-(dimethylphenylammonium]+[5-((propyl)(perfluorophenyl)amino)perfluoroinden-2-yl)(pentafluoroanthracenyl)(perfluoro-naphthyl)(perfluorobiphenyl)aluminate]⁻; [N,N,N-(ethyl)(dioctyl)ammonium]+[6-((hexyl)-(tetrafluorofluorenyl)phosphino)perfluoronaphth-1-yl)(pentalfluoropyrenyl)(2',3',4'-trifluoro-biphenyl)(4,5,7-trifluoronaphthyl)aluminate]⁻; [N,N,N-(ethyl)(methyl)(isopropyl)ammonium]+[4'-((hexyl)(perfluorophenyl)arsino)perfluorobiphen-3-yl)(perfluorophenyl)(perfluorobiphenyl)(perfluorofluorenyl)aluminate]⁻; [N,N,N-(ethyl)(methyl)(octyl)ammonium]+[3'-((triethylsilylpropyl)-(2',3',4'-trifluorobiphenyl)amino)perfluorobiphen-4-yl)bis(pentafluoroanthracenyl)(perfluoro-phenylaluminate]⁻; [tri-N-methylammonium]+[5-((ethyl)(perfluoroanthracenyl)amino)perfluoro-napth-2-yl)(4,5,7-trifluoronaphthyl)(perfluorophenyl)(perfluorofluorenyl)aluminate]⁻; [N,N,N-(ethyl)(dioctyl)ammonium]+[4'-((tri-n-propylsilylhexyl)(perfluoronaphthyl)amino)perfluoro-biphen-4-yl)(4,5,7-trifluoronaphthyl)(perfluorophenyl)(2',3',4'-trifluorobipheny)aluminate]⁻; [tri-N-ethylammonium]+[6-((triethylsilylethyl)(perfluorophenyl)phosphino)perfluoronapth-1-yl)-(4,5,7-trifluoronaphthyl)(perfluorophenyl)(perfluoropyrenyl)aluminate]⁻; [N,N,N-(ethyl)(methyl)-(octyl)ammonium]+[5-((isopropyl)(perfluorofluorenyl)amino)perfluoronapth-1-yl)(pentafluoro-anthracenyl)(2,3,5-trifluorophenyl)(perfluorophenyl)atuminate]⁻; [N,N,N-(ethyl)(methyl)(t-butyl)-ammonium]+[8-((isopropyl)(perfluorophenyl)amino)fluoronapth-3-yl)(5,6,7,8-tetrafluoro-naphthyl)(4,5,6-trifluoronaphthyl)(tetrafluorofluorenyl)aluminate]⁻; [tri-N-(t-butyl)-ammonium]+[5-((n-butyl)(perfluorophenyl)amino)perfluoronapth-2-yl)(2,3,4-trifluorophenyl)-(perfluoropyrenyl)(2',3',4'-trifluorobiphenyl)aluminate]⁻; [N,N,N-(ethyl)(methyl)(n-butyl)-ammonium]+[3'-((tri-n-propylsilylhexyl)(perfluorophenyl)amino)perfluorobiphen-4-yl)(perfluoro-biphenyl)(tetrafluorofluorenyl)(perfluorofluorenyl)aluminate]⁻; [tri-N-octylammonium]+[5-((tri-isopropylsilyloctyl)(perfluorobiphenyl)arsino)perfluoroinden-2-yl)(perfluorophenyl)(perfluoro-anthracenyl)(perfluorobiphenyl)aluminate]⁻; [N,N,N-(ethyl)(methyl)(t-butyl)ammonium]+[6-((tri-isopropylsilyl)(2,3,4-trifluorophenyl)amino)perfluorofluoren-1-yl)(pentafluoroanthracenyl)(2,3,4-trifluorophenyl)(perfluorobiphenyl)aluminate]⁻; [N,N,N-(ethyl)(dioctyl)ammonium]+[7-((methyl)-(4,5,6-trifluoronaphthyl)amino)perfluoronaphth-3-yl)(pentalfluoropyrenyl)(perfluoronaphthyl)-(perfluoroanthracenyl)aluminate]⁻; [N,N,N-(dimethyl)(t-butyl)ammonium]+[5-((methyldiethyl-silyloctyl)(4,5,6-trifluoronaphthyl)amino)perfluoroinden-2-yl)(perfluoroanthracenyl)(pentafluoro-anthracenyl)(perfluorophenyl)aluminate]⁻; [tri-N-(methylphenyl)ammonium]+[5-((isopropyl)-(perfluorobiphenyl)amino)perfluoroinden-1-yl)(2,3,5-trifluorophenyl)(4,5,6,7-tetrafluoro-naphthyl)(2',3',5'-trifluorobiphenyl)aluminate]⁻; [tri-N-propylammonium]+[3'-((methylethylhexyl-silyl)(perfluorobiphenyl)amino)perfluorobiphen-4-yl)(perfluorofluorenyl)(perfluorobiphenyl)(per-fluorophenyl)aluminate]⁻; [N,N,N-(ethyl)(methyl)(isopropyl)ammonium]+[5-((3-ethylnonyl)-(pentalfluoropyrenyl)amino)perfluoronapth-3-yl)(pentalfluoropyrenyl)(perfluorobiphenyl)-(5,6,7,8-tetrafluoronaphthyl)aluminate]⁻; [tri-N-(dimethylphenylammonium]+[3'-((octyl)(5,6,7,8-tetrafluoronaphthyl)amino)perfluorobiphen-4-yl)(perfluoropyrenyl)(perfluoroanthracenyl)(per-fluorofluorenyl)aluminate]⁻; [tri-N-propylammonium]+[6-((tri-isopropylsilyl)(pentafluoro-pyrenyl)phosphino)perfluorofluoren-1-yl)(2,3,4-trifluorophenyl)(perfluorophenyl)(pentalfluoro-pyrenyl)aluminate]⁻; [tri-N-octylammonium]+[6-((hexyl)(2,3,6-trifluorophenyl)amino)perfluoro-napth-2-yl)(perfluorobiphenyl)(2,3,6-trifluorophenyl)(perfluorofluorenyl)aluminate]⁻; [tri-N-methylammonium]+[8-((tri-n-propylsilylhexyl)(perfluoroanthracenyl)amino)perfluoropyren-2-yl)-(5,6,7,8-tetrafluoronaphthyl)(perfluorobiphenyl)(4,5,6-trifluoronaphthyl)aluminate]⁻; [tri-N-(n-butyl)ammonium]+[7-((triethylsilyl)(pentafluoroanthracenyl)phosphino)perfluoroanthracen-1-yl)-(perfluoronaphthyl)(perfluorofluorenyl)(perfluoroanthracenyl)aluminate]⁻; [N,N,N-(ethyl)-(methyl)(n-butyl)ammonium]+[3'-((diethylnonlysilyl)(perfluorophenyl)arsino)perfluorobiphen-4-yl)(perfluorophenyl)(2,3,6-trifluorophenyl)(perfluoropyrenyl)aluminate]⁻; [N,N,N-(ethyl)(methyl)-(octyl)ammonium]+[7-((triethylsilylpropyl)(perfluorophenyl)amino)perfluoronapth-2-yl)-(5,6,7,8-tetrafluoronaphthyl)(2,3,4-trifluorophenyl)(perfluoroanthracenyl)aluminate]⁻; [N,N,N-(ethyl)(methyl)(octyl)ammonium]+[6-((triethylsilylpropyl)(tetrafluorofluorenyl)phosphino)per-fluoroanthracen-1-yl)(2,3,5-trifluorophenyl)(4,5,6,7-tetrafluoronaphthyl)(2',3',5'-trifluoro-biphenyl)aluminate]⁻; [N,N,N-(ethyl)(dioctyl)ammonium]+[3-((benzyl)(perfluorofluorenyl)phos-phino)perfluorophenyl)(perfluoropyrenyl)(pentafluoroanthracenyl)(2',3',4'-trifluorobiphenyl)-aluminate]⁻; [N,N,N-(dimethyl)(t-butyl)ammonium]+[2'-((nonyl)(pentafluoroanthracenyl)amino)-perfluorobiphen-4-yl)(4,5,6,7-tetrafluoronaphthyl)(pentalfluoropyrenyl)-aluminate]⁻; [tri-N- methylammonium]+[3-((triisopropylsilyloctyl)(perfluorobiphenyl)amino)-fluorophen-1-yl)(perfluorofluorenyl)(perfluoroanthracenyl)(2',3',5'-trifluorobiphenyl)aluminate]⁻; [N,N,N-(dimethyl)(t-butyl)ammonium]+[7-((propyl)(4,5,7-trifluoronaphthyl)arsino)perfluoro-pyren-1-yl)(perfluoropyrenyl)(5,6,7,8-tetrafluoronaphthyl)(4,5,6-trifluoronaphthyl)aluminate]⁻; [tri-N-propylammonium]+[5-((methylethylhexylsilyl)(4,5,7-trifluoronaphthyl)phosphino)perfluoro-napth-2-yl)(perfluorobiphenyl)(perfluoropyrenyl)(perfluorophenyl)aluminate]⁻; [tri-N-methyl-ammonium]+[3'-((ethyl)(perfluorobiphenyl)amino)perfluorobiphen-4-yl)(perfluorofluorenyl)-(pentafluoroanthracenyl)(perfluoropyrenyl)aluminate]⁻; [N,N,N-(ethyl)(methyl)(isopropyl)-ammonium]+[3'-((2,2-dimethyloctyl)(4,5,7-trifluoronaphthyl)amino)perfluorobiphen-4-yl)-(5,6,7,8-tetrafluoronaphthyl)(pentalfluoropyrenyl)(perfluorofluorenyl)aluminate]⁻; [tri-N-(methylphenyl)ammonium]+[7-((isopropyl)(4,5,6-trifluoronaphthyl)phosphino)perfluoroinden-2-yl)bis(2,3,4-trifluorophenyl)(perfluoropyrenylaluminate]⁻; [tri-N-(n-butyl)ammonium]+[4'-((octyl)(pentalfluoropyrenyl)arsino)perfluorobiphen-3-yl)(perfluorobiphenyl)(4,5,6-trifluoro-naphthyl)(2,3,4-trifluorophenyl)aluminate]⁻; [tri-N-(t-butyl)ammonium]+[6-((tri-isopropylsilyl-octyl)(perfluorofluorenyl)amino)perfluoronapth-3-yl)(perfluorobiphenyl)(4,5,6-trifluoronaphthyl)-(perfluoroanthracenyl)aluminate]⁻; [N,N,N-(dimethyl)(t-butyl)ammonium]+[5-((2,2-dimethyl-octyl)(pentalfluoropyrenyl)amino)perfluoronapth-3-yl)(5,6,7,8-tetrafluoronaphthyl)(4,5,6-tri-fluoronaphthyl)(tetrafluorofluorenyl)aluminate]⁻; [tri-N-(methylphenyl)ammonium]+[7-((methyl-ethylhexylsilyl)(perfluorophenyl)phosphino)perfluoronaphth-1-yl)(perfluoroanthracenyl)(per-fluorofluorenyl)(4,5,6-trifluoronaphthyl)aluminate]⁻; [tri-N-(n-butyl)ammonium]+[6-((3-ethyl-nonyl)(perfluoronaphthyl)amino)fluoronapth-2-yl)(perfluoronaphthyl)(perfluoropyrenyl)(4,5,6,7-tetrafluoronaphthyl)aluminate]⁻; [tri-N-(n-butyl)ammonium]+[7-((tri-n-propylsilylhexyl)(2,3,4-tri-fluorophenyl)amino)perfluoronapth-2-yl)(tetrafluorofluorenyl)(2',3',4'-trifluorobiphenyl)(per-fluorofluorenyl)aluminate]⁻; [tri-N-(dimethylphenylammonium]+[7-((methyldiethylsilyloctyl)-(2',3',4'-trifluorobiphenyl)amino)perfluoronapth-2-yl)(pentalfluoropyrenyl)(perfluorobiphenyl)-(2',3',4'-trifluorobiphenyl)aluminate]⁻; [tri-N-ethylammonium]+[7-((isopropyl)(2,3,5-trifluoro-phenyl)phosphino)perfluoroinden-2-yl)(perfluorobiphenyl)(4,5,7-trifluoronaphthyl)(perfluoro-anthracenyl)aluminate]⁻; [tri-N-propylammonium]+[6-((nonyl)(perfluoropyrenyl)amino)per-fluoroinden-2-yl)(2',3',5'-trifluorobiphenyl)(perfluorobiphenyl)(perfluoroanthracenyl)aluminate]⁻; [N,N,N-(dimethyl)(t-butyl)ammonium]+[7-((n-butyl)(2,3,4-trifluorophenyl)amino)perfluoropyren-2-yl)(perfluorofluorenyl)(perfluoronaphthyl)(perfluorobiphenyl)aluminate]⁻; [tri-N-methyl-ammonium]+[8-((octyl)(perfluorobiphenyl)arsino)perfluoronapth-3-yl)(tetrafluorofluorenyl)(per-fluorophenyl)(perfluorobiphenyl)aluminate]⁻; [N,N,N-(ethyl)(methyl)(n-butyl)ammonium]+[3-((butyl)(tetrafluorofluorenyl)amino)perfluorophenyl)(tetrafluorofluorenyl)(perfluorophenyl)(4,5,6-trifluoronaphthyl)aluminate]⁻; [tri-N-ethylammonium]+[8-((trimethylsilyl)(2,3,4-trifluoro-phenyl)phosphino)perfluoropyren-2-yl)(perfluoroanthracenyl)(2,3,5-trifluorophenyl)(perfluoro-pyrenyl)aluminate]⁻; [tri-N-(n-butyl)ammonium]+[7-((octyl)(perfluoroanthracenyl)phosphino)-perfluoropyren-2-yl)(5,6,7,8-tetrafluoronaphthyl)(2',3',5'-trifluorobiphenyl)(perfluorophenyl)-aluminate]⁻; [tri-N-methylammonium]+[7-(nonyl)(perfuorophenyl)phosphino)perfuorofluoren-2-yl)(pentafluoroanthracenyl)(2',3',4'-trifluorobiphenyl)(perfluorofluorenyl)aluminate]⁻; [tri-N-propylammonium]+[6-((isopropyl)(perfluorophenyl)amino)perfluoroanthracen-2-yl)bis(5,6,7,8-tetrafluoronaphthyl)(perfluorobiphenyl)aluminate]⁻; [N,N,N-(ethyl)(methyl)(octyl)-ammonium]+[7-((methyldiethylsilyloctyl)(perfluorophenyl)phosphino)perfluoronapth-3-yl)bis(perfluoroanthracenyl)(4,5,7-trifluoronaphthyl)aluminate]⁻; [tri-N-ethylammonium]+[7-((isopropyl)(perfluorobiphenyl)amino)fluoropyren-1-yl)bis(perfluoroanthracenyl)(perfluoro-pyrenylaluminate]⁻; [N,N-diethylanilinium]+[5-((methyldiethylsilyloctyl)(2',3',5'-trifluoro-biphenyl)amino)perfluoronapth-1-yl)(2,3,6-trifluorophenyl)(2,3,5-trifluorophenyl)(perfluoro-anthracenyl)aluminate]⁻; [N,N-diethylanilinium]+[2'-((nonyl)(perfluorobiphenyl)amino)perfluoro-biphen-4-yl)(tetrafluorofluorenyl)(5,6,7,8-tetrafluoronaphthyl)(2',3',5'-trifluorobiphenyl)-aluminate]⁻; [N-methyl-N-dodecylanilinium]+[3'-((diethylnonlysilyl)(perfluorophenyl)amino)per-fluorobiphen-4-yl)(perfluorobiphenyl)(perfluorophenyl)(2,3,5-trifluorophenyl)aluminate]⁻; [N,N-diethylanilinium]+[4'-((benzyl)(perfluoropyrenyl)amino)perfluorobiphen-3-yl)(4,5,6,7-tetrafluoronaphthyl)(perfluorobiphenyl)(perfluoropyrenyl)aluminate]⁻; [N,N-di(dodecyl)-anilinium]+[6-((triethylsilyl)(perfluoroanthracenyl)amino)perfluoronapth-1-yl)(2',3',5'-trifluoro-biphenyl)(5,6,7,8-tetrafluoronaphthyl)(perfluorophenyl)aluminate]⁻; [N,N-di(dodecyl)-anilinium]+[7-((triethylsilylpropyl)(pentafluoroanthracenyl)amino)perfluorofluoren-2-yl)(4,5,7-tri-fluoronaphthyl)(perfluorophenyl)(tetrafluorofluorenyl)aluminate]⁻; [N,N-diethylanilinium]+[3'-((3-ethylnonyl)(pernuorophenyl)amino)perfluorobiphen-4-yl)(perfluorophenyl)(perfluorobiphenyl)-(perfluorofluorenyl)aluminate]⁻; [N-methyl-N-dodecylanilinium]+[7-((octyl)(pentalfluoropyrenyl)-amino)perfluoroinden-2-yl)(pentalfluoropyrenyl)(tetrafluorofluorenyl)(pentafluoroanthracenyl)-aluminate]⁻; [N,N-diethylanilinium]+[8-((isopropyl)(perfluorophenyl)phosphino)perfuoropyren-2-yl)(2',3',5'-trifluorobiphenyl)(2,3,4-trifluorophenyl)(perfluorobiphenyl)aluminate]⁻; [N,N-2,4,6-pentamethylanilinium]+[7-((methyl)(perfluoroanthracenyl)amino)perfluoroanthracen-1-yl)(per-fluorophenyl)(perfluorobiphenyl)(perfluoronaphthyl)aluminate]⁻; [N,N-di(dodecyl)anilinium]+[5-((ethyl)(4,5,7-trifluoronaphthyl)amino)perfluoronapth-1-yl)(pentalfluoropyrenyl)(perfluoro-fluorenyl)(perfluorobiphenyl)aluminate]⁻; [N,N-2,4,6,-pentamethylanilinium]+[7-((tri-isopropyl-silyloctyl)(perfluoronaphthyl)phosphino)perfluoronapth-1-yl)(perfluoropyrenyl)(perfluoro-fluorenyl)(perfluorobiphenyl)aluminate]⁻; [N,N-2,4,6,-pentamethylanilinium]+[6-((diethylnonly-silyl)(perfluoropyrenyl)amino)perfluoronaphth-3-yl)(5,6,7,8-tetrafluoronaphthyl)(pentafluoro-pyrenyl)(perfluorobiphenyl)aluminate]⁻; [N,N-dimethylanilinium]+[6-((octyl)(2,3,4-trifluoro-phenyl)amino)perfluorofluoren-1-yl)(perfluorofluorenyl)(2',3',5'-trifluorobiphenyl)(2,3,4-trifluoro-phenyl)aluminate]⁻; [N,N-di(dodecyl)anilinium]+[4'-((tri-isopropylsilyl)(perfluorobiphenyl)phos-phino)perfluorobiphen-3-yl)(perfluoropyrenyl)(perfluorofluorenyl)(4,5,6,7-tetrafluoronaphthyl)-aluminate]⁻; [N-methyl-N-dodecylanilinium]+[5-((propyl)(pentalfluoropyrenyl)amino)perfluoro-inden-2-yl)(perfluorobiphenyl)(4,5,6,7-tetrafluoronaphthyl)

(pentalfluoropyrenyl)aluminate]⁻; [N,N-di(dodecyl)anilinium]+[6-((2,2-dimethyloctyl)(2',3',5trifluorobiphenyl)amino)perfluoro-anthracen-1-yl)(perfluorobiphenyl)(2,3,4-trifluorophenyl)(4,5,6,7-tetrafluoronaphthyl)-aluminate]⁻; [N,N-di(dodecyl)anilinium]+[8-((tri-isopropylsilyl)(2,3,5-trifluorophenyl)arsino)per-fluoropyren-2-yl)(perfluorobiphenyl)(pentalfluoropyrenyl)(perfluoropyrenyl)aluminate]⁻; [N-methyl-N-dodecylanilinium]+[6-((triethylsilylpropyl)(perfluorobiphenyl)amino)perfluoroanth-racen-1-yl)(perfluoropyrenyl)(perfluoroanthracenyl)(4,5,6-trifluoronaphthyl)aluminate]⁻; [N,N-diethylanilinium]+[6-((benzyl)(pentafluoroanthracenyl)amino)perfluorofluoren-1-yl)bis(2,3,4-tri-fluorophenyl)(perfluorofluorenylaluminate]⁻; [N,N-2,4,6,-pentamethylanilinium]+[6-((triethylsilyl)(pentafluoroanthracenyl)amino)perfluorofluoren-2-yl)(pentalfluoropyrenyl)(4,5,7-trifluoronaphthyl)(perfluoroanthracenyl)aluminate]⁻; [N,N-2,4,6,-pentamethylanilinium]+[5-((isopropyl)(perfluorofluorenyl)amino)perfluoronapth-1-yl)(perfluorofluorenyl)(perfluorophenyl)-(2,3,5-trifluorophenyl)aluminate]⁻; [N,N-di(dodecyl)anilinium]+[7-((cyclohexyl)(perfluoro-naphthyl)amino)perfluoronapth-1-yl)(perfluorobiphenyl)(tetrafluorofluorenyl)(perfluoro-anthracenyl)aluminate]⁻; [N,N-diethylanilinium]+[5-((tri-n-propylsilyl)(perfluorobiphenyl)amino)-perfluoroinden-2-yl)(perfluoroanthracenyl)(5,6,7,8-tetrafluoronaphthyl)(perfluorofluorenyl)-aluminate]⁻; [N,N-diethylanilinium]+[6-((triethylsilylethyl)(perfluoroanthracenyl)amino)per-fluorofluoren-1-yl)(perfluorobiphenyl)(2,3,6-trifluorophenyl)(perfluoroanthracenyl)aluminate]⁻; [N-methyl-N-dodecylanilinium]+[6-((triethylsilylethyl)(perfluorophenyl)phosphino)perfluoro-napth-2-yl)(4,5,7-trifluoronaphthyl)(perfluoronaphthyl)(perfluorobiphenyl)aluminate]⁻; [N,N-diethylanilinium]+[6-((methylethylhexylsilyl)(4,5,6-trifluoronaphthyl)amino)perfluoroinden-2-yl)-(perfluoronaphthyl)(perfluorophenyl)(4,5,6,7-tetrafluoronaphthyl)aluminate]⁻; [N,N-2,4,6-pentamethylanilinium]+[7-((triethylsilylethyl)(2,3,4-trifluorophenyl)amino)perfluoronapth-3-yl)-(4,5,6-trifluoronaphthyl)(perfluoronaphthyl)(perfluorobiphenyl)aluminate]⁻; [N,N-di(dodecyl)-anilinium]+[4'-((methyl)(4,5,7-trifluoronaphthyl)amino)perfluorobiphen-4-yl)(4,5,7-trifluoro-naphthyl)(perfluorophenyl)(perfluoropyrenyl)aluminate]⁻; [N,N,N-(dimethyl)(t-butyl)-phosphonium]+[7-((tri-n-propylsilylhexyl)(perfluorobiphenyl)phosphino)perfluoronapth-3-yl)-(pentalfluoropyrenyl)(perfluoroanthracenyl)(4,5,6,7-tetrafluoronaphthyl)aluminate]⁻; [N,N,N-(ethyl)(methyl)(octyl)phosphonium]+[5-((hexyl)(perfluoropyrenyl)phosphino)perfluoronapth-2-yl)bis(pentalfluoropyrenyl)(perfluoronaphthyl)aluminate]⁻; [tri-N-octylphosphonium]+[4'-((tri-n-propylsilylhexyl)(perfluoroanthracenyl)arsino)perfluorobiphen-4-yl)(4,5,6-trifluoronaphthyl)-(tetrafluorofluorenyl)(perfluorobiphenyl)aluminate]⁻; [tri-N-propylphosphonium]+[5-((isopropyl)-(5,6,7,8-tetrafluoronaphthyl)amino)perfluoroinden-1-yl)(perfluoroanthracenyl)(2,3,6-trifluoro-phenyl)(perfluoropyrenyl)aluminate]⁻; [N,N,N-(ethyl)(dioctyl)phosphonium]+[5-((tri-isopropyl-silyloctyl)(perfluorobiphenyl)amino)perfluoroinden-1-yl)(perfluoropyrenyl)(perfluorophenyl)-(2,3,4-trifluorophenyl)aluminate]⁻; [N,N,N-(dimethyl)(t-butyl)phosphonium]+[7-((tri-n-propyl-silyl)(perfuorophenyl)phosphino)perfluoropyren-2-yl)(perfluorophenyl)(2',3',4'-trifluoro-biphenyl)(perfluoroanthracenyl)aluminate]⁻; [tri-N-(methylphenyl)phosphonium]+[6-((methyl-ethylhexylsilyl)(5,6,7,8-tetrafluoronaphthyl)amino)perfluoroanthracen-1-yl)(pentafluoro-anthracenyl)(2',3',5'-trifluorobiphenyl)(perfluoropyrenyl)aluminate]⁻; [N,N,N-(dimethyl)(t-butyl)-phosphonium]+[7-((hexyl)(perfluorophenyl)amino)perfluorofluoren-1-yl)(2',3',4'-trifluoro-biphenyl)(pentafluoroanthracenyl)(4,5,7-trifluoronaphthyl)aluminate]⁻; [tri-N-(methylphenyl)-phosphonium]+[4'-((butyl)(perfluorofluorenyl)amino)perfluorobiphen-3-yl)(perfluorophenyl)-(2,3,6-trifluorophenyl)(perfluoroanthracenyl)aluminate]⁻; [tri-N-propylphosphonium]+[7-((methyldiethylsilyloctyl)(pentalfluoropyrenyl)amino)fluoroinden-2-yl)(perfluorophenyl)(per-fluoroanthracenyl)(2',3',5'-trifluorobiphenyl)aluminate]⁻; [tri-N-methylphosphonium]+[6-((methyl)(perfluoropyrenyl)phosphino)fluorofluoren-2-yl)(perfluorofluorenyl)(perfluorophenyl)-(4,5,7-trifluoronaphthyl)aluminate]⁻; [tri-N-methylphosphonium]+[6-((3-ethylnonyl)(5,6,7,8-tetrafluoronaphthyl)amino)perfluoroanthracen-2-yl)(pentalfluoropyrenyl)(perfluorophenyl)-(2',3',4'-trifluorobiphenyl)aluminate]⁻; [tri-N-(n-butyl)phosphonium]+[6-((cyclohexyl)(4,5,7-trifluoronaphthyl)arsino)perfluoronaphth-2-yl)(tetrafluorofluorenyl)(perfluorobiphenyl)(2,3,5-trifluorophenyl)aluminate]⁻; [N,N,N-(ethyl)(methyl)(t-butyl)phosphonium]+[6-((octyl)(perfluoro-naphthyl)phosphino)fluoroanthracen-1-yl)bis(perfluorobiphenyl)(2,3,5-trifluorophenyl)aluminate]⁻; [tri-N-(dimethylphenyl)phosphonium]+[6-((diethylnonlysilyl)(perfluorophenyl)-amino)perfluoroanthracen-2-yl)(perfluorophenyl)(pentafluoroanthracenyl)(2',3',5'-trifluoro-biphenyl)aluminate]⁻; [tri-N-ethylphosphonium]+[7-((triethylsilylpropyl)(perfluoro-biphenyl)phosphino)perfluoroanthracen-1-yl)(pentalfluoropyrenyl)(pentafluoroanthracenyl)-(4,5,6,7-tetrafluoronaphthyl)aluminate]⁻; [N,N,N-(ethyl)(methyl)(n-butyl)phosphonium]+[6-((methyl)(perfluorobiphenyl)arsino)perfluoronapth-1-yl)(2,3,6-trifluorophenyl)(4,5,6-trifluoro-naphthyl)(perfluorophenyl)aluminate]⁻; [N,N,N-(ethyl)(methyl)(n-butyl)phosphonium]+[7-((ethyl)(2,3,5-trifluorophenyl)phosphino)perfluoronapth-1-yl)(perfluorobiphenyl)(4,5,6-trifluoro-naphthyl)(perfluorophenyl)aluminate]⁻; [tri-N-ethylphosphonium]+[5-((tri-isopropylsilyloctyl)-(pentafluoroanthracenyl)amino)perfluoronapth-1-yl)(perfluoroanthracenyl)(perfluorobiphenyl)-(2,3,4-trifluorophenyl)aluminate]⁻; [tri-N-ethylphosphonium]+[4'-((3-ethylnonyl)(pentafluoro-anthracenyl)arsino)fluorobiphen-3-yl)(perfluoropyrenyl)(pentalfluoropyrenyl)(perfluorophenyl)-aluminate]⁻; [tri-N-octylphosphonium]+[7-((3-ethylnonyl)(perfluorobiphenyl)amino)fluoroinden-2-yl)(4,5,6-trifluoronaphthyl)(perfluorobiphenyl)(2',3',5'-trifluorobiphenyl)aluminate]⁻; [N,N,N-(ethyl)(methyl)(octyl)phosphonium]+[7-((propyl)(perfluoropyrenyl)amino)perfluoronapth-2-yl)-(pentafluoroanthracenyl)(perfluoropyrenyl)(2',3',5'-trifluorobiphenyl)aluminate]⁻; [tri-N-ethyl-phosphonium]+[6-((triethylsilylpropyl)(perfluorofluorenyl)arsino)perfluoronapth-3-yl)(2,3,4-tri-fluorophenyl)(perfluorofluorenyl)(perfluorophenyl)aluminate]⁻; [tri-N-(t-butyl)phosphonium]+[4'-((propyl)(perfluoropyrenyl)amino)perfluorobiphen-4-yl)bis(perfluoroanthracenyl)(perfluoro-biphenylaluminate]⁻; [tri-N-propylphosphonium]+[7-((triethylsilyl)(perfluorobiphenyl)amino)per-fluoroanthracen-1-yl)(perfluoroanthracenyl)(2',3',4'-trifluorobiphenyl)(4,5,6,7-tetrafluoro-naphthyl)aluminate]⁻; [N,N,N-(ethyl)(methyl)(t-butyl)phosphonium]+[4-((n-butyl)(perfluoro-phenyl)amino)perfluorophenyl)(perfluorobiphenyl)(4,5,7-trifluoronaphthyl)(2',3',5'-trifluoro-biphenyl)aluminate]⁻; [tri-N-(methylphenyl)

phosphonium]+[7-(n-butyl)(perfluorobiphenyl)phos-phino)perfluoronapth-1-yl)(5,6,7,8-tetrafluoronaphthyl)(4,5,6,7-tetrafluoronaphthyl)(perfluoropyrenyl)aluminate]⁻; [tri-N-(methylphenyl)phosphonium]+[6-((nonyl)(perfluorophenyl)phos-phino)perfluoronapth-3-yl)bis(4,5,6-trifluoronaphthyl)(perfluoronaphthylaluminate]⁻; [N N,N-(ethyl)(dioctyl)phosphonium]+[5-((butyl)(perfluorofluorenyl)amino)perfluoronapth-1-yl)(per-fluorofluorenyl)(perfluoropyrenyl)(perfluorophenyl)aluminate]⁻; [N,N,N-(ethyl)(methyl)-(isopropyl)phosphonium]+[6-((tri-isopropylsilyl)(perfluorobiphenyl)amino)perfluoronapth-1-yl)-(pentafluoroanthracenyl)(perfluoropyrenyl)(perfluorofluorenyl)aluminate]⁻; [tri-N-propyl-phosphonium]+[6-((benzyl)(perfluorophenyl)arsino)perfluoroanthracen-2-yl)(5,6,7,8-tetrafluoro-naphthyl)(perfluorophenyl)(2',3',4'-trifluorobiphenyl)aluminate]⁻; [tri-N-(n-butyl)-phosphonium]+[7-((butyl)(2,3,6-trifluorophenyl)amino)perfluorofluoren-1-yl)(perfluorofluorenyl)-(2',3',5'-trifluorobiphenyl)(2',3',4'-trifluorobiphenyl)aluminate]⁻; [tri-N-(dimethylphenyl)-phosphonium]+[3-((hexyl)(perfluorophenyl)amino)perfluorophenyl)(perfluoronaphthyl)(per-fluorobiphenyl)(perfluorofluorenyl)aluminate]⁻; [tri-N-(t-butyl)phosphonium]+[7-((triethylsilyl-propyl)(perfluorobiphenyl)arsino)perfluoroanthracen-1-yl)(perfluorobiphenyl)(perfluoro-biphenyl)(4,5,6,7-tetrafluoronaphthyl)aluminate]⁻; [N,N,N-(ethyl)(dioctyl)phosphonium]+[8-((tri-n-propylsilyl)(perfluoropyreny)amino)perfluoropyren-2-yl)bis(perfluorobiphenyl)(4,5,6,7-tetrafluoronaphthylaluminate]⁻; [tri-N-(dimethylphenyl)phosphonium]+[5-((butyl)(perfluoro-pyrenyl)amino)perfluoroinden-1-yl)(perfluoroanthracenyl)(perfluorophenyl)(4,5,6,7-tetrafluoro-naphthyl)aluminate]⁻; [tri-N-propylphosphonium]+[8-((butyl)(perfluorophenyl)amino)perfluoro-pyren-2-yl)(perfluorobiphenyl)(perfluoropyrenyl)(4,5,6,7-tetrafluoronaphthyl)aluminate]⁻; [tri-N-octylphosphonium]+[5-((tri-isopropysilyloctyl)(2',3',5'-trifluorobiphenyl)amino)fluoroinden-1-yl)-(perfluorobiphenyl)(tetrafluorofluorenyl)(2,3,5-trifluorophenyl)aluminate]⁻; [tri-N-octyl-phosphonium]+[6-((methylethylhexylsilyl)(4,5,7-trifluoronaphthyl)amino)perfluoroanthracen-1-yl)(perfluorobiphenyl)(4,5,6-trifluoronaphthyl)(4,5,6,7-tetrafluoronaphthyl)aluminate]⁻; [tri-N-(methylphenyl)phosphonium]+[8-((tri-isopropylsilyl)(2,3,4-trifluorophenyl)amino)perfluoro-naphth-3-yl)(pentafluoroanthracenyl)(perfluorophenyl)(5,6,7,8-tetrafluoronaphthyl)aluminate]⁻; [tri-N-ethylphosphonium]+[6-((triethylsilylpropyl)(4,5,7-trifluoronaphthyl)amino)perfluoro-fluoren-2-yl)(perfluorofluorenyl)(perfluoropyrenyl)(2,3,5-trifluorophenyl)aluminate]⁻; [N,N,N-(dimethyl)(t-butyl)phosphonium]+[6-((isopropyl)(perfluorophenyl)amino)perfluoronapth-3-yl)-(5,6,7,8-tetrafluoronaphthyl)(pentafluoroanthracenyl)(4,5,7-trifluoronaphthyl)aluminate]⁻; [tri-N-ethylphosphonium]+[4-((hexyl)(perfluoronaphthyl)amino)perfluorophenyl)(pentalfluoropyrenyl)-(perfluoronaphthyl)(perfluoroanthracenyl)aluminate]⁻; [N,N,N-(dimethyl)(t-butyl)-phosphonium]+[4'-((tri-isopropylsilyl)(2,3,6-trifluorophenyl)amino)perfluorobiphen-4-yl)(2,3,6-trifluorophenyl)(perfluorophenyl)(4,5,6,7-tetrafluoronaphthyl)aluminate]⁻; [N,N,N-(ethyl)-(dioctyl)phosphonium]+[6-((propyl)(perfluorophenyl)amino)perfluoronapth-2-yl)(perfluoro-fluorenyl)(perfluoroanthracenyl)(4,5,6,7-tetrafluoronaphthyl)aluminate]⁻; [N,N,N-(ethyl)-(methyl)(octyl)phosphonium]+[4'-((octyl)(tetrafluorofluorenyl)phosphino)perfluorobiphen-3-yl)-(pentalfluoropyrenyl)(4,5,7-trifluoronaphthyl)(perfluorophenyl)aluminate]⁻; [tri-N-(dimethylphenyl)phosphonium]+[4'-((cyclohexyl)(tetrafluorofluorenyl)phosphino)perfluoro-biphen-3-yl)bis(perfluoroanthracenyl)(pentafluoroanthracenylaluminate]⁻; [tri-N-(dimethylphenyl)phosphonium]+[6-((benzyl)(perfluorobiphenyl)amino)perfluorofluoren-2-yl)-(perfluorobiphenyl)(perfluorofluorenyl)(perfluoronaphthyl)aluminate]⁻; [tri-N-ethyl-phosphonium]+[7-((propyl)(perfluorofluorenyl)phosphino)perfluoropyren-1-yl)(pentalfluoro-pyrenyl)(perfluorobiphenyl)(2,3,4-trifluorophenyl)aluminate]⁻; [N,N,N-(ethyl)(methyl)(octyl)-phosphonium]+[7-((nonyl)(perfluorophenyl)phosphino)perfluoropyren-1-yl)(4,5,6-trifluoro-naphthyl)(perfluorobiphenyl)(2',3',5'-trifluorobiphenyl)aluminate]⁻; [tri-N-octylphosphonium]+[5-((triethylsilylethyl)(perfluorophenyl)amino)perfluoronapth-3-yl)(perfluorofluorenyl)(pentalfluoro-pyrenyl)(pentafluoroanthracenyl)aluminate]⁻; [N,N,N-(ethyl)(dioctyl)phosphonium]+[7-((benzyl)(perfluoronaphthyl)amino)perfluoronapth-1-yl)(perfluorobiphenyl)(2,3,4-trifluoro-phenyl)(2',3',5'-trifluorobiphenyl)aluminate]⁻; [N,N,N-(ethyl)(methyl)(n-butyl)phosphonium]+[3-((methyl)(perfluorophenyl)amino)perfluorophenyl)(perfluoropyrenyl)(perfluoroanthracenyl)(per-fluoroanthracenyl)aluminate]⁻; [tri-N-(dimethylphenyl)phosphonium]+[7-((benzyl)(5,6,7,8-tetrafluoronaphthyl)arsino)perfluoroanthracen-1-yl)bis(perfluorobiphenyl)(perfluoronaphthyl-aluminate]⁻; [N,N,N-(ethyl)(methyl)(n-butyl)phosphonium]+[6-((n-butyl)(pentafluoro-anthracenyl)amino)perfluoroanthracen-1-yl)(5,6,7,8-tetrafluoronaphthyl)(4,5,7-trifluoro-naphthyl)(perfluorophenyl)aluminate]⁻; [tri-N-(dimethylphenyl)phosphonium]+[6-((tri-n-propyl-silyl)(2,3,5-trifluorophenyl)phosphino)perfluoroanthracen-1-yl)(perfluorophenyl)(perfluoro-anthracenyl)(2',3',5'-trifluorobiphenyl)aluminate]⁻; [tri-N-(dimethylphenyl)phosphonium]+[7-((methyl)(2',3',4'-trifluorobiphenyl)amino)perfluoroinden-2-yl)bis(perfluoroanthracenyl)(5,6,7,8-tetrafluoronaphthylaluminate]⁻; [tri-N-propylphosphonium]+[4-((triethylsilylpropyl)(perfluoro-phenyl)amino)perfluorophenyl)(pentalfluoropyrenyl)(2,3,6-trifluorophenyl)(2,3,5-trifluoro-phenyl)aluminate]⁻; [tri-N-(dimethylphenyl)phosphonium]+[6-((propyl)(perfluorophenyl)amino)-perfluorofluoren-2-yl)bis(perfluoroanthracenyl)(5,6,7,8-tetrafluoronaphthylaluminate]⁻; [N N,N-(ethyl)(dioctyl)phosphonium]+[6-((hexyl)(perfluorofluorenyl)amino)perfluorofluoren-2-yl)(per-fluoronaphthyl)(4,5,7-trifluoronaphthyl)(perfluorobiphenyl)aluminate]⁻; [N,N,N-(ethyl)(dioctyl)-phosphonium]+[7-((trimethylsilyl)(perfluorobiphenyl)amino)perfluoroinden-2-yl)(perfluoro-fluorenyl)(perfluoropyrenyl)(5,6,7,8-tetrafluoronaphthyl)aluminate]⁻; [N,N,N-(ethyl)(dioctyl)-phosphonium]+[5-((propyl)(5,6,7,8-tetrafluoronaphthyl)amino)perfluoronapth-3-yl)(tetrafluoro-fluorenyl)(2,3,6-trifluorophenyl)(2',3',5'-trifluorobiphenyl)aluminate]⁻; [N,N,N-(ethyl)(dioctyl)-phosphonium]+[3-((3-ethylnonyl)(perfluorophenyl)phosphino)perfluorophenyl)(4,5,7-trifluoro-naphthyl)(perfluorophenyl)(4,5,6-trifluoronaphthyl)aluminate]⁻; [N,N,N-(ethyl)(methyl)(n-butyl)-phosphonium]+[6-((triethylsilylpropyl)(5,6,7,8-tetrafluoronaphthyl)amino)perfluoroanthracen-2-yl)(perfluoroanthracenyl)(2',3',5'-trifluorobiphenyl)(perfluorophenyl)aluminate]⁻; [tri-N-octyl-phosphonium]+[7-((benzyl)(perfluorophenyl)amino)perfluorofluoren-1-yl)(tetrafluorofluorenyl)-(perfluoroanthracenyl)(4,5,6,7- tetrafluoronaphthyl)aluminate]⁻; [tri-N-octylphosphonium]+[4-((nonyl)(tetrafluorofluorenyl)arsino)perfluorophenyl)(pentafluoroanthracenyl)(2,3,4-trifluoro-phenyl)(perfluorobiphenyl)aluminate]⁻; [tri-N-(methylphenyl)phosphonium]+[8-((tri-n-propyl-silyl)(perfluoronaphthyl)amino)fluoronapth-3-yl)(perfluoroanthracenyl)(5,6,7,8-tetrafluoro-naphthyl)(perfluorofluorenyl)aluminate]⁻; [N,N,N-(ethyl)(dioctyl)phosphonium]+[3'-((octyl)(per-fluoropyrenyl)amino)perfluorobiphen-4-yl)(pentalfluoropyrenyl)(perfluorophenyl)(4,5,6,7-tetrafluoronaphthyl)aluminate]⁻; [N,N,N-(ethyl)(methyl)(isopropyl)phosphonium]+[6-((octyl)-(4,5,6,7-tetrafluoronaphthyl)phosphino)perfluoroanthracen-2-yl)(perfluoroanthracenyl)(perfluorobiphenyl)(2,3,4-trifluorophenyl)aluminate]⁻; [tri-N-(methylphenyl)phosphonium]+[3'-((tri-isopropylsilyl)(perfluorophenyl)arsino)perfluorobiphen-4-yl)(pentalfluoropyrenyl)(perfluoro-anthracenyl)(4,5,7-trifluoronaphthyl)aluminate]⁻; [N,N,N-(ethyl)(methyl)(n-butyl)-phosphonium]+[8-((tri-isopropylsilyl)(4,5,7-trifluoronaphthyl)phosphino)perfluoropyren-2-yl)bis(4,5,6,7-tetrafluoronaphthyl)(perfluoropyrenyl)aluminate]⁻; [tri-N-(dimethylphenyl)-phosphonium]+[7-((methyldiethylsilyloctyl)(perfluorophenyl)amino)perfluorofluoren-2-yl)-(4,5,6,7-tetrafluoronaphthyl)(pentalfluoropyrenyl)(4,5,6-trifluoronaphthyl)aluminate]⁻; [N,N,N-(ethyl)(methyl)(t-butyl)phosphonium]+[7-((triethylsilyl)(2',3',5'-trifluorobiphenyl)amino)perfluoro-napth-1-yl)(perfluoronaphthyl)(perfluorobiphenyl)(4,5,6,7-tetrafluoronaphthyl)aluminate]⁻; [tri-N-octylphosphonium]+[6-((n-butyl)(perfluorophenyl)amino)perfluoroanthracen-2-yl)bis(per-fluorobiphenyl)(perfluoroanthracenylaluminate]⁻; [tri-N-(n-butyl)phosphonium]+[5-((trimethyl-silyl)(perfluoroanthracenyl)amino)perfluoroinden-1-yl)bis(2,3,6-trifluorophenyl)(perfluoro-phenyl)aluminate]⁻; [tri-N-(t-butyl)phosphonium]+[7-((octyl)(perfluorobiphenyl)amino)perfluoro-napth-2-yl)(perfluoronaphthyl)(5,6,7,8-tetrafluoronaphthyl)(perfluorobiphenyl)aluminate]⁻; [N,N,N-(ethyl)(methyl)(isopropyl)phosphonium]+[8-((diethylnonlysilyl)(5,6,7,8-tetrafluoro-naphthyl)arsino)perfluoronapth-3-yl)(perfluorofluorenyl)(5,6,7,8-tetrafluoronaphthyl)(perfluoro-phenyl)aluminate]⁻; [tri-N-octylphosphonium]+[4'-((hexyl)(perfluorobiphenyl)amino)perfluoro-biphen-3-yl)(perfluorobiphenyl)(2',3',4'-trifluorobiphenyl)(2,3,5-trifluorophenyl)aluminate]⁻; [tri-N-ethylphosphonium]+[3'-((tri-isopropylsilyloctyl)(perfluorofluorenyl)amino)perfluorobiphen-4-yl)(perfluorophenyl)(tetrafluorofluorenyl)(2,3,6-trifluorophenyl)aluminate]⁻; [tri-N-(n-butyl)-phosphonium]+[6-((tri-isopropylsilyl)(perfluorophenyl)arsino)perfluoroanthracen-2-yl)(5,6,7,8-tetrafluoronaphthyl)(2,3,4-trifluorophenyl)(4,5,7-trifluoronaphthyl)aluminate]⁻; [tri-N-methyl-phosphonium]+[5-((propyl)(perfluorobiphenyl)amino)perfluoronapth-3-yl)(perfluoro-anthracenyl)(perfluoropyrenyl)(2',3',5'-trifluorobiphenyl)aluminate]⁻; [tri-N-(methylphenyl)-phosphonium]+[8-((triethylsilylpropyl)(4,5,6,7-tetrafluoronaphthyl)phosphino)perfluoropyren-2-yl)(perfluorofluorenyl)(4,5,7-trifluoronaphthyl)(pentafluoroanthracenyl)aluminate]⁻; [tri-N-(dimethylphenyl)phosphonium]+[7-((ethyl)(perfluoroanthracenyl)phosphino)perfluoropyren-1-yl)(perfluorobiphenyl)(perfluoropyrenyl)(perfluorofluorenyl)aluminate]⁻; [trityl]+[7-((3-ethyl-nonyl)(2,3,5-trifluorophenyl)arsino)fluoropyren-2-yl)bis(perfluorobiphenyl)(pentafluoro-anthracenyl)aluminate]⁻;

[trityl]+[4'-((nonyl)(perfluorophenyl)amino)perfluorobiphen-4-yl)(per-fluoroanthracenyl)(tetrafluorofluorenyl)(perfluorofluorenyl)aluminate]⁻; [trityl]+[6-((methyl)(per-fluorophenyl)arsino)perfluorofluoren-2-yl)(perfluorophenyl)(perfluorofluorenyl)(4,5,6-trifluoro-naphthyl)aluminate]⁻; [tri-N-(methylphenyl)ammonium]+[7-((nonyl)(perfluorophenyl)arsino)per-fluorofluoren-2-yl)(pentalfluoropyrenyl)(2,3,4-trifluorophenyl)(perfluorophenyl)borate]⁻; [tri-N-methylammonium]+[3-((methyl)(perfluoroanthracenyl)amino)perfluorophenyl)(pentalfluoro-pyrenyl)(2,3,5-trifluorophenyl)(2,3,6-trifluorophenyl)borate]⁻; [tri-N-(dimethylphenyl-ammonium]+[6-((nonyl)(perfluorofluorenyl)amino)perfluorofluoren-1-yl)(4,5,6,7-tetrafluoro-naphthyl)(perfluoropyrenyl)(perfluorobiphenyl)borate]⁻; [tri-N-(n-butyl)ammonium]+[5-((octyl)-(4,5,6-trifluoronaphthyl)amino)perfluoronapth-2-yl)(perfluorobiphenyl)(perfluorofluorenyl)(per-fluoropyrenyl)borate]⁻; [N N,N-(ethyl)(methyl)(n-butyl)ammonium]+[7-((2,2-dimethyloctyl)-(pentalfluoropyrenyl)amino)perfluoronapth-2-yl)(perfluorobiphenyl)(perfluoroanthracenyl)-(pentafluoroanthracenyl)borate]⁻; [tri-N-methylammonium]+[8-((cyclohexyl)(pentafluoro-anthracenyl)amino)perfluoronapth-3-yl)(perfluoronaphthyl)(perfluorobiphenyl)(perfluoro-phenyl)borate]⁻; [N,N,N-(ethyl)(methyl)(isopropyl)ammonium]+[4'-((tri-isopropylsilyloctyl)(per-fluorobiphenyl)amino)perfluorobiphen-3-yl)(perfluorophenyl)(perfluorofluorenyl)(4,5,6-trifluoro-naphthyl)borate]⁻; [tri-N-ethylammonium]+[5-((tri-isopropylsilyl)(2,3,5-trifluorophenyl)arsino)-perfluoronapth-3-yl)bis(perfluorobiphenyl)(perfluorofluorenyl)borate]⁻; [tri-N-methyl-ammonium]+[7-((methylethylhexylsilyl)(perfluorobiphenyl)amino)perfluoronapth-3-yl)(perfluoro-phenyl)(perfluorofluorenyl)(5,6,7,8-tetrafluoronaphthyl)borate]⁻; [tri-N-(methylphenyl)-ammonium]+[4'-((tri-n-propylsilylhexyl)(4,5,7-trifluoronaphthyl)amino)perfluorobiphen-3-yl)(per-fluorofluorenyl)(pentalfluoropyrenyl)(2',3',5'-trifluorobiphenyl)borate]⁻; [N,N,N-(ethyl)(methyl)(t-butyl)ammonium]+[8-((triethylsilyl)(2',3',4'-trifluorobiphenyl)arsino)perfluoronapth-3-yl)(per-fluorofluorenyl)(4,5,7-trifluoronaphthyl)(perfluorophenyl)borate]⁻; [tri-N-(t-butyl)ammonium]+[7-((2,2-dimethyloctyl)(perfluorophenyl)amino)perfluorofluoren-1-yl)(pentalfluoropyrenyl)(5,6,7,8-tetrafluoronaphthyl)(perfluorobiphenyl)borate]⁻; [tri-N-methylammonium]+[4'-((isopropyl)(per-fluoroanthracenyl)amino)perfluorobiphen-4-yl)(perfluoroanthracenyl)(2',3',5'-trifluorobiphenyl)-(4,5,6,7-tetrafluoronaphthyl)borate]⁻; [tri-N-(methylphenyl)ammonium]+[7-((triethylsilyl)(per-fluorophenyl)amino)perfluorofluoren-2-yl)(perfluoronaphthyl)(perfluorophenyl)(perfluoro-biphenyl)borate]⁻; [N,N,N-(ethyl)(methyl)(isopropyl)ammonium]+[7-((methyl)(perfluorophenyl)-amino)perfluoroinden-2-yl)(4,5,7-trifluoronaphthyl)(perfluorophenyl)(perfluorofluorenyl)borate]⁻; [N,N,N-(ethyl)(methyl)(isopropyl)ammonium]+[6-((triethylsilylethyl)(perfluoroanthracenyl)-arsino)perfluoroanthracen-1-yl)bis(perfluorobiphenyl)(4,5,6,7-tetrafluoronaphthylborate]⁻; [N,N,N-(ethyl)(methyl)(n-butyl)ammonium]+[6-((butyl)(4,5,6-trifluoronaphthyl)amino)perfluoro-naphth-1-yl)(pentalfluoropyrenyl)(4,5,6,7-tetrafluoronaphthyl)(perfluoropyrenyl)borate]⁻; [N,N,N-(dimethyl)(t-butyl)ammonium]+[6-((cyclohexyl)(perfluorophenyl)amino)perfluoroinden-2-yl)(pentalfluoropyrenyl)(perfluoroanthracenyl)(perfluorophenyl)borate]⁻; [tri-N-(n-butyl)-ammonium]+[4'-((tri-n-propylsilyl)(4,5,6,7- tetrafluoronaphthyl)amino)perfluorobiphen-4-yl)bis(pentalfluoropyrenyl)(tetrafluorofluorenylborate]⁻; [N,N,N-(ethyl)(methyl)(octyl)-ammonium]+[7-((benzyl)(perfluorophenyl)amino)perfluoronapth-2-yl)(perfluoronaphthyl)(4,5,6-trifluoronaphthyl)(pentalfluoropyrenyl)borate]⁻; [N,N,N-(ethyl)(methyl)(n-butyl)ammonium]+[7-((3-ethylnonyl)(perfluorobiphenyl)amino)perfluoronapth-2-yl)(pentalfluoropyrenyl)(2,3,4-trifluorophenyl)(perfluorophenyl)borate]⁻; [tri-N-propylammonium]+[4'-((trimethylsilyl)(2',3',4'-trifluorobiphenyl)phosphino)perfluorobiphen-3-yl)(tetrafluorofluorenyl)(perfluoropyrenyl)(5,6,7,8-tetrafluoronaphthyl)borate]⁻; [N,N,N-(ethyl)(methyl)(isopropyl)ammonium]+[3'-((isopropyl)(per-fluorophenyl)amino)perfluorobiphen-4-yl)(perfluoropyrenyl)(pentalfluoropyrenyl)(perfluoro-phenyl)borate]⁻; [tri-N-(t-butyl)ammonium]+[7-((triethylsilyl)(4,5,7-trifluoronaphthyl)phosphino)-perfluoroanthracen-1-yl)(2,3,4-trifluorophenyl)(perfluorophenyl)(perfluoroanthracenyl)borate]⁻; [tri-N-(t-butyl)ammonium]+[5-((isopropyl)(2,3,5-trifluorophenyl)phosphino)perfluoronapth-3-yl)bis(2,3,4-trifluorophenyl)(4,5,6-trifluoronaphthyl)borate]⁻; [tri-N-(dimethylphenyl-ammonium]+[6-((tri-n-propylsilylhexyl)(perfluorofluorenyl)amino)perfluorofluoren-1-yl)(2,3,4-trifluorofluorenyl)(perfluoronaphthyl)(perfluorophenyl)borate]⁻; [N,N,N-(ethyl)(methyl)(isopropyl)-ammonium]+[8-((methyldiethylsilyloctyl)(perfluorobiphenyl)phosphino)perfluoronapth-3-yl)bis(perfluorobiphenyl)(4,5,6-trifluoronaphthylborate]⁻; [N,N,N-(ethyl)(methyl)(octyl)-ammonium]+[4'-((3-ethylnonyl)(4,5,6-trifluoronaphthyl)amino)perfluorobiphen-4-yl)(tetrafluoro-fluorenyl)(perfluoronaphthyl)(perfluorobiphenyl)borate]⁻; [N,N,N-(ethyl)(methyl)(n-butyl)-ammonium]+[6-((propyl)(perfluoroanthracenyl)amino)perfluorofluoren-1-yl)(perfluoro-anthracenyl)(2',3',5'-trifluorobiphenyl)(perfluoropyrenyl)borate]⁻; [tri-N-methylammonium]+[6-((tri-n-propylsilyl)(perfluorofluorenyl)amino)fluorofluoren-2-yl)(perfluorophenyl)(2,3,5-trifluoro-phenyl)(2',3',4'-trifluorobiphenyl)borate]⁻; [N,N,N-(ethyl)(methyl)(n-butyl)ammonium]+[6-((triethylsilylethyl)(2',3',5'-trifluorobiphenyl)phosphino)perfluorofluoren-1-yl)bis(2,3,6-trifluoro-phenyl)(4,5,6-trifluoronaphthyl)borate]⁻; [tri-N-ethylammonium]+[5-((octyl)(perfluorophenyl)-amino)perfluoroinden-2-yl)(perfluorobiphenyl)(pentalfluoropyrenyl)(4,5,7-trifluoronaphthyl)-borate]⁻; [tri-N-methylammonium]+[7-((n-butyl)(perfluorophenyl)amino)perfluoropyren-1-yl)-(perfluorofluorenyl)(2',3',5'-trifluorobiphenyl)(2',3',4'-trifluorobiphenyl)borate]⁻; [N,N,N-(ethyl)-(methyl)(isopropyl)ammonium]+[6-((triethylsilyl)(2,3,6-trifluorophenyl)amino)perfluorofluoren-2-yl)(perfluoroanthracenyl)(perfluoropyrenyl)(2,3,5-trifluorophenyl)borate]⁻; [N,N,N-(ethyl)-(dioctyl)ammonium]+[7-((methylethylhexylsilyl)(2',3',5'-trifluorobiphenyl)amino)perfluoroanth-racen-1-yl)(pentalfluoropyrenyl)(perfluoroanthracenyl)(4,5,6,7-tetrafluoronaphthyl)borate]⁻; [tri-N-octylammonium]+[5-((methyldiethylsilyloctyl)(perfluorobiphenyl)phosphino)perfluoroinden-2-yl)(perfluorophenyl)(pentafluoroanthracenyl)(perfluoronaphthyl)borate]⁻; [tri-N-(t-butyl)-ammonium]+[7-((2,2-dimethyloctyl)(perfluoronaphthyl)phosphino)perfluorofluoren-1-yl)(per-fluorobiphenyl)(perfluoropyrenyl)(pentafluoroanthracenyl)borate]⁻; [tri-N-(dimethylphenyl-ammonium]+[7-((triethylsilylethyl)(perfluoronaphthyl)amino)perfluoronapth-2-yl)(tetrafluoro-fluorenyl)(2,3,6-trifluorophenyl)(2',3',5'-trifluorobiphenyl)borate]⁻; [N,N,N-(ethyl)(methyl)(t-butyl)-ammonium]+[6-((tri-n-propylsilylhexyl)(perfluorophenyl) amino)perfluoronapth-3-yl)(perfluoro-pyrenyl)(5,6,7,8-tetrafluoronaphthyl)(perfluoroanthracenyl)borate]⁻; [N,N,N-(ethyl)(methyl)(n-butyl)ammonium]+[6-((2,2-dimethyloctyl)(perfluorophenyl)phosphino)perfluoronapth-1-yl)(per-fluorofluorenyl)(2',3',5'-trifluorobiphenyl)(2',3',4'-trifluorobiphenyl)borate]⁻; [N,N,N-(ethyl)-(methyl)(n-butyl)ammonium]+[7-((methyldiethylsilyloctyl)(perfluorophenyl)amino)perfluoro-napth-2-yl)(tetrafluorofluorenyl)(2',3',4'-trifluorobiphenyl)(perfluorofluorenyl)borate]⁻; [N,N,N-(ethyl)(dioctyl)ammonium]+[7-((tri-n-propylsilyl)(perfluorophenyl)amino)perfluoropyren-2-yl)bis(pentafluoroanthracenyl)(2,3,5-trifluorophenylborate]⁻; [tri-N-(dimethylphenyl-ammonium]+[6-((triethylsilylethyl)(perfluoroanthraceny)amino)perfluoroanthracen-1-yl)(2,3,4-trifluorophenyl)(2',3',4'-trifluorobiphenyl)(2,3,5-trifluorophenyl)borate]⁻; [N,N,N-(ethyl)(methyl)-(octyl)ammonium]+[7-((methyldiethylsilyloctyl)(perfluorobiphenyl)arsino)perfluoronapth-3-yl)-(perfluoropyrenyl)(4,5,7-trifluoronaphthyl)(4,5,6,7-tetrafluoronaphthyl)borate]⁻; [N,N,N-(ethyl)-(methyl)(t-butyl)ammonium]+[6-((methyldiethylsilyloctyl)(perfluorophenyl)amino)fluorofluoren-2-yl)(perfluoronaphthyl)(tetrafluorofluorenyl)(pentalfluoropyrenyl)borate]⁻; [tri-N-propyl-ammonium]+[7-((tri-n-propylsilylhexyl)(perfluorophenyl)amino)perfluorofluoren-1-yl)(2',3',5'-trifluorobiphenyl)(4,5,6,7-tetrafluoronaphthyl)(4,5,6-trifluoronaphthyl)borate]⁻; [N,N,N-(ethyl)-(dioctyl)ammonium]+[8-((isopropyl)(perfluorophenyl)amino)perfluoronapth-3-yl)(2,3,4-trifluoro-phenyl)(perfluorophenyl)(perfluoroanthracenyl)borate]⁻; [N,N,N-(ethyl)(methyl)(isopropyl)-ammonium]+[8-((diethylnonlysilyl)(perfluorophenyl)amino)fluoropyren-2-yl)(perfluorophenyl)-(2,3,6-trifluorophenyl)(2,3,5-trifluorophenyl)borate]⁻; [tri-N-(dimethylphenylammonium]+[6-((benzyl)(2,3,4-trifluorophenyl)phosphino)perfluoroanthracen-1-yl)(pentalfluoropyrenyl)-(tetrafluorofluorenyl)(2',3',5'-trifluorobiphenyl)borate]⁻; [tri-N-(dimethylphenylammonium]+[3'-((trimethylsilyl)(tetrafluorofluorenyl)phosphino)perfluorobiphen-4-yl)(perfluoronaphthyl)(per-fluorobiphenyl)(perfluorophenyl)borate]⁻; [N,N,N-(dimethyl)(t-butyl)ammonium]+[7-((hexyl)-(4,5,6-trifluoronaphthyl)amino)fluorofluoren-1-yl)(4,5,7-trifluoronaphthyl)(perfluorobiphenyl)-(5,6,7,8-tetrafluoronaphthyl)borate]⁻; [tri-N-octylammonium]+[6-((3-ethylnonyl)(pentalfluoro-pyrenyl)amino)perfluoroanthracen-1-yl)(perfluoronaphthyl)(2',3',4'-trifluorobiphenyl)(perfluoro-fluorenyl)borate]⁻; [tri-N-ethylammonium]+[4'-((2,2-dimethyloctyl)(perfluorobiphenyl)phos-phino)perfluorobiphen-3-yl)(5,6,7,8-tetrafluoronaphthyl)(perfluorophenyl)(4,5,7-trifluoro-naphthyl)borate]⁻; [tri-N-(dimethylphenylammonium]+[6-((2,2-dimethyloctyl)(perfluoro-phenyl)phosphino)perfluoroanthracen-1-yl)bis(2,3,4-trifluorophenyl)perfluorobiphenylborate]⁻; [tri-N-methylammonium]+[7-((octyl)(2,3,5-trifluorophenyl)amino)perfluoronapth-2-yl)(perfluoro-fluorenyl)(2',3',5'-trifluorobiphenyl)(2,3,4-trifluorophenyl)borate]⁻; [N,N,N-(ethyl)(methyl)(n-butyl)ammonium]+[6-((tri-n-propylsilylhexyl)(2',3',4'-trifluorobiphenyl)phosphino)perfluoro-fluoren-2-yl)(perfluorophenyl)(perfluoroanthracenyl)(5,6,7,8-tetrafluoronaphthyl)borate]⁻; [tri-N-(methylphenyl)ammonium]+[6-((tri-isopropylsilyloctyl)(4,5,7-trifluoronaphthyl)amino)perfluoro-napth-1-yl)(perfluorobiphenyl)(perfluoroanthracenyl)(2',3',5'-trifluorobiphenyl)borate]⁻; [tri-N-(methylphenyl)

ammonium]+[7-((butyl)(tetrafluorofluorenyl)phosphino) perfluoroanthracen-1-yl)-(perfluorobiphenyl)(2,3,5-trifluorophenyl)(perfluorophenyl)borate]⁻; [N,N,N-(ethyl)(dioctyl)-ammonium]+[7-((n-butyl)(perfluorophenyl)phosphino)perfluoropyren-1-yl)(perfluorophenyl)-(pentafluoroanthracenyl)(perfluorobiphenyl)borate]⁻; [tri-N-(methylphenyl)ammonium]+[7-((iso-propyl)(pentafluoroanthracenyl)arsino)perfluorofluoren-1-yl)(perfluorofluorenyl)(4,5,7-trifluoro-naphthyl)(perfluoropyrenyl)borate]⁻; [N,N,N-(ethyl)(methyl)(isopropyl)ammonium]+[7-((tri-n-propylsilylhexyl)(perfluoroanthracenyl)phosphino)perfluoropyren-1-yl)(perfluoroanthracenyl)-(perfluorobiphenyl)(perfluorophenyl)borate]⁻; [tri-N-(methylphenyl)ammonium]+[3'-((3-ethyl-nonyl)(4,5,7-trifluoronaphthyl)amino)perfluorobiphen-4-yl)(pentalfluoropyrenyl)(pentafluoro-anthracenyl)(2',3',4'-trifluorobiphenyl)borate]⁻; [tri-N-methylammonium]+[6-((benzyl)(perfluoro-biphenyl)amino)fluoroanthracen-2-yl)(perfluorophenyl)(perfluorofluorenyl)(2,3,5-trifluoro-phenyl)borate]⁻; [N,N,N-(ethyl)(dioctyl)ammonium]+[7-((diethylnonlysilyl)(perfluoropyrenyl)-amino)perfluorofluoren-2-yl)(perfluoropyrenyl)(pentalfluoropyrenyl)(perfluoroanthracenyl)-borate]⁻; [tri-N-propylammonium]+[7-((butyl)(perfluorobiphenyl)amino)perfluoronapth-1-yl)-(2,3,6-trifluorophenyl)(perfluorophenyl)(tetrafluorofluorenyl)borate]⁻; [tri-N-(t-butyl)-ammonium]+[8-((octyl)(perfluorofluorenyl)amino)perfluoronapth-3-yl)(5,6,7,8-tetrafluoro-naphthyl)(2,3,4-trifluorophenyl)(tetrafluorofluorenyl)borate]⁻; [N,N,N-(ethyl)(methyl)(n-butyl)-ammonium]+[6-((nonyl)(tetrafluorofluorenyl)amino)perfluoronapth-3-yl)(perfluorobiphenyl)-(2,3,6-trifluorophenyl)(perfluorophenyl)borate]⁻; [N,N,N-(ethyl)(methyl)(octyl)ammonium]+[5-((tri-n-propylsilylhexyl)(2',3',5'-trifluorobiphenyl)amino)perfluoroinden-1-yl)(5,6,7,8-tetrafluoro-naphthyl)(4,5,6,7-tetrafluoronaphthyl)(perfluoropyrenyl)borate]⁻; [N,N,N-(dimethyl)(t-butyl)-ammonium]+[7-((triethylsilylpropyl)(perfluorophenyl)amino)perfluoroanthracen-1-yl)(2,3,4-tri-fluorophenyl)(4,5,6-trifluoronaphthyl)(perfluorobiphenyl)borate]⁻; [N,N,N-(ethyl)(methyl)(t-butyl)ammonium]+[6-((triethylsilylethyl)(perfluoroanthracenyl)amino)fluorofluoren-1-yl)(pentafluoroanthracenyl)(perfluorophenyl)(2',3',4'-trifluorobiphenyl)borate]⁻; [tri-N-ethyl-ammonium]+[3-((octyl)(perfluorobiphenyl)amino)perfluorophenyl)(4,5,7-trifluoronaphthyl)(per-fluorophenyl)(perfluoropyrenyl)borate]⁻; [tri-N-methylammonium]+[5-((octyl)(perfluoro-biphenyl)phosphino)fluoronapth-1-yl)(perfluoropyrenyl)(2',3',5'-trifluorobiphenyl)(perfluoro-naphthyl)borate]⁻; [tri-N-(methylphenyl)ammonium]+[5-((triethylsilyl)(5,6,7,8-tetrafluoro-naphthyl)phosphino)perfluoronapth-1-yl)(2',3',5'-trifluorobiphenyl)(perfluorobiphenyl)(perfluoro-phenyl)borate]⁻; [tri-N-propylammonium]+[6-((tri-isopropylsilyloctyl)(perfluorofluorenyl)phos-phino)perfluoroinden-2-yl)(2,3,5-trifluorophenyl)(4,5,6,7-tetrafluoronaph-2-yl)(2,3,6-trifluoro-phenyl)borate]⁻; [N,N,N-(dimethyl)(t-butyl)ammonium]+[7-((diethylnonlysilyl)(perfluoropyrenyl)-amino)perfluoroinden-2-yl)(perfluoroanthracenyl)(pentafluoroanthracenyl)(2,3,4-trifluoro-phenyl)borate]⁻; [N,N,N-(dimethyl)(t-butyl)ammonium]+[6-((nonyl)(perfluoroanthracenyl)-amino)perfluoronapth-2-yl)(perfluorofluorenyl)(4,5,6,7-tetrafluoronaphthyl)(pentalfluoro-pyrenyl)borate]⁻; [N,N,N-(ethyl)(methyl)(octyl)ammonium]+[7-((methylethylhexylsilyl)(per-fluorophenyl)amino)fluoronapth-1-yl)(perfluoropyrenyl)(4,5,7-trifluoronaphthyl)(perfluoro-biphenyl)borate]⁻; [tri-N-octylammonium]+[6-((benzyl)(perfluorophenyl)amino)perfluoroanth-racen-1-yl)(perfluorobiphenyl)(perfluorophenyl)(tetrafluorofluorenyl)borate]⁻; [N,N,N-(ethyl)-(methyl)(n-butyl)ammonium]+[6-((isopropyl)(perfluorophenyl)amino)perfluoronapth-3-yl)(4,5,7-trifluoronaphthyl)(perfluorofluorenyl)(perfluoropyrenyl)borate]⁻; [N,N,N-(ethyl)(dioctyl)-ammonium]+[5-((ethyl)(4,5,6,7-tetrafluoronaphthyl)amino)perfluoroinden-2-yl)(4,5,7-trifluoro-naphthyl)(perfluorofluorenyl)(2',3',5'-trifluorobiphenyl)borate]⁻; [tri-N-propylammonium]+[7-((propyl)(perfluorophenyl)amino)perfluorofluoren-1-yl)(perfluoroanthracenyl)(4,5,6,7-tetrafluoronaphthyl)(perfluorobiphenyl)borate]⁻; [tri-N-(dimethylphenylammonium]+[6-((2,2-dimethyloctyl)(5,6,7,8-tetrafluoronaphthyl)phosphino)perfluoroanthracen-1-yl)(perfluoro-biphenyl)(pentafluoroanthracenyl)(2,3,4-trifluorophenyl)borate]⁻; [tri-N-methylammonium]+[6-((propyl)(perfluorophenyl)amino)perfluoroanthracen-2-yl)(perfluorofluorenyl)(2,3,5-trifluoro-phenyl)(2,3,4-trifluorophenyl)borate]⁻; [N,N,N-(ethyl)(methyl)(isopropyl)ammonium]+[6-((triethylsilylpropyl)(5,6,7,8-tetrafluoronaphthyl)amino)perfluoroinden-2-yl)(perfluorophenyl)-(2',3',4'-trifluorobiphenyl)(pentalfluoropyrenyl)borate]⁻; [tri-N-ethylammonium]+[7-((hexyl)-(tetrafluorofluorenyl)amino)perfluoroanpth-1-yl)(perfluorobiphenyl)(perfluorofluorenyl)(2',3',5'-trifluorobiphenyl)borate]⁻; [tri-N-(dimethylphenylammonium]+[6-((3-ethylnonyl)(2',3',5'-tri-fluorobiphenyl)arsino)perfluoroinden-2-yl)(2,3,6-trifluorophenyl)(perfluorophenyl)(5,6,7,8-tetrafluoronaphthyl)borate]⁻; [tri-N-octylammonium]+[5-((n-butyl)(perfluoronaphthyl)amino)per-fluoronapth-3-yl)(2',3',5'-trifluorobiphenyl)(perfluorobiphenyl)(perfluorophenyl)borate]⁻; [N,N,N-(dimethyl)(t-butyl)ammonium]+[6-((isopropyl)(pentafuoroanthracenyl)amino)perfluoronapth-2-yl)(perfluorobiphenyl)(2',3',5'-trifluorobiphenyl)(perfluorophenyl)borate]⁻; [N,N,N-(dimethyl)(t-butyl)ammonium]+[5-((tri-isopropylsilyloctyl)(perfluorobiphenyl)amino)perfluoroinden-1-yl)(per-fluoroanthracenyl)(2',3',4'-trifluorobiphenyl)(perfluorobiphenyl)borate]⁻; [tri-N-(methylphenyl)-ammonium]+[4-((cyclohexyl)(perfuorofuorenyl)amino)perfuorophenyl)(4,5,7-trifluoro-naphthyl)(perfluorophenyl)(2,3,4-trifluorophenyl)borate]⁻; [tri-N-(dimethylphenyl-ammonium]+[3'-((trimethylsilyl)(4,5,6,7-tetrafluoronaphthyl)amino)perfuorobiphen-4-yl)(per-fluorophenyl)(pentafluoroanthracenyl)(perfluoropyrenyl)borate]⁻; [tri-N-(methylphenyl)-ammonium]+[7-((triethylsilyl)(2,3,5-trifluorophenyl)arsino)perfluorofluoren-1-yl)(perfluoro-phenyl)(2',3',4'-trifluorobiphenyl)(2,3,5-trifluorophenyl)borate]⁻; [tri-N-methylammonium]+[8-((trimethylsilyl)(4,5,6,7-tetrafluoronaphthyl)amino)perfluoropyren-2-yl)(perfluorobiphenyl)-(4,5,6,7-tetrafluoronaphthyl)(2,3,5-trifluorophenyl)borate]⁻; [tri-N-(n-butyl)ammonium]+[5-((cyclohexyl)(2',3',4'-trifluorobiphenyl)arsino)perfluoronapth-1-yl)(perfluoropyrenyl)(5,6,7,8-tetrafluoronaphthyl)(2,3,5-trifluorophenyl)borate]⁻; [tri-N-octylammonium]+[4'-((n-butyl)(2,3,5-trifluorophenyl)amino)perfluorobiphen-4-yl)(perfluoroanthracenyl)(2,3,6-trifluorophenyl)(per-fluorobiphenyl)borate]⁻; [tri-N-octylammonium]+[7-((nonyl)(perfluorofluorenyl)amino)perfluoro-napth-3-yl)(perfluorofluorenyl)(5,6,7,8-tetrafluoronaphthyl)(perfluoropyrenyl)borate]⁻; [tri-N-(dimethylphenylammonium]+[7-((methylethylhexylsilyl)(2',3',5'-trifluorobiphenyl)phosphino)per-fluoronapth-3-yl)(pentafluoroanthracenyl)(perfluorophenyl)(5,6,7,8- tetrafluoronaphthyl)borate]⁻; [tri-N-(n-butyl)ammonium]+[7-((trimethylsilyl)(perfluorophenyl)amino)perfluoronaphth-2-yl)-(pentafluoroanthracenyl)(perfluorofluorenyl)(perfluorophenyl)borate]⁻; [N,N,N-(ethyl)(methyl)-(n-butyl)ammonium]+[7-((tri-n-propylsilyl)(5,6,7,8-tetrafluoronaphthyl)phosphino)perfluoro-pyren-2-yl)(perfluoroanthracenyl)(2',3',5'-trifluorobiphenyl)(perfluoropyrenyl)borate]⁻; [tri-N-(n-butyl)ammonium]+[7-((propyl)(perfluoroanthracenyl)amino)perfluoropyren-1-yl)(perfluoro-naphthyl)(tetrafluorofluorenyl)(pentalfluoropyrenyl)borate]⁻; [N,N,N-(dimethyl)(t-butyl)-ammonium]+[4-((triethylsilylpropyl)(perfluorobiphenyl)amino)perfluorophenyl)(perfluoro-fluorenyl)(perfluoropyrenyl)(2,3,5-trifluorophenyl)borate]⁻; [tri-N-(t-butyl)ammonium]+[7-((cyclohexyl)(pentafluoroanthracenyl)amino)fluoropyren-1-yl)(pentalfluoropyrenyl)(2',3',5'-tri-fluorobiphenyl)(perfluoronaphthyl)borate]⁻; [N,N,N-(dimethyl)(t-butyl)ammonium]+[4'-((3-ethyl-nonyl)(perfluorobiphenyl)amino)perfluorobiphen-3-yl)(tetrafluorofluorenyl)(5,6,7,8-tetrafluoro-naphthyl)(2,3,6-trifluorophenyl)borate]⁻; [tri-N-ethylammonium]+[8-((ethyl)(perfluoronaphthyl)-amino)perfluoropyren-2-yl)(4,5,7-trifluoronaphthyl)(4,5,6,7-tetrafluoronaphthyl)(tetrafluoro-fluorenyl)borate]⁻; [tri-N-(methylphenyl)ammonium]+[7-((triethylsilylethyl)(tetrafluoro-fluorenyl)phosphino)perfluorofluoren-2-yl)(perfluoronaphthyl)(2',3',5'-trifluorobiphenyl)(per-fluorobiphenyl)borate]⁻; [tri-N-octylammonium]+[6-((3-ethylnonyl)(pentalfluoropyrenyl)amino)-perfluoronapth-2-yl)(perfluoropyrenyl)(perfluorobiphenyl)(pentafluoroanthracenyl)borate]⁻; [N,N,N-(ethyl)(dioctyl)ammonium]+[7-((tri-isopropylsilyl)(perfluorobiphenyl)phosphino)per-fluoroanthracen-1-yl)(perfluorobiphenyl)(4,5,6,7-tetrafluoronaphthyl)(4,5,7-trifluoronaphthyl)-borate]⁻; [N,N,N-(ethyl)(methyl)(octyl)ammonium]+[7-((hexyl)(perfluoronaphthyl)amino)per-fluoronapth-3-yl)bis(perfluoronaphthyl)(2,3,6-trifluorophenyl)borate]⁻; [tri-N-ethyl-ammonium]+[4-((tri-isopropylsilyloctyl)(perfluorophenyl)phosphino)perfluorophenyl)-(pentafluoroanthracenyl)(perfluorobiphenyl)(perfluorophenyl)borate]⁻; [N,N,N-(ethyl)(methyl)-(isopropyl)ammonium]+[5-((isopropyl)(perfluorobiphenyl)phosphino)perfluoronapth-3-yl)(per-fluoropyrenyl)(4,5,6,7-tetrafluoronaphthyl)(5,6,7,8-tetrafluoronaphthyl)borate]⁻; [tri-N-octyl-ammonium]+[7-((tri-n-propylsilylhexyl)(perfluorobiphenyl)amino)perfluoronapth-2-yl)(perfluoro-biphenyl)(perfluorofluorenyl)(pentalfluoropyrenyl)borate]⁻; [tri-N-(dimethylphenyl-ammonium]+[7-((tri-isopropylsilyloctyl)(4,5,6,7-tetrafluoronaphthyl)amino)perfluoronapth-1-yl)-(perfluoronaphthyl)(4,5,7-trifluoronaphthyl)(perfluorobiphenyl)borate]⁻; [N,N,N-(ethyl)(methyl)-(t-butyl)ammonium]+[5-((octyl)(4,5,6-trifluoronaphthyl)phosphino)perfluoroinden-1-yl)(per-fluorofluorenyl)(perfluoroanthracenyl)(pentafluoroanthracenyl)borate]⁻; [tri-N-octyl-ammonium]+[6-((tri-n-propylsilyl)(perfluorophenyl)amino)fluoronapth-2-yl)(perfluorophenyl)-(2,3,4-trifluorophenyl)(perfluorobiphenyl)borate]⁻; [tri-N-methylammonium]+[6-((tri-isopropyl-silyl)(4,5,7-trifluoronaphthyl)phosphino)perfluoroanthracen-1-yl)(perfluoroanthracenyl)(per-fluorobiphenyl)(perfluoropyrenyl)borate]⁻; [N,N,N-(ethyl)(methyl)(octyl)ammonium]+[7-((tri-n-propylsilyl)(pentalfluoropyrenyl)phosphino)perfluoronapth-2-yl)(perfluoropyrenyl)(perfluoro-biphenyl)(2,3,4-trifluorophenyl)borate]⁻; [tri-N-(n-butyl)ammonium]+[6-((tri-n-propylsilylhexyl)-(pentalfluoropyrenyl)amino)fluoronapth-2-yl)(perfluorophenyl)(4,5,7-trifluoronaphthyl)(per-fluorofluorenyl)borate]⁻; [tri-N-(methylphenyl)ammonium]+[7-((2,2-dimethyloctyl)(perfluoro-phenyl)amino)perfluoropyren-2-yl)(perfluorofluorenyl)(perfluorobiphenyl)(perfluorobiphenyl)-borate]⁻; [tri-N-(t-butyl)ammonium]+[6-((hexyl)(4,5,7-trifluoronaphthyl)amino)perfluoroinden-2-yl)(perfluoronaphthyl)(4,5,7-trifluoronaphthyl)(perfluorofluorenyl)borate]⁻; [N,N,N-(ethyl)-(methyl)(octyl)ammonium]+[6-((propyl)(perfluorobiphenyl)amino)perfluoroinden-2-yl)(perfuoro-naphthyl)(2',3',4'-trifluorobiphenyl)(2,3,6-trifluorophenyl)borate]⁻; [N,N,N-(ethyl)(methyl)(octyl)-ammonium]+[7-((tri-n-propylsilylhexyl)(2,3,5-trifluorophenyl)amino)perfluoronapth-1-yl)bis(per-fluoroanthracenyl)(4,5,7-trifluoronaphthyl)borate]⁻; [tri-N-(dimethylphenylammonium]+[7-((trimethylsilyl)(perfluoronaphthyl)phosphino)perfluorofluoren-2-yl)bis(perfluoroanthracenyl)-(2,3,6-trifluorophenyl)borate]⁻; [tri-N-methylammonium]+[6-((isopropyl)(pentalfluoro-pyrenyl)phosphino)perfluoroanthracen-1-yl)(tetrafluorofluorenyl)(perfluorobiphenyl)(4,5,6,7-tetrafluoronaphthyl)borate]⁻; [N,N,N-(dimethyl)(t-butyl)ammonium]+[2'-((isopropyl)(perfluoro-phenyl)arsino)perfluorobiphen-4-yl)(perfluoropyrenyl)(2,3,5-trifluorophenyl)(perfluorophenyl)-borate]⁻; [tri-N-(n-butyl)ammonium]+[5-((hexyl)(2,3,6-trifluorophenyl)phosphino)fluoroinden-1-yl)(perfluorophenyl)(perfluoronaphthyl)(5,6,7,8-tetrafluoronaphthyl)borate]⁻; [tri-N-ethyl-ammonium]+[3'-((butyl)(perfluorobiphenyl)amino)perfluorobiphen-4-yl)(pentalfluoropyrenyl)-(perfluorobiphenyl)(pentafluoroanthracenyl)borate]⁻; [N,N,N-(ethyl)(methyl)(isopropyl)-ammonium]+[6-((methyldiethylsilyloctyl)(perfluorobiphenyl)phosphino)perfluorofluoren-1-yl)-(perfluorophenyl)(2',3',4'-trifluorobiphenyl)(perfluorobiphenyl)borate]⁻; [tri-N-(n-butyl)-ammonium]+[7-((triethylsilyl)(perfluorobiphenyl)amino)perfluoroanthracen-1-yl)(perfluoro-anthracenyl)(2',3',5'-trifluorobiphenyl)(perfluoropyrenyl)borate]⁻; [tri-N-octylammonium]+[4-((methylethylhexylsilyl)(perfluoroanthracenyl)amino)fluorophen-1-yl)(perfluorofluorenyl)-(pentafluoroanthracenyl)(perfluorophenyl)borate]⁻; [N,N,N-(ethyl)(methyl)(isopropyl)-ammonium]+[8-((methyldiethylsilyloctyl)(4,5,6,7-tetrafluoronaphthyl)amino)perfluoropyren-2-yl)(perfluoronaphthyl)(5,6,7,8-tetrafluoronaphthyl)(pentafluoroanthracenyl)borate]⁻; [tri-N-octyl-ammonium]+[4'-((octyl)(5,6,7,8-tetrafluoronaphthyl)amino)perfluorobiphen-4-yl)(pentalfluoro-pyrenyl)(2,3,6-trifluorophenyl)(2,3,5-trifluorophenyl)borate]⁻; [tri-N-(t-butyl)ammonium]+[5-((tri-n-propylsilylhexyl)(perfluorophenyl)arsino)perfluoroinden-2-yl)(tetrafluorofluorenyl)(perfluoro-pyrenyl)(5,6,7,8-tetrafluoronaphthyl)borate]⁻; [N,N,N-(dimethyl)(t-butyl)ammonium]+[7-((nonyl)(2',3',5'-trifluorobiphenyl)amino)perfluoronapth-2-yl)(perfluoroanthracenyl)(5,6,7,8-tetrafluoronaphthyl)(perfluorobiphenyl)borate]⁻; [tri-N-methylammonium]+[6-((tri-n-propylsilyl)-(perfluorobiphenyl)amino)perfluoronaphth-2-yl)(perfluorophenyl)(perfluoronaphthyl)(4,5,6-tri-fluoronaphthyl)borate]⁻; [tri-N-(methylphenyl)ammonium]+[8-((isopropyl)(perfluorophenyl)-amino)perfluoropyren-2-yl)(perfluorofluorenyl)(tetrafluorofluorenyl)(4,5,6-trifluoronaphthyl)-borate]⁻; [tri-N-propylammonium]+[7-((propyl)(perfluoropyrenyl)arsinosperfluoropyren-1-yl)bis(perfluorobiphenyl)(2,3,5-trifluorophenyl)borate]⁻; [tri-N-(methylphenyl)ammonium]+[5-((diethylnonlysilyl)(perfluorobiphenyl)amino)perfluoroinden-1-yl)(tetrafluorofluorenyl)(perfluoronaphthyl)(perfluorobiphenyl)borate]⁻; [tri-N-(methylphenyl)ammonium]+[7-((tri-isopropylsilyl)-(perfluorophenyl)phosphino)perfluoronapth-2-yl)(perfluorophenyl)(pentalfluoropyrenyl)(2,3,5-trifluorophenyl)borate]⁻; [N,N,N-(ethyl)(dioctyl)ammonium]+[7-((tri-isopropylsilyloctyl)(perfluoroanthracenyl)amino)perfluoropyren-2-yl)bis(4,5,6,7-tetrafluoronaphthyl)(2,3,6-trifluoro-phenyl)borate]⁻; [tri-N-methylammonium]+[7-((tri-isopropylsilyl)(perfluorophenyl)amino)per-fluoronapth-2-yl)(perfluoropyrenyl)(2,3,6-trifluorophenyl)(tetrafluorofluorenyl)borate]⁻; [N,N,N-(ethyl)(methyl)(octyl)ammonium]+[6-((n-butyl)(perfluorophenyl)phosphino)perfluorofluoren-1-yl)(pentafluoropyrenyl)(perfluoroanthracenyl)(4,5,7-trifluoronaphthyl)borate]⁻; [N,N-(diethyl-anilinium]+[5-((n-butyl)(perfluorophenyl)phosphino)perfluoronapth-3-yl)(perfluorofuorenyl)-(pentafluoroanthracenyl)(2',3',4'-trifluorobiphenyl)borate]⁻; [N-methyl-N-dodecylanilinium]+[3-((methyl)(perfluorophenyl)amino)perfluorophenyl)bis(2,3,6-trifluorophenyl)(perfluorophenyl)-borate]⁻; [N,N-dimethylanilinium]+[3'-((hexyl)(pentafluoroanthracenyl)amino)perfluorobiphen-4-yl)(perfluorophenyl)(2',3',4'-trifluorobiphenyl)(perfluorobiphenyl)borate]⁻; [N,N-di(dodecyl)-anilinium]+[6-((tri-isopropylsilyl)(pentafluoroanthracenyl)amino)perfluorofluoren-1-yl)(perfluoro-biphenyl)(2,3,6-trifluorophenyl)(tetrafluorofluorenyl)borate]⁻; [N,N-2,4,6,-pentamethyl-anilinium]+[6-((triethylsilylethyl)(2,3,4-trifluorophenyl)amino)perfluoroinden-2-yl)(pentalfluoro-pyrenyl)(perfluoroanthracenyl)(2',3',5'-trifluorobiphenyl)borate]⁻; [N,N-dimethylanilinium]+[3'-((tri-n-propylsilylhexyl)(perfluorophenyl)arsino)perfluorobiphen-4-yl)bis(2,3,4-trifluorophenyl)-(tetrafluorofluorenylborate]⁻; [N,N-diethylanilinium]+[7-((nonyl)(perfluorofluorenyl)amino)per-fluorofluoren-2-yl)(tetrafluorofluorenyl)(perfluorobiphenyl)(4,5,6,7-tetrafluoronaphthyl)borate]⁻; [N,N-di(dodecyl)anilinium]+[8-((benzyl)(2',3',4'-trifluorobiphenyl)amino)perfluoronapth-3-yl)bis(perfluoroanthracenyl)(4,5,6,7-tetrafluoronaphthyl)borate]⁻; [N,N-diethylanilinium]+[5-((3-ethylnonyl)(perfluorobiphenyl)amino)perfluoronapth-2-yl)bis(2,3,4-trifluorophenyl)(2,3,6-tri-fluorophenyl)borate]⁻; [N,N-2,4,6,-pentamethylanilinium]+[4'-((triethylsilylpropyl)(perfluoro-phenyl)phosphino)perfluorobiphen-3-yl)(perfluorophenyl)(perfluorobiphenyl)(perfluoro-anthracenyl)borate]⁻; [N,N-dimethylanilinium]+[5-((diethylnonlysilyl)(perfluorobiphenyl)arsino)-perfluoronapth-3-yl)bis(perfluorobiphenyl)(perfluorofluorenyl)borate]⁻; [N,N-2,4,6,-pentamethylanilinium]+[3-((isopropyl)(4,5,6,7-tetrafluoronaphthyl)phosphino)perfluorophenyl)(per-fluorophenyl)(perfluorofluorenyl)(2,3,6-trifluorophenyl)borate]⁻; [N,N-di(dodecyl)anilinium]+[4-((tri-n-propylsilyl)(perfluorobiphenyl)amino)fluorophen-1-yl)(perfluoroanthracenyl)(2,3,5-tri-fluorophenyl)(2,3,6-trifluorophenyl)borate]⁻; [N,N-2,4,6,-pentamethylanilinium]+[7-((ethyl)(per-fluorobiphenyl)amino)perfluoroanthracen-1-yl)(perfluorofluorenyl)(perfluorobiphenyl)(2,3,6-tri-fluorophenyl)borate]⁻; [N,N-dimethylanilinium]+[5-((n-butyl)(perfluorophenyl)amino)fluoro-inden-2-yl)(5,6,7,8-tetrafluoronaphthyl)(perfluorophenyl)(perfluoronaphthyl)borate]⁻; [N-methyl-N-dodecylanilinium]+[7-((isopropyl)(4,5,6-trifluoronaphthyl)arsino)fluoronapth-3-yl)bis(pentalfluoropyrenyl)(perfluoronaphthyl)borate]⁻; [N,N-diethylanilinium]+[7-((benzyl)-(4,5,6,7-tetrafluoronaphthyl)amino)perfluoropyren-2-yl)(pentalfluoropyrenyl)(4,5,6,7-tetrafluoro-naphthyl)(perfluoropyrenyl)borate]⁻; [N-methyl-N-dodecylanilinium]+[5-((isopropyl)(4,5,6-tri-fluoronaphthyl)amino)perfluoronapth-3-yl)(perfluorophenyl)(2,3,4-trifluorophenyl)(2',3',4'-tri-fluorobiphenyl)borate]⁻; [N-methyl-N-dodecylanilinium]+[7-((triethylsilylpropyl)(4,5,6-trifluoro-naphthyl)phosphino)perfluoroinden-2-yl)(pentalfluoropyrenyl)(pentafluoroanthracenyl)(per-fluorobiphenyl)borate]⁻; [N,N-diethylanilinium]+[6-((tri-isopropylsilyloctyl)(perfluoro-biphenyl)phosphino)perfluoroanthracen-1-yl)(tetrafluorofluorenyl)(perfluorobiphenyl)-(pentalfluoropyrenyl)borate]⁻; [N,N-diethylanilinium]+[4'-((isopropyl)(perfluorofluorenyl)amino)-fluorobiphen-4-yl)(perfluorophenyl)(pentalfluoropyrenyl)(2,3,5-trifluorophenyl)borate]⁻; [N-methyl-N-dodecylanilinium]+[7-((2,2-dimethyloctyl)(perfluorophenyl)phosphino)perfluoro-fluoren-1-yl)(5,6,7,8-tetrafluoronaphthyl)(4,5,7-trifluoronaphthyl)(perfluorophenyl)borate]⁻; [N,N-diethylanilinium]+[4-((tri-n-propylsilylhexyl)(2,3,4-trifluorophenyl)arsino)perfluorophenyl)-(perfluorophenyl)(pentalfluoropyrenyl)(4,5,6-trifluoronaphthyl)borate]⁻; [N-methyl-N-dodecyl-anilinium]+[7-((trimethylsilyl)(4,5,7-trifluoronaphthyl)amino)perfluoro-pyren-1-yl)(perfluoro-pyrenyl)(perfluoronaphthyl)(perfluorophenyl)borate]⁻; [N,N-dimethylanilinium]+[7-((triethylsilyl)-(perfluorobiphenyl)phosphino)perfluorofluoren-2-yl)(perfluoronaphthyl)(5,6,7,8-tetrafluoro-naphthyl)(perfluorobiphenyl)borate]⁻; [N-methyl-N-dodecylanilinium]+[7-((methylethylhexyl-silyl)(pentalfluoropyrenyl)arsino)perfluoronapth-1-yl)(perfluoroanthracenyl)(perfluorophenyl)-(tetrafluorofluorenyl)borate]⁻; [N,N-dimethylanilinium]+[5-((methylethylhexylsilyl)(pentalfluoro-pyrenyl)phosphino)fluoronapth-2-yl)(perfluorofluorenyl)(4,5,7-trifluoronaphthyl)(4,5,6,7-tetrafluoronaphthyl)borate]⁻; [N,N-dimethylanilinium]+[5-((octyl)(perfluorophenyl)phosphino)-perfluoroinden-1-yl)(pentafluoroanthracenyl)(2,3,5-trifluorophenyl)(tetrafluorofluorenyl)borate]⁻; [N,N-2,4,6,-pentamethylanilinium]+[7-((cyclohexyl)(perfluorophenyl)phosphino)perfluoro-fluoren-1-yl)(perfluorobiphenyl)(pentalfluoropyrenyl)(4,5,7-trifluoronaphthyl)borate]⁻; [N-methyl-N-dodecylanilinium]+[6-((2,2-dimethyloctyl)(2,3,4-trifluorophenyl)phosphino)perfluoro-napth-2-yl)bis(perfluoroanthracenyl)(perfluorobiphenylborate]⁻; [N-methyl-N-(dodecyl-anilinium]+[6-((propyl)(perfluorobiphenyl)phosphino)perfluorofluoren-2-yl)bis(perfluoro-biphenyl)(2,3,5-trifluorophenyl)borate]⁻; [N,N-diethylanilinium]+[7-((3-ethylnonyl)(perfluoro-fluorenyl)amino)perfluoroanthracen-1-yl)(perfluoroanthracenyl)(perfluorofluorenyl)(pentafluoro-anthracenyl)borate]⁻; [N-methyl-N-dodecylanilinium]+[5-((trimethylsilyl)(2',3',5'-trifluoro-biphenyl)amino)perfluoroinden-2-yl)(perfluoroanthracenyl)(perfluorophenyl)(tetrafluoro-fluorenyl)borate]⁻; [N,N-diethylanilinium]+[5-((nonyl)(perfluorophenyl)phosphino)perfluoro-naphth-1-yl)(perfluorophenyl)(perfluoroanthracenyl)(4,5,7-trifluoronaphthyl)borate]⁻; [N,N-di(dodecyl)anilinium]+[8-((cyclohexyl)(perfluoropyrenyl)phosphino)perfluoronapth-3-yl)(2,3,5-trifluorophenyl)(pentalfluoropyrenyl)(perfluorophenyl)borate]⁻; [N-methyl-4-dodecyl-anilinium]+[7-((triethylsilylpropyl)(perfluoronaphthyl)phosphino)fluoronapth-2-yl)(perfluoro-biphenyl)(2',3',4'-trifluorobiphenyl)(perfluorophenyl)borate]⁻; [N,N-dimethylanilinium]+[6-((triethylsilylethyl)(4,5,7-trifluoronaphthyl)amino)perfluoroanthracen-2-yl)

(pentalfluoropyrenyl)-(tetrafluorofluorenyl)(pentafluoroanthracenyl)borate]⁻; [N,N-diethylanilinium]+[6-((propyl)(per-fluorophenyl)amino)perfluoroinden-2-yl)(4,5,7-trifluoronaphthyl)(perfluorofluorenyl)(4,5,6-trifluoronaphthyl)borate]⁻; [N,N-dimethylanilinium]+[7-((trimethylsilyl)(perfluorobiphenyl)amino)-perfluoronapth-1-yl)(perfluoropyrenyl)(4,5,7-trifluoronaphthyl)(2,3,5-trifluorophenyl)borate]⁻; [N,N-dimethylanilinium]+[7-((isopropyl)(pentalfluoropyrenyl)phosphino)perfluoronapth-1-yl)bis(pentalfluoropyrenyl)(tetrafluorofluorenylborate]⁻; [N,N-diethylanilinium]+[7-((butyl)(per-fluorophenyl)amino)perfluorofluoren-1-yl)(perfluoroanthracenyl)(2',3',5'-trifluorobiphenyl)(perfluorophenyl)borate]⁻; [N,N-dimethylanilinium]+[5-(diethylnonlysilyl)(perfluorobiphenyl)amino)-perfluoroinden-1-yl)(4,5,7-trifluoronaphthyl)(perfluorobiphenyl)(5,6,7,8-tetrafluoronaphthyl)-borate]⁻; [N-methyl-N-dodecylanilinium]+[6-((tri-n-propylsilylhexyl)(perfluorobiphenyl)phos-phino)perfluoroanthracen-2-yl)(perfluorobiphenyl)(perfluorophenyl)(pentalfluoropyrenyl)-borate]⁻; [N,N-dimethylanilinium]+[6-((tri-n-propylsilyl)(perfluorobiphenyl)amino)perfluoro-naphth-3-yl)(pentalfluoropyrenyl)(perfluorobiphenyl)(2',3',4'-trifluorobiphenyl)borate]⁻; [N,N-dimethylanilinium]+[6-((methyl)(perfluorofluorenyl)amino)perfluoroinden-2-yl)(perfluoro-biphenyl)(2,3,6-trifluorophenyl)(perfluorofluorenyl)borate]⁻; [N,N-diethylanilinium]+[6-((ethyl)-(perfluorobiphenyl)phosphino)perfluoronapth-1-yl)(perfluorobiphenyl)(2',3',5'-trifluorobiphenyl)-(4,5,6,7-tetrafluoronaphthyl)borate]⁻; [N,N-2,4,6,-pentamethylanilinium]+[7-((methylethylhexyl-silyl)(perfluorophenyl)amino)perfluoroanthracen-1-yl)bis(perfluorobiphenyl)(perfluoro-anthracenyl)borate]⁻; [N,N-diethylanilinium]+[2'-((benzyl)(perfluorobiphenyl)phosphino)per-fluorobiphen-4-yl)(perfluoroanthracenyl)(perfluorobiphenyl)-4,5,6,7-tetrafluoronaphthyl) borate]⁻; [N-methyl-N-dodecylanilinium]+[4'-((2,2-dimethyloctyl)(4,5,7-trifluoronaphthyl)amino)perfluoro-biphen-3-yl)(2,3,5-trifluorophenyl)(perfluoronaphthyl)(perfluorofluorenyl)borate]⁻; [N,N,N-(ethyl)(methyl)(octyl)phosphonium]+[8-((octyl)(perfluorofluorenyl)arsino)perfluoronapth-3-yl)-(tetrafluorofluorenyl)(perfluorophenyl)(4,5,7-trifluoronaphthyl)borate]⁻; [N,N,N-(ethyl)(methyl)-(n-butyl)phosphonium]+[5-((2,2-dimethyloctyl)(2,3,6-trifluorophenyl)phosphino)perfluoroinden-1-yl)(perfluorobiphenyl)(4,5,6-trifluoronaphthyl)(pentafluoroanthracenyl)borate]⁻; [tri-N-propyl-phosphonium]+[5-((octyl)(pentafluoroanthracenyl)amino)perfluoroinden-1-yl)(2,3,6-trifluoro-phenyl)(4,5,6-trifluoronaphthyl)(perfluorofluorenyl)borate]⁻; [N,N,N-(ethyl)(methyl)(isopropyl)-phosphonium]+[3-((nonyl)(perfluorophenyl)amino)perfluorophenyl)(4,5,7-trifluoronaphthyl)(per-fluorophenyl)(perfluoropyrenyl)borate]⁻; [N,N,N-(dimethyl)(t-butyl)phosphonium]+[7-((3-ethyl-nonyl)(perfluorophenyl)amino)fluoronapth-3-yl)(perfluorobiphenyl)(2,3,5-trifluorophenyl)(per-fluorophenyl)borate]⁻; [tri-N-(n-butyl)phosphonium]+[7-((triethylsilyl)(perfluorophenyl)phos-phino)perfluoroanthracen-1-yl)(perfluoronaphthyl)(2',3',5'-trifluorobiphenyl)(perfluorofluorenyl)-borate]⁻; [tri-N-(dimethylphenyl)phosphonium]+[8-((diethylnonlysilyl)(perfluorophenyl)amino)-perfluoropyren-2-yl)bis(perfluorophenyl)(perfluoropyrenyl)borate]⁻; [N,N,N-(ethyl)-(methyl)(t-butyl)phosphonium]+[7-((3-ethylnonyl)(2,3,6-trifluorophenyl)amino)perfluoropyren-2-yl)(5,6,7,8-tetrafluoronaphthyl)(2,3,6-trifluorophenyl)(4,5,6-trifluoronaphthyl)borate]⁻; [tri-N-ethylphosphonium]+[5-((tri-isopropylsilyl)(perfluoronaphthyl)arsino)perfluoroinden-1-yl)(4,5,6-trifluoronaphthyl)(2,3,5-trifluorophenyl)(5,6,7,8-tetrafluoronaphthyl)borate]⁻; [N,N,N-(dimethyl)-(t-butyl)phosphonium]+[6-((triethylsilyl)(pentafluoroanthracenyl)amino)perfluoronapth-3-yl)(perfluoropyrenyl)(perfluorophenyl)(5,6,7,8-tetrafluoronaphthyl)borate]⁻; [tri-N-(methylphenyl)-phosphonium]+[3-((benzyl)(4,5,6-trifluoronaphthyl)amino)perfluorophenyl)(2,3,5-trifluoro-phenyl)(4,5,6-trifluoronaphthyl)(perfluorobiphenyl)borate]⁻; [tri-N-ethylphosphonium]+[6-((2,2-dimethyloctyl)(perfluorophenyl)amino)perfluoronapth-2-yl)(perfluoropyrenyl)(2,3,5-trifluoro-phenyl)(4,5,7-trifluoronaphthyl)borate]⁻; [N,N,N-(ethyl)(methyl)(isopropyl)phosphonium]+[6-((hexyl)(perfluoroanthracenyl)amino)perfluorofluoren-2-yl)(tetrafluorofluorenyl)(perfluoro-anthracenyl)(perfluoronaphthyl)borate]⁻; [tri-N-(dimethylphenyl)phosphonium]+[7-((tri-iso-propylsilyl)(perfluorofluorenyl)amino)perfluoroinden-2-yl)(4,5,6-trifluoronaphthyl)(perfluoro-biphenyl)(perfluoroanthracenyl)borate]⁻; [N N,N-(ethyl)(dioctyl)phosphonium]+[5-((tri-iso-propylsilyloctyl)(perfluoroanthracenyl)phosphino)perfluoronapth-3-yl)(4,5,7-trifluoronapththyl)-(perfluoropyrenyl)(perfluorobiphenyl)borate]⁻; [tri-N-octylphosphonium]+[6-((3-ethylnonyl)-(perfluoropyrenyl)amino)perfluorofluoren-1-yl)bis(4,5,6-trifluoronaphthyl)(2',3',4'-trifluoro-biphenylborate]⁻; [tri-N-propylphosphonium]+[5-((methyl)(4,5,6,7-tetrafluoronaphthyl)amino)-perfluoroinden-1-yl)bis(2',3',5'-trifluorobiphenyl)(2,3,5-trifluorophenylborate]⁻; [N,N,N-(dimethyl)(t-butyl)phosphonium]+[5-((tri-n-propylsilylhexyl)(5,6,7,8-tetrafluoronaphthyl)phos-phino)fluoronapth-1-yl)(pentalfluoropyrenyl)(perfluoroanthracenyl)(4,5,7-trifluoronaphthyl)-borate]⁻; [tri-N-ethylphosphonium]+[7-((tri-isopropylsilyl)(perfluorofluorenyl)amino)perfluoro-fluoren-1-yl)(perfluorophenyl)(perfluoropyrenyl)(tetrafluorofluorenyl)borate]⁻; [N,N,N-(ethyl)-(dioctyl)phosphonium]+[5-((propyl)(perfluoronaphthyl)amino)perfluoroinden-1-yl)(perfluoro-fluorenyl)(2',3',5'-trifluorobiphenyl)(2,3,4-trifluorophenyl)borate]⁻; [tri-N-propyl-phosphonium]+[5-((cyclohexyl)(perfluorobiphenyl)amino)perfluoroinden-1-yl)(4,5,6-trifluoro-naphthyl)(4,5,7-trifluoronaphthyl)(perfluoropyrenyl)borate]⁻; [N,N,N-(ethyl)(methyl)(n-butyl)-phosphonium]+[6-((propyl)(2,3,6-trifluorophenyl)arsino)perfluoroanthracen-1-yl)(perfluoro-anthracenyl)(perfluorophenyl)(4,5,6,7-tetrafluoronaphthyl)borate]⁻; [tri-N-octyl-phosphonium]+[5-((tri-isopropylsilyloctyl)(perfluoropyrenyl)phosphino)perfluoronapth-1-yl)(per-fluorophenyl)(2,3,6-trifluorophenyl)(4,5,6,7-tetrafluoronaphthyl)borate]⁻; [N,N,N-(ethyl)-(dioctyl)phosphonium]+[5-((cyclohexyl)(perfluoroanthracenyl)amino)perfluoroinden-2-yl)bis(4,5,6-trifluoronaphthyl)(pentalfluoropyrenylborate]⁻; [tri-N-propylphosphonium]+[7-((nonyl)(perfluorophenyl)amino)perfluoroanthracen-1-yl)(4,5,7-trifluoronaphthyl)(perfluoro-naphthyl)(perfluorobiphenyl)borate]⁻; [tri-N-octylphosphonium]+[7-((diethylnonlysilyl)(per-fluoroanthracenyl)arsino)perfluoronapth-1-yl)(pentalfluoropyrenyl)(4,5,7-trifluoronaphthyl)(per-fluoroanthracenyl)borate]⁻; [tri-N-octylphosphonium]+[6-((tri-isopropylsilyloctyl)(perfluoro-phenyl)amino)perfluoronapth-2-yl)(pentaifluoropyrenyl)(4,5,7-trifluoronaphthyl)(perfluoro-phenyl)borate]⁻; [tri-N-(n-butyl)phosphonium]+[7-((tri-isopropylsilyloctyl)(perfluorophenyl)-amino)perfluoroanthracen-1-yl)

(pentafluoroanthracenyl)(4,5,7-trifluoronaphthyl)(perfluoro-phenyl)borate]⁻; [tri-N-propylphosphonium]+[3'-((methylethylhexylsilyl)(perfluorofluorenyl)-amino)perfluorobiphen-4-yl)(pentafluoroanthracenyl)(perfluorobiphthyl)(perfluorophenyl)borate]⁻; [N,N,N-(ethyl)(methyl)(n-butyl)phosphonium]+[5-((triethylsilyl)(perfluorophenyl)-amino)perfluoronapth-2-yl)(2,3,5-trifluorophenyl)(perfluorofluorenyl)(tetrafluorofluorenyl)-borate]⁻; [N,N,N-(ethyl)(methyl)(octyl)phosphonium]+[5-((methyl)(perfluoroanthracenyl)-amino)perfluoronapth-2-yl)(5,6,7,8-tetrafluoronaphthyl)(2,3,5-trifluorophenyl)(4,5,7-trifluoro-naphthyl)borate]⁻; [tri-N-octylphosphonium]+[7-((benzyl)(perfluoropyrenyl)phosphino)fluoro-pyren-2-yl)(perfluoroanthracenyl)(perfluoropyrenyl)(2',3',5'-trifluorobiphenyl)borate]⁻; [N,N,N-(ethyl)(methyl)(n-butyl)phosphonium]+[4'-((cyclohexyl)(perfluorophenyl)amino)perfluorobiphen-3-yl)(perfluorofluorenyl)(perfluoropyrenyl)(2,3,5-trifluorophenyl)borate]⁻; [N,N,N-(ethyl)-(methyl)(isopropyl)phosphonium]+[7-((triethylsilylpropyl)(perfluorobiphenyl)amino)perfluoro-napth-3-yl)(perfluoropyrenyl)(tetrafluorofluorenyl)(pentafluoroanthracenyl)borate]⁻; [N,N,N-(ethyl)(methyl)(t-butyl)phosphonium]+[6-((methyl)(perfluorofluorenyl)phosphino)perfluoro-napth-1-yl)(4,5,6,7-tetrafluoronaphthyl)(perfluorophenyl)(perfluoropyrenyl)borate]⁻; [N,N,N-(ethyl)(methyl)(t-butyl)phosphonium]+[4'-((triethylsilylethyl)(2,3,4-trifluorophenyl)arsino)perfluorobiphen-4-yl)(tetrafluorofluorenyl)(perfluorofluorenyl)(perfluorophenyl)borate]⁻; [N,N,N-(ethyl)(methyl)(isopropyl)phosphonium]+[7-((ethyl)(perfluorobiphenyl)amino)perfluoroinden-2-yl)(5,6,7,8-tetrafluoronaphthyl)(perfluorophenyl)(2',3',4'-trifluorobiphenyl)borate]⁻; [tri-N-(t-butyl)phosphonium]+[7-((methylethylhexylsilyl)(tetrafluorofluorenyl)amino)perfluoronaphth-2-yl)(2',3',5'-trifluorobiphenyl)(perfluorofluorenyl)(2,3,5-trifluorophenyl)borate]⁻; [tri-N-propyl-phosphonium]+[5-((trimethylsilyl)(2,3,4-trifluorophenyl)amino)perfluoronapth-3-yl)(perfluoro-phenyl)(2',3',4'-trifluorobiphenyl)(perfluorobiphenyl)borate]⁻; [tri-N-methylphosphonium]+[3'-((tri-n-propylsilylhexyl)(perfluoropyrenyl)amino)perfluorobiphen-4-yl)(perfluoropyrenyl)(per-fluoroanthracenyl)(perfluorofluorenyl)borate]⁻; [tri-N-ethylphosphonium]+[8-((trimethylsilyl)-(perfluorobiphenyl)amino)fluoropyren-2-yl)bis(perfluoroanthracenyl)(2,3,6-trifluorophenyl)borate]⁻; [tri-N-(methylphenyl)phosphonium]+[7-((tri-isopropylsilyloctyl)(perfluorophenyl)-amino)perfluoroanthracen-1-yl)(perfluoroanthracenyl)(4,5,7-trifluoronaphthyl)(2,3,4-trifluoro-phenyl)borate]⁻; [N,N,N-(ethyl)(methyl)(octyl)phosphonium]+[8-((tri-isopropylsilyl)(perfluoro-biphenyl)arsino)perfluoropyren-2-yl)(perfluorobiphenyl)(2',3',5'-trifluorobiphenyl)(4,5,6-trifluoro-naphthyl)borate]⁻; [tri-N-(methylphenyl)phosphonium]+[6-((methyl)(perfluoropyrenyl)amino)perfluorofluoren-2-yl)(2,3,5-trifluorophenyl)(perfluorofluorenyl)(tetrafluorofluorenyl)borate]⁻; [tri-N-(dimethylphenyl)phosphonium]+[7-((benzyl)(4,5,6-trifluoronaphthyl)amino)perfluoro-fluoren-2-yl)bis(pentafluoroanthracenyl)(perfluoronaphthyl)borate]⁻; [tri-N-(t-butyl)-phosphonium]+[2'-((triethylsilylpropyl)(perfluorophenyl)amino)perfluorobiphen-4-yl)(perfluoro-anthracenyl)(perfluoronaphthyl)(perfluoropyrenyl)borate]⁻; [tri-N-propylphosphonium]+[7-((tri-n-propylsilyl)(perfluoronaphthyl)amino)perfluoroanthracen-1-yl)(perfluoronaphthyl)(4,5,6-tri-fluoronaphthyl)(perfluorophenyl)borate]⁻; [N,N,N-(ethyl)(methyl)(isopropyl)phosphonium]+[5-((triethylsilyl)(pentalfluoropyrenyl)arsino)perfluoronapth-2-yl)(perfluorobiphenyl)(perfluoro-anthracenyl)(2,3,4-trifluorophenyl)borate]⁻; [tri-N-ethylphosphonium]+[4'-((tri-n-propylsilyl)-(4,5,6,7-tetrafluoronaphthyl)amino)perfluorobiphen-3-yl)(perfluoropyrenyl)(4,5,6,7-tetrafluoro-naphthyl)(4,5,7-trifluoronaphthyl)borate]⁻; [N,N,N-(ethyl)(methyl)(t-butyl)phosphonium]+[4'-((methyldiethylsilyloctyl)(pentalfluoropyrenyl)arsino)perfluorobiphen-3-yl)bis(2',3',4'-trifluoro-biphenyl)(perfluorobiphenylborate]⁻; [tri-N-(methylphenyl)phosphonium]+[6-((cyclohexyl)-(5,6,7,8-tetrafluoronaphthyl)amino)perfluoroanthracen-2-yl)(perfluoropyrenyl)(2',3',4'-trifluoro-biphenyl)(perfluorophenyl)borate]⁻; [tri-N-ethylphosphonium]+[7-((triethylsilylpropyl)(perfluoro-phenyl)amino)perfluoronapth-3-yl)(4,5,7-trifluoronaphthyl)(perfluorofluorenyl)(tetrafluoro-fluorenyl)borate]⁻; [N,N,N-(ethyl)(dioctyl)phosphonium]+[5-((methyl)(perfluorophenyl)amino)-perfluoronapth-3-yl)bis(perfluoroanthracenyl)(perfluorobiphenylborate]⁻; [N,N,N-(ethyl)-(methyl)(isopropyl)phosphonium]+[4-((2,2-dimethyloctyl)(perfluorobiphenyl)amino)perfluoro-phenyl)(2',3',4'-trifluorobiphenyl)(perfluorofluorenyl)(4,5,6,7-tetrafluoronaphthyl)borate]⁻; [N,N,N-(ethyl)(methyl)(n-butyl)phosphonium]+[3'-((triethylsilylpropyl)(perfluorobiphenyl)-amino)perfluorobiphen-4-yl)(perfluorobiphenyl)(4,5,6,7-tetrafluoronaphthyl)(pentafluoro-pyrenyl)borate]⁻; [tri-N-ethylphosphonium]+[6-((2,2-dimethyloctyl)(perfluorophenyl)phos-phino)perfluoronapth-1-yl)(perfluorobiphenyl)(perfluoropyrenyl)(4,5,6,7-tetrafluoronaphthyl)-borate]⁻; [N,N,N-(ethyl)(dioctyl)phosphonium]+[6-((butyl)(perfluorophenyl)phosphino)fluoro-fluoren-1-yl)(perfluorophenyl)(4,5,7-trifluoronaphthyl)(perfluoropyrenyl)borate]⁻; [N,N,N-(ethyl)-(dioctyl)phosphonium]+[6-((trimethylsilyl)(pentafluoroanthracenyl)phosphino)perfluoronapth-3-yl)bis(4,5,6-trifluoronaphthyl)(4,5,6,7-tetrafluoronaphthyl)borate]⁻; [N,N,N-(dimethyl)(t-butyl)-phosphonium]+[7-((cyclohexyl)(perfluorobiphenyl)amino)perfluoropyren-1-yl)(perfluoro-biphenyl)(perfluorophenyl)(pentafluoroanthracenyl)borate]⁻; [tri-N-(t-butyl)phosphonium]+[6-((ethyl)(perfluorobiphenyl)amino)perfluoronapth-1-yl)(perfluorofluorenyl)(2',3',4'-trifluoro-biphenyl)(tetrafluorofluorenyl)borate]⁻; [tri-N-(t-butyl)phosphonium]+[5-((tri-isopropylsilyloctyl)-(2,3,6-trifluorophenyl)phosphino)perfluoroinden-2-yl)(2,3,6-trifluorophenyl)(perfluorophenyl)-(4,5,6,7-tetrafluoronaphthyl)borate]⁻; [N,N,N-(ethyl)(methyl)(n-butyl)phosphonium]+[6-((2,2-dimethyloctyl)(perfluoroanthracenyl)arsino)perfluoronapth-2-yl)(perfluorobiphenyl)(perfluoro-phenyl)(2',3',4'-trifluorobiphenyl)borate]⁻; [tri-N-propylphosphonium]+[5-((nonyl)(perfluoro-phenyl)arsino)perfluoronapth-2-yl)(4,5,7-trifluoronaphthyl)(perfluoronaphthyl)(4,5,6,7-tetrafluoronaphthyl)borate]⁻; [tri-N-octylphosphonium]+[6-((hexyl)(perfluoropyrenyl)amino)per-fluorofluoren-1-yl)(perfluorobiphenyl)(pentafluoroanthracenyl)(2,3,6-trifluorophenyl)borate]⁻; [N,N,N-(ethyl)(methyl)(octyl)phosphonium]+[7-((3-ethylnonyl)(perfluorobiphenyl)phosphino)-perfluoronapth-3-yl)(2',3',5'-trifluorobiphenyl)(perfluorobiphenyl)(perfluorophenyl)borate]⁻; [tri-N-(n-butyl)phosphonium]+[3'-((ethyl)(perfluorobiphenyl)amino)perfluorobiphen-4-yl)(perfluoro-naphthyl)(perfluorobiphenyl)(4,5,6,7-tetrafluoronaphthyl)borate]⁻; [tri-N-ethyl-phosphonium]+[3'-((trimethylsilyl)(perfluoroanthracenyl)amino)perfluorobiphen-4-yl)bis(4,5,6,7-tetrafluoronaphthyl)(tetrafluorofluorenyl)borate]⁻;

[N,N,N-(ethyl)(methyl)(isopropyl)-phosphonium]+[3-((propyl)(4,5,7-trifluoronaphthyl)phosphino)perfluorophenyl)(perfluoro-phenyl)(2,3,5-trifluorophenyl)(perfluoronaphthyl)borate]−; [tri-N-propylphosphonium]+[7-((methylethylhexylsilyl)(4,5,6,7-tetrafluoronaphthyl)phosphino)fluoroinden-2-yl)(perfluoro-anthracenyl)(tetrafluorofluorenyl)(5,6,7,8-tetrafluoronaphthyl)borate]−; [tri-N-(dimethylphenyl)-phosphonium]+[4'-((triethylsilylethyl)(perfluorofluorenyl)phosphino)perfluorobiphen-3-yl)-(5,6,7,8-tetrafluoronaphthyl)(perfluorofluorenyl)(perfluorophenyl)borate]−; [tri-N-propyl-phosphonium]+[4'-((triethylsilylpropyl)(2,3,4-trifluorophenyl)amino)perfluorobiphen-4-yl)-(pentalfluoropyrenyl)(perfluorobiphenyl)(5,6,7,8-tetrafluoronaphthyl)borate]−; [N,N,N-(ethyl)-(methyl)(n-butyl)phosphonium]+[7-((diethylnonlysilyl)(perfluorofluorenyl)amino)perfluoronapth-1-yl)(4,5,7-trifluoronaphthyl)(pentalfluoropyrenyl)(perfluorobiphenyl)borate]−; [tri-N-(t-butyl)-phosphonium]+[6-((triethylsilyl)(perfluorofluorenyl)arsino)perfluoroanthracen-1-yl)(perfluorofluorenyl)(perfluorobiphenyl)(perfluoropyrenyl)borate]−; [tri-N-(n-butyl)phosphonium]+[6-((tri-n-propylsilyl)(2',3',4'-trifluorobiphenyl)amino)perfluoroinden-2-yl)bis(perfluoroanthracenyl)(2,3,4-trifluorophenylborate]−; [tri-N-(methylphenyl)phosphonium]+[6-((2,2-dimethyloctyl)(2,3,4-trifluorophenyl)phosphino)perfluoronapth-3-yl)(perfluoroanthracenyl)(2,3,6-trifluorophenyl)-(2,3,4-trifluorophenyl)borate]−; [N,N,N-(ethyl)(methyl)(t-butyl)phosphonium]+[6-((triethylsilyl-ethyl)(perfluorophenyl)phosphino)perfluoroanthracen-1-yl)(perfluoropyrenyl)(4,5,6,7-tetrafluoronaphthyl)(2',3',4'-trifluorobiphenyl)borate]−; [N,N,N-(ethyl)(methyl)(isopropyl)-phosphonium]+[5-((ethyl)(perfluorophenyl)amino)perfluoroinden-2-yl)(tetrafluorofluorenyl)-(5,6,7,8-tetrafluoronaphthyl)(4,5,6-trifluoronaphthyl)borate]−; [tri-N-(n-butyl)phosphonium]+[8-((butyl)(4,5,6,7-tetrafluoronaphthyl)amino)perfluoronapth-3-yl)(perfluorophenyl)(perfluoro-biphenyl)(2',3',5'-trifluorobiphenyl)borate]−; [tri-N-octylphosphonium]+[5-((trimethylsilyl)(perfluorobiphenyl)amino)fluoroinden-2-yl)(perfluorophenyl)(2,3,6-trifluorophenyl)(2,3,5-trifluoro-phenyl)borate]−; [N,N,N-(ethyl)(methyl)(t-butyl)phosphonium]+[4-((isopropyl)(perfluoro-biphenyl)amino)perfluorophenyl)(perfluorophenyl)(4,5,7-trifluoronaphthyl)(2,3,5-trifluoro-phenyl)borate]−; [tri-N-(n-butyl)phosphonium]+[5-((hexyl)(perfluoropyrenyl)amino)perfluoro-inden-2-yl)(5,6,7,8-tetrafluoronaphthyl)(perfluorofluorenyl)(perfluorobiphenyl)borate]−; [tri-N-octylphosphonium]+[5-((triethylsilyl)(perfluoropyrenyl)amino)perfluoronapth-1-yl)(pentafluoroanthracenyl)(perfluorophenyl)(2,3,4-trifluorophenyl)borate]−; [N,N,N-(ethyl)(dioctyl)-phosphonium]+[6-((methylethylhexylsilyl)(perfluorophenyl)amino)fluorofluoren-2-yl)(perfluoro-pyrenyl)(2,3,4-trifluorophenyl)(2',3',4'-trifluorobiphenyl)borate]−; [tri-N-ethylphosphonium]+[7-((tri-isopropylsilyloctyl)(4,5,7-trifluoronaphthyl)phosphino)perfluoroinden-2-yl)(perfluoro-pyrenyl)(perfluorobiphenyl)(tetrafluorofluorenyl)borate]−; [tri-N-methylphosphonium]+[3-((trimethylsilyl)(perfluorofluorenyl)amino)perfluorophenyl)(5,6,7,8-tetrafluoronaphthyl)(per-fluoronaphthyl)(perfluorophenyl)borate]−; [tri-N-(dimethylphenyl)phosphonium]+[6-((2,2-dimethyloctyl)(5,6,7,8-tetrafluoronaphthyl)amino)perfluoronapth-2-yl)(perfluorobiphenyl)(per-fluoropyrenyl)(pentalfluoropyrenyl)borate]−; [tri-N-propylphosphonium]+[5-((methylethylhexyl-silyl)(perfluorobiphenyl)phosphino)perfluoronapth-1-yl)bis(2,3,6-trifluorophenyl)(perfluoro-anthracenyl)borate]−; [N,N,N-(ethyl)(methyl)(t-butyl)phosphonium]+[7-((trimethylsilyl)(per-fluorobiphenyl)amino)perfluorofluoren-2-yl)(5,6,7,8-tetrafluoronaphthyl)(4,5,6-trifluoro-naphthyl)(tetrafluorofluorenyl)borate]−; [tri-N-propylphosphonium]+[8-((triethylsilylethyl)(4,5,7-trifluoronaphthyl)amino)perfluoropyren-2-yl)bis(4,5,6-trifluoronaphthyl)(perfluoronaphthyl)-borate]−; [tri-N-methylphosphonium]+[7-((ethyl)(perfluorobiphenyl)amino)perfluoropyren-1-yl)-(5,6,7,8-tetrafluoronaphthyl)(4,5,7-trifluoronaphthyl)(perfluoronaphthyl)borate]−; [tri-N-ethyl-phosphonium]+[4'-((methyldiethylsilyloctyl)(pentafluoropyrenyl)amino)perfluorobiphen-3-yl)-(pentalfluoropyrenyl)(perfluorophenyl)(4,5,6,7-tetrafluoronaphthyl)borate]−; [tri-N-(t-butyl)-phosphonium]+[6-((nonyl)(perfluorofluorenyl)phosphino)perfluoroanthracen-1-yl)(4,5,7-tri-fluoronaphthyl)(perfluorobiphenyl)(2',3',5'-trifluorobiphenyl)borate]−; [tri-N-propyl-phosphonium]+[7-((2,2-methyloctyl)(perfluorophenyl)amino)perfluoroinden-2-yl)(perfluoro-biphenyl)(2',3',4'-trifluorobiphenyl)(2',3',5'-trifluorobiphenyl)borate]−; [N,N,N-(ethyl)(methyl)(t-butyl)phosphonium]+[6-((methyldiethylsilyloctyl)(5,6,7,8-tetrafluoronaphthyl)phosphino)per-fluoroanthracen-2-yl)(pentalfluoropyrenyl)(perfluorophenyl)(4,5,6,7-tetrafluoronaphthyl)borate]−; [N,N,N-(dimethyl)(t-butyl)phosphonium]+[8-((tri-n-propylsilyl)(perfluorophenyl)amino)per-fluoropyren-2-yl)(tetrafluorofluorenyl)(5,6,7,8-tetrafluoronaphthyl)(4,5,6-trifluoronaphthyl)-borate]−; [N,N,N-(ethyl)(methyl)(isopropyl)phosphonium]+[6-((propyl)(perfluorobiphenyl)phos-phino)perfluoronapth-3-yl)bis(pentafluoroanthracenyl)(perfluorophenylborate]−; [tri-N-(methylphenyl)phosphonium]+[7-((triethylsilylpropyl)(perfluoropyrenyl)arsino)perfluorofluoren-2-yl)(perfluoropyrenyl)(2,3,5-trifluorophenyl)(4,5,7-trifluoronaphthyl)borate]−; [tri-N-(dimethylphenyl)phosphonium]+[5-((cyclohexyl)(4,5,7-trifluoronaphthyl)phosphino)perfluoro-inden-2-yl)(perfluoronaphthyl)(perfluorobiphenyl)(pentalfluoropyrenyl)borate]−; [N,N,N-(ethyl)-(dioctyl)phosphonium]+[2'-((methylethylhexylsilyl)(perfluorobiphenyl)arsino)perfluorobiphen-4-yl)bis(5,6,7,8-tetrafluoronaphthyl)(perfluorophenylborate]−; [tri-N-propylphosphonium]+[7-((tri-isopropylsilyloctyl)(perfluorofluorenyl)phosphino)perfluoroinden-2-yl)(perfluoropyrenyl)(per-fluoroanthracenyl)(2,3,4-trifluorophenyl)borate]−; [tri-N-ethylphosphonium]+[6-((3-ethylnonyl)-(perfluorobiphenyl)amino)perfluorofluoren-2-yl)bis(perfluorobiphenyl)(2',3',5'-trifluorobiphenyl)-borate]−; [N,N,N-(ethyl)(methyl)(n-butyl)phosphonium]+[7-((hexyl)(2',3',4'-trifluorobiphenyl)-amino)perfluoronapth-3-yl)(perfluorophenyl)(pentafluoroanthracenyl)(2,3,5-trifluorophenyl)-borate]−; [N,N,N-(ethyl)(dioctyl)phosphonium]+[4'-((methylethylhexylsilyl)(perfluorophenyl)-amino)perfluorobiphen-4-yl)(perfluorophenyl)(perfluorofluorenyl)(5,6,7,8-tetrafluoronaphthyl)-borate]−; [N,N,N-(ethyl)(dioctyl)phosphonium]+[4'-((nonyl)(perfluoroanthracenyl)arsino)per-fluorobiphen-3-yl)(tetrafluorofluorenyl)(perfluorobiphenyl)(pentalfluoropyrenyl)borate]−; [tri-N-(dimethylphenyl)phosphonium]+[4'-((propyl)(perfluorobiphenyl)amino)perfluorobiphen-4-yl)-(perfluorobiphenyl)(perfluorophenyl)(pentalfluoropyrenyl)borate]−; [tri-N-(n-butyl)-phosphonium]+[4'-((triethylsilylpropyl)(perfluorophenyl)phosphino)perfluorobiphen-4-yl)(per-fluorophenyl)(perfluorofluorenyl)(pentalfluoropyrenyl)borate]−; [N,N,N-

(ethyl)(methyl)(t-butyl)-phosphonium]+[5-((tri-isopropylsilyl)(perfluorophenyl)amino)perfluoroinden-2-yl)(pentafluoro-anthracenyl)(2',3',4'-trifluorobiphenyl)(2,3,5-trifluorophenyl)borate]⁻; [N,N,N-(ethyl)(methyl)-(isopropyl)phosphonium]+[5-((2,2-dimethyloctyl)(pentafluoroanthracenyl)phosphino)perfluoro-inden-2-yl)(perfluorobiphenyl)(perfluorophenyl)(pentafluoropyrenyl)borate]⁻; [tri-N-ethyl-phosphonium]+[7-((trimethylsilyl)(2,3,4-trifluorophenyl)amino)perfluoronapth-2-yl)(4,5,7-trifluoronaphthyl)(perfluoronaphthyl)(4,5,6,7-tetrafluoronaphthyl)borate]⁻; [N,N,N-(dimethyl)(t-butyl)phosphonium]+[6-((butyl)(2',3',5'-trifluorobiphenyl)arsino)perfluoroinden-2-yl)(5,6,7,8-tetrafluoronaphthyl)(perfluorophenyl)(perfluoronaphthyl)borate]⁻; [tri-N-(methylphenyl)-phosphonium]+[7-((isopropyl)(perfluorophenyl)amino)fluorofluoren-1-yl)(perfluorophenyl)(per-fluoroanthracenyl)(perfluoronaphthyl)borate]⁻; [tri-N-propylphosphonium]+[7-((benzyl)(2,3,5-trifluorophenyl)amino)perfluoronapth-3-yl)bis(2,3,6-trifluorophenyl)(perfluorophenyl)borate]⁻; [N,N,N-(dimethyl)(t-butyl)phosphonium]+[3'-((benzyl)(4,5,6-trifluoronaphthyl)amino)perfluoro-biphen-4-yl)(perfluorophenyl)(2',3',5'-trifluorobiphenyl)(2,3,4-trifluorophenyl)borate]⁻; [tri-N-(methylphenyl)phosphonium]+[5-((tri-isopropylsilyl)(perfluoroanthracenyl)amino)perfluoro-napth-1-yl)(pentalfluoropyrenyl)(perfluorobiphenyl)(2,3,4-trifluorophenyl)borate]⁻; [N,N,N-(ethyl)(methyl)(n-butyl)phosphonium]+[7-((octyl)(5,6,7,8-tetrafluoronaphthyl)arsino)perfluoro-inden-2-yl)(perfluorobiphenyl)(4,5,6-trifluoronaphthyl)(perfluorophenyl)borate]⁻; [N,N,N-(ethyl)-(methyl)(isopropyl)phosphonium]+[5-((triethylsilylethyl)(4,5,6,7-tetrafluoronaphthyl)phosphino)-perfluoroinden-2-yl)(perfluorophenyl)(perfluorofluorenyl)(2,3,5-trifluorophenyl)borate]⁻; [N,N,N-(ethyl)(methyl)(octyl)phosphonium]+[5-((hexyl)(4,5,6-trifluoronaphthyl)amino)perfluoronapth-1-yl)bis(perfluorobiphenyl)(4,5,7-trifluoronaphthylborate]⁻; [tri-N-(dimethylphenyl)-phosphonium]+[7-((diethylnonlysilyl)(perfluoroanthracenyl)amino)perfluoroinden-2-yl)(per-fluoronaphthyl)(perfluorobiphenyl)(perfluorofluorenyl)borate]⁻; [N,N,N-(ethyl)(methyl)(t-butyl)-phosphonium]+[7-((octyl)(perfluoropyrenyl)amino)perfluorofluoren-2-yl)(2,3,4-trifluorophenyl)-(perfluorobiphenyl)(2,3,6-trifluorophenyl)borate]⁻; [tri-N-propylphosphonium]+[3'-((tri-isopropyl-silyloctyl)(4,5,6-trifluoronaphthyl)amino)perfluorobiphen-4-yl)(perfluoropyrenyl)(2,3,4-trifluorophenyl)(2',3',4'-trifluorobiphenyl)borate]⁻; [tri-N-ethylphosphonium]+[7-((tri-isopropysilyl)(perfluorophenyl)amino)perfluoropyren-2-yl)(pentafluoroanthracenyl)(perfluorophenyl)(2',3',4'-trifluorobiphenyl)borate]⁻; [N,N,N-(ethyl)(methyl)(octyl)phosphonium]+[7-((methylethylhexylsilyl)-(perfluoronaphthyl)amino)perfluoronapth-3-yl)(5,6,7,8-tetrafluoronaphthyl)(perfluoropyrenyl)-(perfluoronaphthyl)borate]⁻; [tri-N-(t-butyl)phosphonium]+[7-((ethyl)(perfluorobiphenyl)amino)-perfluoropyren-1-yl)(perfluoropyrenyl)(2',3',4'-trifluorobiphenyl)(4,5,6-trifluoronaphthyl)borate]⁻; [tri-N-(methylphenyl)phosphonium]+[4-((benzyl)(5,6,7,8-tetrafluoronaphthyl)amino)perfluoro-phenyl)(4,5,6-trifluoronaphthyl)(4,5,7-trifluoronaphthyl)(perfluoropyrenyl)borate]⁻; [N,N,N-(ethyl)(methyl)(t-butyl)phosphonium]+[6-((tri-n-propylsilyl)(4,5,7-trifluoronaphthyl)phosphino)-perfluorofluoren-2-yl)(perfluorophenyl)(perfluoropyrenyl)(tetrafluorofluorenyl)borate]⁻; [tri-N-(n-butyl)phosphonium]+[4'-((trimethylsilyl)(4,5,7-trifluoronaphthyl)amino)perfluorobiphen-4-yl)-(2,3,5-trifluorophenyl)(4,5,6,7-tetrafluoronaphthyl)(2',3',5'-trifluorobiphenyl)borate]⁻; [N,N,N-(ethyl)(methyl)(t-butyl)phosphonium]+[5-((triethylsilyl)(perfluorophenyl)arsino)fluoroinden-1-yl)-(4,5,7-trifluoronaphthyl)(perfluorophenyl)(4,5,6-trifluoronaphthyl)borate]⁻; [N,N,N-(ethyl)-(methyl)(octyl)phosphonium]+[7-((cyclohexyl)(2,3,5-trifluorophenyl)phosphino)perfluorofluoren-2-yl)(perfluorofluorenyl)(perfluorobiphenyl)(2,3,6-trifluorophenyl)borate]⁻; [trityl]+[7-((octyl)(per-fluorofluorenyl)phosphino)perfluoropyren-1-yl)(perfluorobiphenyl)(2,3,6-trifluorophenyl)(4,5,7-trifluoronaphthyl)borate]⁻; [trityl]+[6-((nonyl)(perfluoroanthracenyl)phosphino)perfluoroinden-2-yl)(perfluorobiphenyl)(4,5,6,7-tetrafluoronaphthyl)(pentalfluoropyrenyl)borate]⁻; [trityl]+[7-((methyl)(pentalfluoropyrenyl)amino)perfluorofluoren-2-yl)(tetrafluorofluorenyl)(perfluoro-biphenyl)(2,3,5-trifluorophenyl)borate]⁻; [trityl]+[6-((ethyl)(perfluorophenyl)amino)perfluoro-napth-1-yl)(perfluorobiphenyl)(4,5,7-trifluoronaphthyl)(pentafluoroanthracenyl)borate]⁻; [trityl]+[7-((butyl)(perfluorofluorenyl)amino)perfluorofluoren-2-yl)(perfluorobiphenyl)(pentalfluoro-pyrenyl)(2,3,6-trifluorophenyl)borate]⁻; [trityl]+[8-((methylethylhexylsilyl)(perfluorophenyl)-amino)perfluoronapth-3-yl)(perfluorobiphenyl)(perfluorophenyl)(2,3,6-trifluorophenyl)borate]⁻; [trityl]+[3'-((tri-isopropylsilyl)(perfluorophenyl)phosphino)perfluorobiphen-4-yl)(perfluoro-anthracenyl)(tetrafluorofluorenyl)(5,6,7,8-tetrafluoronaphthyl)borate]⁻.

Non-exhaustive List of Invention Catalyst Systems

[tri-N-(n-butyl)ammonium]+[6-((triethylsilylethyl)(perfluorophenyl)amino)perfluorofluoren-2-yl)(perfluorobiphenyl)(perfluorophenyl)(perfluorofluorenyl)aluminate]⁻/oxotris(trimethlsilylmethyl)vanadium.

[tri-N-methylammonium]+[6-((hexyl)(perfluoroanthracenyl)amino)perfluorofluoren-1-yl)(perfluorobiphenyl)(2',3',5'-trifluorobiphenyl)(perfluoropyrenyl)aluminate]⁻/oxotris(trimethlsilylmethyl)vanadium

[tri-N-octylammonium]+[7-((methyldiethylsilyloctyl)(4,5,7-trifluoronaphthyl)phosphino)perfluoronapth-2-yl)(perfluorobiphenyl)(4,5,7-trifluoronaphthyl)(2,3,5-trifluorophenyl)aluminate]⁻/diphenylmethyl(cylcopentadienyl)(2,7-di-tri-butyl-fluorenyl)dimethylhafnium

[N,N,N-(ethyl)(methyl)(n-butyl)ammonium]+[7-((tri-isopropylsilyloctyl)(perfluorophenyl)-amino)perfluorofluoren-1-yl)(perfluorophenyl)(perfluoroanthracenyl)(perfluorofluorenyl)-aluminate]⁻/dimethylsilyl(tetramethycyclopentadienyl)(dodecylamido)dimethylhafnium

[N,N,N-(ethyl)(methyl)(octyl)ammonium]+[6-((ethyl)(perfluorobiphenyl)arsino)perfluoro-napth-1-yl)(perfluorophenyl)(perfluoronaphthyl)(perfluorobiphenyl)aluminate]⁻/dimethylsilylbis(methylindenyl)dimethylhafnium

[N,N,N-(dimethyl)(t-butyl)ammonium]+[4'-((methyl)(perfluorophenyl)amino)perfluorobiphen-4-yl)(4,5,7-trifluoronaphthyl)(perfluorophenyl)(5,6,7,8-tetrafluoronaphthyl)aluminate]⁻/dimethylsilyl(tetramethylcyclopentadienyl)(dodecylamido)dihydridehafnium

[tri-N-octylammonium]+[8-((methylethylhexylsilyl)(perfluorobiphenyl)phosphino)perfluoropyren-2-yl)(perfluorophenyl)(2',3',4'-trifluorobiphenyl)(pentalfluoropyrenyl)aluminate]⁻/diphenylmethyl (cylcopentadienyl)(2,7-di-tri-butyl-fluorenyl)dimethylhafnium

[tri-N-(n-butyl)ammonium]⁺[7-((triethylsilylpropyl)(perfluorobiphenyl)phosphino)perfluoro-napth-2-yl)(perfluorophenyl)(perfluorofluorenyl)(4,5,6,7-tetrafluoronaphthyl)aluminate]⁻/(4-alkyl-1-phenyl)(4-tri-butyl-1-phenyl)methyl(cylcopentadienyl)(fluorenyl)dimethylhafnium

[N,N,N-(ethyl)(methyl)(t-butyl)ammonium]⁺[6-((3-ethylnonyl)(perfluorophenyl)amino)perfluoronapth-1-yl)(perfluorobiphenyl)(pentalfluoropyrenyl)(perfluoroanthracenyl)aluminate]⁻/dimethylsilyl(tetramethylcyclopentadienyl)(dodecylamido)dimethylhafnium

[tri-N-ethylammonium]⁺[7-((tri-n-propylsilylhexyl)(2,3,5-trifluorophenyl)amino)perfluorofluoren-1-yl)(perfluorofluorenyl)(5,6,7,8-tetrafluoronaphthyl)(perfluorophenyl)aluminate]⁻/diphenylmethyl(cylcopentadienyl)(2,7-di-tri-butyl-fluorenyl)dimethylhafnium

[tri-N-propylammonium]⁺[6-((tri-n-propylsilylhexyl)(perfluorophenyl)phosphino)perfluoro-anthracen-1-yl)(pentalfluoropyrenyl)(perfluorophenyl)(pentafluoroanthracenyl)aluminate]⁻/dimethylsilyl(tetramethylcyclopentadienyl)(dodecylamido)dihydridehafnium

[N N,N-(ethyl)(methyl)(t-butyl)ammonium]⁺[6-((benzyl)(perfluoronaphthyl)phosphino)perfluoronapth-3-yl)(perfluorobiphenyl)(perfluoroanthracenyl)(2',3',4'-trifluorobiphenyl)aluminate]⁻/dimethylsilylbis(methylindenyl)dimethylhafnium

[N,N,N-(ethyl)(methyl)(t-butyl)ammonium]⁺[4-((benzyl)(perfluorobiphenyl)amino)perfluorophenyl)(2,3,4-trifluorophenyl)(4,5,6,7-tetrafluoronaphthyl)(perfluoropyrenyl)aluminate]⁻/dimethylsilyl(tetramethylcyclopentadienyl)(dodecylamido)dihydridehafnium

[tri-N-(methylphenyl)ammonium]⁺[3-((tri-isopropylsilyloctyl)(perfluorophenyl)amino)perfluorophenyl)(perfluoropyrenyl)(4,5,7-trifluoronaphthyl)(2,3,5-trifluorophenyl)aluminate]⁻/(4-alkyl-1-phenyl)(4-tri-butyl-1-phenyl)methyl(cylcopentadienyl)(fluorenyl)dimethylhafnium

[N,N,N-(ethyl)(methyl)(isopropyl)ammonium]⁺[5-((nonyl)(perfluoronaphthyl)amino)perfluoronapth-2-yl)(pentafluoroanthracenyl)(2',3',4'-trifluorobiphenyl)(perfluorofluorenyl)aluminate]⁻/dimethylsilyl(tetramethylcyclopentadienyl)(dodecylamido)dimethylhafnium

[tri-N-(dimethylphenylammonium]⁺[6-((2,2-dimethyloctyl)(2,3,6-trifluorophenyl)phosphino)-perfluoroanthracen-2-yl)bis(2,3,4-trifluorophenyl)(tetrafluorofluorenylaluminate]⁻/dimethylsilyl(tetramethylcyclopentadienyl)(dodecylamido)dimethylhafnium

[tri-N-(methylphenyl)ammonium]⁺[6-((cyclohexyl)(5,6,7,8-tetrafluoronaphthyl)amino)perfluoroinden-2-yl)bis(perfluorobiphenyl)(5,6,7,8-tetrafluoronaphthylaluminate]⁻/diphenylmethyl(cylcopentadienyl)(2,7-dimethylfluorenyl)dimethylhafnium

[tri-N-ethylammonium]⁺[5-((methyl)(perfluorophenyl)arsino)fluoronapth-2-yl)(perfluorophenyl)(2',3',4'-trifluorobiphenyl)(pentalfluoropyrenyl)aluminate]⁻/dimethylsilylbis(naphthylmethylindenyl)dimethylhafnium

[tri-N-(dimethylphenylammonium]⁺[8-((3-ethylnonyl)(2,3,6-trifluorophenyl)amino)perfluoropyren-2-yl)(perfluoronaphthyl)(perfluorophenyl)(4,5,6,7-tetrafluoronaphthyl)aluminate]⁻/dimethylsilylbis(naphthylmethylindenyl)dimethylhafnium

[tri-N-methylammonium]⁺[7-((isopropyl)(perfluorophenyl)amino)perfluoroinden-2-yl)(perfluoroanthracenyl)(perfluoropyrenyl)(2,3,5-trifluorophenyl)aluminate]⁻/dimethylsilylbisindenyldimethylhafnium

[N,N,N-(dimethyl)(t-butyl)ammonium]⁺[4'-((benzyl)(pentafluoroanthracenyl)amino)perfluorobiphen-4-yl)bis(pentafluoroanthracenyl)(pentalfluoropyrenyl)aluminate]⁻/dimethylsilylbis(methylindenyl)dimethylhafnium

[tri-N-(t-butyl)ammonium]⁺[4'-((triethylsilyl)(perfluorobiphenyl)amino)perfluorobiphen-4-yl)-(pentafluoroanthracenyl)(2',3',5'-trifluorobiphenyl)(perfluoropyrenyl)aluminate]⁻/tetrabenzylhafnium

[tri-N-(methylphenyl)ammonium]⁺[7-((hexyl)(2',3',5'-trifluorobiphenyl)amino)perfluoroanthracen-1-yl)(perfluorofluorenyl)(2',3',5'-trifluorobiphenyl)(2,3,4-trifluorophenyl)aluminate]⁻/dimethylsilyl(tetramethylcyclopentadienyl)(dodecylamido)dimethylhafnium

[N,N,N-(ethyl)(methyl)(isopropyl)ammonium]⁺[7-((nonyl)(perfluorophenyl)amino)perfluoroinden-2-yl)(perfluorophenyl)(perfluoroanthracenyl)(perfluoropyrenyl)aluminate]⁻/dimethylsilylbisindenyldimethylhafnium

[N,N,N-(ethyl)(methyl)(t-butyl)ammonium](6-((hexyl)(perfluorofluorenyl)amino)perfluoro-napth-1-yl)(perfluorophenyl)(pentalfluoropyrenyl)(2',3',4'-trifluorobiphenyl)aluminate]⁻/dimethylsilyl(tetramethylcyclopentadienyl)(dodecylamido)dimethylhafnium

[tri-N-(t-butyl)ammonium]⁺[6-((2,2-dimethyloctyl)(perfluorobiphenyl)amino)perfluoroinden-2-yl)(perfluorophenyl)(perfluorofluorenyl)(2,3,5-trifluorophenyl)aluminate]⁻/dimethylsilylbis(phenylmethylindenyl)dimethylhafnium

[N N,N-(dimethyl)(t-butyl)ammonium]⁺[5-((tri-isopropylsilyl)(4,5,6-trifluoronaphthyl)amino)-perfluoronapth-2-yl)(perfluoropyrenyl)(perfluoroanthracenyl)(2,3,5-trifluorophenyl)aluminate]⁻/dimethylsilyl(tetramethylcyclopentadienyl)(dodecylamido)dimethylhafnium

[N,N,N-(ethyl)(methyl)(t-butyl)ammonium]⁺[5-((tri-n-propylsilyl)(perfluorophenyl)amino)-fluoronapth-2-yl)(perfluorophenyl)(perfluoropyrenyl)(2,3,4-trifluorophenyl)aluminate]⁻/dimethylsilylbis(naphthylmethylindenyl)dimethylhafnium

[tri-N-(n-butyl)ammonium]⁺[8-((butyl)(2',3',4'-trifluorobiphenyl)amino)perfluoropyren-2-yl)-(perfluorophenyl)(pentalfluoropyrenyl)(pentafluoroanthracenyl)aluminate]⁻/dimethylsilylbis(phenylmethylindenyl)dimethylhafnium

[tri-N-methylammonium]⁺[5-((methylethylhexylsilyl)(perfluorophenyl)amino)perfluoronapth-3-yl)(pentalfluoropyrenyl)(4,5,7-trifluoronaphthyl)(5,6,7,8-tetrafluoronaphthyl)aluminate]⁻/diphenylmethyl(cylcopentadienyl)(2,7-dimethylfluorenyl)dimethylhafnium

[N,N,N-(ethyl)(methyl)(n-butyl)ammonium]⁺[7-((butyl)(2',3',4'-trifluorobiphenyl)amino)perfluoropyren-2-yl)(pentafluoroanthracenyl)(4,5,7-trifluoronaphthyl)(perfluorobiphenyl)aluminate]⁻/diphenylmethyl(fluorenyl)(cyclopentadienyl)dimethylhafnium

[tri-N-ethylammonium]⁺[7-((methyldiethylsilyloctyl)(4,5,7-trifluoronaphthyl)amino)perfluoronapth-2-yl)bis(2',3',5'-trifluorobiphenyl)(pentafluoroanthracenyl)aluminate]⁻/dimethylsilyl(tetramethylcyclopentadienyl)(dodecylamido)dihydridehafnium

[tri-N-propylammonium]⁺[6-((tri-n-propylsilylhexyl)(perfluorophenyl)amino)perfluoroanth-racen-2-yl)(tetrafluorofluorenyl)(5,6,7,8-tetrafluoronaphthyl)(perfluorophenyl)aluminate]⁻/dimethylsilyl(tetramethylcyclopentadienyl)(dodecylamido)dimethylhafnium

[tri-N-methylammonium]⁺[6-((benzyl)(perfluoroanthracenyl)arsino)perfluoroanthracen-1-yl)-(perfluoropyrenyl)(2,3,6-trifluorophenyl)(perfluorobiphenyl)aluminate]⁻/dimethylsilylbis(naphthylmethylindenyl)dimethylhafnium

[N,N,N-(ethyl)(methyl)(t-butyl)ammonium]⁺[7-((benzyl)(perfluorobiphenyl)amino)fluoroanthracen-1-yl)(perfluoroanthracenyl)(2,3,5-trifluorophenyl)(perfluoropyrenyl)aluminate]⁻/diphenylmethyl(cylcopentadienyl)(2,7-dimethylfluorenyl)dimethylhafnium

[tri-N-ethylammonium]⁺[3-((2,2-dimethyloctyl)(perfluoropyrenyl)arsino)perfluorophenyl)(perfluoropyrenyl)(5,6,7,8-tetrafluoronaphthyl)(2,3,6-trifluorophenyl)aluminate]⁻/(4-alkyl-1-phenyl)-(4-tri-butyl-1-phenyl)methyl(cylcopentadienyl)(fluorenyl)dimethylhafnium

[tri-N-ethylammonium]⁺[7-((tri-n-propylsilylhexyl)(tetrafluorofluorenyl)amino)perfluorofluoren-1-yl)(perfluoroanthracenyl)(2',3',5'-trifluorobiphenyl)(tetrafluorofluorenyl)aluminate]⁻/dimethylsilylbis(methylindenyl)dimethylhafnium

[tri-N-ethylammonium]⁺[3-((butyl)(2,3,6-trifluorophenyl)amino)perfluorophenyl)(tetrafluorofluorenyl)(perfluoropyrenyl)(2',3',5'-trifluorobiphenyl)aluminate]⁻/tris(trimethylsilylmethyl)dichlorideniobium

[N,N,N-(ethyl)(methyl)(n-butyl)ammonium]⁺[5-((tri-n-propylsilylhexyl)(perfluorofluorenyl)phosphino)perfluoronapth-1-yl)(2',3',5'-trifluorobiphenyl)(4,5,6,7-tetrafluoronaphthyl)-(4,5,6-trifluoronaphthyl)aluminate]⁻/tris(trimethylsilylmethyl)dichlorideniobium

[N,N,N-(ethyl)(methyl)(n-butyl)ammonium]⁺[8-((methylethylhexylsilyl)(perfluorobiphenyl)amino)perfluoronapth-3-yl)(perfluorobiphenyl)(perfluorophenyl)(2',3',4'-trifluorobiphenyl)aluminate]⁻/tris(trimethylsilylmethyl)dichlorideniobium

[N,N,N-(ethyl)(methyl)(t-butyl)ammonium]⁺[6-((ethyl)(2',3',4'-trifluorobiphenyl)amino)perfluoroinden-2-yl)(pentafluoroanthracenyl)(pentalfluoropyrenyl)(perfluoroanthracenyl)aluminate]⁻/tris(trimethylsilylmethyl)dichlorideniobium

[tri-N-propylammonium]⁺[6-((tri-n-propylsilyl)(2,3,6-trifluorophenyl)amino)perfluoroanthracen-1-yl)(perfluoropyrenyl)(4,5,6,7-tetrafluoronaphthyl)(2,3,5-trifluorophenyl)aluminate]⁻/tris(trimethylsilylmethyl)dichlorideniobium

[N,N,N-(ethyl)(methyl)(octyl)ammonium]⁺[5-((tri-isopropylsilyloctyl)(2',3',4'-trifluorobiphenyl)phosphino)perfluoronaphth-1-yl)(perfluoropyrenyl)(2',3',5'-trifluorobiphenyl)(perfluorobiphenyl)aluminate]⁻/tris(trimethylsilylmethyl)dichloridetantalum

[N,N,N-(ethyl)(methyl)(octyl)ammonium]⁺[6-((triethylsilylethyl)(perfluorobiphenyl)phosphino)perfluoronapth-3-yl)bis(perfluoroanthracenyl)(pentafluoroanthracenylaluminate]⁻/tris(trimethylsilylmethyl)dichloridetantalum

[N,N,N-(ethyl)(methyl)(t-butyl)ammonium]⁺[7-((tri-n-propylsilylhexyl)(5,6,7,8-tetrafluoronaphthyl)amino)perfluoroanthracen-1-yl)(perfluorofluorenyl)(4,5,7-trifluoronaphthyl)(perfluorobiphenyl)aluminate]⁻/pentamethylcyclopentadienylisopropoxidetitanium

[tri-N-propylammonium]⁺[7-((nonyl)(perfluorobiphenyl)arsino)perfluoronaphth-1-yl)(pentafluoroanthracenyl)(2',3',4'-trifluorophenyl)(2,3,5-trifluorophenyl)aluminate]⁻/pentamethyl cyclopentadienylisopropoxidetitanium

[tri-N-(methylphenyl)ammonium]⁺[3-((tri-n-propylsilyl)(perfluoronaphthyl)phosphino)perfluorophenyl)(perfluoropyrenyl)(perfluoroanthracenyl)(perfluorobipheny)aluminate]⁻/dimethylsilyl(tetramethylcyclopentadienyl)(adamantyl-1-amino)dimethyltitanium

[tri-N-(dimethylphenylammonium]⁺[7-((methyl)(perfluoropyrenyl)amino)perfluorofluoren-1-yl)(4,5,6-trifluoronaphthyl)(2,3,6-trifluorophenyl)(perfluorophenyl)aluminate]⁻/dimethylsilyl(tetramethylcyclopentadienyl)(tert-butylamido)dichloridetitanium

[tri-N-(methylphenyl)ammonium]⁺[5-((octyl)(perfluorofluorenyl)amino)perfluoroinden-2-yl)-(perfluorophenyl)(4,5,7-trifluoronaphthyl)(2,3,5-trifluorophenyl)aluminate]⁻/dimethylsilyl(tetramethylcyclopentadienyl)(adamantyl-1-amino)dimethyltitanium

[N,N,N-(ethyl)(methyl)(octyl)ammonium]⁺[7-((methyl)(2',3',5'-trifluorobiphenyl)amino)fluoro-fluoren-1-yl)(perfluorophenyl)(pentalfluoropyrenyl)(2',3',4'-trifluorobiphenyl)aluminate]⁻/dimethylsilyl(tetramethylcyclopentadienyl)(adamantyl-1-amino)dimethyltitanium

[tri-N-ethylammonium]⁺[7-((trimethylsilyl)(perfluorophenyl)amino)perfluoroinden-2-yl)(perfluorophenyl)(4,5,6,7-tetrafluoronaphthyl)(2',3',5'-trifluorobiphenyl)aluminate]⁻/pentamethylcyclopentadienyltribenzyltitanium

[tri-N-octylammonium]⁺[7-((tri-isopropylsilyl)(5,6,7,8-tetrafluoronaphthyl)amino)perfluoro-inden-2-yl)(perfluoropyrenyl)(2,3,5-trifluorophenyl)(4,5,7-trifluoronaphthyl)aluminate]⁻/pentamethylcyclopentadienyltribenzyltitanium

[N,N,N-(ethyl)(dioctyl)ammonium]⁺[6-((butyl)(4,5,6,7-tetrafluoronaphthyl)phosphino)perfluorofluoren-2-yl)(perfluoropyrenyl)(4,5,7-trifluoronaphthyl)(perfluorofluorenyl)aluminate]⁻/pentamethylcyclopentadienylisopropoxidetitanium

[tri-N-(dimethylphenylammonium]⁺[3-((butyl)(perfluorofluorenyl)amino)perfluorophenyl)(per-fluorophenyl)(perfluorobiphenyl)(perfluoroanthracenyl)aluminate]⁻/dimethylsilyl(tetramethylcyclopentadienyl)(adamantyl-1-amino)dimethyltitanium

[N N,N-(dimethyl)(t-butyl)ammonium]⁺[7-((methyldiethylsilyloctyl)(pentafluoroanthracenyl)amino)perfluoropyren-2-yl)(perfluorofluorenyl)(tetrafluorofluorenyl)(perfluorophenyl)aluminate]⁻/pentamethylcyclopentadienylisopropoxidetitanium

[tri-N-ethylammonium]⁺[3-((methyl)(perfluoronaphthyl)phosphino)fluorophen-1-yl)(perfluoroanthracenyl)(5,6,7,8-tetrafluoronaphthyl)(4,5,6-trifluoronaphthyl)aluminate]⁻/tetrabenzyltitanium

[tri-N-(methylphenyl)ammonium]⁺[7-((trimethylsilyl)(perfluoroanthracenyl)amino)fluorofluoren-2-yl)(pentalfluoropyrenyl)(2,3,6-trifluorophenyl)(perfluoropyrenyl)aluminate]⁻/pentamethylcyclopentadienyltribenzyltitanium

[tri-N-propylammonium]⁺[6-((triethylsilylethyl)(4,5,6,7-tetrafluoronaphthyl)amino)perfluoronapth-1-yl)(perfluorophenyl)(2,3,6-trifluorophenyl)(pentafluoroanthracenyl)aluminate]⁻/pentamethylcyclopentadienylisopropoxidetitanium

[N,N,N-(ethyl)(methyl)(n-butyl)ammonium]⁺[6-((tri-n-propylsilyl)(perfluorophenyl)amino)fluoroanthracen-1-yl)

(pentafluoroanthracenyl)(4,5,7-trifluoronaphthyl)(perfluorobiphenyl)aluminate]⁻/tetrabenzyltitanium

[tri-N-(dimethylphenyl)ammonium]⁺[5-((trimethylsilyl)(perfluoroanthracenyl)amino)perfluoroinden-2-yl)(2',3',5'-trifluorobiphenyl)(perfluorobiphenyl)(perfluorophenyl)aluminate]⁻/bis(1,3-dibutyl-methyl-cyclopentadienyl)dimethylzirconium

[N,N,N-(ethyl)(methyl)(t-butyl)ammonium]⁺[7-((benzyl)(perfluorophenyl)phosphino)perfluoropyren-1-yl)(2,3,6-trifluorophenyl)(perfluorophenyl)(perfluoropyrenyl)aluminate]⁻/diphenylmethyl(fluorenyl)(cyclopentadienyl)dimethylzirconium

[tri-N-(methylphenyl)ammonium]⁺[7-((tri-n-propylsilylhexyl)(perfluorobiphenyl)amino)perfluoroinden-2-yl)(perfluorophenyl)(2',3',4'-trifluorobiphenyl)(4,5,7-trifluoronaphthyl)aluminate]⁻/(pentamethylcyclopentadienyl)(cyclopentadienyl)dimethylzirconium

[tri-N-ethylammonium]⁺[5-((methyldiethylsilyloctyl)(perfluoroanthracenyl)phosphino)fluoroinden-1-yl)(2,3,4-trifluorophenyl)(2,3,6-trifluorophenyl)(perfluorophenyl)aluminate]⁻/dimethylsilyl(bisindenyl)dichloridezirconium

[N,N,N-(ethyl)(methyl)(octyl)ammonium]⁺[6-((isopropyl)(tetrafluorofluorenyl)amino)perfluoronapth-1-yl)bis(2,3,4-trifluorophenyl)(4,5,6-trifluoronaphthyl)aluminate)]⁻/dimethylsilylbis(tetrahydroindenyl)dichloridezirconium

[N,N,N-(ethyl)(dioctyl)ammonium]⁺[7-((trimethylsilyl)(perfluorophenyl)phosphino)perfluoronapth-1-yl)(perfluorophenyl)(2',3',4'-trifluorobiphenyl)(2',3',5'-trifluorobiphenyl)aluminate]⁻/dimethylsilylbis(2-methylbenzindenyl)dimethylzirconium

[tri-N-(n-butyl)ammonium]⁺[5-((tri-isopropylsilyloctyl)(perfluorofluorenyl)amino)perfluoroinden-2-yl)(perfluorofluorenyl)(pentafluoroanthracenyl)(perfluorophenyl)aluminate]⁻/tetra(bis(trimethylsilylmethyl))zirconium

[N,N,N-(ethyl)(methyl)(octyl)ammonium]⁺[5-((3-ethylnonyl)(2,3,5-trifluorophenyl)amino)perfluoronapth-1-yl)(perfluoroanthracenyl)(perfluorophenyl)(perfluoropyrenyl)aluminate]⁻/dimethylsily(bisindenyl)dichloridezirconium

[tri-N-(methylphenyl)ammonium]⁺[5-((trimethylsilyl)(perfluoropyrenyl)arsino)perfluoroinden-2-yl)(pentafluoropyrenyl)(pentafluoroanthracenyl)(2',3',4'-trifluorobiphenyl)aluminate]⁻/(tetramethylcyclopentadienyl)(n-propylcyclopentadienyl)dimethylzirconium

[tri-N-propylammonium]⁺[4'-((ethyl)(pentafluoroanthracenyl)phosphino)perfluorobiphen-4-yl)(perfluorophenyl)(perfluoronaphthyl)(2',3',4'-trifluorobiphenyl)aluminate]⁻/tetrabenzylzirconium

[tri-N-octylammonium]⁺[4'-((methyl)(perfluorophenyl)phosphino)perfluorobiphen-3-yl)(perfluorofluorenyl)(perfluorophenyl)(2',3',5'-trifluorobiphenyl)aluminate]⁻/diphenylmethyl(fluorenyl)(cycdopentadienyl)dimethylzirconium

[tri-N-ethylammonium]⁺[7-((tri-n-propylsilyl)(4,5,7-trifluoronaphthyl)phosphino)perfluorofluoren-2-yl)(pentafluoroanthracenyl)(perfluorophenyl)(2,3,4-trifluorophenyl)aluminate]⁻/tetrabenzyl zirconium

[N,N,N-(dimethyl)(t-butyl)ammonium]⁺[5-((nonyl)(tetrafluorofluorenyl)amino)perfluoronaphth-1-yl)(tetrafluorofluorenyl)(4,5,6,7-tetrafluoronaphthyl)(2,3,4-trifluorophenyl)aluminate]⁻/dimethylsily (bisindenyl)dichloridezirconium

[N,N,N-(ethyl)(dioctyl)ammonium]⁺[4'-((propyl)(pentafluoropyrenyl)amino)perfluorobiphen-3-yl)(pentalfluoropyrenyl)(perfluorophenyl)(4,5,6,7-tetrafluoronaphthyl)aluminate]⁻/dimethylsilyl(tetramethylcyclopentadienyl)(t-butylamido)dimethylzirconium

[tri-N-methylammonium]⁺[8-((ethyl)(perfluorofluorenyl)amino)perfluoronapth-3-yl)(perfluorophenyl)(perfluoropyrenyl)(pentalfluoropyrenyl)aluminate]⁻/dimethylsily (bisindenyl)dichloridezirconium

[tri-N-octylammonium]⁺[7-((methyldiethylsilyloctyl)(perfluorophenyl)amino)perfluoropyren-2-yl)(4,5,6,7-tetrafluoronaphthyl)(2,3,5-trifluorophenyl)(perfluorophenyl)aluminate]⁻/(pentamethylcyclopentadienyl)(cyclopentadienyl)dimethylzirconium

[tri-N-propylammonium]⁺[7-((butyl)(perfluoroanthracenyl)amino)perfluorofluoren-1-yl)(perfluorophenyl)(2',3',5'-trifluorobiphenyl)(2,3,4-trifluorophenyl)aluminate]⁻/dimethylsilylbis(tetrahydroindenyl)dichloridezirconium

[N,N,N-(ethyl)(methyl)(isopropyl)ammonium]⁺[5-((tri-isopropylsilyl)(perfluorophenyl)amino)perfluoroinden-1-yl)(pentalfluoropyrenyl)(perfluorophenyl)(tetrafluorofluorenyl)aluminate]⁻/dimethylsilylbis(tetrahydroindenyl)dichloridezirconium

[N,N,N-(ethyl)(methyl)(t-butyl)ammonium]⁺[6-((triethylsilylpropyl)(perfluorofluorenyl)amino)perfluoronapth-2-yl)(perfluorophenyl)(perfluorobiphenyl)(pentafluoroanthracenyl)aluminate]⁻/silacyclobutyl(tetramethylcyclopentadienyl)(n-propylcyclopentadienyl)dimethylzirconium

[tri-N-(methylphenyl)ammonium]⁺[7-((propyl)(perfluorophenyl)amino)perfluoronapth-2-yl)-(perfluoropyrenyl)(pentalfluoropyrenyl)(perfluorobiphenyl)aluminate]⁻/dimethylsily (bisindenyl)dichloridezirconium

[tri-N-(t-butyl)ammonium]⁺[7-((methylethylhexylsilyl)(perfluorofluorenyl)amino)perfluoronapth-2-yl)(pentalfluoropyrenyl)(perfluorofluorenyl)(perfluorophenyl)aluminate]⁻/dimethylsily(bisindenyl)dichloridezirconium

[N,N,N-(ethyl)(dioctyl)ammonium]⁺[3'-((cyclohexyl)(perfluorobiphenyl)phosphino)perfluorobiphen-4-yl)bis(perfluorobiphenyl)(2,3,5-trifluorophenylaluminate]⁻/diphenylmethyl(fluorenyl)(cyclopentadienyl)dimethylzirconium

[N,N,N-(ethyl)(methyl)(n-butyl)ammonium]⁺[5-((methyl)(perfluorophenyl)phosphino)perfluoroinden-2-yl)(pentafluoroanthracenyl)(2',3',4'-trifluorobiphenyl)(perfluorophenyl)aluminate]⁻/diphenylmethyl(fluorenyl)(cyclopentadienyl)dimethylzirconium

[tri-N-(t-butyl)ammonium]⁺[6-((2,2-dimethyloctyl)(2,3,4-trifluorophenyl)phosphino)fluoro-napth-3-yl)(pentafluoroanthracenyl)(5,6,7,8-tetrafluoronaphthyl)(2',3',4'-trifluorobiphenyl)-aluminate]⁻/dimethylsilylbis(2-methylbenzindenyl)dimethylzirconium

[N,N-2,4,6,-pentamethylanilinium]⁺[6-((isopropyl)(perfluoropyrenyl)amino)fluoroinden-2-yl)bis(2,3,6-trifluorophenyl)(perfluorophenylaluminate]⁻/dimethylsilylbis(phenylmethylindenyl)dimethylhafnium

[N,N-di(dodecyl)anilinium]⁺[6-((benzyl)(tetrafluorofluorenyl)amino)perfluoroanthracen-2-yl)-(perfluorofluorenyl)(4,5,6-trifluoronaphthyl)(5,6,7,8-tetrafluoronaphthyl)aluminate]⁻/dimethylsilyl(tetramethylcyclopentadienyl)(dodecylamido)dihydridehafnium

[N,N-di(dodecyl)anilinium]⁺[7-((tri-n-propylsilylhexyl)(5,6,7,8-tetrafluoronaphthyl)amino)perfluoropyren-1-yl)(perfluorofluorenyl)(2',3',5'-trifluorobiphenyl)(4,5,6,7-tetrafluoronaphthyl)aluminate]⁻/dimethylsilylbis(phenylmethylindenyl)dimethylhafnium

[N,N-dimethylanilinium]⁺[4-((tri-n-propylsilylhexyl)(perfluorophenyl)amino)perfluorophenyl)-(perfluoropyrenyl)(perfluorofluorenyl)(pentafluoroanthracenyl)aluminate]⁻/dimethylsilyl(tetramethylcyclopentadienyl)(dodecylamido)dihydridehafnium

[N,N-di(dodecyl)anilinium]⁺[4-((ethyl)(perfluorobiphenyl)phosphino)fluorophen-1-yl)(4,5,7-trifluoronaphthyl)(perfluorofluorenyl)(tetrafluorofluorenyl)aluminate]⁻/dimethylsilyl(tetramethylcyclopentadienyl)(dodecylamido)dihydridehafnium

[N,N-dimethylanilinium]⁺[7-((hexyl)(2,3,4-trifluorophenyl)amino)perfluoronaphth-1-yl)(4,5,7-trifluoronaphthyl)(perfluorofluorenyl)(2',3',5'-trifluorobiphenyl)aluminate]⁻/dimethylsilylbis(naphthylmethylindenyl)dimethylhafnium

[N,N-di(dodecyl)anilinium]⁺[6-((octyl)(perfluorofluorenyl)phosphino)perfluoronaphth-3-yl)-(tetrafluorofluorenyl)(perfluorobiphenyl)(2',3',5'-trifluorobiphenyl)aluminate]⁻/tetrabenzylhafnium

[N,N-2,4,6,-pentamethylanilinium]⁺[5-((triethylsilyl)(2',3',4'-trifluorobiphenyl)phosphino)perfluoroinden-2-yl)(perfluorofluorenyl)(2',3',4'-trifluorobiphenyl)(5,6,7,8-tetrafluoronaphthyl)-aluminate]⁻/(4-alkyl-1-phenyl)(4-tributyl-1-phenyl)methyl(cylcopentadienyl)(fluorenyl)dimethylhafnium

[N,N-diethylanilinium]⁺[6-((triethylsilylpropyl)(perfluoropyrenyl)amino)fluoronaphth-3-yl)(perfluoronaphthyl)(perfluorofluorenyl)(perfluoroanthracenyl)aluminate]⁻/dimethylsilylbis(phenylmethylindenyl)dimethylhafnium

[N,N-2,4,6,-pentamethylanilinium]⁺[5-((methyldiethylsilyloctyl)(perfluorophenyl)amino)perfluoroinden-1-yl)(perfluoronaphthyl)(2,3,5-trifluorophenyl)(perfluoroanthracenyl)aluminate]⁻/diphenylmethyl(cylcopentadienyl)(2,7-dimethylfluorenyl)dimethylhafnium

[N,N-dimethylanilinium]⁺[8-((cyclohexyl)(perfluorobiphenyl)amino)fluoropyren-2-yl)(perfluorobiphenyl)(2,3,6-trifluorophenyl)(perfluorofluorenyl)aluminate]⁻/dimethylsilyl(tetramethylcydopentadienyl)(dodecylamido)dihydridehafnium

[N,N-dimethylanilinium]⁺[7-((trimethylsilyl)(perfluoroanthracenyl)arsino)perfluoronaphth-2-yl)(perfluoroanthracenyl)(perfluorobiphenyl)(perfluorophenyl)aluminate]⁻/tris(trimethylsilylmethyl)dichlorideniobium

[N-methyl-N-dodecylanilinium]⁺[6-((trimethylsilyl)(perfluoroanthracenyl)amino)perfluorofluoren-2-yl)(pentafluoroanthracenyl)(perfluorobiphenyl)(4,5,7-trifluoronaphthyl)aluminate]⁻/tris(trimethylsilylmethyl)dichloridetantalum

[N,N-2,4,6,-pentamethylanilinium]⁺[3-((hexyl)(perfluoroanthracenyl)amino)perfluorophenyl)(5,6,7,8-tetrafluoronaphthyl)(4,5,6,7-tetrafluoronaphthyl)(perfluorobiphenyl)aluminate]⁻/tris(trimethylsilylmethyl)dichloridetantalum

[N,N-diethylanilinium]⁺[5-((ethyl)(perfluoroanthracenyl)phosphino)perfluoroinden-2-yl)bis(2',3',5'-trifluorobiphenyl)(2,3,5-trifluorophenylaluminate]⁻/tetrabenzyltitanium

[N-methyl-N-dodecylanilinium]⁺[4'-((benzyl)(perfluorofluorenyl)amino)perfluorobiphen-3-yl)-(perfluorophenyl)(perfluoroanthracenyl)(tetrafluorofluorenyl)aluminate]⁻/dimethylsilyl(tetramethylcyclopentadienyl)(adamantyl-1-amino)dimethyltitanium

[N,N-2,4,6,-pentamethylanilinium]⁺[7-((n-butyl)(perfluorobiphenyl)amino)perfluoronaphth-2-yl)(5,6,7,8-tetrafluoronaphthyl)(tetrafluorofluorenyl)(perfluorophenyl)aluminate]⁻/dimethylsilyl(tetramethylcyclopentadienyl)(adamantyl-1-amino)dimethyltitanium

[N,N-2,4,6,-pentamethylanilinium]⁺[5-((benzyl)(2,3,6-trifluorophenyl)amino)perfluoroinden-2-yl)(perfluorophenyl)(4,5,6,7-tetrafluoronaphthyl)(2,3,5-trifluorophenyl)aluminate]⁻/pentamethylcyclopentadienyltribenzyltitanium

[N,N-dimethylanilinium]⁺[5-((methylethylhexylsilyl)(2,3,5-trifluorophenyl)arsino)perfluoronaphth-2-yl)(perfluorophenyl)(4,5,6,7-tetrafluoronaphthyl)(perfluoronaphthyl)aluminate]⁻/pentamethylcyclopentadienyltribenzyltitanium

[N,N-2,4,6,-pentamethylanilinium]⁺[7-((diethylnonylsilyl)(pentafluoroanthracenyl)phosphino)perfluoropyren-1-yl)(tetrafluorofluorenyl)(2,3,6-trifluorophenyl)(2',3',5'-trifluorobiphenyl)aluminate]⁻/dimethylsilyl(tetramethylcyclopentadienyl)(tert-butylamido)dichloridetitanium

[N,N-diethylanilinium]⁺[4'-((isopropyl)(perfluorophenyl)phosphino)perfluorobiphen-3-yl)(tetrafluorofluorenyl)(perfluorophenyl)(perfluoropyrenyl)aluminate]⁻/dimethylsily(bisindenyl)dichloridezirconium

[N,N-di(dodecyl)anilinium]⁺[3-((methyl)(perfluoropyrenyl)amino)fluorophen-1-yl)(2',3',5'-trifluorobiphenyl)(tetrafluorofluorenyl)(perfluoropyrenyl)aluminate]⁻/silacyclobutyl(tetramethylcyclopentadienyl)(n-propylcyclopentadienyl)dimethylzirconium

[N,N-diethylanilinium]⁺[5-((tri-n-propylsilylhexyl)(perfluorobiphenyl)phosphino)perfluoronaphth-1-yl)(perfluorophenyl)(2,3,6-trifluorophenyl)(2',3',5'-trifluorobiphenyl)aluminate]⁻/diphenylmethyl(fluorenyl)(cyclopentadienyl)dimethylzirconium

[N-methyl-N-(dodecylanilinium]⁺[7-((tri-isopropylsilyloctyl)(perfluorobiphenyl)phosphino)fluoronaphth-1-yl)(perfluorophenyl)(4,5,7-trifluoronaphthyl)(perfluoropyrenyl)aluminate]⁻/(tetramethylcyclopentadienyl)(n-propylcyclopentadienyl)dimethylzirconium

[N,N-2,4,6,-pentamethylanilinium]⁺[6-((tri-isopropylsilyloctyl)(perfluoronaphthyl)amino)perfluoronaphth-2-yl)(pentafluoroanthracenyl)(perfluorofluorenyl)(perfluorophenyl)aluminate]⁻/dimethylsilylbis(2-methylbenzindenyl)dimethylzirconium

[N,N-dimethylanilinium]⁺[7-((ethyl)(perfluoroanthracenyl)phosphino)perfluoronaphth-1-yl)-(5,6,7,8-tetrafluoronaphthyl)(2,3,5-trifluorophenyl)(4,5,7-trifluoronaphthyl)aluminate]⁻/(pentamethylcyclopentadienyl)(cyclopentadienyl)dimethylzirconium

[N,N-dimethylanilinium]⁺[6-((n-butyl)(perfluorobiphenyl)phosphino)perfluoronaphth-1-yl)-(pentafluoroanthracenyl)(perfluorobiphenyl)(perfluoropyrenyl)aluminate]⁻/tetra(bis(trimethylsilylmethyl))zirconium

[N,N-2,4,6,-pentamethylanilinium]⁺[5-((methyldiethylsilyloctyl)(perfluorobiphenyl)amino)perfluoronaphth-2-yl)(2,3,6-trifluorophenyl)(perfluorophenyl)(4,5,7-trifluoronaphthyl)aluminate]⁻/diphenylmethyl(fluorenyl)(cyclopentadienyl)dimethylzirconium

[N,N-di(dodecyl)anilinium]⁺[7-((butyl)(perfluoronaphthyl)phosphino)perfluoropyren-2-yl)(perfluorophenyl)(2,3,6-trifluorophenyl)(perfluoropyrenyl)aluminate]⁻/(tetramethylcyclopentadienyl)(n-propylcycdopentadienyl)dimethylzirconium

[N,N-2,4,6,-pentamethylanilinium]⁺[5-((methylethylhexylsilyl)(2,3,5-trifluorophenyl)amino)perfluoronapth-2-yl)(perfluorobiphenyl)(perfluorofluorenyl)(2,3,4-trifluorophenyl)aluminate]⁻/(pentamethylcyclopentadienyl)(cyclopentadienyl)dimethylzirconium

[tri-N-(methylphenyl)phosphonium]⁺[7-((cyclohexyl)(perfluorophenyl)arsino)perfluorofluoren-2-yl)(perfluorophenyl)(4,5,6,7-tetrafluoronaphthyl)(2',3',5'-trifluorobiphenyl)aluminate]⁻/oxotris(trimethisilylmethyl)vanadium

[tri-N-(n-butyl)phosphonium]⁺[7-((methyldiethylsilyloctyl)(perfluorofluorenyl)phosphino)perfluoropyren-1-yl)bis(pentalfluoropyrenyl)(pentafluoroanthracenyl)aluminate]⁻/oxotris(trimethlsilylmethyl)vanadium

[N,N,N-(dimethyl)(t-butyl)phosphonium]⁺[6-((tri-n-propylsilylhexyl)(2,3,6-trifluorophenyl)arsino)perfluoronapth-2-yl)(pentalfluoropyrenyl)(perfluorofluorenyl)(4,5,7-trifluoronaphthyl)aluminate]⁻/oxotris(trimethisilylmethyl)vanadium

[tri-N-ethylphosphonium]⁺[4-((triethylsilylethyl)(2',3',5'-trifluorobiphenyl)amino)fluorophen-1-yl)(perfluorofluorenyl)(perfluoronaphthyl)(perfluorobiphenyl)aluminate]⁻/diphenylmethyl(cylcopentadienyl)(2,7-dimethylfluorenyl)dimethylhafnium

[tri-N-(n-butyl)phosphonium]⁺[7-((octyl)(perfluorobiphenyl)arsino)fluoroinden-2-yl)(perfluorophenyl)(perfluoropyrenyl)(perfluorobiphenyl)aluminate]⁻/dimethylsilylbisindenyldimethylhafnium

[N,N,N-(dimethyl)(t-butyl)phosphonium]⁺[7-((isopropyl)(perfluorophenyl)amino)perfluoronaphth-3-yl)bis(2,3,5-trifluorophenyl)(4,5,6-trifluoronaphthylaluminate]⁻/diphenylmethyl(cylcopentadienyl)(fluorenyl)dimethylhafnium

[tri-N-(t-butyl)phosphonium]⁺[7-((octyl)(perfluoropyrenyl)phosphino)perfluoroinden-2-yl)-(perfluoropyrenyl)(tetrafluorofluorenyl)(4,5,6,7-tetrafluoronaphthyl)aluminate]⁻/dimethylsilylbis(methylindenyl)dimethylhafnium

[N,N,N-(ethyl)(dioctyl)phosphonium]⁺[6-((methylethylhexylsilyl)(2,3,5-trifluorophenyl)amino)fluoroanthracen-1-yl)(4,5,7-trifluoronaphthyl)(perfluorophenyl)(2',3',4'-trifluorobiphenyl)aluminate]⁻/diphenylmethyl(fluorenyl)(cyclopentadienyl)dimethylhafnium

[N,N,N-(ethyl)(methyl)(isopropyl)phosphonium]⁺[7-((trimethylsilyl)(perfluorofluorenyl)phosphino)fluoropyren-1-yl)bis(pentalfluoropyrenyl)(pentafluoroanthracenyl)aluminate]⁻/dimethylsily-bisindenyldimethylhafnium

[tri-N-(methylphenyl)phosphonium]⁺[7-((propyl)(2,3,6-trifluorophenyl)amino)perfluoropyren-2-yl)bis(5,6,7,8-tetrafluoronaphthyl)(perfluorofluorenyl)aluminate]⁻/(4-alkyl-1-phenyl)(4-tri-butyl-1-phenyl)methyl(cylcopentadienyl)(fluorenyl)dimethylhafnium

[N,N,N-(dimethyl)(t-butyl)phosphonium]⁺[8-((n-butyl)(perfluorophenyl)amino)perfluoropyren-2-yl)(perfluorophenyl)(4,5,6-trifluoronaphthyl)(tetrafluorofluorenyl)aluminate]⁻/diphenylmethyl(fluorenyl)(cyclopentadienyl)dimethylhafnium

[tri-N-methylphosphonium]⁺[6-((butyl)(perfluorobiphenyl)amino)perfluorofluoren-2-yl)(tetrafluorofluorenyl)(4,5,6,7-tetrafluoronaphthyl)(perfluoropyrenyl)aluminate]⁻/dimethylsilylbisindenyldimethylhafnium

[tri-N-propylphosphonium]⁺[5-((tri-isopropylsilyl)(perfluoroanthracenyl)phosphino)perfluoro-napth-2-yl)(perfluoronaphthyl)(perfluoroanthracenyl)(2',3',5'-trifluorobiphenyl)aluminate]⁻/diphenylmethyl(cylcopentadienyl)(2,7-dimethylfluorenyl)dimethylhafnium

[N,N,N-(ethyl)(methyl)(t-butyl)phosphonium]⁺[7-((ethyl)(tetrafluorofluorenyl)amino)perfluorofluoren-2-yl)(perfluorophenyl)(perfluoroanthracenyl)(4,5,7-trifluoronaphthyl)aluminate]⁻/dimethylsily-bisindenyldimethylhafnium

[N,N,N-(ethyl)(methyl)(isopropyl)phosphonium]⁺[7-((hexyl)(perfluorophenyl)arsino)perfluoropyren-2-yl)(tetrafluorofluorenyl)(2',3',4'-trifluorobiphenyl)(pentalfluoropyrenyl)aluminate]⁻/dimethylsily-bisindenyldimethylhafnium

[tri-N-methylphosphonium]⁺[6-((octyl)(perfluoropyrenyl)arsino)fluoroanthracen-1-yl)(perfluorophenyl)(2',3',5'-trifluorobiphenyl)(4,5,6,7-tetrafluoronaphthyl)aluminate]⁻/dimethylsilylbis(phenylmethylindenyl)dimethylhafnium

[N,N,N-(ethyl)(methyl)(octyl)phosphonium]⁺[7-((tri-n-propylsilylhexyl)(2,3,5-trifluorophenyl)amino)fluoronapth-1-yl)(pentalfluoropyrenyl)(perfluoroanthracenyl)(2',3',5'-trifluorobiphenyl)aluminate]⁻/dimethylsily-bisindenyldimethylhafnium

[N,N,N-(ethyl)(methyl)(t-butyl)phosphonium]⁺[6-((tri-isopropylsilyl)(perfluorophenyl)amino)perfluoroanthracen-2-yl)(perfluorobiphenyl)(tetrafluorofluorenyl)(2,3,5-trifluorophenyl)aluminate]⁻/diphenylmethyl(cylcopentadienyl)(2,7-di-tri-butyl-fluorenyl)dimethylhafnium

[N,N,N-(ethyl)(methyl)(t-butyl)phosphonium]⁺[7-((ethyl)(perfluoroanthracenyl)amino)perfluoropyren-2-yl)bis(perfluoroanthracenyl)(tetrafluorofluorenylaluminate]⁻/dimethylsilylbisindenyldimethylhafnium

[tri-N-(methylphenyl)phosphonium]⁺[8-((triethylsilyl)(perfluorophenyl)amino)perfluoropyren-2-yl)(perfluoroanthracenyl)(perfluorobiphenyl)(5,6,7,8-tetrafluoronaphthyl)aluminate]⁻/diphenylmethyl(cylcopentadienyl)(fluorenyl)dimethylhafnium

[N,N,N-(ethyl)(dioctyl)phosphonium]⁺[6-((methylethylhexylsilyl)(perfluorophenyl)amino)perfluoroanthracen-1-yl)(4,5,7-trifluoronaphthyl)(perfluorophenyl)(tetrafluorofluorenyl)aluminate]⁻/dimethylsilyl(tetramethylcyclopentadienyl)(dodecylamido)dimethylhafnium

[N,N,N-(dimethyl)(t-butyl)phosphonium]⁺[7-((methylethylhexylsilyl)(perfluorobiphenyl)amino)perfluoropyren-2-yl)(perfluorophenyl)(5,6,7,8-tetrafluoronaphthyl)(perfluorobiphenyl)aluminate]⁻/diphenylmethyl(cylcopentadienyl)(2,7-di-tri-butyl-fluorenyl)dimethylhafnium

[tri-N-methylphosphonium]⁺[4'-((benzyl)(tetrafluorofluorenyl)amino)perfluorobiphen-4-yl)(pentafluoroanthracenyl)(4,5,6-trifluoronaphthyl)(perfluorophenyl)aluminate]⁻/(4-alkyl-1-phenyl)(4-tri-butyl-1-phenyl)methyl(cylcopentadienyl)(fluorenyl)dimethylhafnium

[tri-N-methylphosphonium]⁺[7-((3-ethylnonyl)(perfluorobiphenyl)phosphino)perfluoropyren-1-yl)(4,5,7-trifluoronaphthyl)(perfluoropyrenyl)(perfluorophenyl)aluminate]⁻/dimethylsilylbis(phenylmethylindenyl)dimethylhafnium

[N,N,N-(ethyl)(methyl)(n-butyl)phosphonium]⁺[5-((hexyl)(2',3',5'-trifluorobiphenyl)amino)perfluoronapth-2-yl)(pentafluoroanthracenyl)(perfluoroanthracenyl)(4,5,6-trifluoronaphthyl)aluminate]⁻/diphenylmethyl(fluorenyl)(cyclopentadienyl)dimethylhafnium

[tri-N-propylphosphonium]⁺[8-((tri-isopropylsilyl)(perfluoronaphthyl)amino)fluoronapth-3-yl)

(perfluorobiphenyl)(2,3,4-trifluorophenyl)(perfluoropyrenyl)aluminate]⁻/diphenylmethyl(cylcopentadienyl)(2,7-dimethylfluorenyl)dimethylhafnium

[tri-N-(n-butyl)phosphonium]⁺[7-((ethyl)(4,5,7-trifluoronaphthyl)amino)perfluoropyren-2-yl)(pentalfluoropyrenyl)(perfluorofluorenyl)(perfluorophenyl)aluminate]⁻/diphenylmethyl(cylcopentadienyl)(2,7-dimethylfluorenyl)dimethylhafnium

[N,N,N-(ethyl)(methyl)(n-butyl)phosphonium]⁺[7-((triethylsilylethyl)(pentalfluoropyrenyl)amino)perfluoroinden-2-yl)(perfluorobiphenyl)(pentafluoroanthracenyl)(perfluoroanthracenyl)aluminate]⁻/diphenylmethyl(cylcopentadienyl)(2,7-dimethylfluorenyl)dimethylhafnium

[N,N,N-(ethyl)(dioctyl)phosphonium]⁺[6-((n-butyl)(4,5,6-trifluoronaphthyl)amino)perfluorofluoren-1-yl)(perfluorophenyl)(4,5,6-trifluoronaphthyl)(tetrafluorofluorenyl)aluminate]⁻/dimethylsilylbis(methylindenyl)dimethylhafnium

[tri-N-ethylphosphonium]⁺[7-((3-ethylnonyl)(2,3,6-trifluorophenyl)amino)perfluoronapth-1-yl)(4,5,7-trifluoronaphthyl)(perfluorophenyl)(5,6,7,8-tetrafluoronaphthyl)aluminate]⁻/dimethylsily-bisindenyidimethylhafnium

[N,N,N-(ethyl)(methyl)(isopropyl)phosphonium]⁺[3-((benzyl)(perfluorophenyl)amino)perfluorophenyl)(5,6,7,8-tetrafluoronaphthyl)(2,3,5-trifluorophenyl)(tetrafluorofluorenyl)aluminate]⁻/dimethylsilyl(tetramethylcyclopentadienyl)(dodecylamido)dihydridehafnium

[N,N,N-(ethyl)(methyl)(isopropyl)phosphonium]⁺[7-((diethylnonlysilyl)(perfluorobiphenyl)phosphino)perfluoronapth-2-yl)(pentalfluoropyrenyl)(2',3',4'-trifluorobiphenyl)(perfluoroanthracenyl)aluminate]⁻/dimethylsilyl(tetramethylcyclopentadienyl)(dodecylamido)dimethylhafnium

[N,N,N-(ethyl)(dioctyl)phosphonium]⁺[7-((tri-n-propylsilyl)(perfluorofluorenyl)arsino)perfluoronapth-3-yl)(perfluorobiphenyl)(perfluorophenyl)(2,3,5-trifluorophenyl)aluminate]⁻/tetrabenzylhafnium

[tri-N-(dimethylphenyl)phosphonium]⁺[7-((triethylsilyl)(perfluorobiphenyl)amino)perfluoropyren-1-yl)(perfluorobiphenyl)(perfluoronaphthyl)(pentalfluoropyrenyl)aluminate]⁻/diphenylmethyl(cylcopentadienyl)(2,7-di-tri-butyl-fluorenyl)dimethylhafnium

[N,N,N-(ethyl)(methyl)(n-butyl)phosphonium]⁺[4-((triethylsilylethyl)(pentafluoroanthracenyl)amino)perfluorophenyl)(5,6,7,8-tetrafluoronaphthyl)(2,3,5-trifluorophenyl)(perfluoropyrenyl)aluminate]⁻/(4-alkyl-1-phenyl)(4-tri-butyl-1-phenyl)methyl(cylcopentadienyl)(fluorenyl)dimethylhafnium

[tri-N-(t-butyl)phosphonium]⁺[4'-((butyl)(2,3,6-trifluorophenyl)arsino)perfluorobiphen-3-yl)(perfluoroanthracenyl)(perfluoronaphthyl)(2,3,5-trifluorophenyl)aluminate]⁻/dimethylsilyl(tetramethylcyclopentadienyl)(dodecylamido)dimethylhafnium

[N,N,N-(dimethyl)(t-butyl)phosphonium]⁺[6-((propyl)(perfluorophenyl)amino)perfluorofluoren-2-yl)(perfluoroanthracenyl)(perfluoronaphthyl)(2',3',5'-trifluorophenyl)aluminate]⁻/diphenylmethyl(cylcopentadienyl)(2,7-di-tri-butyl-fluorenyl)dimethylhafnium

[tri-N-octylphosphonium]⁺[6-((triethylsilyl)(perfluorobiphenyl)amino)perfluoroanthracen-1-yl)(4,5,7-trifluoronaphthyl)(perfluorophenyl)(pentalfluoropyrenyl)aluminate]⁻/diphenylmethyl(cylcopentadienyl)(2,7-di-tri-butyl-fluorenyl)dimethylhafnium

[tri-N-(dimethylphenyl)phosphonium]⁺[5-((hexyl)(perfluorobiphenyl)amino)perfluoroinden-1-yl)(perfluoroanthracenyl)(perfluorofluorenyl)(5,6,7,8-tetrafluoronaphthyl)aluminate]⁻/dimethylsilyl(tetramethylcyclopentadienyl)(dodecylamido)dihydridehafnium

[N,N,N-(ethyl)(methyl)(isopropyl)phosphonium]⁺[6-((butyl)(perfluorophenyl)amino)fluoronapth-1-yl)(perfluorobiphenyl)(pentalfluoropyrenyl)(pentafluoroanthracenyl)aluminate]⁻/tris(trimethylsilylmethyl)dichlorideniobium

[N,N,N-(dimethyl)(t-butyl)phosphonium]⁺[8-((triethylsilylethyl)(2',3',5'-trifluorobiphenyl)amino)perfluoronapth-3-yl)(tetrafluorofluorenyl)(2,3,4-trifluorophenyl)(perfluoronaphthyl)-aluminate]⁻/tris(trimethylsilylmethyl)dichloridetantalum

[tri-N-methylphosphonium]⁺[7-((nonyl)(perfluorobiphenyl)phosphino)perfluorofluoren-2-yl)-(perfluoroanthracenyl)(perfluoropyrenyl)(2',3',5'-trifluorobiphenyl)aluminate]⁻/tris(trimethylsilylmethyl)dichloridetantalum

[N,N,N-(dimethyl)(t-butyl)phosphonium]⁺[7-((diethylnonlysilyl)(perfluoropyrenyl)amino)perfluoronaphth-1-yl)(4,5,6-trifluoronaphthyl)(2,3,5-trifluorophenyl)(5,6,7,8-tetrafluoronaphthyl)aluminate]⁻/bis(hexamethyldisilido)dimethyltitanium

[N,N,N-(ethyl)(methyl)(octyl)phosphonium]⁺[6-((triethylsilylethyl)(perfluorophenyl)amino)perfluoronapth-2-yl)(perfluorobiphenyl)(2',3',5'-trifluorobiphenyl)(perfluorophenyl)aluminate]⁻/pentamethylcyclopentadienyltrimethyltitanium

[N,N,N-(ethyl)(methyl)(t-butyl)phosphonium]⁺[4'-((triethylsilylethyl)(perfluoropyrenyl)amino)perfluorobiphen-4-yl)bis(perfluoroanthracenyl)(perfluorobiphenylaluminate]⁻/pentamethylcyclopentadienylisopropoxidetitanium

[N,N,N-(ethyl)(dioctyl)phosphonium]⁺[7-((cyclohexyl)(pentafluoroanthracenyl)phosphino)perfluoronapth-2-yl)(perfluorobiphenyl)(perfluorofluorenyl)(perfluoronaphthyl)aluminate]⁻/dimethylsilyl(tetramethylcyclopentadienyl)(tert-butylamido)dichloridetitanium

[N,N,N-(ethyl)(methyl)(t-butyl)phosphonium]⁺[6-((tri-n-propylsilylhexyl)(perfluorofluorenyl)phosphino)perfluoroanthracen-2-yl)(perfluorophenyl)(perfluoronaphthyl)(2',3',4'-trifluorobiphenyl)aluminate]⁻/bis(hexamethyldisilido)dimethyltitanium

[tri-N-(methylphenyl)phosphonium]⁺[7-((n-butyl)(5,6,7,8-tetrafluoronaphthyl)amino)fluoronapth-2-yl)(perfluorophenyl)(2',3',5'-trifluorobiphenyl)(perfluoronaphthyl)aluminate]⁻/pentamethylcyclopentadienylisopropoxidetitanium

[N,N,N-(ethyl)(methyl)(t-butyl)phosphonium]⁺[7-((2,2-dimethyloctyl)(perfluoroanthracenyl)phosphino)perfluoronapth-2-yl)(perfluorophenyl)(2,3,6-trifluorophenyl)(pentafluoroanthracenyl)aluminate]⁻/dimethylsilyl(tetramethylcyclopentadienyl)(tert-butylamido)dichloridetitanium

[N,N,N-(ethyl)(methyl)(t-butyl)phosphonium]⁺[6-((octyl)(2',3',4'-trifluorobiphenyl)amino)perfluorofluoren-1-yl)(perfluorobiphenyl)(2,3,5-trifluorophenyl)(4,5,7-trifluoronaphthyl)aluminate]⁻/dimethylsilyl(tetramethylcyclopentadienyl)(adamantyl-1-amino)dimethyltitanium

[N,N,N-(ethyl)(methyl)(t-butyl)phosphonium]⁺[7-((isopropyl)(pentalfluoropyrenyl)amino)perfluoronapth-1- yl)(perfluoropyrenyl)(pentafluoroanthracenyl)(4,5,6-trifluoronaphthyl)aluminate]⁻/pentamethylcyclopentadienylisopropoxidetitanium

[tri-N-ethylphosphonium]⁺[6-((methyl)(perfluorobiphenyl)amino)perfluorofluoren-2-yl)(perfluorophenyl)(4,5,6-trifluoronaphthyl)(4,5,7-trifluoronaphthyl)aluminate]⁻/dimethylsilyl(tetramethylcyclopentadienyl)(adamantyl-1-amino)dimethyltitanium

[N,N,N-(ethyl)(methyl)(isopropyl)phosphonium]⁺[7-((2,2-dimethyloctyl)(perfluorophenyl)amino)perfluoroanthracen-1-yl)(perfluorobiphenyl)(pentalfluoropyrenyl)(pentafluoroanthracenyl)aluminate]⁻/pentamethylcydopentadienyltribenzyltitanium

[tri-N-methylphosphonium]⁺[6-((diethylnonlysilyl)(2,3,4-trifluorophenyl)amino)perfluorofluoren-1-yl)(perfluoroanthracenyl)(perfluorobiphenyl)(4,5,7-trifluoronaphthyl)aluminate]⁻/pentamethylcyclopentadienyltrimethyltitanium

[N,N,N-(ethyl)(dioctyl)phosphonium]⁺[6-((nonyl)(pentafluoroanthracenyl)amino)perfluoronapth-1-yl)(perfluoropyrenyl)(4,5,6-trifluoronaphthyl)(4,5,7-trifluoronaphthyl)aluminate]⁻/bis(hexamethyl disilido)dimethyltitanium

[N,N,N-(ethyl)(dioctyl)phosphonium]⁺[8-((triethylsilylethyl)(perfluoronaphthyl)arsino)perfluoropyren-2-yl)(2,3,6-trifluorophenyl)(perfluorophenyl)(4,5,6,7-tetrafluoronaphthyl)aluminate]⁻/pentamethyl cyclopentadienylisopropoxidetitanium

[tri-N-methylphosphonium]⁺[7-((methylethylhexylsilyl)(perfluorofluorenyl)amino)perfluoroanthracen-1-yl)(perfluoroanthracenyl)(perfluorofluorenyl)(pentafluoroanthracenyl)aluminate]⁻/pentamethylcyclopentadienyltrimethyltitanium

[N,N,N-(ethyl)(methyl)(octyl)phosphonium]⁺[6-((methyl)(2',3',5'-trifluorobiphenyl)amino)perfluoroanthracen-1-yl)(perfluorophenyl)(4,5,7-trifluoronaphthyl)(2',3',5'-trifluorobiphenyl)aluminate]⁻/pentamethylcyclopentadienylisopropoxidetitanium

[tri-N-propylphosphonium]⁺[7-((2,2-dimethyloctyl)(perfluorofluorenyl)phosphino)perfluoropyren-2-yl)(5,6,7,8-tetrafluoronaphthyl)(2,3,5-trifluorophenyl)(perfluorobiphenyl)aluminate]⁻/dimethylsilyl(tetramethylcyclopentadienyl)(adamantyl-1-amino)dimethyltitanium

[N N,N-(ethyl)(methyl)(octyl)phosphonium]⁺[4'-((methyldiethylsilyloctyl)(perfluorophenyl)amino)perfluorobiphen-4-yl)(pentalfluoropyrenyl)(perfluorophenyl)(perfluoronaphthyl)aluminate]⁻/dimethylsilyl(tetramethylcyclopentadienyl)(tert-butylamido)dichloridetitanium

[N,N,N-(ethyl)(methyl)(isopropyl)phosphonium]⁺[7-((propyl)(perfluorobiphenyl)amino)perfluoropyren-1-yl)(perfluorobiphenyl)(4,5,6,7-tetrafluoronaphthyl)(perfluoropyrenyl)aluminate]⁻/bis(1,3-dibutyl-methyl-cyclopentadienyl)dimethylzirconium

[N,N,N-(ethyl)(methyl)(t-butyl)phosphonium]⁺[7-((benzyl)(2',3',5'-trifluorobiphenyl)amino)perfluoronapth-1-yl)(perfluoroanthracenyl)(2',3',5'-trifluorobiphenyl)(perfluorobiphenyl)aluminate]⁻/dimethylsilyl(tetramethylcyclopentadienyl)(t-butylamido)dimethylzirconium

[tri-N-(dimethylphenyl)phosphonium]⁺[7-((methylethylhexylsilyl)(perfluorobiphenyl)amino)perfluoronaphth-1-yl)(4,5,7-trifluoronaphthyl)(2,3,6-trifluorophenyl)(perfluoroanthracenyl)aluminate]⁻/dimethylsilyl(tetramethylcyclopentadienyl)(t-butylamido)dimethylzirconium

[tri-N-(dimethylphenyl)phosphonium]⁺[3'-((3-ethylnonyl)(perfluoroanthracenyl)phosphino)perfluorobiphen-4-yl)(2,3,5-trifluorophenyl)(perfluorophenyl)(perfluorofluorenyl)aluminate]⁻/tetra(bis(trimethylsilylmethyl))zirconium

[N,N,N-(ethyl)(methyl)(n-butyl)phosphonium]⁺[5-((triethylsilyl)(4,5,7-trifluoronaphthyl)phosphino)perfluoronaphth-2-yl)(pentafluoroanthracenyl)(4,5,7-trifluoronaphthyl)(perfluorobiphenyl)aluminate]⁻/dimethylsilylbis(tetrahydroindenyl)dichloridezirconium

[tri-N-methylphosphonium]⁺[7-((methyl)(5,6,7,8-tetrafluoronaphthyl)phosphino)perfluorofluoren-1-yl)bis(perfluoroanthracenyl)(perfluorofluorenylaluminate]⁻/(pentamethylcyclopentadienyl)(cyclopentadienyl)dimethylzirconium

[N,N,N-(ethyl)(methyl)(isopropyl)phosphonium]⁺[6-((isopropyl)(perfluorofluorenyl)phosphino)perfluoroinden-2-yl)(pentafluoroanthracenyl)(5,6,7,8-tetrafluoronaphthyl)(pentalfluoropyrenyl)aluminate]⁻/dimethylsilylbis(2-methylbenzindenyl)dimethylzirconium

[N,N,N-(ethyl)(methyl)(t-butyl)phosphonium]⁺[5-((tri-n-propylsilylhexyl)(perfluorophenyl)phosphino)perfluoronaphth-2-yl)(perfluoronaphthyl)(perfluorofluorenyl)(perfluorohenyl)aluminate]⁻/silacyclobutyl(tetramethylcyclopentadienyl)(n-propylcyclopentadienyl)dimethylzirconium

[N,N,N-(ethyl)(dioctyl)phosphonium]⁺[7-((tri-n-propylsilylhexyl)(pentafluoroanthracenyl)amino)perfluoroanthracen-1-yl)(perfluorobiphenyl)(4,5,6,7-tetrafluoronaphthyl)(2,3,5-trifluorophenyl)aluminate]⁻/(pentamethylcyclopentadienyl)(cyclopentadienyl)dimethylzirconium

[tri-N-methylphosphonium]⁺[6-((isopropyl)(perfluoroanthracenyl)phosphino)fluoroanthracen-2-yl)(perfluorofluorenyl)(2',3',5'-trifluorobiphenyl)(tetrafluorofluorenyl)aluminate]⁻/diphenyimethyl(fluorenyl)(cyclopentadienyl)dimethylzirconium

[N,N,N-(ethyl)(methyl)(n-butyl)phosphonium]⁺[7-((ethyl)(perfluorophenyl)amino)perfluorofluoren-1-yl)(5,6,7,8-tetrafluoronaphthyl)(2,3,6-trifluorophenyl)(perfluorofluorenyl)aluminate]⁻/bis(1,3-dibutyl-methyl-cyclopentadienyl)dimethylzirconium

[tri-N-(methylphenyl)phosphonium]⁺[6-((propyl)(2,3,4-trifluorophenyl)amino)perfluoroanthracen-2-yl)(pentafluoroanthracenyl)(4,5,6-trifluoronaphthyl)(perfluorophenyl)aluminate]⁻/diphenylmethyl(fluorenyl)(cyclopentadienyl)dimethylzirconium

[tri-N-(dimethylphenyl)phosphonium]⁺[6-((3-ethylnonyl)(perfluorobiphenyl)amino)perfluoroinden-2-yl)(tetrafluorofluorenyl)(5,6,7,8-tetrafluoronaphthyl)(perfluorophenyl)aluminate]⁻/diphenylmethyl(fluorenyl)(cyclopentadienyl)dimethylzirconium

[N,N,N-(ethyl)(methyl)(isopropyl)phosphonium]⁺[7-((diethylnonlysilyl)(2,3,5-trifluorophenyl)amino)perfluoroinden-2-yl)(perfluorobiphenyl)(tetrafluorofluorenyl)(perfluorofluorenyl)aluminate]⁻/(tetramethylcyclopentadienyl)(n-propylcyclopentadienyl)dimethylzirconium

[N,N,N-(ethyl)(methyl)(n-butyl)phosphonium]⁺[3-((methyldiethylsilyloctyl)(perfluorobiphenyl)amino)perfluorophenyl)(tetrafluorofluorenyl)(pentafluoroanthracenyl)(pentalfluoropyrenyl)aluminate]⁻/(pentamethylcyclopentadienyl)(cyclopentadienyl)dimethylzirconium

[tri-N-ethylphosphonium]⁺[6-((nonyl)(perfluoropyrenyl)phosphino)per fluoronapth-1-yl)bis(pentalfluoropyrenyl)(tetrafluorofluorenylaluminate]⁻/bis(1,3-dibutyl-methylcyclopentadienyl)dimethylzirconium

[tri-N-(dimethylphenyl)phosphonium]⁺[6-((cyclohexyl)(perfluoroanthracenyl)amino)perfluorofluoren-1-yl)(pefluorobiphenyl)(perfluoropyrenyl)(pentalfluoropyrenyl)aluminate]⁻/tetra(bis(trimethylsilylmethyl))zirconium

[tri-N-ethylphosphonium]⁺[5-((2,2-dimethyloctyl)(pentafluoroanthracenyl)amino)perfluoronapth-3-yl)(4,5,7-trifluoronaphthyl)(tetrafluorofluorenyl)(perfluorophenyl)aluminate]⁻/diphenylmethyl(fluorenyl)(cyclopentadienyl)dimethylzirconium

[tri-N-(methylphenyl)phosphonium]⁺[6-((methylethylhexylsilyl)(2',3',5'-trifluorobiphenyl)amino)perfluorofluoren-2-yl)(perfluorophenyl)(perfluorobiphenyl)(2',3',5'-trifluorobiphenyl)aluminate]⁻/tetra(bis(trimethylsilylmethyl))zirconium

[N,N,N-(ethyl)(methyl)(isopropyl)phosphonium]⁺[7-((hexyl)(4,5,6-trifluoronaphthyl)arsino)perfluoropyren-1-yl)(4,5,7-trifluoronaphthyl)(perfluorobiphenyl)(perfluoroanthracenyl)aluminate]⁻/tetrabenzylzirconium

[tri-N-methylphosphonium]⁺[6-((triethylsilylpropyl)(4,5,7-trifluoronaphthyl)phosphino)perfluoronapth-2-yl)(perfluoronaphthyl)(perfluorobiphenyl)(2',3',4'-trifluorobiphenyl)aluminate]⁻/dimethylsily(bisindenyl)dichloridezirconium

[tri-N-ethylphosphonium]⁺[5-((octyl)(tetrafluorofluorenyl)amino)perfluoroindenyl)(4,5,6-trifluoronaphthyl)(perfluoronaphthyl)(perfluorobiphenyl)aluminate]⁻/dimethylsily(bisindenyl)dichloridezirconium

[trityl]⁺[7-((triethylsilylethyl)(2,3,4-trifluorophenyl)amino)perfluoronapth-2-yl)(perfluorofluorenyl)(4,5,7-trifluoronaphthyl)(perfluorobiphenyl)aluminate]⁻/dimethylsilylbis(phenylmethylindenyl)dimethylhafnium

[trityl]⁺[4'-((diethylnonlysilyl)(tetrafluorofluorenyl)amino)perfluorobiphen-4-yl)(perfluoronaphthyl)(perfluorophenyl)(4,5,6-trifluoronaphthyl)aluminate]⁻/diphenylmethyl(cylcopentadienyl)(2,7-dimethylfluorenyl)dimethylhafnium

[trityl]⁺[5-((n-butyl)(4,5,6,7-tetrafluoronaphthyl)amino)perfluoronapth-1-yl)(perfluorophenyl)(perfluorobiphenyl)(2',3',5'-trifluorobiphenyl)aluminate]⁻/diphenylmethyl(cylcopentadienyl)(fluorenyl)dimethylhafnium

[trityl]⁺[5-((triethylsilylpropyl)(perfluorophenyl)amino)fluoronapth-2-yl)(perfluoropyrenyl)(perfluorobiphenyl)(pentafluoroanthracenyl)aluminate]⁻/tetrabenzyltitanium

[trityl]⁺[7-((hexyl)(perfluorophenyl)amino)perfluoropyren-2-yl)(perfluorophenyl)(perfluoronaphthyl)(perfluorofluorenyl)aluminate]⁻/dimethylsilyl(tetramethylcyclopentadienyl)(adamantyl-1-amino)dimethyltitanium

[tri-N-octylammonium]⁺[7-((octyl)(4,5,7-trifluoronaphthyl)phosphino)perfluoroanthracen-1-yl)(tetrafluorofluorenyl)(4,5,6,7-tetrafluoronaphthyl)(2,3,4-trifluorophenyl)borate]⁻/oxotris(trimethlsilymethyl)vanadium

[tri-N-methylammonium]⁺[6-((tri-isopropylsilyl)(perfluoroanthracenyl)arsino)perfluorofluoren-2-yl)(4,5,7-trifluoronaphthyl)(perfluorofluorenyl)(perfluoropyrenyl)borate]⁻/oxotris(trimethlsilymethyl)vanadium

[tri-N-(methylphenyl)ammonium]⁺[4'-((diethylnonlysilyl)(tetrafluorofluorenyl)amino)perfluorobiphen-3-yl)(pentafluoroanthracenyl)(perfluoropyrenyl)(perfluorofluorenyl)borate]⁻/oxotris(trimethisilymethyl)vanadium

[tri-N-octylammonium]⁺[6-((cyclohexyl)(perfluorobiphenyl)amino)perfluoroanthracen-1-yl)(perfluorobiphenyl)(4,5,6-trifluoronaphthyl)(perfluoroanthracenyl)borate]⁻/oxotris(trimethlsilymethyl)vanadium

[N,N,N-(ethyl)(dioctyl)ammonium]⁺[7-((cyclohexyl)(4,5,6-trifluoronaphthyl)amino)perfluoronapth-3-yl)(2,3,5-trifluorophenyl)(perfluoronaphthyl)(perfluorofluorenyl)borate]⁻/oxotris(trimethlsilymethyl)vanadium

[tri-N-propylammonium]⁺[6-((cyclohexyl)(2,3,4-trifluorophenyl)amino)perfluoroanthracen-1-yl)(5,6,7,8-tetrafluoronaphthyl)(pentafluoroanthracenyl)(4,5,7-trifluoronaphthyl)borate]⁻/oxotris(trimethlsilymethyl)vanadium

[tri-N-ethylammonium]⁺[5-((diethylnonlysilyl)(perfluorobiphenyl)amino)perfluoronapth-3-yl)bis(4,5,6-trifluoronaphthyl)(perfluoronaphthylborate]⁻/diphenylmethyl(fluorenyl)(cyclopentadienyl)dimethylhafnium

[N,N,N-(ethyl)(methyl)(octyl)ammonium]⁺[6-((ethyl)(perfluoropyrenyl)amino)perfluoroanthracen-1-yl)(pentalfluoropyrenyl)(2',3',4'-trifluorobiphenyl)(2,3,4-trifluorophenyl)borate]⁻/dimethylsilyl(tetramethylcyclopentadienyl)(dodecylamido)dihydridehafnium

[N,N,N-(dimethyl)(t-butyl)ammonium]⁺[7-((2,2-dimethyloctyl)(perfluoropyrenyl)amino)perfluoropyren-1-yl)(perfluorophenyl)(2',3',4'-trifluorobiphenyl)(4,5,7-trifluoronaphthyl)borate]⁻/dimethylsilylbis(methylindenyl)dimethylhafnium

[N,N,N-(ethyl)(methyl)(isopropyl)ammonium]⁺[6-((methyldiethylsilyloctyl)(perfluorobiphenyl)arsino)perfluoronapth-3-yl)(perfluoropyrenyl)(2,3,6-trifluorophenyl)(pentalfluoropyrenyl)borate]⁻/dimethylsilyl(tetramethylcyclopentadienyl)(dodecylamido)dimethylhafnium

[tri-N-(dimethylphenylammonium]⁺[6-((tri-n-propylsilyl)(2',3',5'-trifluorobiphenyl)amino)perfluoronapth-3-yl)(perfluorobiphenyl)(2,3,4-trifluorophenyl)(4,5,6,7-tetrafluoronaphthyl)borate]⁻/diphenylmethyl(fluorenyl)(cyclopentadienyl)dimethylhafnium

[tri-N-methylammonium]⁺[5-((2,2-dimethyloctyl)(perfluorobiphenyl)amino)perfluoroinden-2-yl)(perfluorophenyl)(4,5,6-trifluoronaphthyl)(tetrafluorofluorenyl)borate]⁻/diphenylmethyl(cylcopentadienyl)(fluorenyl)dimethylhafnium

[N,N,N-(ethyl)(methyl)(n-butyl)ammonium]⁺[4-((methylethylhexylsilyl)(perfluorophenyl)amino)perfluorophenyl)(tetrafluorofluorenyl)(4,5,7-trifluoronaphthyl)(pentalfluoropyrenyl)borate]⁻/dimethylsilylbisindenyidimethylhafnium

[N,N,N-(ethyl)(dioctyl)ammonium]⁺[3-((methyldiethylsilyloctyl)(4,5,6-trifluoronaphthyl)amino)perfluorophenyl)(perfluorofluorenyl)(perfluorobiphenyl)(perfluoropyrenyl)borate]⁻/dimethylsilylbis(methylindenyl)dimethylhafnium

[tri-N-(n-butyl)ammonium]⁺[5-((methylethylhexylsilyl)(perfluoropyrenyl)amino)fluoroinden-1-yl)(perfluorofluorenyl)(perfluorophenyl)(2',3',5'-trifluorobiphenyl)borate]⁻/diphenylmethyl(cylcopentadienyl)(fluorenyl)dimethylhafnium

[N,N,N-(ethyl)(methyl)(n-butyl)ammonium]⁺[7-((methylethylhexylsilyl)(perfluorophenyl)amino)perfluoronapth-2-yl)(perfluoroanthracenyl)(2',3',4'-trifluorobiphenyl)(perfluorobiphenyl)borate]⁻/dimethylsilylbis(methylindenyl)dimethylhafnium

[tri-N-(methylphenyl)ammonium]⁺[7-((propyl)(perfluorobiphenyl)amino)fluoropyren-2-yl)bis(perfluorobiphenyl)(perfluoronaphthylborate]⁻/dimethylsilylbis(phenylmethylindenyl)dimethylhafnium

[tri-N-octylammonium]⁺[5-((triethylsilylpropyl)(5,6,7,8-tetrafluoronaphthyl)arsino)perfluoroinden-2-yl)(5,6,7,8- tetrafluoronaphthyl)(perfluorofluorenyl)(perfluorobiphenyl)borate]⁻/dimethylsilyl(tetramethylcyclopentadienyl)(dodecylamido)dihydridehafnium

[tri-N-methylammonium]⁺[7-((tri-n-propylsilyl)(4,5,6-trifluoronaphthyl)amino)perfluoropyren-1-yl)(5,6,7,8-tetrafluoronaphthyl)(2,3,4-trifluorophenyl)(4,5,7-trifluoronaphthyl)borate]⁻/tetrabenzyl hafnium

[N,N,N-(ethyl)(methyl)(isopropyl)ammonium]⁺[7-((triethylsilylethyl)(4,5,6-trifluoronaphthyl)arsino)perfluorofluoren-2-yl)(pentafluoroanthracenyl)(perfluoroanthracenyl)(5,6,7,8-tetrafluoronaphthyl)borate]⁻/dimethylsilylbis(methylindenyl)dimethylhafnium

[tri-N-ethylammonium]⁺[6-((3-ethylnonyl)(5,6,7,8-tetrafluoronaphthyl)amino)perfluoroanthracen-1-yl)(perfluorofluorenyl)(tetrafluorofluorenyl)(perfluorobiphenyl)borate]⁻/diphenylmethyl(cylcopentadienyl)(fluorenyl)dimethylhafnium

[N,N,N-(ethyl)(dioctyl)ammonium]⁺[6-((triethylsilyl)(2,3,6-trifluorophenyl)amino)perfluoronapth-2-yl)(pentafluoroanthracenyl)(perfluoronaphthyl)(perfluorobiphenyl)borate]⁻/dimethylsilylbisindenyldimethylhafnium

[tri-N-(methylphenyl)ammonium]⁺[6-((nonyl)(perfluorobiphenyl)amino)perfluoronapth-2-yl)bis(2,3,6-trifluorophenyl)(4,5,6-trifluoronaphthyl)borate]⁻/diphenylmethyl(cylcopentadienyl)(fluorenyl)dimethylhafnium

[N,N,N-(ethyl)(methyl)(isopropyl)ammonium]⁺[5-((isopropyl)(perfluorophenyl)phosphino)perfluoronapth-1-yl)(2,3,6-trifluorophenyl)(perfluoroanthracenyl)(pentalfluoropyrenyl)borate]⁻/dimethylsilylbis(methylindenyl)dimethylhafnium

[tri-N-(methylphenyl)ammonium]⁺[7-((tri-isopropylsilyl)(pentafluoroanthracenyl)amino)perfluoroinden-2-yl)(perfluorophenyl)(4,5,7-trifluoronaphthyl)(pentafluoroanthracenyl)borate]⁻/dimethylsilylbis(phenylmethylindenyl)dimethylhafnium

[tri-N-ethylammonium]⁺[5-((butyl)(perfluoropyrenyl)amino)perfluoronapth-2-yl)(perfluoronaphthyl)(perfluoroanthracenyl)(perfluorobiphenyl)borate]⁻/diphenylmethyl(cylcopentadienyl)(2,7-di-tri-butyl-fluorenyl)dimethylhafnium

[tri-N-(n-butyl)ammonium]⁺[5-((3-ethylnonyl)(4,5,6-trifluoronaphthyl)amino)perfluoronapth-2-yl)(2,3,6-trifluorophenyl)(2,3,5-trifluorophenyl)(perfluoroanthracenyl)borate]⁻/diphenylmethyl(cylcopentadienyl)(fluorenyl)dimethylhafnium

[tri-N-methylammonium]⁺[4'-((propyl)(perfluorofluorenyl)amino)perfluorobiphen-4-yl)-(pentafluoroanthracenyl)(perfluorophenyl)(5,6,7,8-tetrafluoronaphthyl)borate]⁻/diphenylmethyl(cylcopentadienyl)(2,7-dimethylfluorenyl)dimethylhafnium

[tri-N-methylammonium]⁺[5-((tri-isopropylsilyl)(perfluorobiphenyl)amino)perfluoronapth-2-yl)(perfluoroanthracenyl)(perfluoropyrenyl)(2,3,5-trifluorophenyl)borate]⁻/dimethylsilylbis(phenylmethylindenyl)dimethylhafnium

[tri-N-ethylammonium]⁺[4-((hexyl)(perfluorobiphenyl)amino)perfluorophenyl)(perfluorophenyl)(2',3',4'-trifluorobiphenyl)(2,3,5-trifluorophenyl)borate]⁻/dimethylsilyl(tetramethylcyclopentadienyl)(dodecylamido)dihydridehafnium

[tri-N-methylammonium]⁺[7-((isopropyl)(perfluorobiphenyl)amino)perfluoropyren-2-yl)(perfluoropyrenyl)(perfluorophenyl)(4,5,6,7-tetrafluoronaphthyl)borate]⁻/diphenylmethyl(cylcopentadienyl)(fluorenyl)dimethylhafnium

[tri-N-methylammonium]⁺[5-((methyldiethylsilyloctyl)(perfluoropyrenyl)amino)perfluoronapth-2-yl)(perfluorofluorenyl)(2,3,5-trifluorophenyl)(2',3',4'-trifluorobiphenyl)borate]⁻/diphenylmethyl(cylcopentadienyl)(2,7-di-tri-butyl-fluorenyl)dimethylhafnium

[N,N,N-(ethyl)(dioctyl)ammonium]⁺[7-((octyl)(perfluoronaphthyl)phosphino)perfluoronapth-2-yl)(perfluoropyrenyl)(2,3,6-trifluorophenyl)(2,3,5-trifluorophenyl)borate]⁻/tetrabenzyl hafnium

[tri-N-propylammonium]⁺[6-((ethyl)(perfluorophenyl)amino)perfluorofluoren-2-yl)(perfluorophenyl)(4,5,6,7-tetrafluoronaphthyl)(perfluorobiphenyl)borate]⁻/dimethylsilylbis(naphthylmethylindenyl)dimethylhafnium

[tri-N-(n-butyl)ammonium]⁺[5-((3-ethylnonyl)(2,3,4-trifluorophenyl)amino)perfluoroinden-1-yl)(perfluorophenyl)(4,5,6,7-tetrafluoronaphthyl)(2,3,6-trifluorophenyl)borate]⁻/diphenylmethyl(cylcopentadienyl)(2,7-di-tri-butyl-fluorenyl)dimethylhafnium

[N,N,N-(ethyl)(methyl)(t-butyl)ammonium]⁺[6-((methylethylhexylsilyl)(perfluorofluorenyl)phosphino)perfluoroinden-2-yl)(perfluorofluorenyl)(perfluoroanthracenyl)(5,6,7,8-tetrafluoronaphthyl)borate]⁻/dimethylsilyl(tetramethylcyclopentadienyl)(dodecylamido)dihydridehafnium

[tri-N-(n-butyl)ammonium]⁺[5-((ethyl)(perfluoroanthracenyl)phosphino)perfluoroinden-1-yl)(perfluorophenyl)(2,3,4-trifluorophenyl)(4,5,7-trifluoronaphthyl)borate]⁻/diphenylmethyl(cylcopentadienyl)(fluorenyl)dimethylhafnium

[tri-N-ethylammonium]⁺[3-((tri-n-propylsilylhexyl)(pentafluoroanthracenyl)phosphino)perfluorophenyl)(perfluorophenyl)(perfluoronaphthyl)(perfluoroanthracenyl)borate]⁻/(4-alkyl-1-phenyl)(4-tri-butyl-1-phenyl)methyl(cylcopentadienyl)(fluorenyl)dimethylhafnium

[N,N,N-(dimethyl)(t-butyl)ammonium]⁺[7-((trimethylsilyl)(perfluorobiphenyl)phosphino)perfluoronapth-2-yl)(pentalfluoropyrenyl)(perfluorophenyl)(perfluoronaphthyl)borate]⁻/dimethylsilylbis(phenylmethylindenyl)dimethylhafnium

[tri-N-octylammonium]⁺[7-((ethyl)(2,3,5-trifluorophenyl)phosphino)fluoropyren-1-yl)(4,5,6-trifluoronaphthyl)(perfluorophenyl)(perfluorobiphenyl)borate]⁻/dimethylsilyl(tetramethylcyclopentadienyl)(dodecylamido)dihydridehafnium

[tri-N-ethylammonium]⁺[7-((methylethylhexylsilyl)(perfluoropyrenyl)phosphino)perfluoropyren-1-yl)(pentalfluoropyrenyl)(2',3',4'-trifluorobiphenyl)(2,3,4-trifluorophenyl)borate]⁻/tetrabenzyl hafnium

[tri-N-ethylammonium]⁺[7-((cyclohexyl)(perfluoropyrenyl)amino)perfluoroinden-2-yl)-(pentafluoroanthracenyl)(perfluoroanthracenyl)(5,6,7,8-tetrafluoronaphthyl)borate]⁻/diphenylmethyl(fluorenyl)(cyclopentadienyl)dimethylhafnium

[tri-N-(dimethylphenylammonium]⁺[4'-((octyl)(perfluoronaphthyl)amino)perfluorobiphen-4-yl)(pentafluoroanthracenyl)(perfluorophenyl)(pentalfluoropyrenyl)borate]⁻/diphenylmethyl(cylcopentadienyl)(2,7-dimethylfluorenyl)dimethylhafnium

[tri-N-(methylphenyl)ammonium]⁺[7-((n-butyl)(perfluorophenyl)phosphino)perfluorofluoren-1-yl)bis(pentafluoroanthracenyl)(perfluorophenylborate]⁻/(4-alkyl-1-phenyl)(4-tri-butyl-1-phenyl)methyl(cylcopentadienyl)(fluorenyl)dimethylhafnium

[N,N,N-(ethyl)(methyl)(t-butyl)ammonium]⁺[5-((diethylnonlysilyl)(pentafluoroanthracenyl)amino)

perfluoroinden-1-yl)(2,3,5-trifluorophenyl)(perfluoronaphthyl)(perfluorofluorenyl)borate]⁻/dimethylsilyl(tetramethylcyclopentadienyl)(dodecylamido)dimethylhafnium

[N,N,N-(ethyl)(methyl)(n-butyl)ammonium]⁺[7-((triethylsilylethyl)(perfluoropyrenyl)amino)perfluoropyren-1-yl)(perfluoronaphthyl)(2',3',5'-trifluorobiphenyl)(2,3,5-trifluorophenyl)borate]⁻/dimethylsilylbis(phenylmethylindenyl)dimethylhafnium

[N,N,N-(ethyl)(methyl)(isopropyl)ammonium]⁺[6-((2,2-dimethyloctyl)(perfluorophenyl)amino)fluoronapth-3-yl)bis(2,3,4-trifluorophenyl)(4,5,6,7-tetrafluoronaphthyl)borate]⁻/diphenylmethyl(fluorenyl)(cyclopentadienyl)dimethylhafnium

[N,N,N-(ethyl)(methyl)(t-butyl)ammonium]⁺[7-((cyclohexyl)(perfluoronaphthyl)amino)perfluoroanthracen-1-yl)bis(perfluoroanthracenyl)(perfluoropyrenyl)borate]⁻/dimethylsilylbis(naphthylmethylindenyl)dimethylhafnium

[tri-N-methylammonium]⁺[6-((methyl)(perfluorobiphenyl)phosphino)perfluorofluoren-2-yl)-(perfluorophenyl)(2',3',4'-trifluorobiphenyl)(tetrafluorofluorenyl)borate]⁻/dimethylsilylbis(naphthylmethylindenyl)dimethylhafnium

[tri-N-methylammonium]⁺[5-((tri-n-propylsilylhexyl)(perfluorobiphenyl)amino)perfluoronapth-2-yl)(perfluorophenyl)(2,3,5-trifluorophenyl)(perfluorobiphenyl)borate]⁻/tris(trimethylsilylmethyl)dichloridetantalum

[N,N,N-(ethyl)(dioctyl)ammonium]⁺[7-((triethylsilyl)(5,6,7,8-tetrafluoronaphthyl)phosphino)perfluorofluoren-1-yl)(perfluoropyrenyl)(2,3,6-trifluorophenyl)(perfluorobiphenyl)borate]⁻/tris(trimethylsilylmethyl)dichloridetantalum

[N,N,N-(ethyl)(methyl)(n-butyl)ammonium]⁺[7-((isopropyl)(2,3,6-trifluorophenyl)amino)perfluoronapth-3-yl)(pentafluoroanthracenyl)(perfluorofluorenyl)(perfluoropyrenyl)borate]⁻/tris(trimethylsilylmethyl)dichloridetantalum

[tri-N-propylammonium]⁺[7-((trimethylsilyl)(perfluorobiphenyl)amino)perfluorofluoren-1-yl)-(perfluoroanthracenyl)(perfluorobiphenyl)(5,6,7,8-tetrafluoronaphthyl)borate]⁻/tris(trimethylsilylmethyl)dichloridetantalum

[tri-N-octylammonium]⁺[7-((octyl)(2',3',4'-trifluorobiphenyl)phosphino)perfluoroinden-2-yl)-(perfluoroanthracenyl)(perfluorobiphenyl)(perfluoropyrenyl)borate]⁻/pentamethylcyclopentadienyltribenzyltitanium

[N,N,N-(ethyl)(methyl)(isopropyl)ammonium]⁺[6-((propyl)(perfluorophenyl)amino)perfluoroanthracen-2-yl)(perfluorophenyl)(perfluoroanthracenyl)(2',3',5'-trifluorobiphenyl)borate]⁻/tetrabenzyl titanium

[N,N,N-(ethyl)(methyl)(t-butyl)ammonium]⁺[6-((tri-isopropylsilyloctyl)(2,3,4-trifluorophenyl)phosphino)perfluoroanthracen-1-yl)(pentalfluoropyrenyl)(4,5,6,7-tetrafluoronaphthyl)(perfluoronaphthyl)borate]⁻/bis(hexamethyldisilido)dimethyltitanium

[N,N,N-(ethyl)(methyl)(n-butyl)ammonium]⁺[3-((butyl)(perfluoroanthracenyl)amino)perfluorophenyl)(4,5,7-trifluoronaphthyl)(perfluorophenyl)(perfluoropyrenyl)borate]⁻/tetrabenzyltitanium

[tri-N-propylammonium]⁺[5-((tri-n-propylsilylhexyl)(perfluorobiphenyl)arsino)fluoronapth-2-yl)(4,5,7-trifluoronaphthyl)(perfluorobiphenyl)(4,5,6-trifluoronaphthyl)borate]⁻/pentamethylcyclopentadienyltrimethyltitanium

[N,N,N-(ethyl)(methyl)(isopropyl)ammonium]⁺[5-((triethylsilyl)(perfluorophenyl)arsino)perfluoroinden-1-yl)(perfluorobiphenyl)(2,3,4-trifluorophenyl)(perfluoroanthracenyl)borate]⁻/pentamethylcyclopentadienyltribenzyltitanium

[N,N,N-(ethyl)(methyl)(n-butyl)ammonium]⁺[6-((methyldiethylsilyloctyl)(2,3,5-trifluorophenyl)phosphino)perfluoroinden-2-yl)(perfluoroanthracenyl)(2,3,4-trifluorophenyl)(tetrafluorofluorenyl)borate]⁻/dimethylsilyl(tetramethylcyclopentadienyl)(adamantyl-1-amino)dimethyltitanium

[tri-N-(n-butyl)ammonium]⁺[7-((ethyl)(2,3,6-trifluorophenyl)phosphino)perfluoropyren-2-yl)-(perfluorophenyl)(pentalfluoropyrenyl)(pentafluoroanthracenyl)borate]⁻/pentamethylcyclopentadienyltrimethyltitanium

[tri-N-(methylphenyl)ammonium]⁺[6-((2,2-dimethyloctyl)(perfluoronaphthyl)amino)fluoronapth-2-yl)(2,3,4-trifluorophenyl)(2',3',4'-trifluorobiphenyl)(2,3,5-trifluorophenyl)borate]⁻/pentamethyl cyclopentadienyl tribenzyl titanium

[N,N,N-(ethyl)(methyl)(n-butyl)ammonium]⁺[4'-((diethylnonlysilyl)(perfluoropyrenyl)phosphino)perfluorobiphen-4-yl)(tetrafluorofluorenyl)(2,3,4-trifluorophenyl)(perfluoroanthracenyl)borate]⁻/dimethylsily(tetramethylcyclopentadienyl)(tert-butylamido)dichloridetitanium

[tri-N-(methylphenyl)ammonium]⁺[6-((2,2-dimethyloctyl)(perfluoropyrenyl)amino)perfluoroinden-2-yl)(perfluoropyrenyl)(perfluoronaphthyl)(perfluoroanthracenyl)borate]⁻/pentamethyl cyclopentadienyl tribenzyl titanium

[tri-N-(n-butyl)ammonium]⁺[4'-((benzyl)(perfluoroanthracenyl)amino)perfluorobiphen-3-yl)(perfluoropyrenyl)(perfluorobiphenyl)(tetrafluorofluorenyl)borate]⁻/pentamethyl cyclopentadienylisopropoxidetitanium

[N,N,N-(ethyl)(dioctyl)ammonium]⁺[4-((octyl)(perfluorophenyl)phosphino)perfluorophenyl)(pentafluoroanthracenyl)(perfluorobiphenyl)(2,3,4-trifluorophenyl)borate]⁻/dimethylsilyl(tetramethylcyclopentadienyl)(tert-butylamido)dichloridetitanium

[tri-N-ethylammonium]⁺[5-((cyclohexyl)(perfluorobiphenyl)amino)perfluoronaphth-2-yl)bis(pentafluoroanthracenyl)(pentalfluoropyrenyl)borate]⁻/tetrabenzyltitanium

[N,N,N-(ethyl)(methyl)(octyl)ammonium]⁺[7-((methyldiethylsilyloctyl)(perfluorobiphenyl)phosphino)perfluorofluoren-1-yl)(4,5,7-trifluoronaphthyl)(perfluorofluorenyl)(tetrafluorofluorenyl)borate]⁻/bis(hexamethyldisilido)dimethyltitanium

[tri-N-(n-butyl)ammonium]⁺[7-((tri-isopropylsilyloctyl)(perfluoropyrenyl)amino)perfluoronapth-1-yl)(perfluorobiphenyl)(2',3',5'-trifluorobiphenyl)(4,5,6-trifluoronaphthyl)borate]⁻/bis(hexamethyldisilido)dimethyltitanium

[N,N,N-(dimethyl)(t-butyl)ammonium]⁺[6-((methylethylhexylsilyl)(4,5,6,7-tetrafluoronaphthyl)amino)perfluoronapth-1-yl)(perfluorophenyl)(2,3,4-trifluorophenyl)(perfluoronaphthyl)borate]⁻/dimethylsilyl(tetramethylcyclopentadienyl)(tert-butylamido)dichloridetitanium

[N,N,N-(dimethyl)(t-butyl)ammonium]⁺[5-((butyl)(2',3',5'-trifluorobiphenyl)amino)perfluoronapth-1-yl)(perfluoroanthracenyl)(2',3',5'-trifluorobiphenyl)(perfluoronaphthyl)borate]⁻/tetrabenzyltitanium

[N,N,N-(ethyl)(methyl)(octyl)ammonium]⁺[6-((triethylsilyl)(perfluorobiphenyl)phosphino) perfluorofluoren-1-yl)(perfluorofluorenyl)(2',3',4'-trifluorobiphenyl)(2,3,6-trifluorophenyl)borate]⁻/dimethylsilyl(tetramethylcyclopentadienyl)(tert-butylamido)dichloridetitanium

[tri-N-ethylammonium]⁺[3-((propyl)(perfluorofluorenyl) phosphino)perfluorophenyl)(perfluoroanthracenyl)(perfluorofluorenyl)(4,5,6-trifluoronaphthyl)borate]⁻/pentamethylcyclopentadienylisopropoxidetitanium

[tri-N-octylammonium]⁺[7-((trimethylsilyl)(perfluorobiphenyl)amino)perfluoroinden-2-yl) (perfluorobiphenyl)(2,3,6-trifluorophenyl)(perfluoroanthracenyl)borate]⁻/pentamethylcyclopentadienyltrimethyltitanium

[N,N,N-(dimethyl)(t-butyl)ammonium]⁺[6-((methyldiethylsilyloctyl)(perfluorobiphenyl)amino)perfluoroinden-2-yl)(5,6,7,8-tetrafluoronaphthyl)(2',3',4'-trifluorobiphenyl)(perfluorophenyl)borate]⁻/pentamethylcyclopentadienyltrimethyltitanium

[N,N,N-(ethyl)(methyl)(t-butyl)ammonium]⁺[6-((triethylsilylethyl)(5,6,7,8-tetrafluoronaphthyl)amino)perfluorofluoren-1-yl)(perfluorobiphenyl)(4,5,6-trifluorobiphenyl)(2,3,6-trifluorophenyl)borate]⁻/dimethylsilyl(tetramethylcyclopentadienyl)(tert-butylamido)dichloridetitanium

[N,N,N-(ethyl)(dioctyl)ammonium]⁺[5-((octyl)(perfluorophenyl)phosphino)perfluoronapth-2-yl) (perfluorobiphenyl)(4,5,6-trifluoronaphthyl) (perfluoropyrenyl)borate]⁻/dimethylsilyl (tetramethylcyclopentadienyl)(tert-butylamido) dichloridetitanium

[tri-N-(t-butyl)ammonium]⁺[7-((2,2-dimethyloctyl)(2',3', 4'-trifluorobiphenyl)amino)perfluoropyren-2-yl) (perfluoroanthracenyl)(2',3',5'-trifluorobiphenyl)(perfluorophenyl)borate]⁻/dimethylsilyl (tetramethylcyclopentadienyl)(tert-butylamido) dichloridetitanium

[tri-N-(t-butyl)ammonium]⁺[3'-((trimethylsilyl)(4,5,6,7-tetrafluoronaphthyl)phosphino)fluorobiphen-4-yl) (pentafluoroanthracenyl)(perfluorobiphenyl) (perfluoronaphthyl)borate]⁻/pentamethylcyclopentadienyltrimethyltitanium

[N,N,N-(ethyl)(methyl)(t-butyl)ammonium]⁺[6-((n-butyl)(4,5,6,7-tetrafluoronaphthyl)phosphino)fluoroinden-2-yl)(perfluoroanthracenyl)(perfluorobiphenyl) (perfluoropyrenyl)borate]⁻/dimethylsilyl (tetramethylcyclopentadienyl)(tert-butylamido) dichloridetitanium

[tri-N-octylammonium]⁺[7-((tri-n-propylsilyl)(4,5,7-trifluoronaphthyl)amino)perfluorofluoren-1-yl)(4,5,7-trifluoronaphthyl)(2,3,6-trifluorophenyl) (perfluoroanthracenyl)borate]⁻/pentamethylcyclopentadienyltrimethyltitanium

[tri-N-ethylammonium]⁺[7-((triethylsilylpropyl)(pentafluoroanthracenyl)phosphino)perfluoropyren-2-yl) (perfluoropyrenyl)(2,3,4-trifluorophenyl) (perfluoroanthracenyl)borate]⁻/dimethylsilyl (tetramethylcyclopentadienyl)(tert-butylamido) dichloridetitanium

[tri-N-(methylphenyl)ammonium]⁺[7-((ethyl) (perfluorophenyl)amino)perfluoronapth-2-yl)-(4,5,6-trifluoronaphthyl)(perfluorobiphenyl)(perfluoronaphthyl) borate]⁻/pentamethylcyclopentadienyltrimethyltitanium

[N,N,N-(ethyl)(methyl)(isopropyl)ammonium]⁺[6-((n-butyl)(4,5,6,7-tetrafluoronaphthyl)phosphino)perfluorofluoren-2-yl)(perfluorobiphenyl)(2,3,4-trifluorophenyl)(perfluoroanthracenyl)borate]⁻/pentamethylcyclopentadienylisopropoxidetitanium

[tri-N-octylammonium]⁺[4'-((3-ethylnonyl)(perfluorobiphenyl)amino)perfluorobiphen-3-yl)bis (perfluorobiphenyl)(pentafluoroanthracenyl)borate]⁻/dimethylsilylbis(tetrahydroindenyl)dichloridezirconium

[tri-N-(t-butyl)ammonium]⁺[5-((nonyl)(perfluorophenyl)amino)perfluoronapth-1-yl)(perfluoroanthracenyl)(5,6,7,8-tetrafluoronaphthyl)(perfluorophenyl)borate]⁻/bis(1,3-dibutyl-methylcyclopentadienyl)dimethylzirconium

[tri-N-(n-butyl)ammonium]⁺[6-((octyl)(4,5,6,7-tetrafluoronaphthyl)phosphino)perfluoroanthracen-2-yl)(pentafluoroanthracenyl)(2,3,4-trifluorophenyl)(5,6,7,8-tetrafluoronaphthyl)borate]⁻/dimethylsilylbis (tetrahydroindenyl)dichloridezirconium

[tri-N-(methylphenyl)ammonium]+(7-((benzyl) (perfluorophenyl)phosphino)perfluoropyren-2-yl) (perfluoronaphthyl)(tetrafluorofluorenyl) (perfluoroanthracenyl)borate]⁻/silacyclobutyl (tetramethylcyclopentadienyl)(n-propylcyclopentadienyl) dimethylzirconium

[tri-N-(t-butyl)ammonium]⁺[5-((cyclohexyl) (perfluoropyrenyl)amino)perfluoroinden-2-yl) (perfluorobiphenyl)(4,5,6-trifluoronaphthyl) (pentafluoropyrenyl)borate]⁻/dimethylsilyl (tetramethylcyclopentadienyl)(t-butylamido) dimethylzirconium

[N,N,N-(ethyl)(dioctyl)ammonium]⁺[7-((tri-n-propylsilyl)(pentalfluoropyrenyl)amino)perfluorofluoren-2-yl)(perfluoroanthracenyl)(2',3',4'-trifluorobiphenyl)(2,3,5-trifluorophenyl)borate]⁻/(pentamethylcyclopentadienyl) (cyclopentadienyl)dimethylzirconium

[N,N,N-(ethyl)(dioctyl)ammonium]⁺[6-((triethylsilylethyl)(perfluorobiphenyl)amino) perfluorofluoren-2-yl)(perfluorophenyl)(2',3',4'-trifluorobiphenyl)(tetrafluorofluorenyl)borate]⁻/tetrabenzylzirconium

[tri-N-octylammonium]⁺[7-((nonyl)(5,6,7,8-tetrafluoronaphthyl)amino)perfluoronapth-2-yl)-(perfluoropyrenyl)(perfluorofluorenyl)(2',3',4'-trifluorobiphenyl)borate]⁻/(pentamethylcyclopentadienyl) (cyclopentadienyl)dimethylzirconium

[N,N,N-(ethyl)(methyl)(octyl)ammonium]⁺[5-((tri-n-propylsilylhexyl)(perfluorobiphenyl)arsino)perfluoroinden-2-yl)(pentafluoroanthracenyl)(4,5,7-trifluoronaphthyl) (perfluorophenyl)borate]⁻/tetrabenzylzirconium

[N,N,N-(ethyl)(methyl)(isopropyl)ammonium]⁺[6-((propyl)(4,5,7-trifluoronaphthyl)phosphino) perfluoroanthracen-1-yl)(perfluorophenyl)(4,5,6,7-tetrafluoronaphthyl)(4,5,7-trifluoronaphthyl)borate]⁻/dimethylsilyl(tetramethylcyclopentadienyl)(t-butylamido) dimethylzirconium

[N,N,N-(ethyl)(methyl)(isopropyl)ammonium]⁺[7-((propyl)(perfluorobiphenyl)amino)fluoropyren-1-yl) (perfluorophenyl)(4,5,7-trifluoronaphthyl)(2',3',4'-trifluorobiphenyl)borate]⁻/dimethylsilyl (tetramethylcyclopentadienyl)(t-butylamido) dimethylzirconium

[N,N,N-(dimethyl)(t-butyl)ammonium]⁺[3'-((methyldiethylsilyloctyl)(perfluorobiphenyl)phosphino) fluorobiphen-4-yl)(perfluoroanthracenyl) (perfluorofluorenyl)(2,3,4-trifluorophenyl)borate]⁻/tetra(bis (trimethylsilylmethyl))zirconium

[N,N,N-(ethyl)(methyl)(octyl)ammonium]⁺[5-((nonyl)(2, 3,5-trifluorophenyl)amino)perfluoronapth-2-yl)(5,6,7,8-tetrafluoronaphthyl)(perfluorophenyl)(4,5,7-trifluoronaphthyl)borate]⁻/tetrabenzylzirconium

[tri-N-ethylammonium]⁺[8-((isopropyl)(perfluoroanthracenyl)amino)perfluoropyren-2-yl)(perfluorobiphenyl)(2',3',4'-trifluorobiphenyl)(perfluoroanthracenyl)borate]⁻/silacyclobutyl(tetramethylcyclopentadienyl)(n-propylcyclopentadienyl)dimethylzirconium

[tri-N-octylammonium]⁺[6-((isopropyl)(5,6,7,8-tetrafluoronaphthyl)arsino)perfluoronapth-2-yl)(perfluorobiphenyl)(4,5,6,7-tetrafluoronaphthyl)(pentalfluoropyrenyl)borate]⁻/(tetramethylcyclopentadienyl)(n-propylcyclopentadienyl)dimethylzirconium

[N,N,N-(ethyl)(methyl)(isopropyl)ammonium]⁺[6-((2,2-dimethyloctyl)(perfluoropyrenyl)amino)perfluoroinden-2-yl)(perfluoropyrenyl)(perfluorophenyl)(perfluoronaphthyl)borate]⁻/tetra(bis(trimethylsilylmethyl))zirconium

[tri-N-octylammonium]⁺[7-((methyl)(perfluorobiphenyl)arsino)perfluorofluoren-2-yl)(4,5,7-tri-fluoronaphthyl)(tetrafluorofluorenyl)(2',3',4'-trifluorobiphenyl)borate]⁻/tetra(bis(trimethylsilylmethyl))zirconium

[tri-N-propylammonium]⁺[6-((n-butyl)(perfluoronaphthyl)amino)perfluorofluoren-1-yl)(perfluorobiphenyl)(pentalfluoropyrenyl)(5,6,7,8-tetrafluoronaphthyl)borate]⁻/dimethylsilyl(tetramethylcyclopentadienyl)(t-butylamido)dimethylzirconium

[N,N,N-(ethyl)(methyl)(t-butyl)ammonium]⁺[3'-((triethylsilyl)(perfluorophenyl)amino)perfluorobiphen-4-yl)(4,5,7-trifluoronaphthyl)(perfluorobiphenyl)(2,3,4-trifluorophenyl)borate]⁻/tetra(bis(trimethylsilylmethyl))zirconium

[N,N,N-(ethyl)(methyl)(octyl)ammonium]⁺[5-((diethylnonlysilyl)(2,3,6-trifluorophenyl)amino)perfluoronapth-2-yl)(perfluoroanthracenyl)(perfluoronaphthyl)(perfluorophenyl)borate]⁻/dimethylsilylbis(2-methylbenzindenyl)dimethylzirconium

[tri-N-propylammonium]⁺[3'-((triethylsilyl)(2,3,6-trifluorophenyl)phosphino)perfluorobiphen-4-yl)bis(perfluoroanthracenyl)(5,6,7,8-tetrafluoronaphthylborate]⁻/(pentamethylcyclopentadienyl)(cyclopentadienyl)dimethylzirconium

[tri-N-(dimethylphenylammonium]⁺[3-((tri-n-propylsilylhexyl)(perfluorophenyl)phosphino)perfluorophenyl)(perfluoroanthracenyl)(2,3,4-trifluorophenyl)(4,5,6-trifluoronaphthyl)borate]⁻/dimethylsilylbis(tetrahydroindenyl)dichloridezirconium

[N,N,N-(ethyl)(dioctyl)ammonium]⁺[5-((benzyl)(perfluorophenyl)phosphino)perfluoronapth-1-yl)(5,6,7,8-tetrafluoronaphthyl)(2,3,5-trifluorophenyl)(perfluorofluorenyl)borate]⁻/silacyclobutyl(tetramethylcyclopentadienyl)(n-propylcyclopentadienyl)dimethylzirconium

[N,N,N-(dimethyl)(t-butyl)ammonium]⁺[6-((hexyl)(perfluoropyrenyl)amino)perfluoroanthracen-1-yl)(5,6,7,8-tetrafluoronaphthyl)(2,3,5-trifluorophenyl)(2,3,4-trifluorophenyl)borate]⁻/dimethylsilyl(tetramethylcyclopentadienyl)(t-butylamido)dimethylzirconium

[tri-N-ethylammonium]⁺[5-((tri-n-propylsilylhexyl)(perfluorobiphenylamino)perfluoroinden-1-yl)(perfluoronaphthyl)(4,5,6-trifluoronaphthyl)(pentalfluoropyrenyl)borate]⁻/diphenylmethyl(fluorenyl)(cyclopentadienyl)dimethylzirconium

[N,N,N-(ethyl)(dioctyl)ammonium]⁺[5-((tri-n-propylsilyl)(perfluorobiphenyl)phosphino)fluoroinden-1-yl)(perfluoropyrenyl)(perfluorofluorenyl)borate]⁻/dimethylsilylbis(2-methylbenzindenyl)dimethylzirconium

[tri-N-ethylammonium]⁺[6-((triethylsilylpropyl)(4,5,7-trifluoronaphthyl)amino)perfluorofluoren-2-yl)(perfluoropyrenyl)(pentafluoropyrenyl)(2',3',5'-trifluorobiphenyl)borate]⁻/(tetramethylcyclopentadienyl)(n-propylcyclopentadienyl)dimethylzirconium

[tri-N-propylammonium]⁺[4-((octyl)(tetrafluorofluorenyl)arsino)perfluorophenyl)(perfluoroanthracenyl)(2,3,4-trifluorophenyl)(tetrafluorofluorenyl)borate]⁻/dimethylsily(bisindenyl)dichloridezirconium

[tri-N-(n-butyl)ammonium]⁺[6-((tri-n-propylsilylhexyl)(perfluorophenyl)amino)perfluoronapth-1-yl)(2',3',5'-trifluorobiphenyl)(perfluorofluorenyl)(perfluoropyrenyl)borate]⁻/dimethylsilylbis(tetrahydroindenyl)dichloridezirconium

[N,N,N-(ethyl)(methyl)(n-butyl)ammonium]⁺[2'-((methyl)(perfluorophenyl)phosphino)perfluorobiphen-4-yl)(perfluoropyrenyl)(4,5,6-trifluoronaphthyl)(perfluorobiphenyl)borate]⁻/(tetramethylcyclopentadienyl)(n-propylcyclopentadienyl)dimethylzirconium

[N,N,N-(ethyl)(methyl)(isopropyl)ammonium]⁺[5-((cyclohexyl)(perfluoroanthracenyl)amino)perfluoronapth-2-yl)(perfluorobiphenyl)(tetrafluorofluorenyl)(perfluorofluorenyl)borate]⁻/dimethylsilylbis(tetrahydroindenyl)dichloridezirconium

[tri-N-(dimethylphenylammonium]⁺[8-((tri-n-propylsilyl)(4,5,6-trifluoronaphthyl)amino)perfluoropyren-2-yl)(2,3,4-trifluorophenyl)(perfluorobiphenyl)(perfluoropyrenyl)borate]⁻/dimethylsilylbis(2-methylbenzindenyl)dimethylzirconium

[tri-N-octylammonium]⁺[7-((ethyl)(pentafluoroanthracenyl)amino)perfluoropyren-2-yl)bis(5,6,7,8-tetrafluoronaphthyl)(2',3',4'-trifluorobiphenyl)borate]⁻/dimethylsilyl(tetramethylcyclopentadienyl)(t-butylamido)dimethylzirconium

[N,N,N-(ethyl)(methyl)(octyl)ammonium]⁺[5-((n-butyl)(perfluorobiphenyl)amino)perfluoronapth-1-yl)(perfluoroanthracenyl)(2,3,4-trifluorophenyl)(4,5,6,7-tetrafluoronaphthyl)borate]⁻/dimethylsilylbis(2-methylbenzindenyl)dimethylzirconium

[N,N,N-(ethyl)(methyl)(t-butyl)ammonium]⁺[6-((butyl)(perfluoronaphthyl)amino)perfluorofluoren-2-yl)(pentalfluoropyrenyl)(4,5,7-trifluoronaphthyl)(perfluoroanthracenyl)borate]⁻/dimethylsilylbis(2-methylbenzindenyl)dimethylzirconium

[tri-N-(n-butyl)ammonium]⁺[6-((tri-isopropylsilyl)(perfluorophenyl)amino)perfluorofluoren-2-yl)(perfluorofluorenyl)(perfluoroanthracenyl)(4,5,6,7-tetrafluoronaphthyl)borate]⁻/bis(1,3-dibutyl-methyl-cyclopentadienyl)dimethylzirconium

[tri-N-(methylphenyl)ammonium]⁺[6-((nonyl)(2,3,5-trifluorophenyl)amino)perfluoroanthracen-1-yl)(perfluorophenyl)(2,3,4-trifluorophenyl)(5,6,7,8-tetrafluoronaphthyl)borate]⁻/(pentamethylcyclopentadienyl)(cyclopentadienyl)dimethylzirconium

[tri-N-ethylammonium]⁺[4-((methyldiethylsilyloctyl)(perfluorophenyl)amino)perfluorophenyl)(pentafluoroanthracenyl)(pentalfluoropyrenyl)(perfluoroanthracenyl)borate]⁻/tetrabenzylzirconium

[N,N,N-(ethyl)(methyl)(octyl)ammonium]⁺[6-((diethylnonlysilyl)(2,3,6-trifluorophenyl)amino)fluorofluoren-2-yl)(4,5,7-trifluoronaphthyl)(perfluorobiphenyl)(perfluoroanthracenyl)borate]⁻/dimethylsily(bisindenyl)dichloridezirconium

[tri-N-(methylphenyl)ammonium]⁺[7-((n-butyl)(2,3,6-trifluorophenyl)amino)perfluorofluoren-2-yl)bis(2,3,4- trifluorophenyl)(tetrafluorofluorenylborate]⁻/dimethylsily(bisindenyl)dichloridezirconium

[N,N,N-(ethyl)(methyl)(t-butyl)ammonium]⁺[8-((methyldiethylsilyloctyl)(perfluorophenyl)amino)perfluoronapth-3-yl)(2,3,6-trifluorophenyl)(perfluorophenyl)(tetrafluorofluorenyl)borate]⁻/dimethylsilyl(tetramethylcyclopentadienyl)(t-butylamido)dimethylzirconium

[tri-N-octylammonium]⁺[6-((methylethylhexylsilyl)(pentalfluoropyrenyl)phosphino)perfluoronapth-1-yl)bis(2,3,6-trifluorophenyl)(perfluoropyrenyl)borate]⁻/dimethylsilylbis(2-methylbenzindenyl)dimethylzirconium

[tri-N-propylammonium]⁺[4'-((triethylsilylpropyl)(pentafluoroanthracenyl)amino)fluorobiphen-4-yl)(perfluoroanthracenyl)(perfluorofluorenyl)(2',3',5'-trifluorobiphenyl)borate]⁻/tetra(bis(trimethylsilylmethyl))zirconium

[N,N,N-(ethyl)(methyl)(octyl)ammonium]⁺[6-((propyl)(pentafluoroanthracenyl)phosphino)perfluoroanthracen-2-yl)(perfluorophenyl)(2,3,5-trifluorophenyl)(2',3',4'-trifluorobiphenyl)borate]⁻/dimethylsilyl(tetramethylcyclopentadienyl)(t-butylamido)dimethylzirconium

[tri-N-octylammonium]⁺[7-((tri-n-propylsilyl)(perfluorophenyl)amino)perfluoronapth-1-yl)bis(2,3,4-trifluorophenyl)(2,3,5-trifluorophenyl)borate]⁻/dimethylsilylbis(tetrahydroindenyl)dichloridezirconium

[tri-N-propylammonium]⁺[6-((tri-n-propylsilyl)(perfluorobiphenyl)amino)perfluoroanthracen-2-yl)(2',3',5'-trifluorobiphenyl)(perfluorobiphenyl)(perfluorophenyl)borate]⁻/diphenylmethyl(fluorenyl)(cyclopentadienyl)dimethylzirconium

[tri-N-(t-butyl)ammonium]⁺[6-((tri-isopropylsilyl)(perfluoropyrenyl)arsino)perfluoroanthracen-2-yl)(perfluoronaphthyl)(perfluorophenyl)(perfluorobiphenyl)borate]⁻/dimethylsilylbis(tetrahydroindenyl)dichloridezirconium

[tri-N-octylammonium]⁺[7-((diethylnonlysilyl)(perfluorobiphenyl)phosphino)perfluoropyren-2-yl)(perfluorophenyl)(4,5,6,7-tetrafluoronaphthyl)(2',3',5'-trifluorobiphenyl)borate]⁻/silacyclobutyl(tetramethylcyclopentadienyl)(n-propylcyclopentadienyl)dimethylzirconium

[tri-N-(dimethylphenylammonium]⁺[6-((benzyl)(pentalfluoropyrenyl)amino)perfluoroinden-2-yl)(perfluorophenyl)(perfluorobiphenyl)(4,5,6-trifluoronaphthyl)borate]⁻/tetra(bis(trimethylsilylmethyl))zirconium

[N,N,N-(ethyl)(methyl)(t-butyl)ammonium]⁺[6-((2,2-dimethyloctyl)(perfluorobiphenyl)amino)fluoronapth-3-yl)(perfluorophenyl)(2',3',4'-trifluorobiphenyl)(perfluoroanthracenyl)borate]⁻/silacyclobutyl(tetramethylcyclopentadienyl)(n-propylcyclopentadienyl)dimethylzirconium

[N,N,N-(ethyl)(methyl)(octyl)ammonium]⁺[7-((tri-n-propylsilylhexyl)(perfluorophenyl)phosphino)fluoropyren-1-yl)(perfluoroanthracenyl)(2,3,4-trifluorophenyl)(perfluorophenyl)borate]⁻/(tetramethylcyclopentadienyl)(n-propylcyclopentadienyl)dimethylzirconium

[N,N-2,4,6,-pentamethylanilinium]⁺[8-((n-butyl)(perfluorofluorenyl)amino)perfluoronaphth-3-yl)(perfluoronaphthyl)(5,6,7,8-tetrafluoronaphthyl)(pentafluoroanthracenyl)borate]⁻/oxotris(trimethisilylmethyl)vanadium

[N-methyl-N-dodecylanilinium]⁺[6-((cyclohexyl)(perfluoropyrenyl)phosphino)perfluorofluoren-1-yl)(perfluorophenyl)(2,3,4-trifluorophenyl)(2',3',4'-trifluorobiphenyl)borate]⁻/oxotris(trimethlsilylmethyl)vanadium

[N-methyl-N-dodecylanilinium]⁺[5-((triethylsilyl)(perfluorobiphenyl)amino)perfluoroinden-1-yl)(perfluorofluorenyl)(tetrafluorofluorenyl)(perfluorophenyl)borate]⁻/dimethylsilylbis(phenylmethylindenyl)dimethylhafnium

[N-methyl-N-dodecylanilinium]⁺[3-((3-ethylnonyl)(2,3,5-trifluorophenyl)amino)perfluorophenyl)(perfluorophenyl)(perfluoroanthracenyl)(pentalfluoropyrenyl)borate]⁻/tetrabenzylhafnium

[N,N-2,4,6,-pentamethylanilinium]⁺[6-((triethylsilylethyl)(perfluorobiphenyl)amino)perfluoroanthracen-1-yl)(perfluorobiphenyl)(perfluoroanthracenyl)(tetrafluorofluorenyl)borate]⁻/diphenylmethyl(fluorenyl)(cyclopentadienyl)dimethylhafnium

[N,N-di(dodecyl)anilinium]⁺[3-((butyl)(perfluorobiphenyl)arsino)perfluorophenyl)(pentalfluoropyrenyl)(2',3',5'-trifluorobiphenyl)(perfluorophenyl)borate]⁻/dimethylsilyl bisindenyidimethylhafnium

[N,N-2,4,6,-pentamethylanilinium]⁺[6-((methylethylhexylsilyl)(perfluoropyrenyl)amino)perfluoroanthracen-2-yl)(perfluorophenyl)(2,3,4-trifluorophenyl)(4,5,6,7-tetrafluoronaphthyl)borate]⁻/dimethylsilyl(tetramethylcyclopentadienyl)(dodecylamido)dihydridehafnium

[N-methyl-N-dodecylanilinium]⁺[7-((octyl)(5,6,7,8-tetrafluoronaphthyl)amino)perfluoronapth-1-yl)(perfluorobiphenyl)(perfluoropyrenyl)(pentalfluoropyrenyl)borate]⁻/diphenylmethyl(cyclopentadienyl)(2,7-di-tri-butyl-fluorenyl)dimethylhafnium

[N,N-di(dodecyl)anilinium]⁺[7-((triethylsilyl)(4,5,7-trifluoronaphthyl)amino)fluorofluoren-2-yl)-(perfluorofluorenyl)(perfluoropyrenyl)(2,3,5-trifluorophenyl)borate]⁻/dimethylsilylbis(methylindenyl)dimethylhafnium

[N,N-di(dodecyl)anilinium]⁺[6-((trimethylsilyl)(perfluorobiphenyl)amino)perfluorofluoren-1-yl)(pentalfluoropyrenyl)(perfluorophenyl)(2',3',4'-trifluorobiphenyl)borate]⁻/dimethylsilylbis(methylindenyl)dimethylhafnium

[N,N-diethylanilinium]⁻[6-((methyldiethylsilyloctyl)(perfluorophenyl)amino)perfluoroinden-2-yl)(perfluorobiphenyl)(4,5,6-trifluoronaphthyl)(perfluoropyrenyl)borate]⁻/dimethylsilylbisindenyldimethylhafnium

[N-methyl-N-dodecylanilinium]⁺[5-((triethylsilylpropyl)(perfluorobiphenyl)amino)fluoroinden-2-yl)(perfluorofluorenyl)(perfluoropyrenyl)(perfluorophenyl)borate]⁻/dimethylsilyl(tetramethylcyclopentadienyl)(dodecylamido)dimethylhafnium

[N,N-diethylanilinium]⁺[3'-((tri-n-propylsilyl)(perfluorophenyl)phosphino)perfluorobiphen-4-yl)(tetrafluorofluorenyl)(2,3,6-trifluorophenyl)(pentafluoroanthracenyl)borate]⁻/diphenyimethyl(cyclopentadienyl)(fluorenyl)dimethylhafnium

[N,N-di(dodecyl)anilinium]⁺[6-((methylethylhexylsilyl)(perfluoropyrenyl)phosphino)perfluorofluoren-2-yl)(tetrafluorofluorenyl)(5,6,7,8-tetrafluoronaphthyl)(perfluoropyrenyl)borate]⁻/diphenylmethyl(fluorenyl)(cyclopentadienyl)dimethylhafnium

[N,N-2,4,6,-pentamethylanilinium]⁺[7-((n-butyl)(pentafluoroanthracenyl)amino)perfluoronapth-3-yl)bis(perfluorobiphenyl)(2,3,5-trifluorophenylborate]⁻/dimethylsilylbis(phenylmethylindenyl)dimethylhafnium

[N,N-di(dodecyl)anilinium]⁺[6-((tri-n-propylsilylhexyl)(4,5,6-trifluoronaphthyl)amino)perfluoroanthracen-2-yl)

(perfluorobiphenyl)(perfluoroanthracenyl)borate]⁻/(4-alkyl-1-phenyl)(4-tri-butyl-1-phenyl)methyl(cyclopentadienyl)(fluorenyl)dimethylhafnium

[N,N-di(dodecyl)anilinium]⁺[5-((benzyl)(pentaffluoropyrenyl)amino)perfluoroinden-2-yl)(perfluorobiphenyl)(perfluoronaphthyl)(2,3,6-trifluorophenyl)borate]⁻/dimethylsilylbisindenyldimethylhafnium

[N,N-diethylanilinium]⁺[7-((methylethylhexylsilyl)(perfluorobiphenyl)phosphino)perfluoronapth-2-yl)(2,3,4-trifluorophenyl)(perfluoropyrenyl)(2',3',4'-trifluorobiphenyl)borate]⁻/diphenylmethyl(cyclopentadienyl)(2,7-di-tri-butyl-fluorenyl)dimethylhafnium

[N,N-di(dodecyl)anilinium]⁺[5-((methylethylhexylsilyl)(perfluorophenyl)amino)perfluoronapth-1-yl)bis(4,5,6,7-tetrafluoronaphthyl)(perfluorofluorenylborate]⁻/diphenylmethyl(cyclopentadienyl)(2,7-di-tri-butyl-fluorenyl)dimethylhafnium

[N,N-dimethylanilinium]⁺[5-((nonyl)(perfluorophenyl)amino)perfluoroinden-2-yl)(perfluorobiphenyl)(perfluoronaphthyl)(2,3,6-trifluorophenyl)borate]⁻/dimethylsilyl(tetramethylcyclopentadienyl)(dodecylamido)dimethylhafnium

[N,N-diethylanilinium]⁺[6-((tri-isopropylsilyl)(2,3,5-trifluorophenyl)amino)perfluoroinden-2-yl)(perfluorofluorenyl)(perfluoronaphthyl)(2,3,6-trifluorophenyl)borate]⁻/diphenylmethyl(cyclopentadienyl)(fluorenyl)dimethylhafnium

[N,N-di(dodecyl)anilinium]⁺[5-((tri-n-propylsilyl)(perfluorophenyl)amino)perfluoronapth-3-yl)-(2,3,5-trifluorophenyl)(perfluorophenyl)(4,5,7-trifluoronaphthyl)borate]⁻/dimethylsilyl(tetramethylcyclopentadienyl)(dodecylamido)dimethylhafnium

[N,N-2,4,6,-pentamethylanilinium]⁺[5-((benzyl)(perfluorobiphenyl)amino)perfluoronapth-3-yl)(perfluorobiphenyl)(pentafluoroanthracenyl)(perfluorophenyl)borate]⁻/tris(trimethylsilylmethyl)dichlorideniobium

[N,N-dimethylanilinium]⁺[7-((tri-isopropylsilyloctyl)(pentafluoroanthracenyl)amino)perfluoronapth-3-yl)(perfluorobiphenyl)(2,3,4-trifluorophenyl)(perfluorophenyl)borate]⁻/tris(trimethylsilylmethyl)dichlorideniobium

[N,N-2,4,6,-pentamethylanilinium]⁺[7-((tri-n-propylsilylhexyl)(perfluorobiphenyl)amino)perfluoroanthracen-1-yl)(2',3',5'-trifluorobiphenyl)(5,6,7,8-tetrafluoronaphthyl)(perfuorophenyl)borate]⁻/tris(trimethylsilylmethyl)dichlorideniobium

[N,N-2,4,6,-pentamethylanilinium]⁺[7-((nonyl)(perfluorobiphenyl)arsino)perfluoropyren-1-yl)(perfluorophenyl)(perfluorobiphenyl)(2,3,5-trifluorophenyl)borate]⁻/tris(trimethylsilylmethyl)dichlorideniobium

[N,N-di(dodecyl)anilinium]⁺[6-((3-ethylnonyl)(perfluorophenyl)amino)perfluoroinden-2-yl)-(perfluoropyrenyl)(2,3,6-trifluorophenyl)(perfluoroanthracenyl)borate]⁻/tris(trimethylsilylmethyl)dichlorideniobium

[N,N-2,4,6,-pentamethylanilinium]⁺[7-((triethylsilylpropyl)(perfluoroanthracenyl)amino)fluorofluoren-1-yl)(perfluorofluorenyl)(perfluoropyrenyl)(2,3,6-trifluorophenyl)borate]⁻/tris(trimethylsilylmethyl)dichloridetantalum

[N,N-2,4,6,-pentamethylanilinium]⁺[4-((methyldiethylsilyloctyl)(2',3',4'-trifluorobiphenyl)amino)perfluorophenyl)(2,3,6-trifluorophenyl)(perfluorophenyl)(4,5,7-trifluoronaphthyl)borate]⁻/tetrabenzyltitanium

[N,N-diethylanilinium]⁺[6-((hexyl)(perfluorobiphenyl)amino)perfluorofluoren-2-yl)(pentafluoroanthracenyl)(perfluoropyrenyl)(perfluorofluorenyl)borate]⁻/bis(hexamethyldisilido)dimethyltitanium

[N,N-diethylanilinium]⁺[5-((2,2-dimethyloctyl)(perfluoropyrenyl)amino)fluoronapth-3-yl)(perfluorofluorenyl)(tetrafluorofluorenyl)(4,5,6-trifluoronaphthyl)borate]⁻/dimethylsilyl(tetramethylcyclopentadienyl)(tert-butylamido)dichloridetitanium

[N,N-diethylanilinium]⁺[4'-((nonyl)(perfluoropyrenyl)amino)perfluorobiphen-4-yl)(perfluorofluorenyl)(perfluoropyrenyl)(2,3,4-trifluorophenyl)borate]⁻/pentamethylcyclopentadienyltribenzyltitanium

[N,N-2,4,6,-pentamethylanilinium]⁺[7-((tri-isopropylsilyloctyl)(pentalfluoropyrenyl)amino)perfluoronapth-3-yl)(perfluoronaphthyl)(perfluorophenyl)(tetrafluorofluorenyl)borate]⁻/dimethylsilyl(tetramethylcyclopentadienyl)(tert-butylamido)dichloridetitanium

[N,N-diethylanilinium]⁺[6-((methylethylhexylsilyl)(perfluoropyrenyl)amino)perfluoroanthracen-1-yl)(perfluorofluorenyl)(perfluorobiphenyl)(2',3',4'-trifluorobiphenyl)borate]⁻/bis(hexamethyldisilido)dimethyltitanium

[N-methyl-N-dodecylanilinium]⁺[5-((ethyl)(4,5,6,7-tetrafluoronaphthyl)amino)perfluoronapht-3-yl)(perfluoropyrenyl)(2,3,6-trifluorophenyl)(tetrafluorofluorenyl)borate]⁻/pentamethylcyclopentadienyltrimethylutanium

[N-methyl-N-dodecylanilinium]⁺[6-((triethylsilylethyl)(perfluoronaphthyl)amino)perfluoronapth-1-yl)(perfluorofluorenyl)(perfluorophenyl)(2,3,6-trifluorophenyl)borate]⁻/bis(hexamethyldisilido)dimethyltitanium

[N-methyl-N-dodecylanilinium]⁺[7-((methylethylhexylsilyl)(perfluorobiphenyl)amino)perfluoroinden-2-yl)(2',3',5'-trifluorobiphenyl)(2',3',4'-trifluorobiphenyl)(perfluorobiphenyl)borate]⁻/dimethylsily(bisindenyl)dichloridezirconium

[N,N-2,4,6,-pentamethylanilinium]⁺[7-((isopropyl)(perfluorobiphenyl)amino)perfluoronapth3-yl)(perfluoropyrenyl)(4,5,6,7-tetrafluoronaphthyl)(4,5,7-trifluoronaphthyl)borate]⁻/dimethylsily(bisindenyl)dichloridezirconium

[N,N-2,4,6,-pentamethylanilinium]⁺[7-((triethylsilylethyl)(5,6,7,8-tetrafluoronaphthyl)amino)fluorofluoren-1-yl)(perfluoroanthracenyl)(perfluorofluorenyl)(2,3,4-trifluorophenyl)borate]⁻/silacyclobutyl(tetramethylcyclopentadienyl)(n-propylcyclopentadienyl)dimethylzirconium

[N,N-dimethylanilinium]⁺[6-((octyl)(perfluorophenyl)amino)perfluoroanthracen-2-yl)(4,5,6,7-tetrafluoronaphthyl)(2,3,5-trifluorophenyl)(perfluorophenyl)borate]⁻/bis(1,3-dibutyl-methylcyclopentadienyl)dimethylzirconium

[N-methyl-N-dodecylanilinium]⁺[7-((hexyl)(2,3,4-trifluorophenyl)amino)perfluorofluoren-2-yl)(tetrafluorofluorenyl)(2,3,4-trifluorophenyl)(perfluoronaphthyl)borate]⁻/(tetramethylcyclopentadienyl)(n-propylcyclopentadienyl)dimethylzirconium

[N,N-dimethylanilinium]⁺[6-((triethylsilyl)(perfluorophenyl)amino)perfluoroanthracen-1-yl)-(2',3',5'-trifluorobiphenyl)(perfluorophenyl)(pentalfluoropyrenyl)borate]⁻/(pentamethylcyclopentadienyl)(cyclopentadienyl)dimethylzirconium

[N,N-diethylanilinium]⁺[7-((cyclohexyl)(5,6,7,8-tetrafluoronaphthyl)amino)perfluoronapth-1-yl)(2,3,5- trifluorophenyl)(perfluorophenyl)(4,5,6-trifluoronaphthyl)borate]⁻/dimethylsilylbis(2-methylbenzindenyl)dimethylzirconium

[N-methyl-N-dodecylanilinium]⁺[7-((3-ethylnonyl)(perfluorophenyl)phosphino)perfluoroanthracen-1-yl)bis(pentalfluoropyrenyl)(perfluorobiphenyl)borate]⁻/dimethylsilylbis(2-methylbenzindenyl)dimethylzirconium

[N,N-di(dodecyl)anilinium]⁺[2'-((diethylnonlysilyl)(4,5,6,7-tetrafluoronaphthyl)amino)perfluorobiphen-4-yl)(2,3,4-trifluorophenyl)(4,5,6-trifluoronaphthyl)(4,5,6,7-tetrafluoronaphthyl)borate]⁻/bis(1,3-dibutyl-methyl-cyclopentadienyl)dimethylzirconium

[N-methyl-N-dodecylanilinium]⁺[7-((trimethylsilyl)(perfluorobiphenyl)amino)perfluoronapth-1-yl)(perfluorofluorenyl)(4,5,7-trifluoronaphthyl)(pentafluoroanthracenyl)borate]⁻/dimethylsilylbis(2-methylbenzindenyl)dimethylzirconium

[N-methyl-N-dodecylanilinium]⁺[4'-((tri-isopropylsilyloctyl)(4,5,7-trifluoronaphthyl)amino)perfluorobiphen-4-yl)bis(2',3',4'-trifluorobiphenyl)(perfluorobiphenylborate]⁻/dimethylsily(bisindenyl)dichloridezirconium

[N,N-di(dodecyl)anilinium]⁺[5-((propyl)(pentalfluoropyrenyl)phosphino)fluoronapth-3-yl)(perfluorobiphenyl)(perfluoropyrenyl)(perfluoronaphthyl)borate]⁻/dimethylsily(bisindenyl)dichloridezirconium

[N,N-dimethylanilinium]⁺[5-((methyldiethylsilyloctyl)(perfluorophenyl)amino)perfluoronapth-1-yl)(perfluorofluorenyl)(perfluorophenyl)(pentalfluoropyrenyl)borate]⁻/dimethylsilylbis(tetrahydroindenyl)dichloridezirconium

[N,N,N-(ethyl)(methyl)(n-butyl)phosphonium]⁺[7-((benzyl)(perfluorobiphenyl)amino)perfluoroanthracen-1-yl)(perfluoroanthracenyl)(2',3',5'-trifluorobiphenyl)(perfluorophenyl)borate]⁻/oxotris(trimethlsilylmethyl)vanadium

[N,N,N-(ethyl)(methyl)(octyl)phosphonium]⁺[3'-((tri-isopropylsilyl)(tetrafluorofluorenyl)amino)fluorobiphen-4-yl)(perfluorobiphenyl)(perfluoronaphthyl)(2,3,5-trifluorophenyl)borate]⁻/oxotris(trimethlsilylmethyl)vanadium

[N,N,N-(ethyl)(methyl)(n-butyl)phosphonium]⁺[6-((cyclohexyl)(pentafluoroanthracenyl)phosphino)perfluoronapth-1-yl)(perfluorophenyl)(2',3',5'-trifluorobiphenyl)(2,3,5-trifluorophenyl)borate]⁻/oxotris(trimethisilylmethyl)vanadium

[tri-N-octylphosphonium]⁺[5-((propyl)(perfluorophenyl)amino)perfluoroinden-2-yl)(perfluorofluorenyl)(pentafluoroanthracenyl)(perfluorophenyl)borate]⁻/oxotris(trimethlsilylmethyl)vanadium

[tri-N-propylphosphonium]⁺[5-((isopropyl)(perfluorophenyl)phosphino)perfluoroinden-1-yl)(perfluoronaphthyl)(perfluorofluorenyl)(perfluorophenyl)borate]⁻/diphenylmethyl(cyclopentadienyl)(2,7-dimethylfluorenyl)dimethylhafnium

[tri-N-(t-butyl)phosphonium]⁺[6-((nonyl)(perfluorophenyl)amino)perfluoronapth-1-yl)(perfluoroanthracenyl)(perfluorobiphenyl)(2,3,4-trifluorophenyl)borate]⁻/dimethylsilylbis(methylindenyl)dimethylhafnium

[tri-N-(n-butyl)phosphonium]⁺[6-((nonyl)(2,3,5-trifluorophenyl)phosphino)perfluoroanthracen-1-yl)(pentafluoroanthracenyl)(4,5,6-trifluoronaphthyl)(perfluorobiphenyl)borate]⁻/dimethylsilyl(tetramethylcyclopentadienyl)(dodecylamido)dihydridehafnium

[N,N,N-(ethyl)(methyl)(octyl)phosphonium]⁺[6-((triethylsilylethyl)(2,3,6-trifluorophenyl)arsino)perfluorofluoren-1-yl)bis(perfluorobiphenyl)(2',3',5'-trifluorobiphenyl)borate]⁻/tetrabenzylhafnium

[N,N,N-(ethyl)(methyl)(isopropyl)phosphonium]⁺[5-((2,2-dimethyloctyl)(tetrafluorofluorenyl)amino)perfluoroinden-2-yl)(4,5,7-trifluoronaphthyl)(5,6,7,8-tetrafluoronaphthyl)(perfluorophenyl)borate]⁻/dimethylsily-bisindenyldimethylhafnium

[N,N,N-(ethyl)(methyl)(n-butyl)phosphonium]⁺[7-((methyl)(perfluorophenyl)amino)perfluoroanthracen-1-yl)(perfluorofluorenyl)(perfluorophenyl)(pentalfluoropyrenyl)borate]⁻/diphenylmethyl(fluorenyl)(cyclopentadienyl)dimethylhafnium

[N,N,N-(ethyl)(dioctyl)phosphonium]⁺[3-((triethylsilylpropyl)(2',3',5'-trifluorobiphenyl)amino)perfluorophenyl)(perfluorophenyl)(2,3,6-trifluorophenyl)(4,5,6-trifluoronaphthyl)borate]⁻/dimethylsily-bisindenyldimethylhafnium

[tri-N-methylphosphonium]⁺[4'-((methyldiethylsilyloctyl)(2',3',4'-trifluorobiphenyl)phosphino)perfluorobiphen-3-yl)(5,6,7,8-tetrafluoronaphthyl)(perfluoropyrenyl)(perfluoronaphthyl)borate]⁻/diphenylmethyl(fluorenyl)(cyclopentadienyl)dimethylhafnium

[tri-N-propylphosphonium]⁺[7-((octyl)(2,3,5-trifluorophenyl)amino)perfluoronapth-1-yl)(perfluorobiphenyl)(perfluorofluorenyl)(perfluoronaphthyl)borate]⁻/diphenylmethyl(fluorenyl)(cyclopentadienyl)dimethylhafnium

[tri-N-(methylphenyl)phosphonium]⁺[7-((benzyl)(perfluorobiphenyl)amino)perfluoroanthracen-1-yl)(perfluoronaphthyl)(perfluorophenyl)(4,5,6,7-tetrafluoronaphthyl)borate]⁻/diphenylmethyl(cyclopentadienyl)(fluorenyl)dimethylhafnium

[N,N,N-(ethyl)(methyl)(octyl)phosphonium]⁺[4-((n-butyl)(perfluorobiphenyl)phosphino)perfluorophenyl)(perfluorobiphenyl)(perfluoropyrenyl)(perfluoroanthracenyl)borate]⁻/dimethylsilylbis(methylindenyl)dimethylhafnium

[tri-N-ethylphosphonium]⁺[6-((triethylsilylpropyl)(tetrafluorofluorenyl)arsino)perfluoronapth-3-yl)(perfluoronaphthyl)(pentafluoroanthracenyl)(perfluorobiphenyl)borate]⁻/diphenylmethyl(cyclopentadienyl)(2,7-di-tri-butyl-fluorenyl)dimethylhafnium

[N,N,N-(ethyl)(methyl)(n-butyl)phosphonium]⁺[5-((methylethylhexylsilyl)(tetrafluorofluorenyl)amino)perfluoroinden-2-yl)bis(2',3',4'-trifluorobiphenyl)(4,5,6,7-tetrafluoronaphthyl)borate]⁻/dimethylsilyl(tetramethylcyclopentadienyl)(dodecylamido)dimethylhafnium

[N,N,N-(ethyl)(methyl)(isopropyl)phosphonium]⁺[7-((trimethylsilyl)(2',3',4'-trifluorobiphenyl)amino)perfluoronapth-1-yl)(5,6,7,8-tetrafluoronaphthyl)(perfluorophenyl)(perfluorofluorenyl)borate]⁻/dimethylsilylbisindenyidimethylhafnium

[tri-N-octylphosphonium]⁺[6-((triethylsilylpropyl)(perfluorofluorenyl)arsino)perfluoroanthracen-1-yl)bis(pentalfluoropyrenyl)(perfluoroanthracenylborate]⁻/dimethylsilylbis(methylindenyl)dimethylhafnium

[N,N,N-(dimethyl)(t-butyl)phosphonium]⁺[6-((tri-isopropylsilyloctyl)(perfluoronaphthyl)amino)perfuoronapth-3-yl)(pentalfluoropyrenyl)(perfluorobiphenyl)(2,3,4-trifluorophenyl)borate]⁻/diphenylmethyl(cyclopentadienyl)(2,7-dimethylfluorenyl)dimethylhafnium

[N,N,N-(dimethyl)(t-butyl)phosphonium]⁺[7-((trimethylsilyl)(perfluoronaphthyl)amino)perfluoropyren- 1-yl)(pentalfluoropyrenyl)(perfluoroanthracenyl)(4,5,7-trifluoronaphthyl)borate]⁻/(4-alkyl-1-phenyl)(4-tri-butyl-1-phenyl)methyl(cyclopentadienyl)(fluorenyl)dimethylhafnium

[tri-N-propylphosphonium]⁺[4-((3-ethylnonyl)(perfluorophenyl)amino)perfluorophenyl)(perfluorophenyl)(pentafluoroanthracenyl)(2,3,5-trifluorophenyl)borate]⁻/dimethylsilylbisindenyldimethylhafnium

[N,N,N-(dimethyl)(t-butyl)phosphonium]⁺[3-((butyl)(perfluorobiphenyl)phosphino)perfluorophenyl)bis(perfluorobiphenyl)(perfluorofluorenylborate]⁻/dimethylsilyl(tetramethylcyclopentadienyl)(dodecylamido)dimethylhafnium

[tri-N-propylphosphonium]⁺[5-((tri-isopropylsilyl)(perfluorophenyl)phosphino)perfluoroinden-2-yl)bis(5,6,7,8-tetrafluoronaphthyl)(perfluorobiphenyl)borate]⁻/diphenylmethyl(cyclopentadienyl)(2,7-dimethylfluorenyl)dimethylhafnium

[tri-N-ethylphosphonium]⁺[5-((triethylsilyl)(4,5,6,7-tetrafluoronaphthyl)phosphino)perfluoronapth-2-yl)(perfluorophenyl)(perfluorobiphenyl)(perfluorofluorenyl)borate]⁻/(4-alkyl-1-phenyl)-(4-tri-butyl-1-phenyl)methyl(cyclopentadienyl)(fluorenyl)dimethylhafnium

[tri-N-propylphosphonium]⁺[7-((ethyl)(perfluoronaphthyl)amino)perfluoronaphth-1-yl)bis(4,5,6-trifluoronaphthyl)(2',3',4'-trifluorobiphenylborate]⁻/dimethylsilylbis(phenylmethylindenyl)dimethylhafnium

[N,N,N-(ethyl)(methyl)(n-butyl)phosphonium]⁺[5-((isopropyl)(perfluorophenyl)amino)perfluoroinden-1-yl)(perfluorobiphenyl)(2',3',4'-trifluorobiphenyl)(perfluorofluorenyl)borate]⁻/(4-alkyl-1-phenyl)(4-tri-butyl-1-phenyl)methyl(cyclopentadienyl)(fluorenyl)dimethylhafnium

[N,N,N-(ethyl)(methyl)(t-butyl)phosphonium]⁺[3-((3-ethylnonyl)(perfluorobiphenyl)amino)perfluorophenyl)(perfluoroanthracenyl)(perfluorobiphenyl)(perfluoropyrenyl)borate]⁻/dimethylsilylbis(phenylmethylindenyl)dimethylhafnium

[N,N,N-(dimethyl)(t-butyl)phosphonium]⁺[6-((triethylsilylethyl)(perfluorofluorenyl)amino)perfluoroinden-2-yl)(perfluoropyrenyl)(perfluorofluorenyl)(2',3',5'-trifluorobiphenyl)borate]⁻/tetrabenzylhafnium

[tri-N-propylphosphonium]⁺[5-((tri-n-propylsilylhexyl)(perfluorobiphenyl)amino)perfluoroinden-2-yl)(perfluorophenyl)(2',3',4'-trifluorobiphenyl)(perfluoropyrenyl)borate]⁻/dimethylsilyl(tetramethylcyclopentadienyl)(dodecylamido)dihydridehafnium

[N,N,N-(ethyl)(methyl)(octyl)phosphonium]⁺[8-((tri-isopropylsilyl)(perfluoropyrenyl)phosphino)fluoronapth-3-yl)(2',3',5'-trifluorobiphenyl)(perfluorophenyl)(4,5,6-trifluoronaphthyl)borate]⁻/tetrabenzylhafnium

[tri-N-(dimethylphenyl)phosphonium]⁺[5-((tri-n-propylsilylhexyl)(perfluorophenyl)amino)perfluoronapth-1-yl)(perfluorophenyl)(pentalfluoropyrenyl)(pentafluoroanthracenyl)borate]⁻/dimethylsilyl(tetramethylcyclopentadienyl)(dodecylamido)dimethylhafnium

[N,N,N-(ethyl)(methyl)(n-butyl)phosphonium]⁺[7-((2,2-dimethyloctyl)(perfluorobiphenyl)arsino)perfluorofluoren-2-yl)(perfluorophenyl)(2',3',4'-trifluorobiphenyl)(pentafluoroanthracenyl)borate]⁻/tetrabenzylhafnium

[tri-N-(dimethylphenyl)phosphonium]⁺[5-((triethylsilylpropyl)(4,5,7-trifluoronaphthyl)amino)perfluoronapth-1-yl)bis(pentafluoroanthracenyl)(pentalfluoropyrenyl)borate]⁻/dimethylsilylbis(phenylmethylindenyl)dimethylhafnium

[tri-N-ethylphosphonium]⁺[6-((trimethylsilyl)(4,5,7-trifluoronaphthyl)amino)perfluorofluoren-1-yl)(5,6,7,8-tetrafluoronaphthyl)(2,3,4-trifluorophenyl)(perfluorofluorenyl)borate]⁻/dimethylsilylbisindenyldimethylhafnium

[tri-N-(methylphenyl)phosphonium]⁺[6-((trimethylsilyl)(perfluoropyrenyl)amino)perfluorofluoren-1-yl)(2,3,6-trifluorophenyl)(4,5,6-trifluoronaphthyl)(perfluorofluorenyl)borate]⁻/diphenylmethyl(cyclopentadienyl)(fluorenyl)dimethylhafnium

[tri-N-(t-butyl)phosphonium]⁺[3-((butyl)(2,3,4-trifluorophenyl)amino)perfluorophenyl)(4,5,6,7-tetrafluoronaphthyl)(4,5,6-trifluoronaphthyl)(perfluorofluorenyl)borate]⁻/dimethylsilylbis(phenylmethylindenyl)dimethylhafnium

[tri-N-methylphosphonium]⁺[7-((diethylnonlysilyl)(perfluoroanthracenyl)amino)perfluoronapth-2-yl)(perfluoronaphthyl)(2',3',5'-trifluorobiphenyl)(2,3,5-trifluorophenyl)borate]⁻/dimethylsilylbis(methylindenyl)dimethylhafnium

[tri-N-(methylphenyl)phosphonium]⁺[6-((nonyl)(perfluorophenyl)amino)perfluoroanthracen-1-yl)(pentafluoroanthracenyl)(4,5,6-trifluoronaphthyl)(perfluorobiphenyl)borate]⁻/dimethylsilylbis(naphthylmethylindenyl)dimethylhafnium

[tri-N-octylphosphonium]⁺[8-((3-ethylnonyl)(perfluoropyrenyl)phosphino)perfluoronapth-3-yl)(2',3',5'-trifluorobiphenyl)(4,5,6,7-tetrafluoronaphthyl)(4,5,6-trifluoronaphthyl)borate]⁻/tetrabenzylhafnium

[tri-N-(dimethylphenyl)phosphonium]⁺[5-((2,2-dimethyloctyl)(tetrafluorofluorenyl)amino)perfluoroinden-2-yl)bis(pentafluoropyrenyl)(5,6,7,8-tetrafluoronaphthyl)borate]⁻/diphenylmethyl(cyclopentadienyl)(2,7-di-tri-butyl-fluorenyl)dimethylhafnium

[N,N,N-(ethyl)(methyl)(octyl)phosphonium]⁺[5-((benzyl)(5,6,7,8-tetrafluoronaphthyl)amino)perfluoronapth-1-yl)(tetrafluorofluorenyl)(perfluorobiphenyl)(perfluoroanthracenyl)borate]⁻/diphenylmethyl(cyclopentadienyl)(fluorenyl)dimethylhafnium

[N,N,N-(ethyl)(methyl)(isopropyl)phosphonium]⁺[6-((hexyl)(perfluorophenyl)amino)perfluoroanthracen-2-yl)(perfluorophenyl)(perfluorobiphenyl)(2,3,5-trifluorophenyl)borate]⁻/diphenylmethyl(fluorenyl)(cyclopentadienyl)dimethylhafnium

[tri-N-methylphosphonium]⁺[5-((trimethylsilyl)(perfluoroanthracenyl)amino)perfluoronapth-1-yl)(tetrafluorofluorenyl)(perfluorofluorenyl)(perfluorophenyl)borate]⁻/dimethylsilylbisindenyldimethylhafnium

[tri-N-(methylphenyl)phosphonium]⁺[4-((isopropyl)(2,3,6-trifluorophenyl)arsino)perfluorophenyl)(perfluoropyrenyl)(5,6,7,8-tetrafluoronaphthyl)(2,3,6-trifluorophenyl)borate]⁻/diphenylmethyl(cyclopentadienyl)(2,7-dimethylfluorenyl)dimethylhafnium

[tri-N-octyl phosphonium]⁺[8-((triethylsilytethyl)(perfluorofluorenyl)phosphino)perfluoronapth-3-yl)(perfluorobiphenyl)(perfluoroanthracenyn)(2',3',5'-trifluorobiphenyl)borate]⁻/diphenylmethyl(cyclopentadienyl)(2,7-di-tri-butyl-fluorenyl)dimethylhafnium

[tri-N-(dimethylphenyl)phosphonium]⁺[7-((octyl)(2,3,5-trifluorophenyl)amino)perfluorofluoren-2-yl)(perfluorofluorenyl)(2,3,5-trifluorophenyl)(2,3,4-trifluorophenyl)borate]⁻/diphenylmethyl(cyclopentadienyl)(2,7-dimethylfluorenyl)dimethylhafnium

[tri-N-ethylphosphonium]⁺[6-((tri-n-propylsilylhexyl)(perfluorofluorenyl)amino)perfluoroinden-2-yl)

(perfluorophenyl)(pentafluoroanthracenyl)(perfluoronaphthyl)borate]⁻/dimethylsilylbisindenyldimethylhafnium

[N,N,N-(ethyl)(dioctyl)phosphonium]⁺[5-((tri-n-propylsilylhexyl)(perfluorobiphenyl)arsino)perfluoronapth-2-yl)(4,5,6-trifluoronaphthyl)(perfluorophenyl)(tetrafluorofluorenyl)borate]⁻/dimethylsilylbis(naphthylmethylindenyl)dimethylhafnium

[tri-N-(n-butyl)phosphonium]⁺[5-((hexyl)(5,6,7,8-tetrafluoronaphthyl)amino)perfluoroinden-2-yl)(perfluoronaphthyl)(4,5,6-trifluoronaphthyl)(pentalfluoropyrenyl)borate]⁻/dimethylsilylbis(phenylmethylindenyl)dimethylhafnium

[tri-N-(methylphenyl)phosphonium]⁺[4-((tri-isopropylsilyloctyl)(perfluoroanthracenyl)amino)perfluorophenyl)bis(4,5,7-trifluoronaphthyl)(2,3,4-trifluorophenyl)borate]⁻/dimethylsilylbisindenyidimethylhafnium

[N,N,N-(ethyl)(methyl)(isopropyl)phosphonium]⁺[3'-((isopropyl)(perfluoronaphthyl)arsino)fluorobiphen-4-yl)(tetrafluorofluorenyl)(2,3,4-trifluorophenyl)(pentalfluoropyrenyl)borate]⁻/diphenylmethyl(cyclopentadienyl)(2,7-dimethylfluorenyl)dimethylhafnium

[tri-N-(methylphenyl)phosphonium]⁺[7-((hexyl)(2',3',4'-trifluorobiphenyl)amino)perfluoropyren-2-yl)(pentalfluoropyrenyl)(perfluorophenyl)(pentafluoroanthracenyl)borate]⁻/dimethylsilyl(tetramethylcyclopentadienyl)(dodecylamido)dihydridehafnium

[tri-N-(n-butyl)phosphonium]⁺[4'-((triethylsilylethyl)(perfluorobiphenyl)amino)perfluorobiphen-3-yl)(tetrafluorofluorenyl)(perfluorophenyl)(2,3,4-trifluorophenyl)borate]⁻/tris(trimethylsilylmethyl)dichlorideniobium

[N,N,N-(ethyl)(methyl)(n-butyl)phosphonium]⁺[7-((triethylsilylpropyl)(perfluoropyrenyl)amino)perfluoroanthracen-1-yl)(perfluorobiphenyl)(2,3,5-trifluorophenyl)(2',3',4'-trifluorobiphenyl)borate]⁻/tris(trimethylsilylmethyl)dichlorideniobium

[tri-N-(t-butyl)phosphonium]⁺[6-((triethylsilylethyl)(2',3',5'-trifluorobiphenyl)phosphino)fluoroanthracen-2-yl)(5,6,7,8-tetrafluoronaphthyl)(2,3,6-trifluorophenyl)(4,5,7-trifluoronaphthyl)borate]⁻/tris(trimethylsilylmethyl)dichlorideniobium

[tri-N-(t-butyl)phosphonium]⁺[6-((triethylsilylpropyl)(perfluorobiphenyl)amino)perfluoronapth-2-yl)bis(perfluoroanthracenyl)(2,3,4-trifluorophenylborate]⁻/tris(trimethylsilylmethyl)dichlorideniobium

[tri-N-propylphosphonium]⁺[5-((methyldiethylsilyloctyl)(perfluorofluorenyl)phosphino)perfluoroinden-1-yl)(perfluorophenyl)(2,3,5-trifluorophenyl)(2',3',4'-trifluorobiphenyl)borate]⁻/tris(trimethylsilylmethyl)dichlorideniobium

[N,N,N-(dimethyl)(t-butyl)phosphonium]⁺[3-((butyl)(2,3,4-trifluorophenyl)amino)perfluorophenyl)(perfluoronaphthyl)(4,5,7-trifluoronaphthyl)(4,5,6-trifluoronaphthyl)borate]⁻/tris(trimethylsilylmethyl)dichloridetantalum

[tri-N-(n-butyl)phosphonium]⁺[6-((hexyl)(perfluorobiphenyl)arsino)fluorofluoren-2-yl)(2,3,5-trifluorophenyl)(perfluorobiphenyl)(perfluorophenyl)borate]⁻/tris(trimethylsilylmethyl)dichloridetantalum

[tri-N-(t-butyl)phosphonium]⁺[6-((trimethylsilyl)(perfluorobiphenyl)amino)perfluoroanthracen-1-yl)(pentalfluoropyrenyl)(4,5,7-trifluoronaphthyl)(5,6,7,8-tetrafluoronaphthyl)borate]⁻/tris(trimethylsilylmethyl)dichloridetantalum

[N,N,N-(ethyl)(dioctyl)phosphonium]⁺[6-((hexyl)(perfluorobiphenyl)amino)perfluoroinden-2-yl)(perfluorobiphenyl)(2,3,6-trifluorophenyl)(perfluorofluorenyl)borate]⁻/tetrabenzyltitanium

[N,N,N-(ethyl)(methyl)(n-butyl)phosphonium]⁺[5-((methyl)(perfluoropyrenyl)amino)fluoronapth-3-yl)bis(pentalfluoropyrenyl)(perfluoronaphthyl)borate]⁻/pentamethyl cyclopentadienylisopropoxidetitanium

[N,N,N-(ethyl)(methyl)(isopropyl)phosphonium]⁺[6-((benzyl)(perfluorophenyl)amino)perfluoronapth-3-yl)(pentafluoroanthracenyl)(perfluorofluorenyl)(perfluoropyrenyl)borate]⁻/dimethylsilyl(tetramethylcyclopentadienyl)(tert-butylamido)dichloridetitanium

[N,N,N-(ethyl)(methyl)(t-butyl)phosphonium]⁺[6-((methyldiethylsilyloctyl)(perfluorophenyl)amino)perfluoronapth-2-yl)bis(2,3,6-trifluorophenyl)(perfluorophenyl)borate]⁻/pentamethylcyclopentadienyl tribenzyl titanium

[tri-N-methylphosphonium]⁺[3'-((benzyl)(perfluorophenyl)amino)perfluorobiphen-4-yl)bis(perfluorobiphenyl)(perfluoronaphthylborate]⁻/pentamethyl cyclopentadienyl tribenzyltitanium

[tri-N-ethylphosphpnium]⁺[8-((tri-n-propylsilyl)(perfluorophenyl)amino)perfluoronapth-3-yl)-(perfluoronaphthyl)(perfluorofluorenyl)(2',3',5'-trifluorobiphenyl)borate]⁻/pentamethyl cyclopentadienyl tribenzyl titanium

[tri-N-ethylphosphonium]⁺[6-((tri-n-propylsilylhexyl)(4,5,6,7-tetrafluoronaphthyl)amino)perfluoronapth-2-yl)(2,3,6-trifluorophenyl)(perfluoronaphthyl)(perfluorophenyl)borate]⁻/tetrabenzyltitanium

[N,N,N-(ethyl)(methyl)(n-butyl)phosphonium]⁺[7-((benzyl)(perfluorobiphenyl)phosphino)perfluoroinden-2-yl)(perfluoropyrenyl)(perfluorobiphenyl)(perfluoronaphthyl)borate]⁻/tetrabenzyltitanium

[tri-N-ethylphosphonium]⁺[7-((cyclohexyl)(perfluorobiphenyl)amino)perfluoronapth-2-yl)-(pentalfluoropyrenyl)(perfluorophenyl)(pentafluoroanthracenyl)borate]⁻/dimethylsilyl(tetramethylcyclopentadienyl)(tert-butylamido)dichloridetitanium

[N,N,N-(dimethyl)(t-butyl)phosphonium]⁺[4'-((methylethylhexylsilyl)(4,5,7-trifluoronaphthyl)amino)fluorobiphen-3-yl)(pentalfluoropyrenyl)(perfluoroanthracenyl)(perfluorofluorenyl)borate]⁻/bis(hexamethyldisilido)dimethyltitanium

[N,N,N-(ethyl)(dioctyl)phosphonium]⁺[6-((cyclohexyl)(perfluorophenyl)amino)perfluorofluoren-2-yl)bis(4,5,7-trifluoronaphthyl)(tetrafluorofluorenyl)borate]⁻/dimethylsilyl(tetramethylcyclopentadienyl)(tert-butylamido)dichloridetitanium

[tri-N-(n-butyl)phosphonium]⁺[7-((methyldiethylsilyloctyl)(perfluorobiphenyl)amino)perfluoroanthracen-1-yl)(perfluorophenyl)(pentafluoroanthracenyl)(perfluorobiphenyl)borate]⁻/pentamethyl cyclopentadienylisopropoxidetitanium

[N N,N-(dimethyl)(t-butyl)phosphonium]⁺[7-((tri-n-propylsilylhexyl)(perfluorofluorenyl)amino)perfluorofluoren-1-yl)(perfluorophenyl)(4,5,6-trifluoronaphthyl)(perfluoroanthracenyl)borate]⁻/dimethylsilyl(tetramethylcyclopentadienyl)(tert-butylamido)dichloridetitanium

[tri-N-(methylphenyl)phosphonium]⁺[7-((tri-n-propylsilyl)(2',3',4'-trifluorobiphenyl)amino)fluoroinden-2-yl)(perfluoronaphthyl)(2',3',4'-trifluorobiphenyl)(perfluorofluorenyl)borate]⁻/pentamethylcyclopentadienyltribenzyltitanium

[tri-N-methylphosphonium]⁺[5-((trimethylsilyl)(perfluorophenyl)arsino)perfluoronapth-2-yl)-(perfluoroanthracenyl)(pentafluoroanthracenyl)(4,5,7-trifluoronaphthyl)borate]⁻/pentamethyl cyclopentadienyl tribenzyl titanium

[tri-N-propylphosphonium]⁺[5-((tri-n-propylsilylhexyl)(5,6,7,8-tetrafluoronaphthyl)amino)perfluoronapth-1-yl)(pentalfluoropyrenyl)(perfluorobiphenyl)(tetrafluorofluorenyl)borate]⁻/pentamethylcyclopentadienyltrimethyltitanium

[tri-N-methylphosphonium]⁺[6-((triethylsilyl)(perfluorofluorenyl)amino)perfluorofluoren-2-yl)-(perfluorophenyl)(2,3,4-trifluorophenyl)(5,6,7,8-tetrafluoronaphthyl)borate]⁻/pentamethylcyclopentadienyltrimethyltitanium

[N,N,N-(ethyl)(dioctyl)phosphonium]⁺[5-((2,2-dimethyloctyl)(perfluorophenyl)amino)perfluoronapth-3-yl)(4,5,6,7-tetrafluoronaphthyl)(pentalfluoropyrenyl)(5,6,7,8-tetrafluoronaphthyl)borate]⁻/tetrabenzyltitanium

[tri-N-(dimethylphenyl)phosphonium]⁺[7-((triethylsilylethyl)(4,5,7-trifluoronaphthyl)arsino)perfluoropyren-1-yl)(pentalfluoropyrenyl)(perfluorobiphenyl)(5,6,7,8-tetrafluoronaphthyl)borate]⁻/dimethylsilyl(tetramethylcyclopentadienyl)(adamantyl-1-amino)dimethyltitanium

[N,N,N-(ethyl)(methyl)(isopropyl)phosphonium]⁺[4'-((methyldiethylsilyloctyl)(perfluorofluorenyl)phosphino)perfluorobiphen-3-yl)bis(perfluoroanthracenyl)(5,6,7,8-tetrafluoronaphthylborate]⁻/pentamethylcyclopentadienyltribenzyltitanium

[N,N,N-(dimethyl)(t-butyl)phosphonium]⁺[6-((tri-isopropylsilyl)(perfluoropyrenyl)amino)perfluoronapth-2-yl)(pentalfluoropyrenyl)(4,5,7-trifluoronaphthyl)(perfluorophenyl)borate]⁻/pentamethyl cyclopentadienyl tribenzyl titanium

[N,N,N-(dimethyl)(t-butyl)phosphonium]⁺[7(ethyl)(2',3',5'-trifluorobiphenyl)phosphino)perfluoropyren-1-yl)(4,5,6-trifluoronaphthyl)(2,3,4-trifluorophenyl)(perfluorofluorenyl)borate]⁻/tetrabenzyltitanium

[tri-N-ethylphosphonium]⁺[5-((diethylnonylsilyl)(tetrafluorofluorenyl)amino)perfluoroinden-1-yl)(perfluorophenyl)(perfluoronaphthyl)(perfluorobiphenyl)borate]⁻/bis(hexamethyldisilido)dimethyltitanium

[tri-N-propylphosphonium]⁺[7-((tri-isopropylsilyl)(perfluorobiphenyl)amino)perfluoronapth-2-yl)(perfluoronaphthyl)(2',3',5'-trifluorobiphenyl)(2,3,5-trifluorophenyl)borate]⁻/dimethylsilyl(tetramethylcyclopentadienyl)(t-butylamido)dimethylzirconium

[tri-N-(methylphenyl)phosphonium]⁺[7-((triethylsilylethyl)(perfluorophenyl)amino)perfluoroinden-2-yl)(perfluorophenyl)(pentalfluoropyrenyl)(pentafluoroanthracenyl)borate]⁻/dimethylsilylbis(tetrahydroindenyl)dichloridezirconium

[tri-N-(methylphenyl)phosphonium]⁺[5-((tri-n-propylsilylhexyl)(perfluorobiphenyl)amino)perfluoroinden-1-yl)(perfluoroanthracenyl)(2',3',5'-trifluorobiphenyl)(4,5,6,7-tetrafluoronaphthyl)borate]⁻/silacyclobutyl(tetramethylcyclopentadienyl)(n-propylcyclopentadienyl)dimethylzirconium

[tri-N-(n-butyl)phosphonium]⁺[7-((trimethylsilyl)(perfluoropyrenyl)arsino)fluorofluoren-1-yl)(perfluoropyrenyl)(perfluorofluorenyl)(tetrafluorofluorenyl)borate]⁻/(tetramethylcyclopentadienyl)(n-propylcyclopentadienyl)dimethylzirconium

[N,N,N-(ethyl)(methyl)(n-butyl)phosphonium]⁺[6-((hexyl)(5,6,7,8-tetrafluoronaphthyl)phosphino)perfluoroanthracen-1-yl)(pentalfluoropyrenyl)(perfluorobiphenyl)(tetrafluorofluorenyl)borate]⁻/tetra(bis(trimethylsilylmethyl))zirconium

[tri-N-methylphosphonium]⁺[4'-((tri-n-propylsilyl)(perfluorobiphenyl)amino)perfluorobiphen-3-yl)(4,5,7-trifluoronaphthyl)(perfluoropyrenyl)(perfluorophenyl)borate]⁻/tetra(bis(trimethylsilylmethyl))zirconium

[N,N,N-(ethyl)(methyl)(t-butyl)phosphonium]⁺[5-((methyldiethylsilyloctyl)(perfluorofluorenyl)phosphino)perfluoroinden-2-yl)(4,5,7-trifluoronaphthyl)(perfluorophenyl)(2,3,4-trifluorophenyl)borate]⁻/silacyclobutyl(tetramethylcyclopentadienyl)(n-propylcyclopentadienyl)dimethylzirconium

[N,N,N-(dimethyl)(t-butyl)phosphonium]⁺[3'-((triethylsilylethyl)(perfluoroanthracenyl)amino)fluorobiphen-4-yl)(perfluorophenyl)(4,5,7-trifluoronaphthyl)(perfluoropyrenyl)borate]⁻/dimethylsilyl(tetramethylcyclopentadienyl)(t-butylamido)dimethylzirconium

[tri-N-(n-butyl)phosphonium]⁺[6-((octyl)(5,6,7,8-tetrafluoronaphthyl)amino)perfluoroanthracen-2-yl)(perfluorobiphenyl)(4,5,7-trifluoronaphthyl)(perfluoroanthracenyl)borate]⁻/bis(1,3-dibutyl-methyl-cyclopentadienyl)dimethylzirconium

[tri-N-(dimethylphenyl)phosphonium]⁺[7-((2,2-dimethyloctyl)(perfluorophenyl)arsino)perfluoronapth-1-yl)(perfluorofluorenyl)(5,6,7,8-tetrafluoronaphthyl)(perfluoroanthracenyl)borate]⁻/dimethylsilylbis(2-methylbenzindenyl)dimethylzirconium

[tri-N-(t-butyl)phosphonium]⁺[6-((tri-isopropylsilyloctyl)(perfluoronaphthyl)amino)perfluorofluoren-2-yl)(perfluoroanthracenyl)(pentalfluoropyrenyl)(2,3,4-trifluorophenyl)borate]⁻/dimethylsilylbis(tetrahydroindenyl)dichloridezirconium

[N,N,N-(ethyl)(methyl)(isopropyl)phosphonium]⁺[6-((tri-n-propylsilyl)(2,3,6-trifluorophenyl)amino)perfluoronapth-1-yl)(tetrafluorofluorenyl)(2',3',4'-trifluorobiphenyl)(pentalfluoropyrenyl)borate]⁻/tetrabenzylzirconium

[tri-N-(n-butyl)phosphonium]⁺[6-((butyl)(2',3',4'-trifluorobiphenyl)phosphino)perfluoroinden-2-yl)(4,5,7-trifluoronaphthyl)(perfluorobiphenyl)(2',3',5'-trifluorobiphenyl)borate]⁻/(pentamethylcyclopentadienyl)(cyclopentadienyl)dimethylzirconium

[N,N,N-(dimethyl)(t-butyl)phosphonium]⁺[4-((tri-n-propylsilyl)(perfluoropyrenyl)phosphino)perfluorophenyl)(2,3,4-trifluorophenyl)(perfluorobiphenyl)(2,3,6-trifluorophenyl)borate]⁻/dimethylsilylbis(tetrahydroindenyl)dichloridezirconium

[tri-N-octylphosphonium]⁺[3-((triethylsilyl)(2',3',4'-trifluorobiphenyl)arsino)perfluorophenyl)(perfluorophenyl)(perfluorobiphenyl)(2',3',5'-trifluorobiphenyl)borate]⁻/dimethylsily (bisindenyl)dichloridezirconium

[tri-N-(t-butyl)phosphonium]⁺[5-((cyclohexyl)(2',3',5'-trifluorobiphenyl)amino)fluoronapth-3-yl)(4,5,7-trifluoronaphthyl)(perfluorophenyl)(4,5,6-trifluoronaphthyl)borate]⁻/diphenylmethyl(fluorenyl)(cyclopentadienyl)dimethylzirconium

[N,N,N-(ethyl)(methyl)(n-butyl)phosphonium]⁺[7-((trimethylsilyl)(perfluorophenyl)phosphino)perfluoropyren-2-yl)(5,6,7,8-tetrafluoronaphthyl)(perfluorobiphenyl)(4,5,6-trifluoronaphthyl)borate]⁻/(pentamethylcyclopentadienyl)(cydlopentadienyl)dimethylzirconium

[tri-N-propylphosphonium]⁺[5-((propyl)(perfluorofluorenyl)amino)perfluoronapth-1-yl)(perfluoronaphthyl)(perfluorofluorenyl)

(perfluoroanthracenyl)borate]⁻/dimethylsilyl(tetramethylcyclopentadienyl)(t-butylamido)dimethylzirconium

[N,N,N-(ethyl)(methyl)(octyl)phosphonium]⁺[3'-((triethylsilylethyl)(perfluorobiphenyl)amino)perfluorobiphen-4-yl)(perfluoronaphthyl)(5,6,7,8-tetrafluoronaphthyl)(perfluorobiphenyl)borate]⁻/(tetramethylcyclopentadienyl)(n-propylcyclopentadienyl)dimethylzirconium

[tri-N-methylphosphonium]⁺[7-((triethylsilylpropyl)(perfluorobiphenyl)amino)fluoropyren-1-yl)(perfluorophenyl)(perfluoropyrenyl)(perfluorobiphenyl)borate]⁻/dimethylsilylbis(tetrahydroindenyl)dichloridezirconium

[tri-N-octylphosphonium]⁺[6-((triethylsilyl)(perfluorobiphenyl)arsino)perfluorofluoren-1-yl)-(perfluorobiphenyl)(pentalfluoropyrenyl)(5,6,7,8-tetrafluoronaphthyl)borate]⁻/tetrabenzylzirconium

[tri-N-(t-butyl)phosphonium]⁺[5-((methyldiethylsilyloctyl)(4,5,6,7-tetrafluoronaphthyl)amino)fluoroinden-2-yl)(perfluoroanthracenyl)(perfluorofluorenyl)(5,6,7,8-tetrafluoronaphthyl)borate]⁻/tetra(bis(trimethylsilylmethyl))zirconium

[tri-N-(n-butyl)phosphonium]⁺[5-((n-butyl)(perfluoropyrenyl)amino)perfluoronaphth-3-yl)(perfluorofluorenyl)(5,6,7,8-tetrafluoronaphthyl)(perfluoroanthracenyl)borate]⁻/diphenylmethyl(fluorenyl)(cyclopentadienyl)dimethylzirconium

[tri-N-(t-butyl)phosphonium]⁺[6-((tri-n-propylsilylhexyl)(perfluoronaphthyl)amino)perfluorofluoren-2-yl)(perfluorophenyl)(perfluoronaphthyl)(perfluorofluorenyl)borate]⁻/silacyclobutyl(tetramethylcyclopentadienyl)(n-propylcyclopentadienyl)dimethylzirconium

[tri-N-(n-butyl)phosphonium]⁺[6-((ethyl)(4,5,6-trifluoronaphthyl)amino)perfluorofluoren-2-yl)(tetrafluorofluorenyl)(2,3,5-trifluorophenyl)(perfluoropyrenyl)borate]⁻/(pentamethylcyclopentadienyl)(cyclopentadienyl)dimethylzirconium

[N,N,N-(ethyl)(methyl)(n-butyl)phosphonium]⁺[7-((tri-ethylsilyl)(perfluorobiphenyl)amino)fluorofluoren-2-yl)(perfluorobiphenyl)(perfluorofluorenyl)(perfluorophenyl)borate]⁻/diphenylmethyl(fluorenyl)(cyclopentadienyl)dimethylzirconium

[N,N,N-(ethyl)(methyl)(octyl)phosphonium]⁺[7-((octyl)(4,5,6,7-tetrafluoronaphthyl)amino)perfluorofluoren-2-yl)(pentalfluoropyrenyl)(4,5,6,7-tetrafluoronaphthyl)(perfluoropyrenyl)borate]⁻/bis(1,3-dibutyl-methyl-cyclopentadienyl)dimethylzirconium

[tri-N-(methylphenyl)phosphonium]⁺[8-((methyl)(perfluorophenyl)arsino)perfluoropyren-2-yl)(2',3',4'-trifluorobiphenyl)(perfluorophenyl)(2,3,4-tyfluorophenyl)borate]⁻/dimethylsilyl(tetramethylcyclopentadienyl)(t-butylamido)dimethylzirconium

[N,N,N-(ethyl)(methyl)(t-butyl)phosphonium]⁺[4-((triethylsilyl)(perfluorophenyl)amino)fluorophen-1-yl)(perfluorophenyl)(perfluoroanthracenyl)(perfluoropyrenyl)borate]⁻/dimethylsilylbis(2-methylbenzindenyl)dimethylzirconium

[N,N,N-(ethyl)(methyl)(t-butyl)phosphonium]⁺[6-((ethyl)(2,3,4-trifluorophenyl)amino)perfluoronapth-1-yl)(tetrafluorofluorenyl)(2',3',4'-trifluorobiphenyl)(perfluorofluorenyl)borate]⁻/dimethylsilylbis(tetrahydroindenyl)dichloridezirconium

[N,N,N-(ethyl)(methyl)(t-butyl)phosphonium]⁺[6-((triethylsilylpropyl)(tetrafluorofluorenyl)arsino)perfluoroanthracen-2-yl)(perfluoronaphthyl)(perfluorophenyl)(perfluorobiphenyl)borate]⁻/silacyclobutyl(tetramethylcyclopentadienyl)(n-propylcyclopentadienyl)dimethylzirconium

[tri-N-(dimethylphenyl)phosphonium]⁺[7-((nonyl)(pentalfluoropyrenyl)amino)perfluorofluoren-2-yl)(2,3,6-trifluorophenyl)(perfluorophenyl)(tetrafluorofluorenyl)borate]⁻/diphenylmethyl(fluorenyl)(cyclopentadienyl)dimethylzirconium

[tri-N-(methylphenyl)phosphonium]⁺[3-((octyl)(4,5,7-trifluoronaphthyl)phosphino)perfluorophenyl)(perfluorobiphenyl)(2',3',5'-trifluorobiphenyl)(perfluorofluorenyl)borate]⁻/tetra(bis(trimethylsilylmethyl))zirconium

[tri-N-propylphosphonium]⁺[6-((propyl)(perfluoropyrenyl)amino)perfluoroanthracen-2-yl)-(perfluoroanthracenyl)(2,3,4-trifluorophenyl)(perfluorophenyl)borate]⁻/dimethylsilyl(tetramethylcycdopentadienyl)(t-butylamido)dimethylzirconium

[tri-N-(methylphenyl)phosphonium]⁺[5-((nonyl)(pentalfluoropyrenyl)amino)perfluoronapth-3-yl)(perfluorophenyl)(2,3,6-trifluorophenyl)(perfluoropyrenyl)borate]⁻/tetrabenzylzirconium

[tri-N-(dimethylphenyl)phosphonium]⁺[8-((triethylsilylethyl)(perfluorophenyl)amino)perfluoropyren-2-yl)(perfluorobiphenyl)(2,3,4-trifluorophenyl)(perfluoropyrenyl)borate]⁻/tetrabenzylzirconium

[tri-N-octylphosphonium]⁺[4'-((ethyl)(tetrafluorofluorenyl)amino)perfluorobiphen-3-yl)(tetrafluorofluorenyl)(pentafluoroanthracenyl)(2',3',4'-trifluorobiphenyl)borate]⁻/diphenylmethyl(fluorenyl)(cyclopentadienyl)dimethylzirconium

[tri-N-propylphosphonium]⁺[7-((trimethylsilyl)(4,5,6,7-tetrafluoronaphthyl)phosphino)perfluoroinden-2-yl)(perfluorophenyl)(perfluorobiphenyl)(perfluoroanthracenyl)borate]⁻/dimethylsily(bisindenyl)dichloridezirconium

[trityl]⁺[5-((cyclohexyl)(pentafluoropyrenyl)amino)perfluoroinden-2-yl)(perfluorophenyl)(2,3,4-trifluorophenyl)(perfluoropyrenyl)borate]⁻/dimethylsilyl(tetramethylcyclopentadienyl)(dodecylamido)dihydridehafnium

[trityl]⁺[7-((methyldiethylsilyloctyl)(perfluorophenyl)phosphino)perfluoropyren-1-yl)(perfluorophenyl)(2,3,6-trifluorophenyl)(2',3',5'-trifluorobiphenyl)borate]⁻/tetrabenzyltitanium

[trityl]⁺[5-((tri-n-propylsilylhexyl)(2,3,5-trifluorophenyl)amino)perfluoroinden-2-yl)(perfluorobiphenyl)(5,6,7,8-tetrafluoronaphthyl)(pentafluoroanthracenyl)borate]⁻/tetrabenzyltitanium

[trityl]⁺[7-((3-ethylnonyl)(perfluorobiphenyl)phosphino)perfluoroanthracen-1-yl)(4,5,7-trifluoronaphthyl)(perfluorofluorenyl)(pentafluoroanthracenyl)borate]⁻/dimethylsilyl(tetramethylcyclopentadienyl)(t-butylamido)dimethylzirconium

[trityl]⁺[6-((ethyl)(2,3,4-trifluorophenyl)amino)perfluoronapth-1-yl)(perfluorophenyl)(perfluoroanthracenyl)(5,6,7,8-tetrafluoronaphthyl)borate]⁻/(tetramethylcyclopentadienyl)(n-propylcyclopentadienyl)dimethylzirconium

[trityl]⁺[5-((methyl)(perfluoropyrenyl)amino)perfluoronapth-1-yl)(2',3',5'-trifluorobiphenyl)(perfluorophenyl)(tetrafluorofluorenyl)borate]⁻/diphenylmethyl(fluorenyl)(cyclopentadienyl)dimethylzirconium

[trityl]⁺[3-((butyl)(perfluorophenyl)phosphino)perfluorophenyl)(perfluoropyrenyl)(perfluoroanthracenyl)(4,5,6-trifluoronaphthyl)borate]⁻/bis(1,3-dibutyl-methylcyclopentadienyl)dimethylzirconium

EXAMPLES

The following examples are presented to illustrate the foregoing discussion. All parts, proportions and percentages are by weight unless otherwise indicated. All examples were carried out in dry, oxygen-free environments and solvents. Although the examples may be directed to certain embodiments of the present invention, they are not to be viewed as limiting the invention in any specific respect. In these examples certain abbreviations are used to facilitate the description. These include standard chemical abbreviations for the elements and certain commonly accepted abbreviations, such as: Me=methyl, Et=ethyl, n-Pr=normal-propyl, t-Bu=tertiary-butyl, Ph=phenyl, pfp=pentafluorophenyl, Cp=cyclopentadienyl, Ind=indenyl, Flu=fluorenyl, TMS=trimethylsilyl, TES=triethylsilyl and THF (or thf)=tetrahydrofuran.

All molecular weights are weight average molecular weight unless otherwise noted. Molecular weights (weight average molecular weight (Mw) and number average molecular weight (Mn) were measured by Gel Permeation Chromatography, unless otherwise noted, using a Waters 150 Gel Permeation Chromatograph equipped with a differential refractive index (DRI) and low angle light scattering (LS) detectors and calibrated using polystyrene standards. Samples were run in 1,2,4-trichlorobenzene (135° C.) using three Polymer Laboratories PC Gel mixed B columns in series. This general technique is discussed in "Liquid Chromatography of Polymers and Related Materials III" J. Cazes Ed., Marcel Decker, 1981, page 207, which is incorporated by reference for purposes of U.S. patent practice herein. No corrections for column spreading were employed; however, data on generally accepted standards, e.g. National Bureau of Standards Polyethylene 1475, demonstrated a precision with 0.2 units for Mw/Mn which was calculated from elution times.

Catalyst Preparation

Example 1

Synthesis of 4-($C_6F_5$NH)—$C_6F_4$Br. To a suspension of sodium hydroxide (11 grams) in methyl sulfoxide (300 milliliters, DMSO) was added $C_6F_5NH_2$ (50 grams in 100 milliliters of DMSO). The mixture darkened immediately upon the addition of the amine. To this solution was added $C_6F_5$Br (67 grams in 100 milliliters of DMSO). The mixture was stirred for 16 hours. The reaction mixture was added to 300 milliliters of diluted hydrochloric acid (HCl). To the quenched mixture was added 300 milliliters of diethyl ether ($Et_2O$). The two layers were separated. The aqueous layer was extracted a second time with 300 milliliters of diethyl ether. The purple ether layers are combined and dried with magnesium sulfate ($MgSO_4$). After an appropriate drying period the $MgSO_4$ was removed by filtration. The solvent was removed and the product was sublimed (oil bath temperature was 80–90° C., pressure was approximately $10^{-4}$ millitorr). The white solid collected on the cold finger was crystallized from hexanes to afford a white crystalline solid. The product was characterized by $^{19}$F NMR. The yield was 24.56 grams of 4-($C_6F_5$NH)—$C_6F_4$Br. $^{19}$F NMR (CDCl$_3$, 25° C., referenced from CFCl$_3$(0.0)): δ –134.5 (m, 2F), –152.6 (d, 2F), –154.4 (d, 2F), –161.7 (t, 1F), –162.9 (q, 2F).

Example 2

Synthesis of 4-($C_6F_5$N{TMS})—$C_6F_4$Br. To a potassium hydride (0.610 grams) suspension in tetrahydrofuran (50 milliliters, THF) was added a solution of 4-($C_6F_5$NH)—$C_6F_4$Br (6.245 grams in 50 milliliters of THF). After the gas generation stopped, TMS-Cl(1.65 grams) was added. The solution was allowed to stir for 16 hours. The solid precipitate was separated by filtration and the THF was replaced with hexanes. The colorless liquid product was isolated from the yellow mixture by column chromatography (200 mesh silica gel, hexanes). This procedure yields 4.0 grams of product. The product was characterized by $_{19}$F NMR. $_{19}$F NMR (CDCl$_3$, 25° C., referenced from CFCl$_3$(0.0)): δ –134.2 (m, 2F), –143.8 (m, 2F), –144.4 (m, 2F), –157.8 (t, 1F), –163.0 (m, 2F).

Example 3

Synthesis of [4-($C_6F_5$N{TMS})—$C_6F_4$]$_4$B Li($Et_2O$)$_{2.5}$: To a cold $Et_2O$ solution of 4-($C_6F_5$N{TMS})—$C_6F_4$Br (1.493 grams) was added nButyl Lithium (2.0 milliliters, 2.1 M in hexanes, Aldrich). The lithiation was allowed to stir over 2 hours at which point boron chloride (0.77 milliliters, 1.0 M in hexanes, Aldrich) was added to the reaction mixture. The cold bath was removed and the reaction was stirred for 3 hours. The white precipitate was separated by filtration. The volume of the filtrate was reduced to approximately 30% and pentane was added to induce precipitation. The two-layered mixture was chilled to $-35°$ C. The product precipitates as a white solid (1.135 grams). The product was characterized by $^{19}$F and $^1$H NMR. $^1$H NMR (Toluene-d, 25° C.): δ 3.25 (q, 10H), 1.09 (t, 15H), 0.11 (s, 36H). $^{19}$F NMR (Toluene-d, 25° C.): δ –133.2 (m, 2F), –145.5 (m, 2F), –150.3 (m, 2F), –160.0 (t, 1F), –164.7 (m, 2F).

Example 4

Synthesis of [$C_6H_5NMe_2$(H)][4-($C_6F_5$N{TMS})—$C_6F_4$]$_4$ B: To a methylene chloride solution of [4-($C_6F_5$N{TMS})—$C_6F_4$]$_4$B Li($Et_2O$)$_{2.5}$ (2.121 grams) was added a methylene chloride solution of $C_6H_5NMe_2$HCl (0.185 grams). The mixture was stirred for 1 hour and the white precipitate was separated by filtration. The volume of the filtrate was reduced to 30% and pentane was added to induce precipitation. After chilling the mixture for 16 hours at 35° C., the product was collected by filtration and washed with cold pentane to afford 1.512 grams of product. The product was characterized by $^{19}$F and $^1$H NMR. $^{19}$F NMR (Toluene-d$^8$, 25° C.): δ –133.7 (m, 2F), –145.6 (m, 2F), –149.3 (m, 2F), –159.3 (t, 1F), –164.2 (m, 2F). $^1$H NMR δ 6.82 (bm, 3H), 6.45 (bm, 2H), 2.13 (s, 6H), 0.07 (S, 36H).

Example 5

Synthesis of 4-($C_6F_5$N{TES})—$C_6F_4$Br. To a potassium hydride (0.489 grams) suspension in tetrahydrofuran (50 milliliters, THF) was added a solution of 4-($C_6F_5$NH)—$C_6F_4$Br (6.245 grams in 50 milliliters of THF). After the gas generation stopped, chlorotriethylsilane (TES-Cl, 1.65 grams) was added The solution was allowed to stir for 16 hours. The solvent was replaced with hexanes and the solid precipitate was separated by filtration. The colorless liquid product was isolated from the yellow mixture by column chromatography (200 mesh silica gel, hexanes). This procedure yields 5.03 grams of product. The product was characterized by $_{19}$F NMR. $_{19}$F NMR (CDCl$_3$, 25° C., referenced from CFCl$_3$(0.0)): δ –134.2 (m, 2F), –143.1 (m, 2F), –143.8 (m, 2F), –157.8 (t, 1F), –163.1 (m, 2F).

Example 6

Synthesis of [4-($C_6F_5$N{TES})—$C_6F_4$]$_4$B Li($Et_2$O)$_{2.5}$: To a cold $Et_2$O solution of 4-($C_6F_5$N{TES})—$C_6F_4$Br (4.604 grams) was added nButyl lithium (4.2 milliliters, 2.1 M in hexanes, Aldrich). The lithiation was allowed to complete over 2 hours at which point boron chloride (2.2 milliliters, 1.0 M in hexanes, Aldrich) was added to the reaction mixture. The cold bath was removed and the reaction was stirred for 3 hours. The white precipitate was separated by filtration. The volume of the filtrate was reduced to approximately 30% and pentane was added to induce precipitation. The two-layered mixture was chilled to 35° C. The product precipitates as a white solid (3.956 grams). The product was characterized by $^{19}$F and $^1$H NMR. $^1$H NMR (Toluene-d$^8$, 25° C.): δ 3.27 (q, 10H), 1.13 (t, 15H), 0.83 (t, 36H), 0.69 (q, 24H). $^{19}$F NMR (Toluene-d$^8$, 25° C.): δ −135.1 (m, 2F), −144.6 (m, 2F), −150.6 (m, 2F), −160.7 (t, 1F), −164.9 (m, 2F).

Example 7

Synthesis of [$C_6H_5$NBu$_2$(H)][4-($C_6F_5$N{TES})—$C_6F_4$]$_4$B: To a methylene chloride solution of [4-($C_6F_5$N{TES})—$C_6F_4$]$_4$B Li($Et_2$O)$_{2.5}$ (1.618 grams) was added a methylene chloride solution of $C_6H_5$NBu$_2$HCl (0.200 grams). The mixture was stirred for 1 hour and the white precipitate was separated by filtration. The volume of the filtrate was reduced to 30% and pentane was added to induce precipitation. The solution was chilled for 16 hours at −35° C. The solvents were remove and the product was collected to afford 1.218 grams of product. The product was characterized by $^{19}$F and $^1$H NMR. $^{19}$F NMR (Toluene-d$^8$, 25° C.): δ −133.2 (m, 2F), −144.6 (m, 2F), −149.0 (m, 2F), −159.3 (t, 1F), −164.3 (m, 2F). $^1$H NMR δ 6.88 (bm, 3H), 6.48 (bm, 2H), 2.95 (bs, 2H), 2.72 (bs, 2H), 1.25 (m, 4H), 1.50 (m, 4H), 0.80–0.07 (m, 66H).

Example 8

Synthesis of Br$C_6F_4$—N(n-Pr)$_2$: To a solution of $C_6F_6$ in DMSO was added HN(n-Pr)$_2$. The reaction was allowed to stir for 16 hours. The resulting orange solution was quenched with an aqueous NaHSO$_4$ solution (200 milliliters). Chloroform was added to extract the product (300 milliliters). The organic layer was separated and dried with MgSO$_4$. The drying agent was removed by filtration and the solvent evaporated. A vacuum distillation failed to afford pure amine. The final purification was accomplished by column chromatography (silica gel, hexanes). This procedure results in a clear, colorless oil (5.21 grams). $_{19}$F NMR (CDCl$_3$, 25° C.): δ −136.4 (m, 2F), −147.9 (m, 2F). $^1$H NMR (CDCl$_3$, 25° C.): 3.10 (t, 4H), 1.48 (m, 4H), 0.81 (t, 6H).

Example 9

Synthesis of Li($Et_2$O)$_{1/2}$B($C_6F_4$N(n-Pr)$_2$)$_4$: To a cold diethylether (50 milliliters) solution of Br$C_6F_4$—N(n-Pr)$_2$ (2.1 grams) was added Butyl lithium (4.0 milliliters). The reaction was allowed to stir for 1 hour at −78° C. One quarter of an equivalent of boron trichloride was added and the mixture stirred for 30 minutes. The reaction was then allowed to stir at room temperature for 14 hours. The resulting yellow solution was filtered to remove the LiCl by-product. The solvent was replaced with pentane to induce trituration (14 hours). The mixture was chilled to −35° C. and the product collected by filtration (1.06 grams). $^{19}$F NMR (Toluene/THF-d$^8$, 25° C.): δ −133.8 (bs, 8F), −153.5 (bs, 8F). $^1$H NMR (Toluene/THF-d$^8$, 25° C.): δ 3.26 (q, 2H), 2.91 (t, 16H), 1.37 (q, 16H), 1.10 (t, 3H), 0.77 (t, 24H).

Example 10

Synthesis of Comparative Compound B($C_6F_4$N(n-Pr)$_2$)$_4$: To a methylene chloride (5 milliliters) solution of Li($Et_2$O)$_{1/2}$B($C_6F_4$N(n-Pr)$_2$)$_4$ (0.604 grams) was added $C_6H_5$NMe$_2$HCl (0.091 grams) in 5 milliliters of methylene chloride. The solution was stirred for 1 hour and the solid LiCl by-product remove by filtration. The product was titrated with pentane and collected to afford 0.435 grams of (n-Pr)$_2$N(H)$C_6F_4$B($C_6F_4$N(n-Pr)$_2$)$_3$. Attempts to remove all of the N,N'-dimethylaniline ("DMA") were unsuccessful.

Example 11

Solubility Test

Procedure: To 0.023 g of the invention compound [$C_6H_5$NBu$_2$(H)][4-($C_6H_5$ {$Et_3$Si})—$C_6F_4$]$_4$B was added 0.735 grams of pentane. The mixture was stirred for 30 minutes. The resulting mixture was filtered to remove undissolved solids. An portion of the filtrate weighing 0.423 grams was evaporated. After solvent removal the vessel contents, the borate salt, weighed 0.011 grams (2.6 wt %). Under analogous experimental conditions with another invention compound [$C_6H_5$NMe$_2$(H)][4-($C_6F_5$N{Me$_3$Si})—$C_6F_4$]$_4$B, no visible amount of activator remained from the filtrate after evaporation. Accordingly, the solubility of the —SiMe$_3$-trialkyl silyl substituent of the second compound appeared to be <0.01 wt %, and is significantly less than that of the —SiEt$_3$-trialkylsilyl containing first compound.

Batch Propylene Polymerization

Example 12

Propylene polymerization reactions were carried out in a well-stirred 1 liter batch reactor equipped to perform coordination polymerization in the presence of an inert hydrocarbon (hexanes) solvent at pressures up to 500 psig and temperatures up to 150° C. In the vapor-liquid polymerization system, the polymerization occurred in the liquid phase where propylene was fed into the reactor prior to the addition of the catalyst solutions. In all experiments, the reactor temperature was kept constant at 60° C. by electronically controlling the amount of steam added to the reactor jacket. In a typical experiment, hexanes (125 milliliters) were fed into the dry reactor. A toluene solution (20 microliters, 25% wt) of TIBAL was added to the reactor. Propylene (125 ml) was added to the reactor. The reactor was sealed and heated to 60° C. The catalyst solution (catalyst and activator dissolved in 40 milliliters toluene) was added to the reactor via a catalyst feed pump. Polymerization began immediately upon addition of the catalyst, and was allowed to continue under controlled temperature for the indicated times. After the indicated time, the reactor was allowed to reach room temperature and depressurized by venting. The polymerization solution was poured into methanol to induce precipitation. The polymer was collected and allowed to dry over 16 h under ambient condition. The polymer was dried further under vacuum at 60° C. Polymerization results are presented in Tables 1 and 2.

TABLE 1

Propylene Polymerization.[1]

| Act | Yield (g) | time (min) | Activity (g/mmol*min)[3] | Mn | Mw | Mw/Mn |
|---|---|---|---|---|---|---|
| A[2] | 22.15 | 15 | 353 | 108,222 | 181,669 | 1.68 |
| A[2] | 20.40 | 15 | 292 | 113,554 | 189,136 | 1.67 |
| A[2] | 34.56 | 15 | 722 | 107,500 | 189,730 | 1.76 |
| A[2] | 13.30 | 15 | 168 | 140,761 | 237,646 | 1.69 |
| A[2] | 17.04 | 15 | 259 | 108,001 | 191,813 | 1.78 |
| A[2] | 26.18 | 15 | 635 | 114,817 | 183,040 | 1.59 |

[1]Catalyst: dimethylsilyl (bis-indenyl) hafnium dimethyl;
[2]Cocatalyst: N,N-dimethyl anilinium tetrakis (4-(N-pentafluorophenyl-N-trimethylsilylamino)tetrafluorophenyl) borate.
[3]g/mmol*min: gram of polymer per millimole of activated catalyst per minute.

TABLE 2

Comparative Propylene Polymerization.[1]

| Act | Yield (g) | time (min) | Activity (g/mmol*min)[3] | Mn | Mw | Mw/Mn |
|---|---|---|---|---|---|---|
| A[4] | 7.1 | 15 | 127 | 56,259 | 109,863 | 2.11 |
| A[4] | 10.50 | 15 | 54 | 27,767 | 57,832 | 2.08 |
| A[4] | 3.0 | 15 | 91 | 34,105 | 40,145 | 2.06 |
| A[4] | 13.70 | 15 | 30 | 57,952 | 109,863 | 1.90 |

[1,3]Same as noted in Table 1.
[4]Cocatalyst: N,N-dimethyl anilinium tetrakis(4-N-pentafluorophenyl-N-trimethylsilylamino)tetrafluorophenyl) borate.

As can be seen from Tables 1 and 2, there is a significant and surprisingly large difference in relative activity and molecular weight values. Without intending to be bound thereby, it is suspected that the N,N'-dimethyl anilinium cation is protonating the unshared electron pair of the nitrogen of the dialkylamino group on the fluoroaryl ligand of the borate anion. A zwitterionic activator is the likely reaction product and will compete with any [Ct]$^+$ [A]$^-$ ionic salt that may exist in some equilibrium with the zwitterionic reaction product. By contrast, the use of the fluoraryl group in place of one alkyl group of the dialkylamino provides a significant unexpected improvement in activity, likely because of a decrease in the basicity (and protonation reactivity) from the unshared electron pair of the nitrogen atom due to added electron-withdrawing capacity of the fluoraryl group.

High Temperature Batch Ethylene/octene Copolymerization

Example 13

Ethylene/1-octene copolymerizations were carried out in a well-stirred 1 L batch reactor equipped to perform coordination polymerization in the presence of an inert hydrocarbon (hexane) solvent at pressures up to 600 psig and temperatures up to 150° C. In the vapor-liquid (VL) polymerization system, the polymerization occurs in the liquid phase whereas ethylene was continuously fed to the reactor to keep the vapor phase overhead pressure constant at 265 psig during the polymerization. The reactor temperature was kept constant at 140° C. by throttling the amount of steam added to the reactor mantle and by adjusting the amount of catalyst fed to the reactor by the pump. Typically, 250 mL of dried hexane, 18 mL of dried 1-octene, and 1.0 mL of a 10 wt % triisobutylaluminum solution (toluene or hexane), a poison scavenger, were fed to the reactor, which was then brought to 140° C. The reactor content was then pressurized with 265 psi ethylene by feeding ethylene and maintained at constant ethylene pressure throughout the polymerization. The polymerization was started by continuously feeding a pre-activated solution (toluene or hexane) of the catalyst during the polymerization. The catalyst flow rate was stopped and the reactor was allowed to cool to room temperature and depressurized. The product was precipitated out of solution and then dried in a hood at room temperature overnight. Polymerization results are presented in Table 3.

TABLE 3

Ethylene-Octene copolymerization.[5,7]

| Act | Yield (g) | time (min) | Activity (g/mmol*min)[3] | Mn | Mw | Mw/Mn |
|---|---|---|---|---|---|---|
| A[6] | 10.24 | 30 | 91 | 58,369 | 152,858 | 2.62 |
| A[6] | 12.36 | 30 | 110 | 75,681 | 161,667 | 2.14 |
| A[6] | 12.90 | 30 | 108 | 76,764 | 166,130 | 2.16 |
| A[6] | 11.92 | 30 | 93 | 60,485 | 147,384 | 2.44 |
| A[6] | 10.25 | 30 | 77 | 91,132 | 173,438 | 1.90 |

[5]Catalyst: bis(3,5-(bistriethylsilyl)phenyl)methylene cyclopentadienyl fluorenyl hafnium dimethyl;
[6]Cocatalyst: N,N-dibutyl anilinium tetrakis(4-(N-pentafluoro-N-triethylsilylamino)tetrafluorophenyl)borate;
[3]Same as noted in Table 1;
[7]Co-monomer incorporation: ranged from 18–23 wt. % 1-octene.

While certain representative embodiments and details have been provided to illustrate the invention, it will be apparent to skilled artisans that various process and product changes from those disclosed in this specification may be made without departing from this invention's scope, which the appended claims define. These are considered to be within the scope of the current invention.

All patents, test procedures, and other documents cited in this specification are fully incorporated by reference to the extent that this material is consistent with this specification and for all jurisdictions in which such incorporation is permitted.

I claim:

1. A composition of matter comprising a cation [Ct]$^+$ and an anion [A]$^-$, wherein the anion comprises a Group-13-element core connected to at least one fluoroaryl ligand, wherein the fluoroaryl ligand has a substitution that comprises a Group-15 element connected to an electron-withdrawing group that renders the Group-15 element's lone pair substantially unreactive.

2. The composition of claim 1 represented by the formula:

wherein
   (a) [Ct]$^+$ is an activating cation;
   (b) M is a Group-13 element;
   (c) ArF are each independently fluoroaryl groups, wherein each fluoroaryl group has at least one fluorine substitution;
   (d) E is a Group-15 element;
   (e) R is a $C_1$–$C_{20}$ hydrocarbyl or hydrocarbylsilyl substituent; and
   (f) n=0, 1, 2, or 3.

3. The composition of claim 2 wherein each fluoroaryl group is one of phenyl, biphenyl, naphthyl, indenyl, anthracenyl, fluorenyl, azulenyl, phenanthrenyl, or pyrenyl.

4. The composition of claim 3 wherein each fluoroanyl group is one of phenyl, biphenyl, or napthyl.

5. The composition of claim 3 wherein R is a $C_1$–$C_{10}$, linear, branched, or cyclic, aliphatic hydrocarbyl or hydrocarbylsilyl substituent.

6. The composition of claim 5 wherein R is trialkyl silyl, the alkyl groups contain from 1 to 20 carbon atoms, and the alkyl groups may be the same or different.

7. The composition of claim 1 wherein the Group-15 element is nitrogen or phosphorous.

8. The composition of claim 2 wherein each fluoroaryl group is perfluorinated.

9. The composition of claim 2 wherein ArF in each position is perfluoro-phenyl, E is nitrogen and is in the para-position of the ArF ligand connected to M, and R is a $C_3$–$C_{12}$ hydrocarbyl or hydrocarbylsilyl substituent.

10. A composition of matter represented by the formula:

wherein (a) $[Ct]^+$ is an activating cation;

(b) B is boron;

(c) ArF are each independently fluoroaryl groups, wherein each fluorinated aryl group has at least one fluorine substitution;

(d) N is nitrogen;

(e) R is a $C_1$–$C_{20}$ hydrocarbyl or hydrocarbylsilyl substituent; and n=1, 2, or 3.

11. The composition of claim 10 wherein the aryl portion of each fluoroaryl group is independently one of phenyl, biphenyl, naphthyl, indenyl, anthracenyl, fluorenyl, azulenyl, phenanthrenyl, or pyrenyl.

12. The composition of claim 11 wherein the aryl portion of each fluoroaryl group is independently one of phenyl, biphenyl, or napthyl.

13. The composition of claim 12 wherein R is a $C_1$–$C_{20}$ a linear, branched, or cyclic aliphatic hydrocarbyl or hydrocarbylsilyl substituent.

14. The composition of claim 13 wherein R is a silyl group substituted with a multiplicity of the same or different, 1-to-20-carbon-atom alkyl groups.

15. A composition of matter consisting of a cation $[Ct]^+$ and an anion $[A]^-$, wherein the anion comprises a Group-13 element core connected to at least one fluoroaryl ligand, wherein the fluoroaryl ligand is para-substituted with a fluoroaryl-trialkylsilyl-tertiary amino group.

16. The composition of claim 15 wherein the Group-13 element is boron or aluminum, and the amino-group fluoroaryl ligands are perfluorophenyl.

17. The composition of claim 16 wherein each of the fluoroaryl ligands is para-substituted with a fluoroaryl-trialkylsilyl-tertiary amino group.

18. An olefin polymerization catalyst that is the reaction product of (a) a transition metal compound having at least one stabilizing ligand and at least one ligand suitable for olefin insertion and a scissile metal-carbon connection that, upon scission, forms at least one active olefin polymerization catalysis center and (b) a Group-13-element-based cocatalyst comprising a cation $[Ct]^+$ and an anion $[A]^-$, wherein the anion comprises a core Group-13 element connected to at least one fluoroaryl ligand, wherein at least one fluoroaryl ligand has a substitution that comprises a Group-15 element connected to an electron-withdrawing group that renders the Group-15 element's lone-pair substantially unreactive.

19. The catalyst composition of claim 18 wherein the cocatalyst compound is represented by the formula:

wherein (a) $[Ct]^+$ is an activating cation;

(b) M is a Group-13 element;

(c) ArF are each independently fluoroaryl groups, wherein each fluoroaryl group has at least one fluorine substitution;

(d) E is a Group-15 element;

(e) R is a $C_1$–$C_{20}$ hydrocarbyl or hydrocarbylsilyl substituent; and (f) n=1, 2, or 3.

20. The composition of claim 19 wherein each fluoroaryl group is perfluorinated.

21. The composition according to any of the claims 18–20 wherein the transition metal compound is a Group-3–10 metal catalyst precursor activable to a cation for olefin polymerization.

22. The composition of claim 21 wherein the transition metal compound is a metallocene catalyst precursor with the formula:

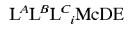

where, $L_A$ is a substituted or unsubstituted cyclopentadienyl ligand connected to Mc; $L^B$ is a member of the class of ligands defined for $L_A$, or is J, a heteroatom ligand connected to Mc; the $L_A$ and $L_B$ ligands may be bridged together through a Group-13–16-element-containing linking group; $L^C_i$ is an optional neutral, non-oxidizing ligand connected to Mc (i equals 0 to 3); Mc is a Group-3–6-transition metal; and, D and E are independently labile ligands, each having a metal-carbon connection with M, optionally bridged to each other or to $L^A$ or $L_B$, wherein the D- or E-M connection is breakable by the Group-13-element cocatalyst and into which a monomer or macromer can insert for polymerization.

23. The composition of claim 22 wherein M is titanium and $L_B$ is J, a heteroatom ligand connected to M.

24. The composition of claim 22 wherein M is zirconium or hafnium and $L_B$ is independently a substituted or unsubstituted cyclopentadienyl ligand connected to M.

25. A catalyst for olefin polymerization comprising the reaction product of (a) an organometallic transition metal catalyst compound having at least one stabilizing ligand and at least one labile ligand suitable for olefin insertion and (b) the composition of any of claims 1–20.

26. A process for preparing polyolefins comprising combining one or more olefins under polymerization conditions with a catalyst that is the reaction product of (a) a transition metal compound having at least one stabilizing ligand and at least one ligand suitable for olefin insertion and (b) the composition of claims 1–20.

27. The process of claims 26 wherein the transition metal compound is activable for olefin polymerization and comprises a Group-3–10 metal.

28. The process of claim 27 wherein the transition metal compound has the formula:

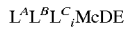

where, $L_A$ is a substituted or unsubstituted cyclopentadienyl ligand connected to Mc; $L^B$ is a member of the class of ligands defined for $L^A$, or is J, a heteroatom ligand connected to Mc; the $L_A$ and $L_B$ ligands may be bridged together through a Group-13-16-element-containing linking group; $L^C_i$ is an optional neutral, non-oxidizing ligand connecting to Mc (i equals 0 to 3); Mc is a Group-3–6-transition metal; and, D and E are independently labile ligands, connected to M, optionally bridged to each other or to $L^A$ or $L_B$, wherein the D- or E-M connection is breakable by the Group-13-element cocatalyst and into which a monomer or macromer can insert for polymerization.

29. The process of claim 27 wherein M is titanium and $L_B$ is J, a heteroatom ligand connected to M.

30. The process of claim 27 wherein M is zirconium or hafnium and $L_B$ is independently a substituted or unsubstituted cyclopentadienyl ligand connected to M.

31. The process of claim 29 wherein polymerization conditions comprise solution, supercritical pressure, bulk, slurry or gas-phase processes conducted at temperatures from greater than or equal to 30° C. to 300° C. and pressures from greater than or equal to 0 to greater than or equal to 2000 bar.

32. The process of claim 30 wherein the process is an adiabatic solution process conducted at a temperature greater than or equal to 40° C. to greater than or equal to 250° C.

33. The process of claim 30 wherein the process is bulk, slurry, or gas phase, and the transition metal compound, after activation for olefin polymerization, is carried on or affixed to a particulate support.

34. The process of claim 30 wherein the monomers are one or more of ethylene, $C_3$–$C_{20}$ olefins, $C_5$–$C_{20}$ diolefins, $C_7$–$C_{20}$ vinyl aromatic monomers, $C_4$–$C_{20}$ geminally-disubstituted olefins, and $C_5$–$C_{20}$ cyclic olefins.

35. A catalyst system for olefin polymerization comprising:
   (a) a transition metal compound having at least one stabilizing ligand and at least one ligand suitable for olefin insertion, and
   (b) the composition of claims 1–19.

36. The catalyst system of claim 35 wherein the transition metal compound comprises a metal from Groups 3–6 of the periodic table.

37. The catalyst system of claim 35 wherein the transition metal compound is a metallocene.

38. The catalyst system of claim 35 wherein the transition metal compound is a metallocene.

* * * * *